(12) United States Patent
Kendall et al.

(10) Patent No.: US 11,179,553 B2
(45) Date of Patent: Nov. 23, 2021

(54) DELIVERY DEVICE

(71) Applicant: Vaxxas Pty Limited, Sydney (AU)

(72) Inventors: Mark Anthony Fernance Kendall, Chelmer (AU); Stefano Meliga, West End (AU); Alexandra Christina Isabelle Depelsenaire, Yeerongpilly (AU); Michael Lawrence Crichton, Auchenflower (AU); Christopher Flaim, Kenmore (AU)

(73) Assignee: VAXXAS PTY LIMITED, Sydney (AU)

( * ) Notice: Subject to any disclaimer, the term of this patent is extended or adjusted under 35 U.S.C. 154(b) by 0 days.

(21) Appl. No.: 14/351,499

(22) PCT Filed: Oct. 12, 2012

(86) PCT No.: PCT/AU2012/001289
§ 371 (c)(1),
(2) Date: Apr. 11, 2014

(87) PCT Pub. No.: WO2013/053022
PCT Pub. Date: Apr. 18, 2013

(65) Prior Publication Data
US 2014/0257188 A1    Sep. 11, 2014

(30) Foreign Application Priority Data
Oct. 12, 2011    (AU) .................................. 2011904174

(51) Int. Cl.
*A61M 37/00* (2006.01)
*A61K 9/00* (2006.01)
*A61B 17/20* (2006.01)

(52) U.S. Cl.
CPC ........ *A61M 37/0015* (2013.01); *A61B 17/205* (2013.01); *A61K 9/0021* (2013.01);
(Continued)

(58) Field of Classification Search
CPC ...... A61M 37/0015; A61M 2037/0053; A61M 2037/0046; A61M 2037/0023;
(Continued)

(56) References Cited

U.S. PATENT DOCUMENTS

| 2,213,830 A | 9/1940 | Anastasi |
| 2,881,500 A | 4/1959 | Furness |

(Continued)

FOREIGN PATENT DOCUMENTS

| CN | 1149018 A | 5/1997 |
| CN | 101214395 A | 7/2008 |

(Continued)

OTHER PUBLICATIONS

Garafalo et al., Histamine Release and Therapy of Severe Dematographism, Aug. 1981, J. Allergy Clin. Immunol., vol. 68, No. 2, pp. 103-105.*

(Continued)

*Primary Examiner* — William R Carpenter
(74) *Attorney, Agent, or Firm* — Seed IP Law Group LLP

(57) ABSTRACT

A device for delivery of material to a biological subject, the device including a base and a number of projections extending from the base, each projection including a tip for penetrating tissue of the biological subject, at least a portion of at least one of the projections being coated with a non-liquid coating including the material. At least the tip of at least one of the coated projections may have a convex effective profile. The device may be for delivery of material to a dermal layer of the biological subject. In another aspect an applicator for applying the device to the biological subject applies a preload force to the tissue such that the force at least partially compresses a subcutaneous tissue layer of the biological subject prior to application of the device, and applies the device with a predetermined velocity, (Continued)

wherein tissue stiffness is maintained and/or the projections penetrate the tissue to a predetermined depth.

9 Claims, 112 Drawing Sheets

(52) U.S. Cl.
CPC ..... *A61M 37/00* (2013.01); *A61M 2037/0023* (2013.01); *A61M 2037/0046* (2013.01)

(58) Field of Classification Search
CPC ........... A61K 9/0021; B81B 2201/055; B81B 1/008; A61B 5/150984
See application file for complete search history.

(56) References Cited

U.S. PATENT DOCUMENTS

| | | | |
|---|---|---|---|
| 4,702,799 A | 10/1987 | Tuot | |
| 5,017,007 A | 5/1991 | Milne et al. | |
| 5,201,992 A | 4/1993 | Marcus et al. | |
| 5,353,792 A | 10/1994 | Lübbers et al. | |
| 5,449,064 A | 9/1995 | Hogan et al. | |
| 5,457,041 A | 10/1995 | Ginaven et al. | |
| 5,461,482 A | 10/1995 | Wilson et al. | |
| 5,499,474 A | 3/1996 | Knooihuizen | |
| 5,527,288 A | 6/1996 | Gross et al. | |
| 5,611,806 A | 3/1997 | Jang | |
| 5,657,138 A | 8/1997 | Lewis et al. | |
| 5,859,937 A | 1/1999 | Nomura | |
| 5,922,356 A | 7/1999 | Koseki et al. | |
| 5,928,207 A | 7/1999 | Pisano et al. | |
| 5,943,075 A | 8/1999 | Lee et al. | |
| 6,052,652 A | 4/2000 | Lee | |
| 6,233,797 B1 | 5/2001 | Neely et al. | |
| 6,287,556 B1 | 9/2001 | Portnoy et al. | |
| 6,299,621 B1 | 10/2001 | Fogarty et al. | |
| 6,334,856 B1 | 1/2002 | Allen et al. | |
| 6,352,697 B1 | 3/2002 | Cox et al. | |
| 6,454,755 B1 | 9/2002 | Godshall | |
| 6,463,312 B1 | 10/2002 | Bergveld et al. | |
| 6,478,738 B1 | 11/2002 | Hirabayashi et al. | |
| 6,503,231 B1 | 1/2003 | Prausnitz et al. | |
| 6,533,949 B1 | 3/2003 | Yeshurun et al. | |
| 6,537,242 B1 | 3/2003 | Palmer | |
| 6,537,264 B1 | 3/2003 | Cormier et al. | |
| 6,551,849 B1 | 4/2003 | Kenney | |
| 6,557,849 B2 | 5/2003 | Wyss | |
| 6,558,361 B1* | 5/2003 | Yeshurun | A61B 5/1411 604/272 |
| 6,565,532 B1 | 5/2003 | Yuzhakov et al. | |
| 6,589,202 B1 | 7/2003 | Powell | |
| 6,591,124 B2 | 7/2003 | Sherman et al. | |
| 6,610,382 B1 | 8/2003 | Kobe et al. | |
| 6,743,211 B1 | 6/2004 | Prausnitz et al. | |
| 6,749,575 B2 | 6/2004 | Matriano et al. | |
| 6,855,372 B2 | 2/2005 | Trautman et al. | |
| 6,881,203 B2* | 4/2005 | Delmore | A61B 5/1411 604/272 |
| 6,908,453 B2 | 6/2005 | Fleming et al. | |
| 6,923,764 B2 | 8/2005 | Aceti et al. | |
| 6,931,277 B1* | 8/2005 | Yuzhakov | A61M 37/0015 604/21 |
| 6,945,952 B2 | 9/2005 | Kwon | |
| 7,022,071 B2 | 4/2006 | Schaupp et al. | |
| 7,045,069 B2 | 5/2006 | Ozeryansky | |
| 7,048,723 B1 | 5/2006 | Frazier et al. | |
| 7,097,631 B2 | 8/2006 | Trautman et al. | |
| 7,169,600 B2 | 1/2007 | Hoss et al. | |
| 7,211,062 B2 | 5/2007 | Kwon | |
| 7,250,037 B2 | 7/2007 | Shermer et al. | |
| 7,316,665 B2 | 1/2008 | Laurent et al. | |
| 7,753,888 B2 | 7/2010 | Mukerjee et al. | |
| 8,052,633 B2 | 11/2011 | Kendall | |
| 8,062,573 B2 | 11/2011 | Kwon | |
| 8,267,889 B2 | 9/2012 | Cantor et al. | |
| 8,414,548 B2 | 4/2013 | Yuzhakov | |
| 8,540,672 B2 | 9/2013 | McAllister | |
| 8,734,697 B2 | 5/2014 | Chen et al. | |
| 8,883,015 B2 | 11/2014 | Kendall et al. | |
| 9,283,365 B2 | 3/2016 | Kendall et al. | |
| 2002/0008530 A1 | 1/2002 | Kim et al. | |
| 2002/0016562 A1 | 2/2002 | Cormier et al. | |
| 2002/0032415 A1 | 3/2002 | Trautman et al. | |
| 2002/0128599 A1 | 9/2002 | Cormier et al. | |
| 2002/0133129 A1* | 9/2002 | Arias | A61M 37/0015 604/272 |
| 2002/0169411 A1 | 11/2002 | Sherman et al. | |
| 2002/0177839 A1 | 11/2002 | Cormier et al. | |
| 2003/0036710 A1 | 2/2003 | Matriano et al. | |
| 2003/0199810 A1 | 10/2003 | Trautman et al. | |
| 2003/0199811 A1 | 10/2003 | Sage, Jr. et al. | |
| 2004/0002121 A1 | 1/2004 | Regan et al. | |
| 2004/0004649 A1 | 1/2004 | Bibl et al. | |
| 2004/0008241 A1 | 1/2004 | Junhua | |
| 2004/0039397 A1 | 2/2004 | Weber et al. | |
| 2004/0049150 A1 | 3/2004 | Dalton et al. | |
| 2004/0087992 A1 | 5/2004 | Gartstein et al. | |
| 2004/0161470 A1 | 8/2004 | Andrianov et al. | |
| 2005/0042866 A1 | 2/2005 | Klapproth et al. | |
| 2005/0089553 A1* | 4/2005 | Cormier | A61K 9/0021 424/448 |
| 2005/0089554 A1 | 4/2005 | Cormier et al. | |
| 2005/0126710 A1 | 6/2005 | Laermer et al. | |
| 2005/0137531 A1* | 6/2005 | Prausnitz | A61B 5/14514 604/173 |
| 2005/0143713 A1 | 6/2005 | Delmore et al. | |
| 2005/0197308 A1 | 9/2005 | Dalton et al. | |
| 2005/0261632 A1* | 11/2005 | Xu | A61K 9/0021 604/173 |
| 2006/0012780 A1 | 1/2006 | Nishiyama et al. | |
| 2006/0015061 A1 | 1/2006 | Kuo et al. | |
| 2006/0055724 A1 | 3/2006 | Krawczyk et al. | |
| 2006/0074376 A1 | 4/2006 | Kwon | |
| 2006/0195125 A1 | 8/2006 | Sakakine et al. | |
| 2006/0202385 A1 | 9/2006 | Xu et al. | |
| 2006/0264782 A1 | 11/2006 | Holmes et al. | |
| 2007/0027474 A1 | 2/2007 | Lasner | |
| 2007/0060867 A1 | 3/2007 | Xu | |
| 2007/0078376 A1 | 4/2007 | Smith | |
| 2007/0224252 A1 | 9/2007 | Trautman et al. | |
| 2007/0264749 A1 | 11/2007 | Birkmeyer | |
| 2007/0270738 A1 | 11/2007 | Wu et al. | |
| 2007/0293815 A1 | 12/2007 | Chan et al. | |
| 2007/0299388 A1 | 12/2007 | Chan et al. | |
| 2008/0009811 A1 | 1/2008 | Cantor | |
| 2008/0108959 A1 | 5/2008 | Jung et al. | |
| 2008/0114298 A1 | 5/2008 | Cantor et al. | |
| 2008/0136874 A1 | 6/2008 | Tsukamura | |
| 2008/0245764 A1 | 10/2008 | Pirk et al. | |
| 2008/0287858 A1 | 11/2008 | Duan | |
| 2008/0312610 A1* | 12/2008 | Binks | A61K 9/0021 604/272 |
| 2008/0312669 A1 | 12/2008 | Vries et al. | |
| 2009/0017210 A1* | 1/2009 | Andrianov | A61M 37/0015 427/256 |
| 2009/0041810 A1* | 2/2009 | Andrianov | A61K 9/0021 424/400 |
| 2009/0198189 A1 | 8/2009 | Simons et al. | |
| 2009/0292254 A1 | 11/2009 | Tomono | |
| 2010/0221314 A1 | 9/2010 | Matsudo et al. | |
| 2010/0222743 A1 | 9/2010 | Frederickson et al. | |
| 2010/0256568 A1 | 10/2010 | Frederickson et al. | |
| 2011/0021996 A1 | 1/2011 | Lee et al. | |
| 2011/0028905 A1 | 2/2011 | Takada | |
| 2011/0059150 A1 | 3/2011 | Kendall et al. | |
| 2011/0160069 A1 | 6/2011 | Corrie et al. | |
| 2011/0223542 A1* | 9/2011 | Kendall | A61M 37/0015 430/320 |
| 2011/0245776 A1* | 10/2011 | Kendall | A61B 17/205 604/173 |
| 2011/0276027 A1 | 11/2011 | Trautman et al. | |

(56) References Cited

U.S. PATENT DOCUMENTS

| | | | |
|---|---|---|---|
| 2011/0288484 A1* | 11/2011 | Kendall | A61B 17/205 604/173 |
| 2012/0027810 A1 | 2/2012 | Chen et al. | |
| 2012/0041412 A1* | 2/2012 | Roth | A61M 25/10 604/500 |
| 2012/0083741 A1 | 4/2012 | Kendall | |
| 2012/0083762 A1 | 4/2012 | Kendall | |
| 2012/0109065 A1 | 5/2012 | Backes | |
| 2012/0136312 A1* | 5/2012 | Terahara | A61B 5/150984 604/173 |
| 2012/0220981 A1* | 8/2012 | Soo | A61M 37/0015 604/506 |
| 2012/0265141 A1 | 10/2012 | Kalpin et al. | |
| 2012/0277629 A1 | 11/2012 | Bernstein et al. | |
| 2012/0330250 A1 | 12/2012 | Kuwahara et al. | |
| 2013/0079666 A1 | 3/2013 | Gonzalez-Zugasti et al. | |
| 2013/0131598 A1 | 5/2013 | Trautman et al. | |
| 2013/0150822 A1 | 6/2013 | Ross | |
| 2013/0158482 A1 | 6/2013 | Davis et al. | |
| 2013/0190794 A1 | 7/2013 | Kendall et al. | |
| 2013/0337150 A1 | 12/2013 | Biemans | |
| 2014/0243747 A1 | 8/2014 | Tokumoto et al. | |
| 2014/0276366 A1 | 9/2014 | Bourne et al. | |
| 2014/0276378 A1 | 9/2014 | Chen et al. | |
| 2015/0057604 A1 | 2/2015 | Arami et al. | |
| 2015/0080844 A1 | 3/2015 | Donovan et al. | |
| 2016/0015952 A1 | 1/2016 | Omachi et al. | |
| 2016/0058697 A1 | 3/2016 | Kendall et al. | |
| 2016/0220803 A1 | 8/2016 | Kendall et al. | |
| 2016/0310412 A1 | 10/2016 | Tanoue et al. | |
| 2017/0182301 A1 | 6/2017 | Kendall | |
| 2017/0239458 A1 | 8/2017 | Kato et al. | |
| 2017/0282417 A1 | 10/2017 | Okano et al. | |
| 2017/0296465 A1 | 10/2017 | Yoshida et al. | |
| 2017/0361082 A1 | 12/2017 | Okano et al. | |
| 2017/0368322 A1 | 12/2017 | Kato et al. | |
| 2018/0015271 A1 | 1/2018 | Junger et al. | |
| 2018/0161050 A1 | 6/2018 | Kendall | |
| 2018/0263641 A1 | 9/2018 | Crichton et al. | |
| 2018/0264244 A1 | 9/2018 | Meliga et al. | |
| 2018/0326726 A1 | 11/2018 | Wang et al. | |
| 2019/0046479 A1 | 2/2019 | Pathak | |
| 2020/0246545 A1 | 8/2020 | Langer et al. | |

FOREIGN PATENT DOCUMENTS

| | | | |
|---|---|---|---|
| CN | 101297989 A | 11/2008 | |
| EP | 0 139 286 A2 | 5/1985 | |
| EP | 0 732 208 A1 | 9/1996 | |
| EP | 1 695 734 B1 | 6/2008 | |
| EP | 2 213 284 A1 | 8/2010 | |
| EP | 2 327 419 A1 | 6/2011 | |
| EP | 2 568 174 A1 | 3/2013 | |
| EP | 2 835 147 A1 | 2/2015 | |
| JP | 2003-127430 A | 5/2003 | |
| JP | 2007-260889 A | 10/2007 | |
| JP | 2010-071845 A | 4/2010 | |
| JP | 2016-166769 A | 9/2016 | |
| WO | 91/06571 A1 | 5/1991 | |
| WO | 94/24281 A1 | 10/1994 | |
| WO | 98/28037 A1 | 7/1998 | |
| WO | 98/28038 A1 | 7/1998 | |
| WO | 99/02694 A1 | 1/1999 | |
| WO | 99/42564 A2 | 8/1999 | |
| WO | 99/64580 A1 | 12/1999 | |
| WO | 00/05339 A1 | 2/2000 | |
| WO | 00/42215 A1 | 7/2000 | |
| WO | 00/74763 A2 | 12/2000 | |
| WO | 00/74764 A1 | 12/2000 | |
| WO | 01/03361 A1 | 1/2001 | |
| WO | 01/33614 A1 | 5/2001 | |
| WO | 01/85207 A2 | 11/2001 | |
| WO | 02/064193 A2 | 8/2002 | |
| WO | 02/074173 A1 | 9/2002 | |
| WO | 02/075794 A2 | 9/2002 | |
| WO | 02/085446 A2 | 10/2002 | |
| WO | 02/085447 A2 | 10/2002 | |
| WO | 02/100476 A2 | 12/2002 | |
| WO | 03/020359 A2 | 3/2003 | |
| WO | 03/026732 A2 | 4/2003 | |
| WO | 03/048031 A2 | 6/2003 | |
| WO | 03/053258 A1 | 7/2003 | |
| WO | 03/092785 A1 | 11/2003 | |
| WO | 2004/000389 A2 | 12/2003 | |
| WO | 2004/024224 A1 | 3/2004 | |
| WO | 2005/049108 A2 | 6/2005 | |
| WO | 2005/060621 A2 | 7/2005 | |
| WO | 2005/069736 A2 | 8/2005 | |
| WO | 2005/072360 A2 | 8/2005 | |
| WO | 2005/072630 A1 | 8/2005 | |
| WO | 2005/123173 A1 | 12/2005 | |
| WO | 2006/055799 A1 | 5/2006 | |
| WO | 2006/101459 A1 | 9/2006 | |
| WO | 2006/108185 A1 | 10/2006 | |
| WO | 2006/116281 A1 | 11/2006 | |
| WO | 2006/138719 A2 | 12/2006 | |
| WO | 2007/002123 A2 | 1/2007 | |
| WO | 2007/002521 A2 | 1/2007 | |
| WO | 2007/012114 A1 | 2/2007 | |
| WO | 2007/030477 A2 | 3/2007 | |
| WO | 2007/054090 A1 | 5/2007 | |
| WO | 2007/061781 A1 | 5/2007 | |
| WO | 2007/061871 A1 | 5/2007 | |
| WO | 2007/070004 A2 | 6/2007 | |
| WO | 2007/080427 A2 | 7/2007 | |
| WO | 2007/127976 A2 | 11/2007 | |
| WO | 2008/010681 A1 | 1/2008 | |
| WO | 2008/011625 A2 | 1/2008 | |
| WO | 2008/053481 A1 | 5/2008 | |
| WO | 2008/069566 A1 | 6/2008 | |
| WO | 2008/083209 A2 | 7/2008 | |
| WO | 2008/091602 A2 | 7/2008 | |
| WO | 2009/040548 A1 | 4/2009 | |
| WO | 2009/066763 A1 | 5/2009 | |
| WO | 2009/079712 A1 | 7/2009 | |
| WO | 2009/081122 A1 | 7/2009 | |
| WO | 2009/097660 A1 | 8/2009 | |
| WO | WO 2009097660 A1 * | 8/2009 | A61M 37/0015 |
| WO | 2009/140735 A1 | 11/2009 | |
| WO | 2010/042996 A1 | 4/2010 | |
| WO | WO 2010042996 A1 * | 4/2010 | A61B 17/205 |
| WO | 2010/071918 A1 | 7/2010 | |
| WO | WO-2010071918 A1 * | 7/2010 | A61M 37/0015 |
| WO | 2010/109471 A1 | 9/2010 | |
| WO | 2011/105496 A1 | 9/2011 | |
| WO | 2011/116388 A1 | 9/2011 | |
| WO | 2012/119907 A1 | 9/2012 | |
| WO | 2012/122162 A1 | 9/2012 | |
| WO | 2013/053022 A1 | 4/2013 | |
| WO | 2013/055641 A1 | 4/2013 | |
| WO | 2015/034924 A1 | 3/2015 | |
| WO | 2016/123665 A1 | 8/2016 | |
| WO | 2016/143514 A1 | 9/2016 | |
| WO | 2017/123652 A1 | 7/2017 | |
| WO | 2018/119174 A1 | 6/2018 | |

OTHER PUBLICATIONS

Aichele et al., "Antiviral Cytotoxic T Cell Response Induced by In Vivo Priming With a Free Synthetic Peptide," *J. Exp. Med.* 171:1815-1820, 1990.

Albert et al., "Dendritic cells acquire antigen from apoptotic cells and induce class I-restricted CTLs," *Nature* 392:86-89, 1998.

Albert et al., "Tumor-specific killer cells in paraneoplastic cerebellar degeneration," *Nature Medicine* 4(11):1321-1324, 1998.

Anderson, "Cutaneous Microdialysis: Is it Worth the Sweat?," *Journal of Investigative Dermatology* 126:1207-1209, 2006.

Athanasopoulos et al., "Gene therapy vectors based on adeno-associated virus: Characteristics and applications to acquired and inherited diseases (Review)," *International Journal of Molecular Medicine* 6:363-375, 2000.

(56) References Cited

OTHER PUBLICATIONS

Bachmann et al., "Dendritic cells process exogenous viral proteins and virus-like particles for class I presentation to CD8+ cytotoxic T lymphocytes," *Eur. J. Immunol.* 26:2595-2600, 1996.

Camilli et al., "*Listeria monocytogenes* Mutants Lacking Phosphatidylinositol-specific Phospholipase C Are Avirulent," *J. Exp. Med.* 173:751-754, 1991.

Cormier et al., "Transdermal delivery of desmopressin using a coated microneedle array patch system," *Journal of Controlled Release* 97:503-511, 2004.

Cox et al., "Adjuvants—a classification and review of their modes of action," *Vaccine* 15(3):248-256, 1997.

Dreyer, "Microneedles: Microprocessing in Medicine," ENMA 465: Microprocessing, May 10, 2004, 23 pages.

Feng et al., "Molecular Biomarkers for Cancer Detection in Blood and Bodily Fluids," *Critical Reviews in Clinical Laboratory Sciences* 43(5-6):497-560, 2006.

Gao et al., "Priming of Influenza Virus-Specific Cytotoxic T Lymphocytes Vivo by Short Synthetic Peptides," *The Journal of Immunology* 147:3268-3273, 1991.

Gardeniers et al., "Silicon Micromachined Hollow Microneedles for Transdermal Liquid Transport," *Journal of Microelectromechanical Systems* 12(6):855-862, 2003.

Gill et al., "Coated microneedles for transdermal delivery," *Journal of Controlled Release* 117:227-237, 2007.

Gill et al., "Coating Formulations for Microneedles," *Pharmaceutical Research* 24(7):1369-1380, 2007.

International Preliminary Report on Patentability, dated Jul. 8, 2010, for International Application No. PCT/AU2008/001903, 8 pages.

International Preliminary Report on Patentability, completed Nov. 14, 2012, for International Application No. PCT/AU2011/000890, 6 pages.

International Preliminary Report on Patentability, dated Jun. 7, 2006, for International Application No. PCT/GB2005/000336, 11 pages International Search Report, dated Feb. 20, 2009, for International Application No. PCT/AU2008/001903, 5 pages.

International Search Report, dated Oct. 25, 2011, for International Application No. PCT/AU2011/000890, 4 pages.

Ito et al., "Feasibility of microneedles for percutaneous absorption of insulin," *European Journal of Pharmaceutical Sciences* 29:82-88, 2006.

Ito et al., "Self-dissolving microneedles for the percutaneous absorption of EPO in mice," *Journal of Drug Targeting* 14(5):255-261, 2006.

Ito et al., "Evaluation of self-dissolving needles containing low molecular weight heparin (LMWH) in rats," *International Journal of Pharmaceutics* 349:124-129, 2008.

Jondal et al., "MHC Class I-Restricted CTL Responses to Exogenous Antigens," *Immunity* 5:295-302, 1996.

Kay et al., "Viral vectors for gene therapy: the art of turning infectious agents into vehicles of therapeutics," *Nature Medicine* 7(1):33-40, 2001.

Kendall et al., "The mechanical properties of the skin epidermis in relation to targeted gene and drug delivery," *Biomaterials* 28:4968-4977, 2007.

Kuzu et al., "In vivo priming effect during various stages of ontogeny of an influenza A virus nucleoprotein peptide," *Eur. J. Immunol.* 23:1397-1400, 1993.

Kwon, "In Vitro Evaluation of Transdermal Drug Delivery by a Micro-needle Patch," Controlled Release Society 31$^{st}$ Annual Meeting, 2004, 2 pages.

Kwon, "Acne Treatment by a Dissolvable Micro-Needle Patch," TheraJect Inc., 2006, 2 pages.

Kwon et al., "Rapid Intradermal Drug Delivery by a Dissolvable Micro-Needle Patch," Controlled Release Society 32$^{nd}$ Annual Meeting, 2005, 2 pages.

Kwon et al., "In Vitro Modeling of Transdermal PTH Delivery by Dissolving Micro-needle Patch," TheraJect Inc., 2007, 2 pages.

Lee et al., "Dissolving microneedles for transdermal drug delivery," *Biomaterials* 29:2113-2124, 2008.

Lin et al., "Silicon-Processed Microneedles," *IEEE Journal of Microelectromechanical Systems* 8(1):78-84, 1999.

Matriano et al., "Macroflux® Microprojection Array Patch Technology: A New and Efficient Approach for Intracutaneous Immunization," *Pharmaceutical Research* 19(1):63-70, 2002.

Mengaud et al., "Expression in *Escherichia coli* and Sequence Analysis of the Listeriolysin O Determinant of *Listeria monocytogenes*," *Infection and Immunity* 56(4):766-772, 1988.

Miyano et al., "Sugar Micro Needles as Transdermic Drug Delivery System," *Biomedical Microdevices* 7(3):185-188, 2005.

Miyano et al., "Hydrolytic Microneedles as Transdermal Drug Delivery System," *Transducers & Eurosensors '07*, The 14$^{th}$ International Conference on Solid-State Sensors, Actuators and Microsystems, Lyon, France, Jun. 10-14, 2007, 4 pages.

Moore et al., "Introduction of Soluble Protein into the Class I Pathway of Antigen Processing and Presentation," *Cell* 54:777-785, 1988.

Mukerjee et al., "Microneedle array for transdermal biological fluid extraction and in situ analysis," *Sensors and Actuators A* 114:267-275, 2004.

Office Action, dated Feb. 17, 2012, for Chinese Patent Application No. 200980104635.3, 7 pages. (English Translation).

Oh et al., "Intradermal influenza vaccine delivery using skin-penetrating dissolvable vaccine microneedles," 2006 AAPS Annual Meeting and Exposition, 1 page.

Oh et al., "Demonstration of Dose-controlled Delivery by Dissolvable Micro-needle Arrays," 34$^{th}$ Annual CRS Conference, Jun. 2007, 2 pages.

Palmer et al., "Streptolysin O: A Proposed Model of Allosteric Interaction between a Pore-Forming Protein and Its Target Lipid Bilayer," *Biochemistry* 37:2378-2383, 1998.

Park et al., "Biodegradable polymer microneedles: Fabrication, mechanics and transdermal drug delivery," *Journal of Controlled Release* 104:51-66, 2005.

Park et al., "Polymer Microneedles for Controlled-Release Drug Delivery," *Pharmaceutical Research* 23(5):1008-1019, 2006.

Park et al., "Towards the silicon nanowire-based sensor for intracellular biochemical detection," *Biosensors and Bioelectronics* 22:2065-2070, 2007.

Portnoy et al., "Capacity of Listeriolysin O, Streptolysin O, and Perfringolysin O to Mediate Growth of *Bacillus subtilis* within Mammalian Cells," *Infection and Immunity* 60(7):2710-2717, 1992.

Rossjohn et al., "Structure of a Cholesterol-Binding, Thiol-Activated Cytolysin and a Model of Its Membrane Form," *Cell* 89:685-692, 1997.

Schulz et al., "Peptide-induced antiviral protection by cytotoxic T cells," *Proc. Natl. Acad. Sci. USA* 88:991-993, 1991.

Silver et al., "Viscoelastic Properties of Young and Old Human Dermis: A Proposed Molecular Mechanism for Elastic Energy Storage in Collagen and Elastin," *J. Appl Polym Sci* 86:1978-1985, 2002.

Stoeber et al., "Arrays of Hollow Out-of-Plane Microneedles for Drug Delivery," *Journal of Microelectromechanical Systems* 14(3):472-479, 2005.

Sullivan et al., "Minimally Invasive Protein Delivery with Rapidly Dissolving Polymer Microneedles," *Adv. Mater.* 20:933-938, 2008.

Tao et al., "A systematic study of dry etch process for profile control of silicon tips," *Microelectronic Engineering* 78-79:147-151, 2005.

Tsuchiya et al., "Development of Blood Extraction System for Health Monitoring System," *Biomedical Microdevices* 7(4):347-353, 2005.

Tyagi et al., "Molecular Beacons: Probes that Fluoresce upon Hybridization," *Nature Biotechnology* 14:303-308, 1996.

Vigna et al., "Lentiviral vectors: excellent tools for experimental gene transfer and promising candidates for gene therapy," *The Journal of Gene Medicine* 2:308-316, 2000.

Walther et al., "Viral Vectors for Gene Transfer—A Review of Their Use in the Treatment of Human Diseases," *Drugs* 60(2):249-271, 2000.

(56) References Cited

OTHER PUBLICATIONS

Wang et al., "Label-free hybridization detection of a single nucleotide mismatch by immobilization of molecular beacons on an agarose film," *Nucleic Acids Research* 30(12):e61, 2002. (9 pages).
Widera et al., "Effect of delivery parameters on immunization to ovalbumin following intracutaneous administration by a coated microneedle array patch system," *Vaccine* 24:1653-1664, 2006.
Written Opinion of the International Searching Authority, dated Feb. 20, 2009, for International Application No. PCT/AU2008/001903, 6 pages.
Wu et al., "Production of viral vectors for gene therapy applications," *Current Opinions in Biotechnology* 11:205-208, 2000.
Yuan et la., "Measuring microelastic properties of stratum corneum," *Colloids and Surfaces B: Biointerfaces* 48:6-12, 2006.
Zheng et al., "Multiplexed electrical detection of cancer markers with nanowire sensor arrays," *Nature Biotechnology* 23(10):1294-1301, 2005.
Zhou et al., "Liposome-Mediated Cytoplasmic Delivery of Proteins: An Effective Means of Accessing the MHC Class I-Restricted Antigen Presentation Pathway," *Immunomethods* 4:229-235, 1994.
International Search Report, dated Feb. 20, 2013, for corresponding International Application No. PCT/AU2012/001289, 13 pages.
Crichton et al., "The viscoelastic, hyperelastic and scale dependent behaviour of freshly excised individual skin layers," *Biomaterials* 32:4670-4681, 2011.
Fernando et al., "Potent Immunity to Low Doses of Influenza Vaccine by Probabilistic Guided Micro-Targeted Skin Delivery in a Mouse Model," *PLoS One* 5(4):e10266, 2010. (11 pages).
Henry et al., "Microfabricated Microneedles: A Novel Approach to Transdermal Drug Delivery," *Journal of Pharmaceutical Sciences* 87(8):922-925, 1998.
McAllister et al., "Microfabricated needles for transdermal delivery of macromolecules and nanoparticles: Fabrication methods and transport studies," *PNAS* 100(24):13755-13760, 2003.
Extended European Search Report, dated Nov. 10, 2015, for European Application No. 12840561.0-1506 / 2765927, 11 pages.
Patent Examination Report No. 1, dated Apr. 11, 2016, for Australian Application No. 2012323782, 3 pages.
Australian Examination report No. 2 for standard patent application, dated Jan. 9, 2017, for corresponding Australian application No. 2012323782, 4 pages.
Australian Patent Examination Report No. 1, dated Mar. 27, 2013, for corresponding Australian application No. 2009212106, 5 pages.
Canadian Examination Report, dated Apr. 23, 2015, for corresponding Canadian application No. 2,749,347, 4 pages.
Canadian Examination Report, dated Feb. 17, 2015, for corresponding Canadian application No. 2,745,339, 4 pages.
Chinese 2nd Office Action, dated Sep. 24, 2012, for corresponding Chinese application No. 200980104635.3, 9 pages. (with English Translation).
Chinese 3rd Office Action, dated Dec. 28, 2012, for corresponding Chinese application No. 200980104635.3, 6 pages. (with English Translation).
Extended European Search Report and Written Opinion, dated Jul. 20, 2012, for corresponding EP application No. 09833918.7, 9 pages.
Extended European Search Report and Written Opinion, dated Sep. 26, 2014, for corresponding EP application No. 09707729.1, 9 pages.
International Search Report and Written Opinion of the International Searching Authority, dated Mar. 7, 2016, for corresponding international application No. PCT/AU2016/050056, 13 pages.
International Search Report and Written Opinion of the International Searching Authority, dated Dec. 6, 2016, for corresponding international application No. PCT/AU2016/050867, 20 pages.
International Search Report and Written Opinion of the International Searching Authority, dated Dec. 22, 2016, for corresponding international application No. PCT/AU2016/050907, 14 pages.

Ma et al., "A PZT Insulin Pump Integrated with a Silicon Micro Needle Array for Transdermal Drug Delivery," 56th Electronic Components & Technology Conference, San Diego, CA, May 30-Jun. 2, 2006, 5 pages.
Crichton et al., "The effect of strain rate on the precision of penetration of short densely-packed microprojection array patches coated with vaccine," *Biomaterials* 31(16):4562-4572, 2010.
Boehm et al., "Inkjet printing for pharmaceutical applications," *Materials Today* 17(5):247-252, 2014.
Desai et al., "Understanding release kinetics of biopolymer drug delivery microcapsules for biomedical applications," *Materials Science and Engineering B* 168:127-131, 2010.
European Search Report dated Sep. 10, 2018, for European Application No. 16746000.5, 3 pages.
International Search Report dated Jul. 30, 2018, for International Application No. PCT/AU2018/050298, 6 pages.
International Search Report dated Sep. 13, 2018, for International Application No. PCT/AU2018/050847, 4 pages.
International Search Report dated Aug. 1, 2018, for International Application No. PCT/AU2018/050586, 4 pages.
International Search Report dated Dec. 22, 2016, for International Application No. PCT/AU2016/050907, 4 pages.
International Search Report dated Nov. 8, 2018, for International Application No. PCT/AU2018/050810, 8 pages.
Ma et al., "Coating solid dispersions on microneedles via a molten dip coating method: development and in vitro evaluation for transdermal delivery of a water insoluble drug," *J Pharm Sci* 103(11):3621-3630, 2014. (21 pages).
Meléndez et al., "Thermal Inkjet Application in the Preparation of Oral Dosage Forms: Dispensing of Prednisolone Solutions and Polymorphic Characterization by Solid-State Spectroscopic Techniques," *Journal of Pharmaceutical Sciences* 97(7):2619-2636, 2008.
Radulescu et al., "Uniform Paclitaxel-Loaded Biodegradable Microspheres Manufactured by Ink-Jet Technology," *Proc., the Winter Symposium and 11th International Symposium on Recent Advantages in Drug-Delivery Systems, Controlled Release Society*, Salt Lake City, Utah, 2003, 5 pages.
Sandler et al., "Inkjet Printing of Drug Substances and Use of Porous Substrates-Towards Individualized Dosing," *Journal of Pharmaceutical Sciences* 100(8):3386-3395, 2011.
Scoutaris et al., "ToF-SIMS analysis of chemical heterogenities in inkjet micro-array printed drug/polymer formulations," *J Mater Sci: Mater Med* 23:385-391, 2012.
Tarcha et al., "The Application of Ink-Jet Technology for the Coating and Loading of Drug-Eluting Stents," *Annals of Biomedical Engineering* 35(10):1791-1799, 2007.
Wu et al., "Solid free-form fabrication of drug delivery devices," *Journal of Controlled Release* 40:77-87, 1996.
U.S. Appl. No. 15/401,950, filed Jan. 9, 2017, Delivery Device.
U.S. Appl. No. 15/849,134, filed Dec. 20, 2017, Method of Delivering Material or Stimulus to a Biological Subject.
U.S. Appl. No. 15/548,065, filed Aug. 1, 2017, Microprojection Array Applicator and Method.
U.S. Appl. No. 15/760,869, filed Mar. 16, 2018, Microprojection Arrays With Microprojections Having Large Surface Area Profiles.
U.S. Appl. No. 15/762,913, filed Mar. 23, 2018, Microprojection Arrays With Enhanced Skin Penetrating Properties and Methods Thereof.
U.S. Appl. No. 15/942,895, filed Apr. 2, 2018, Device and Method for Coating Surfaces.
U.S. Appl. No. 16/622,092, filed Dec. 12, 2019, Quality Control of Substrate Coatings.
U.S. Appl. No. 16/636,467, filed Feb. 4, 2020, Compact High Mechanical Energy Storage and Low Trigger Force Actuator for the Delivery of Microprojection Array Patches (MAP).
U.S. Appl. No. 16/638,072, filed Feb. 25, 2020, Differential Coating of Microprojections and Microneedles on Arrays.
Australian Examination Report No. 1 dated Oct. 9, 2020 for Australian Application No. 2016333148, 5 pages.
Chinese Office Action dated Jan. 11, 2021 for Chinese Application No. 201880036675.8, 31 pages. (w/ machine translation).

(56) References Cited

OTHER PUBLICATIONS

Communication pursuant to Article 94(3) EPC, dated Jan. 19, 2021, for European Application No. 16 746 000.5, 4 pages.
Extended European Search Report dated Feb. 15, 2021 for European Application No. 18 81 6698, 8 pages.
Extended European Search Report dated Nov. 30, 2020 for European Application No. 18 77 6793, 10 pages.
Fernando et al., "Influenza nucleoprotein DNA vaccination by a skin targeted, dry coated, densely packed microprojection array (Nanopatch) induces potent antibody and CD8+ T cell responses," *Journal of Controlled Release* 237:35-41, 2016.
Fernando et al., "Safety, tolerability, acceptability and immunogenicity of an influenza vaccine delivered to human skin by a novel high-density microprojection array patch (Nanopatch™)," *Vaccine* 36:3779-3788, 2018.
International Preliminary Report on Patentability dated Feb. 4, 2020 for International Application No. PCT/AU2018/050810, 9 pages.
International Search Report dated May 25, 2020 for International Application No. PCT/AU2020/050296, 6 pages.
Muller et al., "High-density microprojection array delivery to rat skin of low doses of trivalent inactivated poliovirus vaccine elicits potent neutralising antibody responses," *Scientific Reports* 7:12644, 2017, (10 pages).
Ng et al., "Potent response of QS-21 as a vaccine adjuvant in the skin when delivered with the Nanopatch, resulted in adjuvant dose sparing," *Scientific Reports* 6:29368, 2016. (12 pages).
Scoutaris et al., "Current Trends on Medical and Pharmaceutical Applications of Inkjet Printing Technology," *Pharm Res.* 33:1799-1816, 2016.

\* cited by examiner

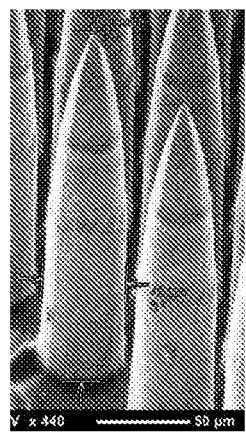
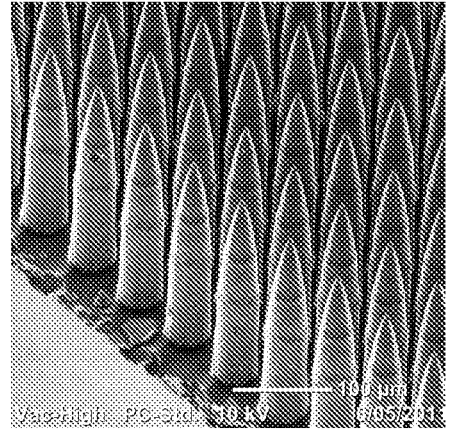
Fig. 2A  Fig. 2B
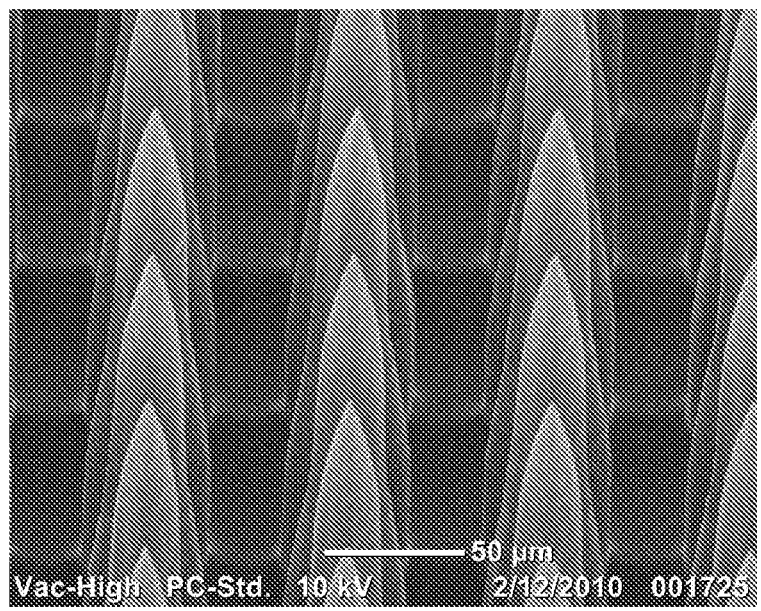
Fig. 2C

A

B

Day 0     Day 1     Day 7

Fig. 32A
Fig. 32B
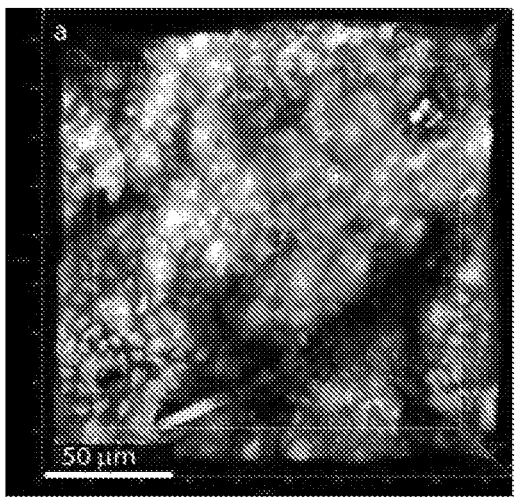
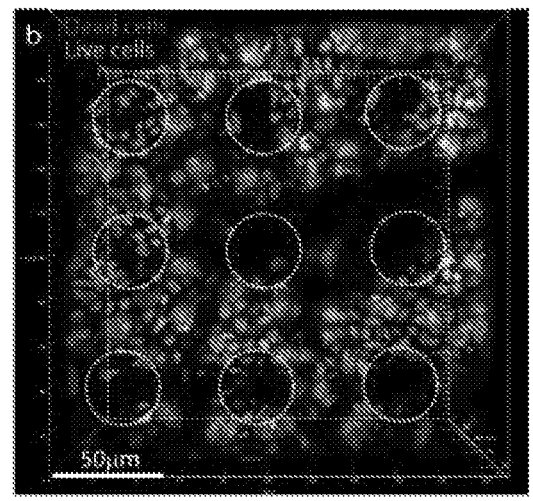
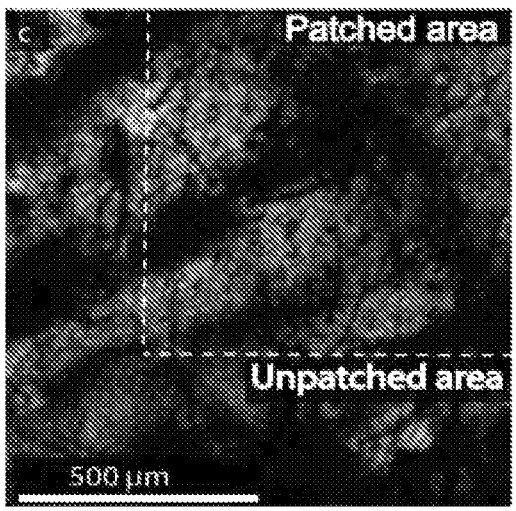
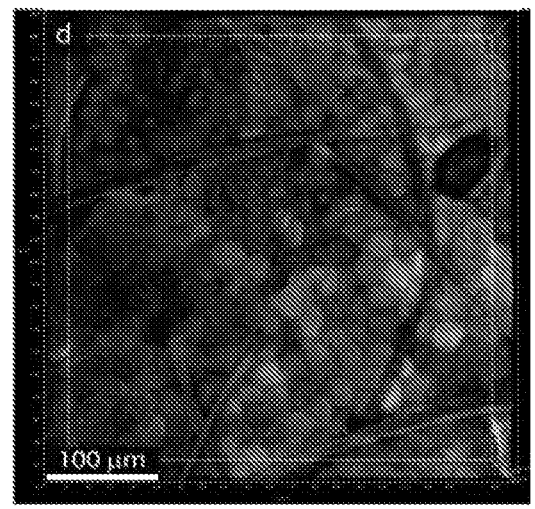
Fig. 32C
Fig. 32D

A/Solomon Islands/3/2006 (H1N1)
A/Brisbane/10/2007 (H3N2)
B/Florida/4/2006

DELIVERY DEVICE

BACKGROUND OF THE INVENTION

The present invention relates to a device for delivering material or stimulus to a biological subject, and in particular to a device including projections for penetrating a surface of the biological surface.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

In recent years, attempts have been made to devise new methods of delivering drugs and other bioactive materials, for vaccination and other purposes, which provide alternatives that are more convenient and/or enhanced in performance to the customary routes of administration such as intramuscular and intradermal injection. Limitations of intradermal injection include: cross-contamination through needle-stick injuries in health workers; injection phobia from a needle and syringe; and most importantly, as a result of its comparatively large scale and method of administration, the needle and syringe cannot target key cells in the outer skin layers. This is a serious limitation to many existing and emerging strategies for the prevention, treatment and monitoring of a range of untreatable diseases.

US 2011245776 describes a device for delivery of material or stimulus to targets within a body to produce a desired response, the targets being at least one of cells of interest, cell organelles of interest and cell nuclei of interest. The device includes a number of projections for penetrating a body surface, with the number of projections being selected to produce a desired response, and the number being at least 500. A spacing between projections is also at least partially determined based on an arrangement of the targets within the body. The document describes delivering material to specific targets by configuring the projection spacing and dimensions based on the target, with a particular focus on Langerhans cells in the epidermis.

SUMMARY OF THE PRESENT INVENTION

In a first broad form the present invention seeks to provide a device for delivery of material to a biological subject, the device including:
 a) a base; and,
 b) a number of projections extending from the base, each projection including a tip for penetrating tissue of the biological subject, at least a portion of at least one of the projections being coated with a non-liquid coating including the material, wherein at least the tip of at least one of the coated projections has a convex effective profile.

Typically the effective profile of at least one of the coated projections tapers from the base to the tip.

Typically a cone angle measured from a centerline of the projection to an edge of the effective profile varies along the length of at least one of the projections.

Typically the cone angle increases along the length of at least one of the projections from the base towards the tip.

Typically the cone angle at the tip of at least one of the projections is at least one of:
 a) between 20° and 25°;
 b) between 15° and 20°;
 c) between 10° and 15°;
 d) between 10° and 12.5°;
 e) between 1° and 10°;
 f) between 10° and 30°;
 g) between 15° and 25°;
 h) between 18° and 22°; and,
 i) about 20°.

Typically a radius of curvature of the effective profile varies along the length of at least one of the projections.

Typically the radius of curvature decreases along the length of at least one of the projections from the base towards the tip.

Typically the effective profile of at least one of the coated projections is substantially bullet-shaped.

Typically at least one of the projections is formed to have a substantially convex surface profile, and wherein the non-liquid coating has a substantially constant thickness so that a coating surface substantially conforms to the surface profile of the projection to provide the convex effective profile.

Typically at least one of the projections is formed to have a non-convex surface profile, and wherein the non-liquid coating has a variable thickness to provide the convex effective profile.

Typically at least one of the projections is formed to have a surface profile with at least one profile discontinuity, and wherein the non-liquid coating has a thickness which varies to thereby provide the convex effective profile.

Typically at least one of the projections is formed to have a stepped surface profile, and wherein the non-liquid coating has a thickness that is increased near a step of the stepped surface profile to thereby provide the convex effective profile.

Typically the convex effective profile includes a discontinuity.

In a second broad form the present invention seeks to provide a device for delivery of material to a biological subject, the device including:
 a) a base; and,
 b) a number of projections extending from the base, at least one of the projections including a tip for penetrating tissue of the biological subject, at least a portion of at least one of the projections being coated with a non-liquid coating including the material, wherein at least one of the coated projections has an effective profile including a discontinuity.

Typically the discontinuity generates a pressure wave within the tissue thereby inducing a bystander response when the device is applied to the tissue so that the projections penetrate the tissue.

Typically the discontinuity interacts with the tissue to at least partially control penetration of the projections into the tissue, when the device is applied to the tissue so that the projections penetrate the tissue.

Typically the discontinuity is located at a distance from the tip end of the projections, the distance being from:
 a) between 10 and 100 μm; or
 b) between 20 and 90 μm; or
 c) between 30 and 80 μm; or,
 d) between 40 and 60 μm.

Typically at least one of the coated projections has a convex effective profile.

Typically at least one of the projections has a length of at least one of:
a) between 1 and 5 times a penetration depth;
b) between 2 and 4 times a penetration depth;
c) between 2 and 3 times a penetration depth;
d) between 100 µm and 1000 µm;
e) between 150 µm and 800 µm;
f) between 150 µm and 500 µm;
g) between 200 µm and 600 µm;
h) between 200 µm and 300 µm;
i) between 200 µm and 250 µm; and,
j) between 250 µm and 300 µm.

In a third broad form the present invention seeks to provide a device for delivery of material or stimulus to a dermal layer of a biological subject, the device including:
a) a base; and,
b) a number of projections extending from the base, at least one of the projections including a tip for penetrating a tissue of the biological subject and wherein the projections have a length of between 200 and 300 µm.

Typically at least a portion of at least one of the projections is coated with a non-liquid coating including a material to thereby deliver material into the biological subject, wherein the coated projections have at least one of:
a) a convex effective profile; and,
b) an effective profile including a discontinuity.

Typically material is delivered to at least one dermal cell when the device is applied to the biological subject.

Typically the length is selected to penetrate the dermis by at least one of:
a) about 50 µm;
b) a depth up to 2 times the epidermal thickness of the subject; and,
c) a depth approximately equal to a depth of the viable epidermis of the biological subject.

Typically the length is selected to substantially prevent stimulation of nerve endings within the biological subject when the projections penetrate the tissue.

Typically the length is selected to prevent the base from contacting a tissue surface of the biological subject when the projections penetrate the tissue.

Typically the projections are solid.

Typically the projections are non-porous and non-hollow.

Typically the projections have varying dimensions.

Typically at least part of at least one of the projections is coated with two or more different non-liquid materials on the same projection.

Typically the device is for delivering material to at least one cell within the biological subject.

Typically at least part of the projections are coated with a non-liquid coating including the material to thereby deliver the material to the biological subject.

Typically the material includes at least one of:
a) nanoparticles;
b) a nucleic acid or protein;
c) an antigen, allergen, or adjuvant;
d) parasites, bacteria, viruses, or virus-like particles;
e) live, weakened, inactivated, split or fragmented parasites, bacteria, viruses, or virus-like particles;
f) quantum dots, SERS tags, raman tags or other nano-biosensors;
g) metals or metallic compounds;
h) molecules, elements or compounds;
i) contrast agents for imaging;
j) radio-isotopes;
k) an agent for inducing a response in cells;
l) a modulating agent for modulating cell activity; and,
m) mixtures thereof.

Typically the material includes a vaccine for delivery to cells within the biological subject to thereby induce an immunological response in the biological subject.

Typically at least some material is delivered into cells surrounding the projection by at least one of:
a) diffusion;
b) movement of fluids within the tissue; and,
c) contact between the non-liquid coating and the cells.

Typically at least a tip of the projections penetrate the dermal layer to thereby deliver material by diffusion into the dermal layer.

Typically at least one of the projections perturbs cells within the biological subject to thereby induce a bystander response when the device is applied to the tissue so that the projections penetrate the tissue.

Typically the projections cause cell damage of at least one cell near the projections to thereby induce a bystander response when the device is applied to the tissue so that the projections penetrate the tissue.

Typically cell damage causes the release of signalling agents which propagate to nearby living cells.

Typically material is delivered to at least one cell that receives signalling agents, thereby generating an improved immunological response when the device is applied to the tissue so that the projections penetrate the tissue.

Typically the device includes at least one uncoated projection to thereby stimulate or perturb cells within the biological subject in use.

Typically at least part of at least one of the projections at least partially dissolves upon penetrating the tissue of the biological subject.

Typically a material is incorporated into the projections, wherein the material is delivered to cells within the biological subject as the at least part of one of more of the projections dissolve.

Typically the number of projections is at least one of:
a) between 100 and 10000000;
b) between 500 and 1000000; and,
c) between 1000 and 100000.

Typically at least one of the projections has a base width of at least one of:
a) between 5 µm and 100 µm;
b) between 10 µm and 80 µm;
c) between 20 µm and 70 µm; and,
d) between 30 µm and 50 µm.

Typically at least one of the projections has a tip radius of at least one of:
a) between 0.1 µm and 5 µm;
b) between 0.1 µm and 2.5 µm;
c) between 0.1 µm and 1 µm; and,
d) between 0.1 µm and 0.5 µm.

Typically the projections are separated by a spacing of at least one of:
a) between 10 µm and 200 µm;
b) between 30 µm and 150 µm;
c) between 50 µm and 120 µm; and,
d) between 70 µm and 100 µm.

Typically the projections are arranged in an array.

Typically the array has a projection distribution of at least one of:
a) between 10 and 1000 projections per $mm^2$; and
b) between 100 and 300 projections per $mm^2$.

Typically the device has a size of at least one of:
a) between 0.5×0.5 mm and 20×20 mm;
b) between 0.5×0.5 mm and 15×15 mm; and,
c) between 1×1 mm and 10×10 mm.

Typically at least one projection is flared towards the base.

Typically the device includes hydrophobic surfaces that are uncoated.

Typically the hydrophobic surfaces are provided on at least one of:
 a) the projections; and,
 b) the base and at least a portion of the projections.

Typically the non-liquid coating includes an indicator material for indicating a degree of penetration of the projections into the biological subject.

Typically at least one of the projections is mechanically reinforced.

Typically projections are mechanically reinforced using at least one of an increased diameter and buttressing.

Typically:
 a) at least one projection is configured for providing increased mechanical strength; and,
 b) at least one projection is configured for delivery of material.

In a fourth broad form the present invention seeks to provide a device for delivery of material to a biological subject, the device including:
 a) a base; and,
 b) a number of projections extending from the base, at least one of the projections including a tip for penetrating tissue of the biological subject, at least a portion of the device is coated with a non-liquid coating, the non-liquid coating including an indicator material, and wherein application of the device to a subject causes at least some indicator material to be released, thereby providing a visual indication of device application.

Typically indicator material is provided on at least part of the projections.

Typically an amount of indicator material released depends at least partially on at least one of:
 a) a depth of penetration of the projections; and,
 b) an application velocity.

Typically the indicator material is provided in a concentration so that a visual indication is discernable if the projections have penetrated to a desired depth.

Typically indicator material is provided on the base so that indicator material is transferred to the subject if the base contacts a tissue surface.

Typically a colour of the indicator material depends on environmental conditions, a colour being used to determine if the projections have penetrated to a desired depth.

Typically the indicator material is at least one of:
 a) a pH sensitive indicator material;
 b) a redox sensitive indicator material; and,
 c) a cell viability indicator material.

In a fifth broad form the present invention seeks to provide apparatus for delivery of material or stimulus to a biological subject, the apparatus including:
 a) a device including:
  i) a base; and,
  ii) a number of projections extending from the base, at least one of the projections including a tip for penetrating a tissue surface of the biological subject; and,
 b) an applicator for applying the device to the biological subject so that at least some of the projections penetrate the tissue, wherein the applicator:
  i) applies a preload force to the tissue such that the force at least partially compresses a subcutaneous tissue layer of the biological subject prior to application of the device; and,
  ii) applies the device with a predetermined velocity, wherein tissue stiffness is maintained and/or the projections penetrate the tissue to a predetermined depth.

Typically the applicator is configured to apply the preload force to a region surrounding an application area of the tissue of the biological subject.

Typically the preload force is at least one of:
 a) between 0.1 N and 50 N;
 b) between 2 N and 40 N;
 c) between 5 N and 30 N;
 d) between 10 N and 20 N;
 e) between 1 N and 5 N;
 f) between 5 N and 10 N;
 g) between 10 N and 15 N; and,
 h) between 15 N and 20 N.

Typically the velocity is at least one of:
 a) between 1 $ms^{-1}$ and 50 $ms^{-1}$;
 b) between 1 $ms^{-1}$ and 10 $ms^{-1}$;
 c) between 1 $ms^{-1}$ and 5 $ms^{-1}$;
 d) between 1 $ms^{-1}$ and 2 $ms^{-1}$;
 e) between 2 $ms^{-1}$ and 3 $ms^{-1}$;
 f) between 3 $ms^{-1}$ and 4 $ms^{-1}$;
 g) between 4 $ms^{-1}$ and 5 $ms^{-1}$; and,
 h) between 5 $ms^{-1}$ and 10 $ms^{-1}$.

Typically the applicator includes a surface ring that contacts the tissue of the subject thereby providing the preload force.

Typically the surface is in the form of an annular ring.

Typically, the device is applied to a region radially inwardly of the annular ring.

Typically the ring is at least one of flexible and rigid.

Typically the applicator includes an actuator for automatically applying the device once a predetermined preload force has been provided by a user.

Typically the predetermined application velocity is determined based on mechanical properties of the tissues within the biological subject to be penetrated.

Typically the predetermined application velocity is selected to cause the projections to penetrate the dermis of the biological subject.

Typically the projections deliver material or stimulus to a dermal layer of a biological subject, and wherein the projections have a length of between 150 and 300 μm.

Typically at least a portion of at least some of the projections are coated with a non-liquid, coating, wherein at least the coated projections have at least one of:
 a) a convex effective profile; and,
 b) an effective profile including a discontinuity.

In a sixth broad form the present invention seeks to provide a device for delivery of vaccine to dermal cells within a biological subject to produce an immunological response within the biological subject, the device including:
 a) a base; and,
 b) a number of projections extending from the base, at least one of the projections including a tip for penetrating tissue of the biological subject, at least a portion of at least some of the projections being coated with a non-liquid material including a vaccine, wherein:
  i) the number of projections is at least 500;
  ii) at least one of the projections has a length of between 200 μm and 350 μm;
  iii) at least one of the projections has a base width of between 20 μm and 50 μm;
  iv) at least one of the projections has a tip radius of less than 2 μm;
  v) projections are separated by a spacing of between 70 μm and 100 μm; and, vi) wherein the projections have at least one of:
(1) a convex effective profile; and,
(2) an effective profile including a discontinuity.

In a seventh broad form the present invention seeks to provide apparatus for delivery of vaccine to dermal cells within a biological subject to produce an immunological response within the biological subject, the device including:
a) a device including:
i) a base; and,
ii) a number of projections extending from the base, at least one of the projections including a tip for penetrating tissue of the biological subject, at least a portion of at least some of the projections being coated with a non-liquid material including a vaccine, wherein:
(1) the number of projections is at least 500;
(2) at least one of the projections has a length of between 200 μm and 350 μm;
(3) at least one of the projections has a base width of between 20 μm and 50 μm;
(4) at least one of the projections has a tip radius of less than 2 μm;
(5) projections are separated by a spacing of between 70 μm and 100 μm; and,
(6) wherein the projections have at least one of:
(a) a convex effective profile; and,
(b) an effective profile including a discontinuity.
b) an applicator for applying the device to the biological subject so that at least some of the projections penetrate the tissue, wherein the applicator is adapted to:
i) apply a preload force to the tissue to at least partially compress a subcutaneous tissue layer prior to application of the device; and,
ii) apply the device with a predetermined application velocity to thereby at least one of:
(1) maintain tissue stiffness; and,
(2) cause penetration of the projections to a predetermined depth.

In an eighth broad form the present invention seeks to provide a method for delivery of material or stimulus to a biological subject, the method including:
a) applying a preload force to tissue to at least partially compress a subcutaneous tissue layer; and,
b) applying a device with a predetermined application velocity, the device including:
i) a base; and,
ii) a number of projections extending from the base, at least one of the projections including a tip for penetrating a tissue surface of the biological subject.

In a ninth broad form the present invention seeks to provide a device for delivery of material to a dermis of a biological subject, the device including:
a) a base; and,
b) a number of projections extending from the base, each projection including a tip for penetrating tissue of the biological subject, at least a portion of at least one of the projections being coated with a non-liquid coating including the material, wherein the projections have a length that is at least one of:
i) between 4 and 8 times an epidermal thickness of the subject;
ii) greater than 2.5 times a desired dermis penetration distance; and,
iii) sufficient to penetrate the dermis by an amount up to 2 times the epidermal thickness of the subject.

Typically the projections have a length that is at least one of:
a) between 4 and 6 times an epidermal thickness of the subject;
b) between 6 and 8 times an epidermal thickness of the subject;
c) between 5 and 7 times an epidermal thickness of the subject;
d) between 100 μm and 1000 μm;
e) between 150 μm and 800 μm;
f) between 150 μm and 500 μm;
g) between 200 μm and 600 μm;
h) between 200 μm and 300 μm;
i) between 200 μm and 250 μm; and,
j) between 250 μm and 300 μm.

Typically a ratio of the dermal penetration distance and projection length is at least one of:
a) between 0 and 0.4;
b) between 0.1 and 0.3;
c) about 0.18; and,
d) about 0.2.

Typically a ratio of the dermal penetration distance and epidermal thickness is at least one of:
a) between 0 and 2;
b) between 0.5 and 1.5;
c) about 1; and,
d) about 1.25.

In a tenth broad form the present invention seeks to provide a device for delivery of material to an epidermis of a biological subject, the device including:
a) a base; and,
b) a number of projections extending from the base, each projection including a tip for penetrating tissue of the biological subject, at least a portion of at least one of the projections being coated with a non-liquid coating including the material, wherein the projections have a length that is at least one of:
i) between 2 and 25 times a stratum corneum thickness of the subject;
ii) up to 6 times a desired epidermis penetration distance; and,
iii) sufficient to penetrate the epidermis by an amount up to 5 times the stratum corneum thickness of the subject.

Typically the projections have a length that is at least one of:
a) between 2 and 10 times a stratum corneum thickness of the subject; and,
b) between 2 and 5 times a stratum corneum thickness of the subject.
c) between 20 μm and 250 μm; and,
d) between 40 μm and 100 μm.

Typically the number of projections is at least one of:
a) at least 500;
b) between 100 and 10000000;
c) between 500 and 1000000; and,
d) between 1000 and 100000.

Typically the projections are separated by a spacing of at least one of:
a) between 10 μm and 200 μm;
b) between 30 μm and 150 μm;
c) between 50 μm and 120 μm; and,
d) between 70 μm and 100 μm.

Typically at least one projection has a length to width ratio of less than about 6.

Typically the array has a projection distribution of at least one of:
a) between 10 and 1000 projections per $mm^2$; and
b) between 100 and 300 projections per $mm^2$.

Typically the device has a size of at least one of:
a) between 0.5×0.5 mm and 20×20 mm;
b) between 0.5×0.5 mm and 15×15 mm; and,
c) between 1×1 mm and 10×10 mm.

In an eleventh broad form the present invention seeks to provide a device for delivery of vaccine to dermal cells within a biological subject to produce an immunological response within the biological subject, the device including:
a) a base; and,
b) a number of projections extending from the base, each projection including a tip for penetrating tissue of the biological subject, at least a portion of at least one of the projections being coated with a non-liquid coating including the vaccine, wherein the projections have a length that is at least one of:
  i) between 4 and 8 times an epidermal thickness of the subject;
  ii) greater than 2.5 times a desired dermis penetration distance; and,
  iii) sufficient to penetrate the dermis by an amount up to 2 times the epidermal thickness of the subject.

In a twelfth broad form the present invention seeks to provide a device for delivery of an allergen to an epidermis of a biological subject, the device including:
a) a base; and,
b) a number of projections extending from the base, each projection including a tip for penetrating tissue of the biological subject, at least a portion of at least one of the projections being coated with a non-liquid coating including the allergen, wherein the projections have a length that is at least one of:
  i) between 2 and 25 times a stratum corneum thickness of the subject;
  ii) up to 6 times a desired epidermis penetration distance; and,
  iii) sufficient to penetrate the epidermis by an amount up to 5 times the stratum corneum thickness of the subject.

In a thirteenth broad form the present invention seeks to provide a method for applying a device to a biological subject to thereby deliver material to a dermis of the subject, the device including a base and a number of projections extending from the base, each projection including a tip for penetrating tissue of the biological subject, at least a portion of at least one of the projections being coated with a non-liquid coating including the material, and wherein the method includes applying the device with at least one of:
  i) an application velocity is at least 1 m/s;
  ii) an application momentum of between 50 and 200 gram m/s;
  iii) an application momentum of between 0.005-1 gram m/s per projection;
  iv) an application energy of up to 400 mJ; and,
  v) an application energy of up to 2 mJ per projection.

Typically the application velocity is at least one of:
a) less than 10 m/s;
b) less than 5 m/s; and,
c) approximately 2 m/s.

In a fourteenth broad form the present invention seeks to provide a method for applying a device to a biological subject to thereby deliver material to an epidermis of the subject, the device including a base and a number of projections extending from the base, each projection including a tip for penetrating tissue of the biological subject, at least a portion of at least one of the projections being coated with a non-liquid coating including the material, and wherein the method includes applying the device with at least one of:
  i) an application velocity is at least 0.05 m/s;
  ii) an application momentum of between 35 and 150 gram m/s;
  iii) an application momentum of between 0.003-0.2 gram m/s per projection;
  iv) an application energy of up to 200 mJ; and,
  v) an application energy of up to 1 mJ per projection.

Typically the device includes projections having a length of between 100 µm and 250 µm, and wherein the application velocity is between 0.05 m/s and 1 m/s.

Typically the device includes projections having a length of between 40 µm and 100 µm, and wherein the application velocity is greater than 1 m/s.

Typically the application momentum is at least one of:
a) between 0.01-0.25 gram m/s per projection;
b) between 0.03-0.125 gram m/s per projection;
c) between 50 and 150 gram ms;
d) between 50 and 100 gram m/s; and,
e) between 100 and 150 gram m/s.

Typically the application energy is at least one of:
a) 0.25 mJ/projection;
b) 0.1-0.5 mJ/projection;
c) 0.05-2 mJ/projection;
d) less than 350 mJ;
e) less than 300 mJ;
f) greater than 50 mJ;
g) greater than 100 mJ;
h) between 100 and 300 mJ; and,
i) between 150 and 250 mJ.

Typically the method includes retaining the device in an applied position for at least one of:
a) up to 3600 seconds;
b) up to 600 seconds;
c) up to 120 seconds;
d) at least one second;
e) at least 2 seconds;
f) at least 5 seconds; and,
g) at least 10 seconds.

Typically the method includes applying a preload force to tissue to at least partially compress a subcutaneous tissue layer prior to applying the device.

In a fifteenth broad form the present invention seeks to provide a method for applying a device to a biological subject to thereby deliver vaccine to dermal cells within a biological subject to produce an immunological response within the biological subject, the device including a base and a number of projections extending from the base, each projection including a tip for penetrating tissue of the biological subject, at least a portion of at least one of the projections being coated with a non-liquid coating including the vaccine, and wherein the method includes applying the device with at least one of:
  i) an application velocity is at least 1 m/s;
  ii) an application momentum of between 50 and 200 gram m/s;
  iii) an application momentum of between 0.005-1 gram m/s per projection;
  iv) an application energy of up to 400 mJ; and,
  v) an application energy of up to 2 mJ per projection.

In a sixteenth broad form the present invention seeks to provide a method for applying a device to a biological subject to thereby deliver an allergen to an epidermis of the subject, the device including a base and a number of projections extending from the base, each projection including a tip for penetrating tissue of the biological subject, at least a portion of at least one of the projections being coated with a non-liquid coating including the allergen, and wherein the method includes applying the device with at least one of:
    i) an application velocity is at least 0.05 m/s;
    ii) an application momentum of between 35 and 150 gram m/s;
    iii) an application momentum of between 0.003-0.2 gram m/s per projection;
    iv) an application energy of up to 200 mJ; and,
    v) an application energy of up to 1 mJ per projection.

In a seventeenth broad form the present invention seeks to provide an applicator for applying a device to a biological subject to thereby deliver material to a dermis of the subject, the device including a base and a number of projections extending from the base, each projection including a tip for penetrating tissue of the biological subject, at least a portion of at least one of the projections being coated with a non-liquid coating including the material, and wherein the applicator includes:
    a) a body;
    b) a piston for receiving the device; and,
    c) a biasing mechanism for urging the piston towards the biological subject at a velocity selected so that at least some of the projections penetrate the tissue, and wherein at least one of:
    (1) the piston has a mass of between 5 grams to 100 grams;
    (2) the piston has a mass of between 0.003 grams to 0.0625 grams per projection;
    (3) an application velocity is at least 1 m/s;
    (4) an application momentum of between 50 and 200 gram m/s;
    (5) an application momentum of between 0.005-1 gram m/s per projection;
    (6) an application energy of up to 400 mJ; and,
    (7) an application energy of up to 2 mJ per projection.

Typically the application velocity is at least one of:
    a) less than 10 m/s;
    b) less than 5 m/s; and,
    c) approximately 2 m/s.

In an eighteenth broad form the present invention seeks to provide an applicator for applying a device to a biological subject to thereby deliver material to an epidermis of the subject, the device including a base and a number of projections extending from the base, each projection including a tip for penetrating tissue of the biological subject, at least a portion of at least one of the projections being coated with a non-liquid coating including the material, and wherein the applicator includes:
    a) a body;
    b) a piston for receiving the device; and,
    c) a biasing mechanism for urging the piston towards the biological subject at a velocity selected so that at least some of the projections penetrate the tissue, and wherein at least one of:
    i) the piston has a mass of between 5 grams to 100 grams;
    ii) the piston has a mass of between 0.003 grams to 0.0625 grams per projection;
    iii) an application velocity is at least 0.05 m/s;
    iv) an application momentum of between 35 and 150 gram m/s;
    v) an application momentum of between 0.003-0.2 gram m/s per projection;
    vi) an application energy of up to 200 mJ; and,
    vii) an application energy of up to 1 mJ per projection.

Typically the device includes projections having a length of between 100 µm and 250 µm, and wherein the application velocity is between 0.05 m/s and 1 m/s.

Typically the device includes projections having a length of between 40 µm and 100 µm, and wherein the application velocity is greater than 1 m/s.

Typically the application momentum is at least one of:
    a) between 50 and 150 gram m/s;
    b) between 50 and 100 gram m/s; and,
    c) between 100 and 150 gram m/s.

Typically the application energy is at least one of:
    a) 0.25 mJ/projection;
    b) 0.1-0.5 mJ/projection;
    c) less than 350 mJ;
    d) less than 300 mJ;
    e) greater than 50 mJ;
    f) greater than 100 mJ;
    g) between 100 and 300 mJ; and,
    h) between 150 and 250 mJ.

Typically the applicator includes a device support that in use is coupled to the piston and operates to support the device during application to the subject.

Typically the device support includes a profiled portion extending around at least part of an inner region, the device being mounted to the inner region in use so that the profiled portion at least partially surrounds the device.

Typically the profiled portion includes a ridge that can be used to shield edges of the patch substrate from a surface of the biological subject.

Typically the device support includes a compliant or semi-compliant material for cushioning the device during application.

Typically the device support includes an inner portion for receiving the device and an outer portion coupled to the piston, the inner and outer portions being selectively attached to allow the device to be mounted to the applicator.

Typically the device is supplied coupled to the inner portion and including a removable cap for preventing contact with the device during attachment to the piston.

In a twentieth broad form the present invention seeks to provide an applicator for applying a device to a biological subject to thereby deliver vaccine to dermal cells within a biological subject to produce an immunological response within the biological subject, the device including a base and a number of projections extending from the base, each projection including a tip for penetrating tissue of the biological subject, at least a portion of at least one of the projections being coated with a non-liquid coating including the vaccine, and wherein the applicator includes:
    a) a body;
    b) a piston for receiving the device; and,
    c) a biasing mechanism for urging the piston towards the biological subject at a velocity selected so that at least some of the projections penetrate the tissue, and wherein at least one of:
    (1) the piston has a mass of between 5 grams to 100 grams;
    (2) the piston has a mass of between 0.003 grams to 0.0625 grams per projection;
    (3) an application velocity is at least 0.05 m/s;
    (4) an application momentum of between 35 and 150 gram m/s;

(5) an application momentum of between 0.003-0.2 gram m/s per projection;
(6) an application energy of up to 200 mJ; and,
(7) an application energy of up to 1 mJ per projection.

In a twenty-first broad form the present invention seeks to provide an applicator for applying a device to a biological subject to thereby deliver an allergen to an epidermis of the subject, the device including a base and a number of projections extending from the base, each projection including a tip for penetrating tissue of the biological subject, at least a portion of at least one of the projections being coated with a non-liquid coating including the allergen, and wherein the applicator includes:
a) a body;
b) a piston for receiving the device; and,
c) a biasing mechanism for urging the piston towards the biological subject at a velocity selected so that at least some of the projections penetrate the tissue, and wherein at least one of:
(1) the piston has a mass of between 5 grams to 100 grams;
(2) the piston has a mass of between 0.003 grams to 0.0625 grams per projection;
(3) an application velocity is at least 0.05 m/s;
(4) an application momentum of between 35 and 150 gram m/s;
(5) an application momentum of between 0.003-0.2 gram m/s per projection;
(6) an application energy of up to 200 mJ; and,
(7) an application energy of up to 1 mJ per projection.

In a twenty-second broad form the present invention seeks to provide apparatus for applying a device to a biological subject to thereby deliver material to a dermis of the subject, the apparatus including:
a) a device including:
i) a base; and,
ii) a number of projections extending from the base, each projection including a tip for penetrating tissue of the biological subject, at least a portion of at least one of the projections being coated with a non-liquid coating including the material, and wherein the projections have a length of at least one of:
(1) between 2 and 25 times a stratum corneum thickness of the subject;
(2) up to 6 times a desired epidermis penetration distance; and,
(3) sufficient to penetrate the epidermis by an amount up to 5 times the stratum corneum thickness of the subject.
b) an applicator including:
i) a body;
ii) a piston for receiving the device; and,
iii) a biasing mechanism for urging the piston towards the biological subject at a velocity selected so that at least some of the projections penetrate the tissue, and wherein at least one of:
(1) the piston has a mass of between 5 grams to 100 grams;
(2) the piston has a mass of between 0.003 grams to 0.0625 grams per projection;
(3) an application velocity is at least 1 m/s;
(4) an application momentum of between 50 and 200 gram m/s;
(5) an application momentum of between 0.005-1 gram m/s per projection;
(6) an application energy of up to 400 mJ; and,
(7) an application energy of up to 2 mJ per projection.

In a twenty-third broad form the present invention seeks to provide apparatus for applying a device to a biological subject to thereby deliver material to an epidermis of the subject, the apparatus including:
a) a device including:
i) a base; and,
ii) a number of projections extending from the base, each projection including a tip for penetrating tissue of the biological subject, at least a portion of at least one of the projections being coated with a non-liquid coating including the material, and wherein the projections have a length of at least one of:
(1) between 4 and 8 times an epidermal thickness of the subject;
(2) greater than 2.5 times a desired dermis penetration distance; and,
(3) sufficient to penetrate the dermis by an amount up to 2 times the epidermal thickness of the subject; and,
b) an applicator including:
i) a body;
ii) a piston for receiving the device; and,
iii) a biasing mechanism for urging the piston towards the biological subject at a velocity selected so that at least some of the projections penetrate the tissue, and wherein at least one of:
(1) the piston has a mass of between 5 grams to 100 grams;
(2) the piston has a mass of between 0.003 grams to 0.0625 grams per projection;
(3) an application velocity is at least 0.05 m/s;
(4) an application momentum of between 35 and 150 gram m/s;
(5) an application momentum of between 0.003-0.2 gram m/s per projection;
(6) an application energy of up to 200 mJ; and,
(7) an application energy of up to 1 mJ per projection.

Typically the device includes projections having a length of between 100 µm and 250 µm, and wherein the application velocity is between 0.05 m/s and 1 m/s.

Typically the device includes projections having a length of between 40 µm and 100 µm, and wherein the application velocity is greater than 1 m/s.

BRIEF DESCRIPTION OF THE DRAWINGS

An example of the present invention will now be described with reference to the accompanying drawings, in which:

FIGS. 2A to 2F are scanning electron microscope images of examples of projections;

FIGS. 32A to 32D are confocal images of projection patch treated and untreated murine ear skin stained with acridine orange and ethidium bromide;

DETAILED DESCRIPTION OF THE PREFERRED EMBODIMENTS

Figure 1A:
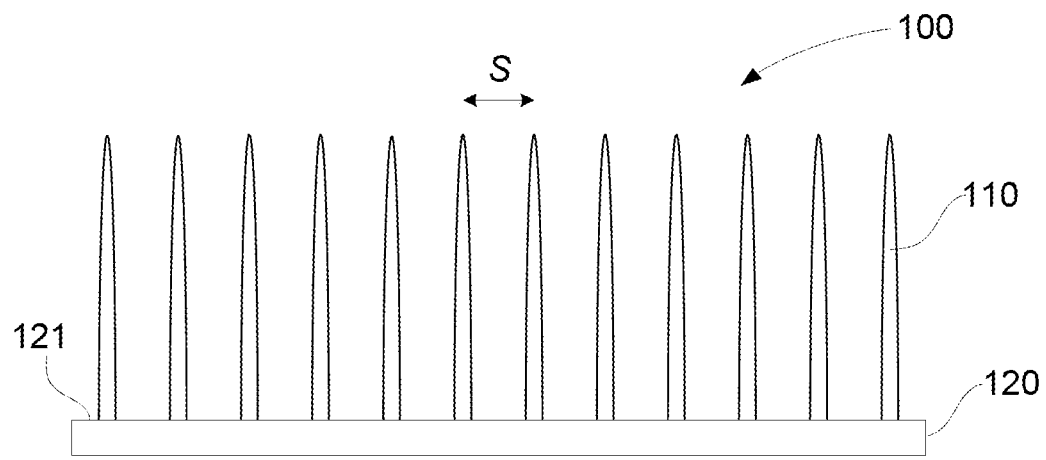
FIGS. 1A and 1B are schematic diagrams of an example of a device for delivery of material or stimulus to targets within a body.
Figure 1B:
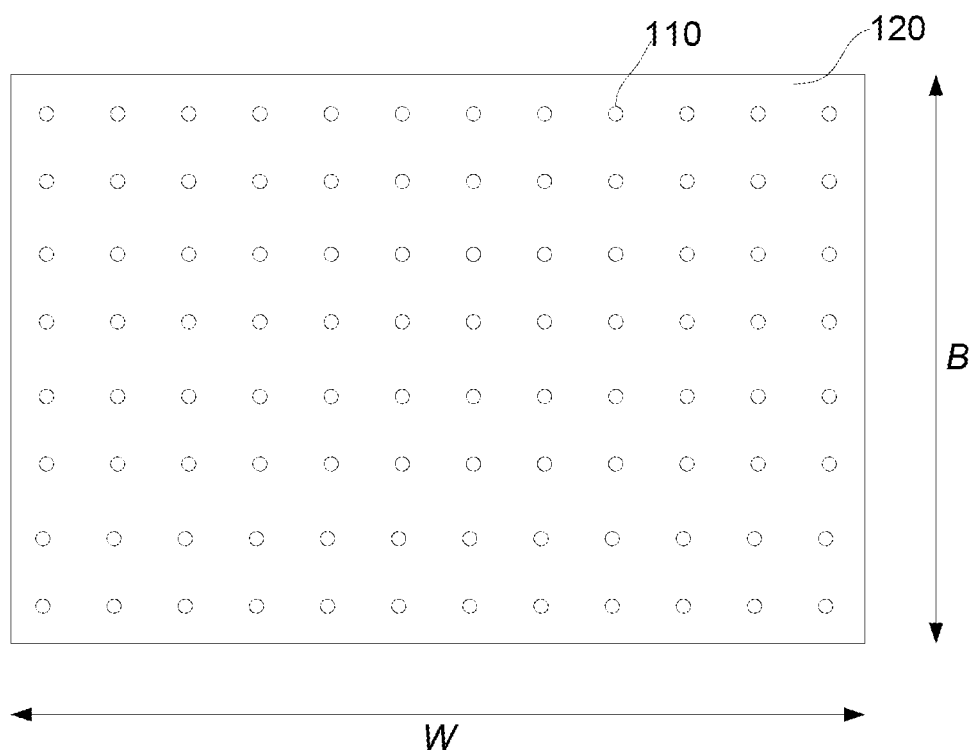
Figure 1C:
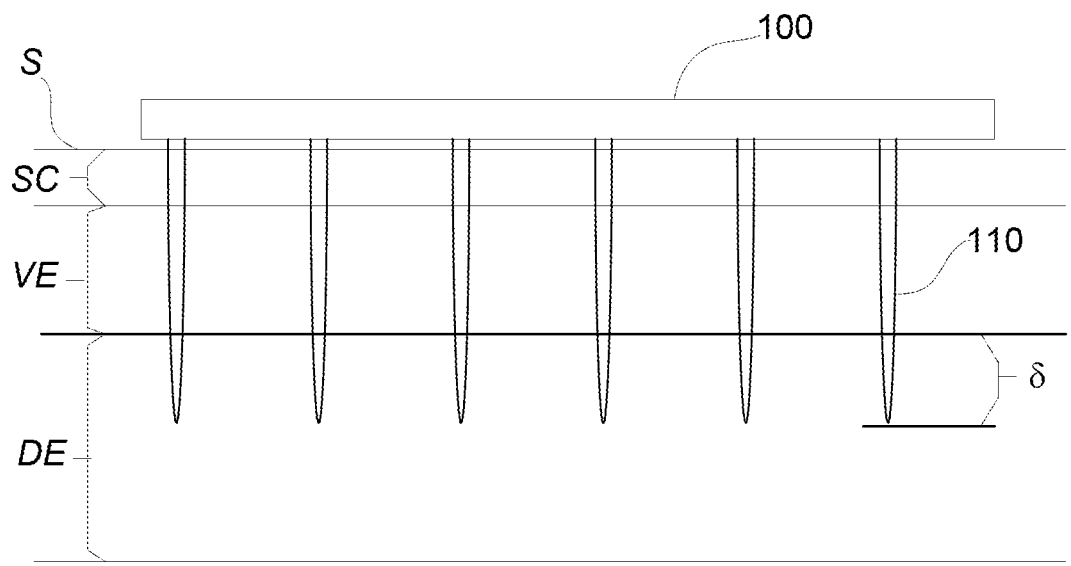
FIG. 1C is a schematic diagram of an example of the device of FIG. 1A in use.

An example of a device for delivering material or stimulus to a biological subject will now be described with reference to FIGS. 1A to 1H.

In this example, the device is in the form of patch 100 having projections 110 extending from a surface 121 of a base 120. The projections 110 and base 120 may be formed from any suitable material, but in one example, are formed from a silicon type material. The projections may be solid, non-porous and non-hollow, although this is not essential.

For example, porous and/or hollow projections can be used. Porous and/or hollow projections could be used to increase the volume of coating that can be accommodated on each projection, for example so that coating is contained in pores or hollow portions of the projections. In this example, this can result in material being delivered over time as coating on the outer surface of the patch dissolves first, with coating in the porosities dissolving subsequently when the outer coating has dissolved and the pores are exposed to the wetness of the surrounding tissues. Hollow projections can also be used for delivery of non-liquid coatings.

In the example shown, the patch 100 has a width W and a breadth B with the projections 110 being separated by spacing S. The projections 110 are preferably provided in an array as shown but other arrangements of projections 110 may also be used.

Each projection 110 includes a tip 111 for penetrating tissue of the biological subject. Projections 110 will typically have a profile which tapers from the base 120 to the tip 111.

In use, the patch 100 is applied to the biological subject by positioning the patch 100 against a surface of a subject. The tip 111 of each projection 110 is allowed to penetrate the surface and to further penetrate tissue beneath the surface as the patch 100 is applied. It will therefore be appreciated that the patch 100 can be used to deliver material or stimulus to internal tissues of the biological subject. An example application of the patch 100 is shown in FIG. 1C.

In this example, the patch 100 is urged against a subject's skin shown generally at S, so that the projections 110 pierce the Stratum Corneum SC, and penetrate through the Viable Epidermis VE to penetrate the Dermis DE by a dermal penetration depth δ. However, this is not essential and the patch can be used to deliver material or stimulus to any part or region in the subject.

The patch 100 can be provided in a variety of different configurations to suit different material or stimulus delivery requirements. Accordingly, the specific configuration of the patch 100 can be selected to allow the delivery of material and stimulus to particular tissues, at a specific depth, to induce a desired response.

For instance, the overall configuration of the patch 100 may be adjusted by varying parameters such as the width W and breadth B of the patch 100 and the spacing S separating the projections 110.

Furthermore, the geometry of the projections 110 can be adjusted in numerous ways to allow the effective delivery of material and stimulus to particular tissues, at a specific depth, to induce a desired response. Particularly suitable geometries for achieving desired material and stimulus delivery outcomes will be described in detail below.

At least a portion of the projections 100 may be coated. Accordingly, one way of providing material for delivery to the biological subject is by providing the material within the coating. For example, the coating may include a vaccine for providing an immunological response within the subject. However, the projections 110 may also be provided in an uncoated state to provide physical stimulus to tissues within the biological subject without actually delivering material. This can result in bystander interactions in neighbouring cells, which may provide a physical adjuvant effect, irrespective of whether materials are delivered, as will be described in further detail below.

The coating may be provided in liquid or non-liquid forms, and may further include ingredients other than the material to be delivered, such as an adjuvant. Suitable coating formulations for use with projections patches and methods of applying such coatings to the projections are known, as described, for example, in WO/2010/042996 and WO/2009/079712.

Although any type of coating may be used, particularly advantageous embodiments of the patch 100 are provided with at least a portion of the projections 110 coated with a non-liquid coating. In this regard, the term "non-liquid" coating will be understood to include a coating that is applied in a liquid form and allowed to dry or otherwise solidify to thereby form a non-liquid coating.

The non-liquid coating may act as an additional substantially solid layer of material which can be used to even further adjust the geometry of the projections 110, by optionally causing the projections 110 to have an effective profile of a different shape to the underlying uncoated profile of the projections 110 as initially fabricated.

The term "effective profile" therefore generally refers to an external profile of a projection 110, and as such defines the shape of the projection 110 which penetrates the tissues of the biological subject in use. As mentioned above, the effective profile can be different from the uncoated profile of the projections; however, it should be understood that any projection 110 will have an effective profile irrespective of whether the projection 110 is coated or uncoated.

For instance, in examples where projections 110 are uncoated, the effective profile is the same as the uncoated profile of the projections 110. In certain examples where a coating is applied to the projections 110, the coating may be of an even thickness such that the effective profile is substantially similar to the uncoated profile. However, in other examples, a coating may be applied to the projections 110 in a manner which significantly alters the effective profile of the projections 110. For example, the coating may have a variable thickness which causes the effective profile to differ from the uncoated profile depending on the variations in thickness of the coating.

Accordingly, by modifying the effective profile using different coating configurations, the shape of the projection 110 which penetrates the tissues of the biological subject in use can be further adjusted following fabrication of the projections.

In some embodiments, more than one non-liquid coatings can be applied to the same projections. For instance, different coatings may be applied in layers to provide different materials for delivery to the tissues within the subject at different times, as the layers dissolve in sequence. A first coating may be applied to modify surface properties of the projection and improve the ability of the second coating to coat the projection in a desirable manner. Multiple layers of the same coating formulation may be used with drying between each layer to allow a progressive build up coating to achieve an increased thickness and thus modify the effective cross section even further.

In other embodiments, at least a portion of the projection 110 may be formed from a dissolvable material within which a material for delivery to the subject, such as a vaccine, is incorporated. The dissolvable material is configured so that, after the projection 110 penetrates tissues, the dissolvable material will at least partially dissolve and release the material for delivery into the tissues. Suitable methods for producing dissolvable projections are described, for example, in WO/2010/071918.

It will be appreciated that this technique allows a projection 110 for delivery of material to tissues of the subject to be formed with a specific effective profile, without necessarily requiring a non-liquid coating to be applied to the projection 110.

In any event, it will be appreciated that a projection 110 can be provided with a desirable effective profile in numerous ways.

Projections Having Convex Effective Profile

In particular embodiments, at least the tips of the projections 110 may have a convex effective profile. In view of the above, it will be appreciated that the convex effective profile may be provided, for example, by fabricating the projections 110 to have a convex effective profile and applying coating that substantially conforms with the uncoated profiled of the projection, or by fabricating the projections 110 to have a profile other than convex and subsequently coating the projections 110 in such a way as to cause the effective profile to be convex.

Figure 1D:
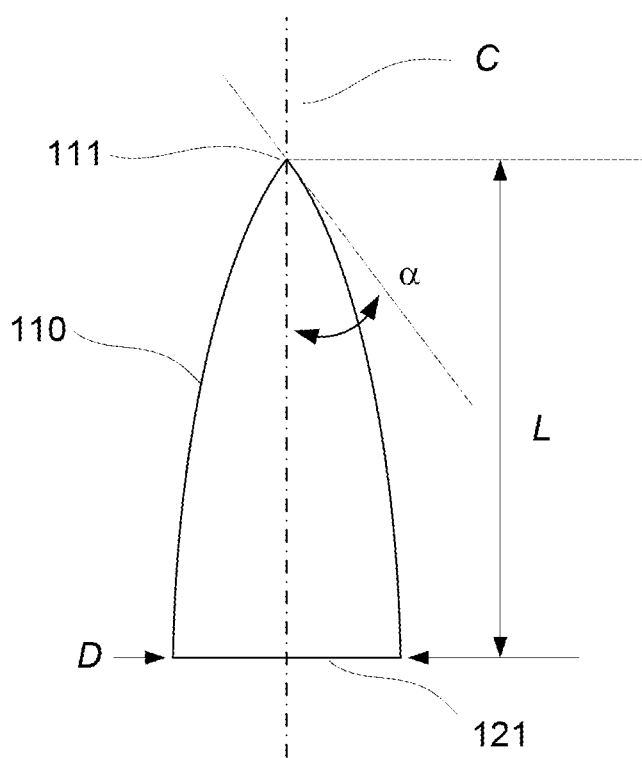
FIGS. 1D to 1H are schematic diagrams of examples of projections used in the device of FIG. 1A.

A simple example of a projection 110 having a convex effective profile is shown in FIG. 1D.

It should be noted that this example projection and subsequent examples are shown in schematic form to illustrate variations of geometric features of the projections, but in order to better highlight these variations, the features have been exaggerated. Therefore it should be understood that the example projections are not drawn to scale and do not necessarily reflect practical projection configurations.

The overall dimensions of the projection 110 can be broadly defined in terms of the length L measured from the surface 121 of the base 120 to the tip 111, and the base width or diameter D.

It will be appreciated that a base diameter D is a convenient measurement for projections 110 having a generally axisymmetric configuration, as is the case in FIG. 1D, where the effective profile is the same from different viewpoints rotated about an axis defined along the centerline C of the effective profile. However, a width measurement can be more broadly applied to other configurations of projections 110 which do not have a rotational axis of symmetry.

As can be seen, the effective profile of the projection 110 has a convex or outwardly curved shape. In this example, the convex effective profile extends along the entire length L of the projection, however, in other embodiments, the convex effective profile may be applied to only a portion of the length L, extending from the tip 111 towards the base 120.

In any event, a projection having a convex effective profile will generally occupy a greater volume and have a larger external surface area than would be the case for a projection having a purely conical effective profile having the same length and width/diameter parameters.

A useful parameter for characterising the effective profile of a projection 110 is the cone angle $\alpha$ measured between the centerline C and surface of the effective profile, as depicted in FIG. 1D.

In the case of a projection 110 having a purely conical effective profile, the cone angle $\alpha$ will be constant along the length of the projection 110. However, in the case of a convex effective profile, the cone angle $\alpha$ will vary along the length of the projection 110.

In the particular example of FIG. 1D, the cone angle $\alpha$ increases along the length of the projection 110 from the base 120 towards the tip 111. As can be seen, the surface of the effective profile is almost parallel with the centerline C near the base 120 resulting in a cone angle $\alpha$ approaching 0° when measured at the base 120. The surface of the effective profile gradually slopes towards the centerline C as the distance from the base 120 increases, resulting in a progressively increasing cone angle $\alpha$, with the maximum cone angle $\alpha$ for the projection 110 being at the tip 111 in this example.

It will be appreciated that the cone angle $\alpha$ can vary along the length of the projection 110 in different ways whilst still providing a convex effective profile. It should be noted that the cone angle $\alpha$ can increase or decrease along portions of the length of the projection. For example, the projection effective profile may include an inflection in the cone angle $\alpha$ where the rate of change of cone angle $\alpha$ transitions from increasing to decreasing, to define features such as steps, or the like.

The specific shape of the effective profile may also be characterised by the radius of curvature of the surface in a plane through the length of the projection as illustrated in FIG. 1D. The radius of curvature at a point along the length of the projection is indicative of the radius of an imaginary circle having the same curvature as the surface at that point. A relatively large radius of curvature measurement will therefore be indicative of a gradually curved effective profile whilst a relatively small radius of curvature measurement will be indicative of a more drastically curved effective profile. It is generally desirable to provide a sharp tip to 111 to improve penetration, and therefore the tip 111 will typically have a very small radius of curvature.

As per the cone angle $\alpha$, the radius of curvature may vary along the length of the projection. For example, in the embodiment shown in FIG. 1D the radius of curvature gradually decreases along the length of the projection 110 from the base towards the tip 111. When measured near the base 120, the radius of curvature may approach infinite, indicating a substantially straight surface, whilst more highly curved portions of the effective profile will have correspondingly smaller radius of curvature measurements.

A convex effective profile has been found to offer significant benefits compared to conventional purely conical profiles. For example, a convex effective profile will typically be thicker near the tip 111 compared to a purely conical profile which has a constant taper towards the tip, which results in improved tip strength and thus a reduced likelihood of tip breakage during application. A convex effective profile also provides a larger surface area compared to a conical profile, allowing increases in the quantity of coating that can be provided under constant coating thicknesses. It has also been determined that a convex effective profile offers other improvements with regard, to penetration performance and effectiveness in delivering materials or stimulus to the biological subject, as will be explained further below.

Although the entire projection 110 can have a convex effective profile as shown in FIG. 1D, this is not essential. Advantages as discussed above can still be provided where only a portion of the projection 110 including the tip 111 has a convex effective profile.

The effective profile near the tip 111 will generally have a larger impact on the penetration performance of the patch 100 compared to the effective profile along portions of the projection 110 closer to the base 120. This is because it is the tip 111 which actually penetrates the tissues of the biological subject during application of the patch 100. Accordingly, providing a convex effective profile near the tip 111 can still offer significant benefits in use, even if the effective profile away from the tip is not convex.

Figure 1E:
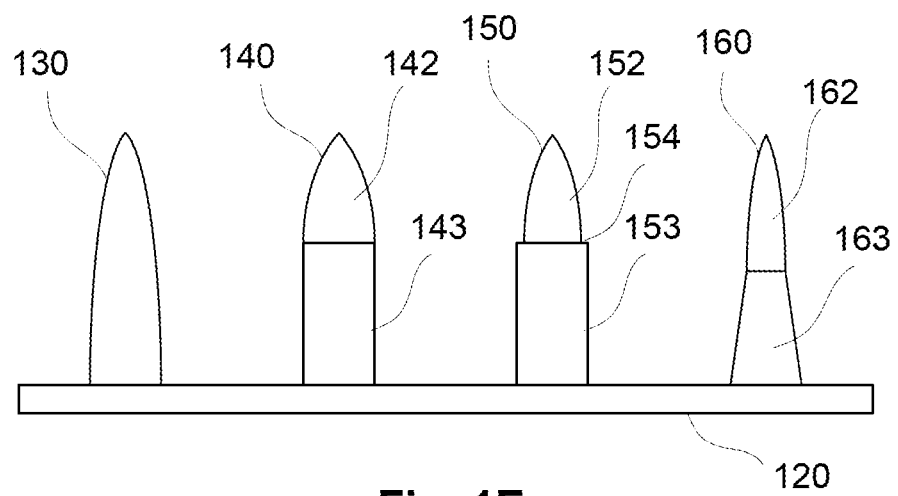
Figure 1F:
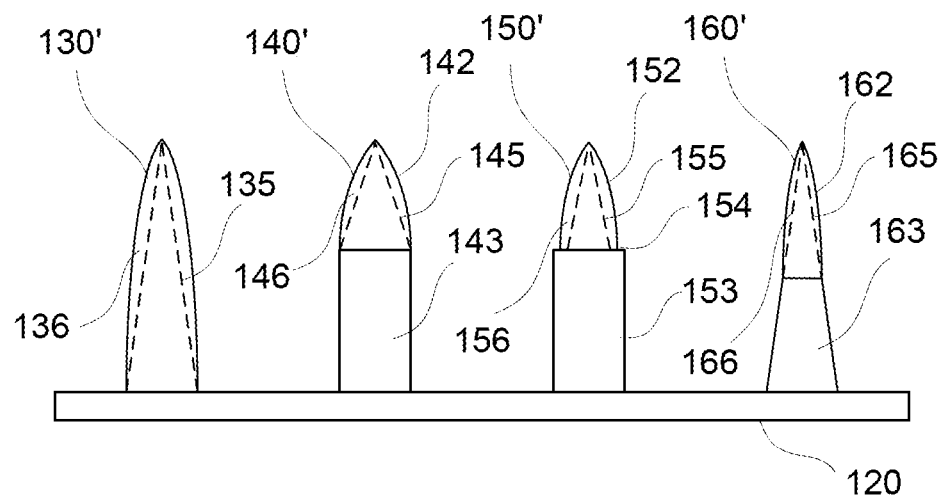

In view of the above, it will be appreciated that many different projection shapes may be provided which have a convex effective profile, and illustrative examples of these are shown in FIGS. 1E and 1F.

With regard to FIG. 1E, it will be seen that the example projection 130 has an overall convex effective profile similar to that of FIG. 1D; however, it will also be seen that example projections 140, 150 and 160 have effective profiles where only a portion thereof is convex. In general terms the example projections 140, 150 and 160 include a convex end section extending from a support section having an effective profile other than convex. As can be seen, the convex effective profile may result in projections having an overall bullet-shaped appearance, with a pointed tip.

The example projection 140 includes an end section 142 having a convex effective profile which smoothly transitions from a substantially cylindrical support section 143. The example projection 150 has a similar configuration to the example projection 140, but in this case the transition from the substantially cylindrical support section 153 to the convex end section 152 is not smooth, and instead occurs at a discontinuity in the effective profile in the form of step 154. As will be outlined in further detail below, there can also be particular benefits associated with projections including a discontinuity or step as shown, and thus the example projection 150 allows these benefits to be combined with the benefits of a convex effective profile.

Example projection 160 shows a further potential shape where the convex end section 162 extends from a supports section 163 having a tapered conical shape, which can provide improved structural strength towards the base compared to substantially cylindrical support section 163.

As discussed above, the projections may be formed to have a desired substantially convex surface profile, and may subsequently be coated with a coating having a substantially constant thickness so that a coating surface substantially conforms to the surface profile of the projection to provide the convex effective profile. Therefore the effective profiles of the example projections 130, 140, 150, 160 may be provided primarily due to the uncoated profile resulting from the fabrication of the projections.

However, FIG. 1F illustrates examples of how the convex effective profiles of the example projections 130, 140, 150, 160 can alternatively be provided using projections which have uncoated profiles that are not convex, by applying the coating with varying thickness to modify the external effective profile.

With regard to the example projection 130', the uncoated profile 135 of the projection 130' is substantially conical, and the coating 136 is provided with a thickness that varies across the length of the projection 130' to result in the overall convex effective profile.

In the case of example projection 140', only the end section 142 is coated, such that the substantially cylindrical support section 143 contributes to the effective profile without being modified by the coating, whilst the effective profile for the end section 142 is provided through variations in the thickness of the coating 146 to modify the conical uncoated profile 145 of the end section 142. It can be seen that the coating thickness is substantially zero at the transition between the support section 143 and end section 142, to maintain smoothness in the transition.

Example projection 150' is similar to the previously described example, except in this case the step 154 between the cylindrical support section 153 and the uncoated profile 155 of the end section 152 is more pronounced than in the effective profile. The coating 156 has an increased thickness at the step 154, although a step feature having a reduced step offset x is nevertheless retained in the effective profile. It will therefore be appreciated that the coating 156 in this case is used to modify, or optionally eliminate, discontinuities in the uncoated profile.

Finally, example projection 160' is formed using a substantially conical uncoated profile 165 which has an even taper along the entire length of the projection as per example projection 130' discussed above, but in this case only the end portion 162 is coated with coating 166 so as to provide a convex effective profile along the end portion 162, whilst retaining a conical support section 163.

It will be appreciated that numerous other shapes may also be provided in view of the above discussion.

Projections Having Discontinuities in Effective Profile

As mentioned above, it can be desirable to incorporate a discontinuity into the effective profile of the projections 110, and this can have benefits either in combination with the convex effective profile, or in isolation.

Figure 1G:
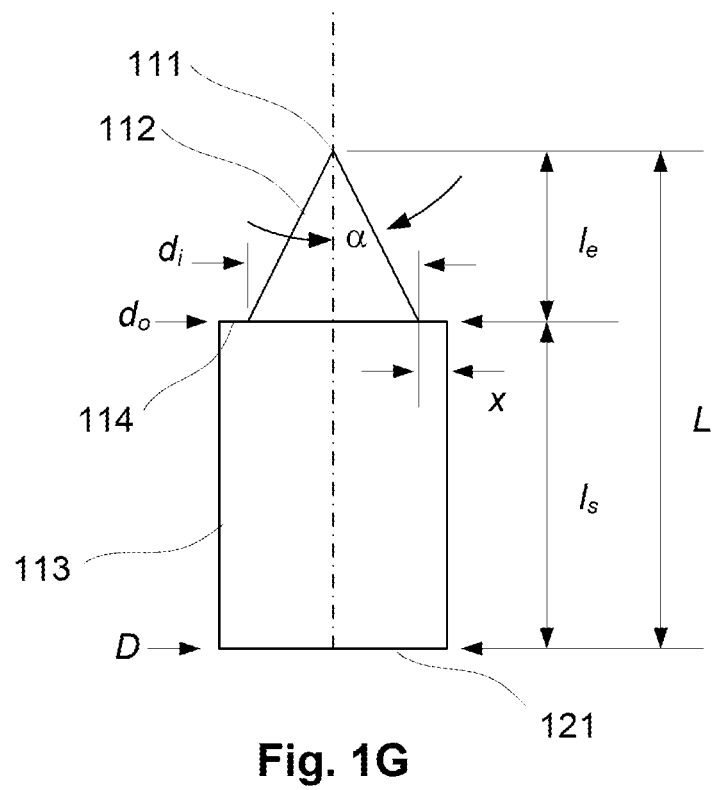

Accordingly, FIG. 1G shows a simplified example of a projection 110 having a stepped effective profile, to further illustrate additional parameters which may be controlled to obtain a desired penetration performance or to induce a desired response within the subject. The basic geometry of the projection 110 may still be defined in terms of length L and diameter D, but in this case it is also useful to measure other dimensions.

The length of the end section 112 is denoted $l_e$ whilst the length of the support section 113 is denoted $l_s$, and it will be appreciated that independently varying these parameters can allow more control over the overall length L without necessitating compromises in other aspects of the geometry. For example, the length L can be adjusted by varying the support section 113 length $l_s$ without having any impact on the shape of the end section 112. In contrast, when a purely conical projection is used, an increase in length L will result in a higher aspect ratio projection, assuming the base diameter is not also increased.

The step 114 can be characterised in terms of the outer diameter $d_o$ and inner diameter $d_i$ and/or by a step offset dimension x as illustrated in FIG. 1G, where $d_o - d_i = 2_x$.

As will be explained in further detail below, the step 114 can assist in ensuring more consistent depth of penetration in different biological subjects, despite variations in the tissue properties from subject to subject. In particular, during insertion of the projection, the step can impact on the dermal tissues, which typically present an increased resistance to penetration compared to tissues in outer layers of the skin (such as the viable epidermis, for example), thereby limiting further penetration of the projection. By providing projections with a suitably configured stepped effective profile, and using controlled application parameters, it is therefore possible to ensure that the tips of the projections extend into the dermis by a predetermined distance δ.

Additionally, the discontinuity can help create additional physical stimulus within the biological subject in use. As projections penetrate the skin and tissue during an impact application of a patch, the projections generate a pressure wave, which can assist in causing cell damage. This in enhances the immunological response generated within the subject by acting as a "physical adjuvant", as will be described in more detail below.

Providing a step or discontinuity in the effective profile can cause even higher magnitude pressure waves to be generated, to thus provide even further exaggerated physical adjuvant effects. For example, as the step penetrates the skin layers, the step will impact stiffer underlying tissues within the dermis, which will generate additional pressure waves emanating from the impact region which may cause even further cell damage in the vicinity of the impact. Further details on these mechanisms will be provided below.

Figure 1H:
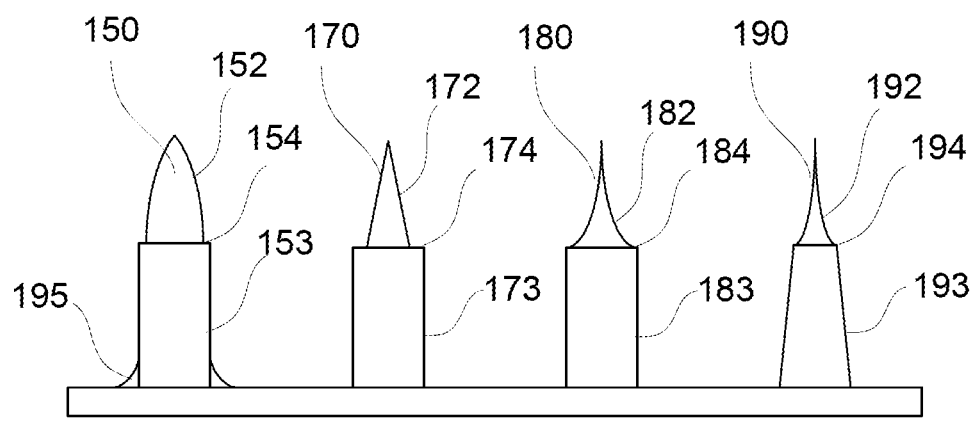

Illustrative examples of projections having discontinuities or steps are shown in FIG. 1H.

The first example projection 150, which has already been described in greater detail with reference to FIG. 1F, shows the option of having a convex effective profile at the end section 152 in combination with a step 154.

The example projection 170 generally corresponds to the uncoated profile 155 in example 150', and has an end section 172 provided atop a support section 173 with a significant step offset x defined at the step 174.

Example projection 180 includes an end section 182 having a concave effective profile. It will be seen that although the discontinuity 184 in this case is not strictly a step, the highly concave profile extending from the support section 183 has a large cone angle which results in a step-like feature despite no step offset x actually being defined on the projection 180. It will be appreciated that a concave profile can be coated in such a way as to provide a conical or convex effective profile, to allow a drastic increase in the coating supplied at the end section 182.

Finally, example projection 190 is similar to projection 180 but has a tapering conical support section 193. The overall effective profile of the projection 190 is generally conical, but the discontinuity 194 results in a rapid change in diameter in the transition between the support section 193 and the end section 192.

An advantage of using a stepped effective profile as discussed above is that the support section may be configured to effectively provide mechanical reinforcement for the projection, without impacting on the effective profile of the penetrating end section. This mechanical reinforcement may be provided by merely increasing the diameter of the projections along desired portions of the projection, but may also be provided in other ways, such as by providing buttress features radiating from the base of the projections, to even further strengthen the projections.

It will be appreciated that patches having projections of the forms described above can be fabricated using known techniques. For instance, etching techniques as described in WO/2009/097660 can be used to form the desired projection geometries from a substrate of silicon or any other suitable material. Moulding techniques as described in WO/2010/071918 may also be used, and as mentioned above, these techniques may allow projections to be moulded from a dissolvable material incorporating a material for delivery.

FIGS. 2A to 2D show SEM images of examples of fabricated projections which embody aspects of the advantageous effective profiles described in general terms above.

FIGS. 2A and 2B show examples of projections having convex effective profile with a cone angle that varies from about 3° near the base to about 8.7° at the pointed tip. These projections have a length of about 190 μm and a base diameter of about 45 μm. The projections in FIG. 2C illustrate longer projections having a length of about 226 μm and further include a flared base.

Figure 2D:
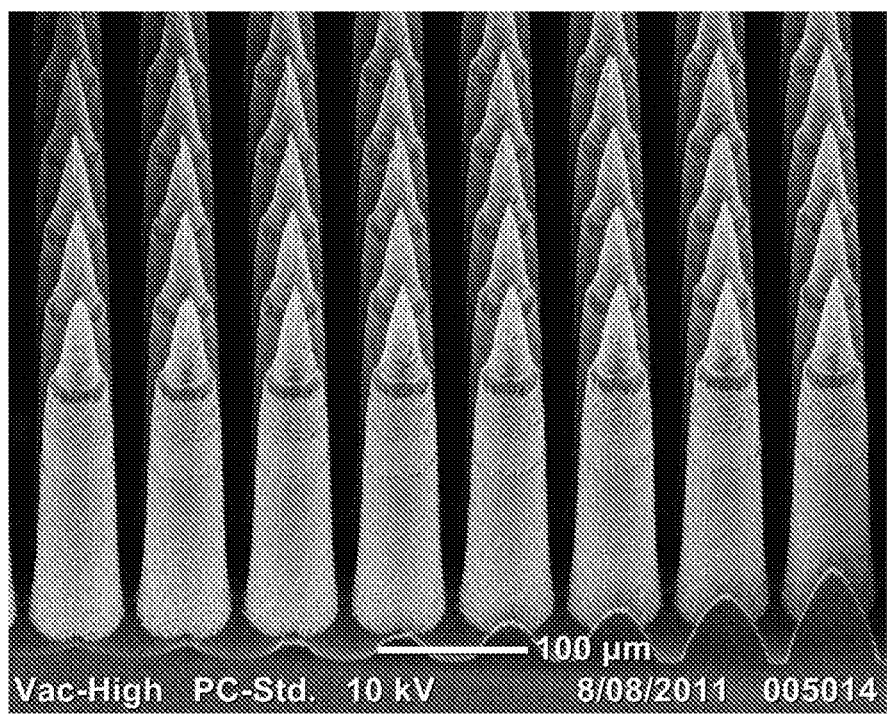
Figure 2E:
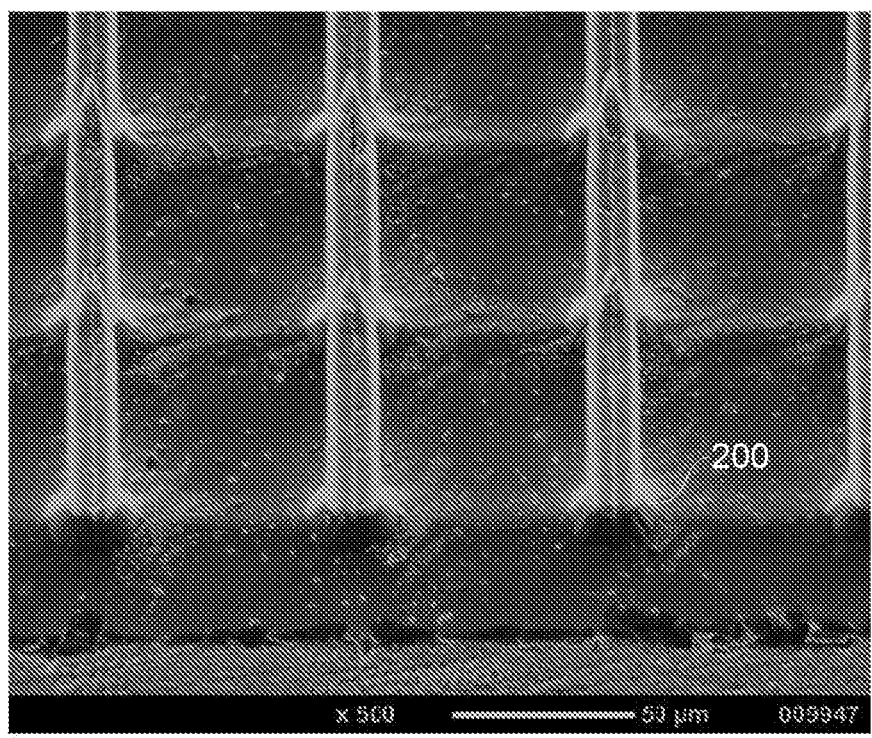
Figure 2F:
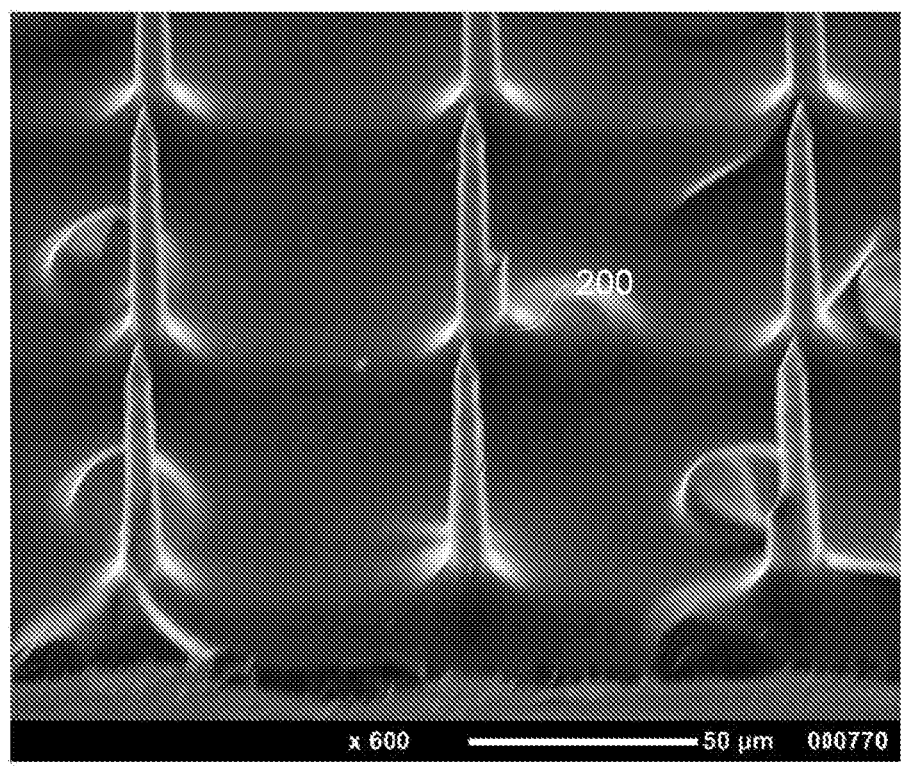

FIG. 2D shows an example of 315 μm long projections having a stepped geometry. As can be seen these projections are provided in a very closely spaced array with a small spacing relative to the base diameter of the projections. The support section of these projections has a conical profile towards the base but transitions to a convex profile towards the step, and the end section provides a similar profile as the support section ending with a pointed tip.

Projections having geometries such as those shown in FIGS. 2A to 2D can be fabricated using masked etching processes as described in WO2009/097660, where flow rates of an etchant and a passivant may be controlled in a continuous process, to thereby provide a "morphed" geometry which varies along the length of the projection to result in a desired profile.

In preferred fabrication processes, the etchant is sulphur hexa-fluoride (SF6) and the passivant is octafluorocyclobutane (C4F8). The flow rates of the etchant and passivant gases can be varied under different control strategies to provide different projection geometries.

These processes enable the production of high aspect ratio projections having convex profiles at least in the vicinity of the tip, at lengths ranging between 150-500 μm and more particularly between 200-300 μm, which are particularly suitable for penetrating the dermis in humans.

Example parameters for a typical etching process of the above type used to fabricate such projections will now be described.

First, a photoresist mask is provided on a substrate of silicon material. In one suitable example, the mask has 45-50 μm diameter dots arranged with 70 μm spacing.

Figure 3:
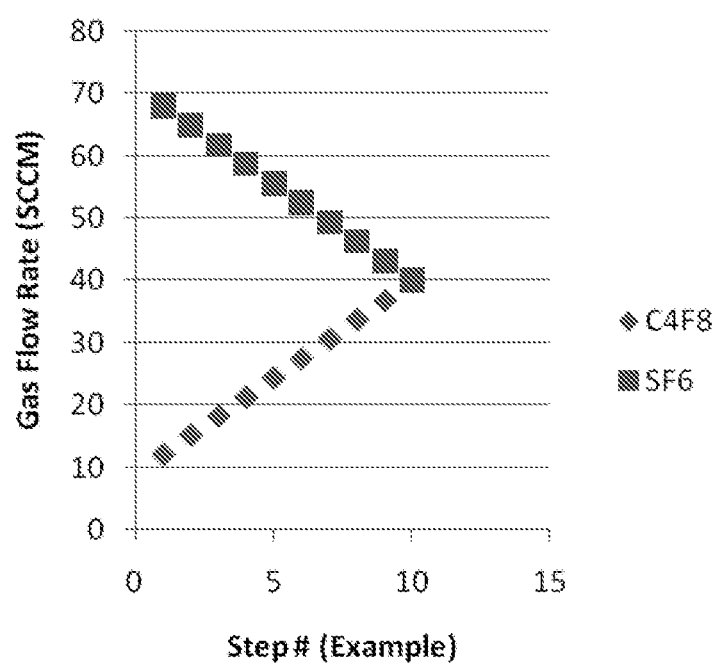
FIG. 3 is a graph of an example gas flow rate control strategy for use in fabricating projections using etching techniques.

The tip geometry may be formed with a continuous etching process as described above, using the following parameters:

Pressure: 10 mT
Power: 1500 W
SF6 flow rate: 68 to 40 seem (standard cubic centimeters per minute)
C4F8 flow rate: 12 to 40
Bias: 100 V
Loops: 1000
Loop time: 5 seconds FIG. 3 shows a plot representing an example of how the gas flow rates of SF6 and C4F8 are varied throughout the etching process in a linear fashion, resulting in a linear morphing of the projection geometry, which can be used to form a convex projection profile. It will be appreciated that it is also possible to vary the gas flow rates to result in other, nonlinear morphing of the projection geometry. For instance, convex or concave gas-flow profiles may be used to alter the final etched shape of the projection.

Following the generation of the tip geometry, a Deep Silicon Etch (DSE) process can be used to effectively extend the length of the projection, whilst maintaining the morphed projection geometry as the end section of the projection. A typical DSE etch will be performed using 800 loops with a loop time of 10 seconds.

Finally, an isotropic etching process can be performed. This isotropic etching is primarily used to remove the photoresist mask as the silicon underneath the photoresist mask "necks" down to several microns, but can also be used to ensure that the tip has a desired sharpness and/or to adjust the smoothness of the projection. The isotropic etch can be suitably conducted using the following etch parameters:

Power: 1500 W
Pressure: 10 mT
Bias: 100 V
SF6: 60 sccm
Time: 6 minutes

Modifying Effective Profile Using Coating

Figure 4:
FIG. 4 is a scanning electron microscope image of examples of projections where an effective profile is modified using a coating.

As discussed above with reference to FIG. 1F, the coating can be applied in such a way as to modify the effective profile of the projections. FIG. 4 shows a SEM image of coated projections, in which the coating has been applied on the projections to provide a convex effective profile which is convex, despite the underlying uncoated profile of the projections having a conical end section and a pronounced step.

As can be seen in FIG. 4, whilst an inflection point exists in the effective profile in the transition from the support section to the end section of the projections, the step has been substantially smoothed by the coating, and the coated projection has a curved effective profile including convex portions along each of the support section and end section of the projection.

Such modification of the effective profile not only provides a smoother effective profile, but also results in the ability to control the quantity of coating provided at desirable depths within the subject. For instance, providing a relatively thick layer of coating in the step region and upon the end section as shown in FIG. 4 allows a greater quantity of coating to be delivered to the subject at the depth to which the end section penetrates, compared to an even layer of coating on a projection having the same geometry.

Certain projection fabrication techniques can be used to even further enhance the amount of coating that can be provided upon selected portions of the projections. Although providing a step is a relatively straightforward means of promoting higher coating depositions towards the end section, as seen in FIG. 4 an inflection may remain after the step is coated. This indicates that even further coating might be applied to allow a greater quantity of material within the coating to be delivered, although there may be practical limitations to the thickness of coating that might be applied to a surface to modify the effective profile.

However, further structures may be provided as part of the projection geometry which can cause the coating to accumulate to even greater extents.

Figure 5:
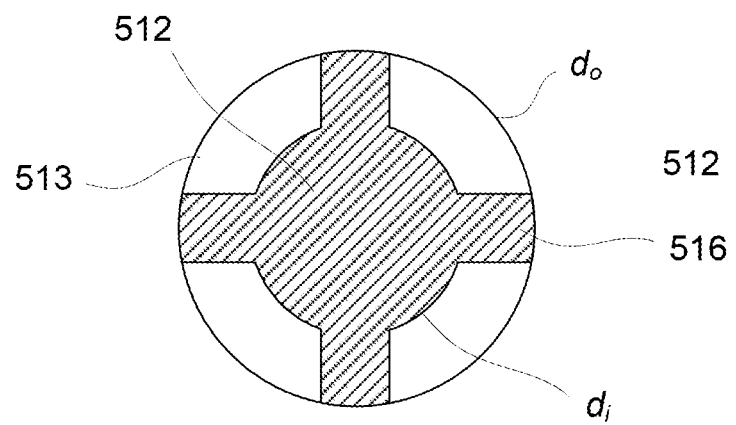
FIG. 5 is a schematic cross-section diagram of an example of a projection for promoting the modification of the effective profile of the projection using a coating.
Figure 6A:
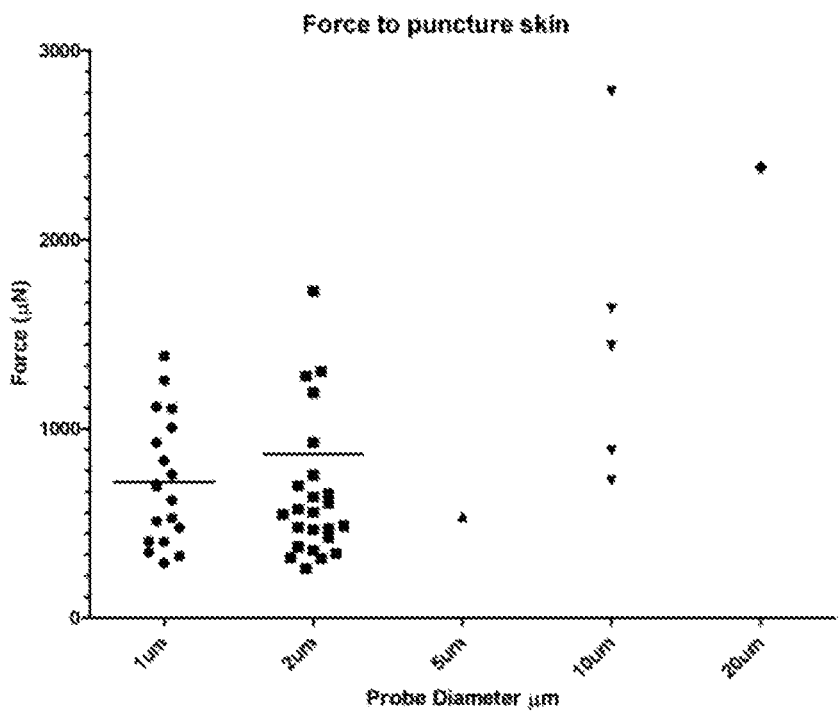
FIGS. 6A and 6B are graphs of results from micro-probe skin penetration studies.
Figure 6B:
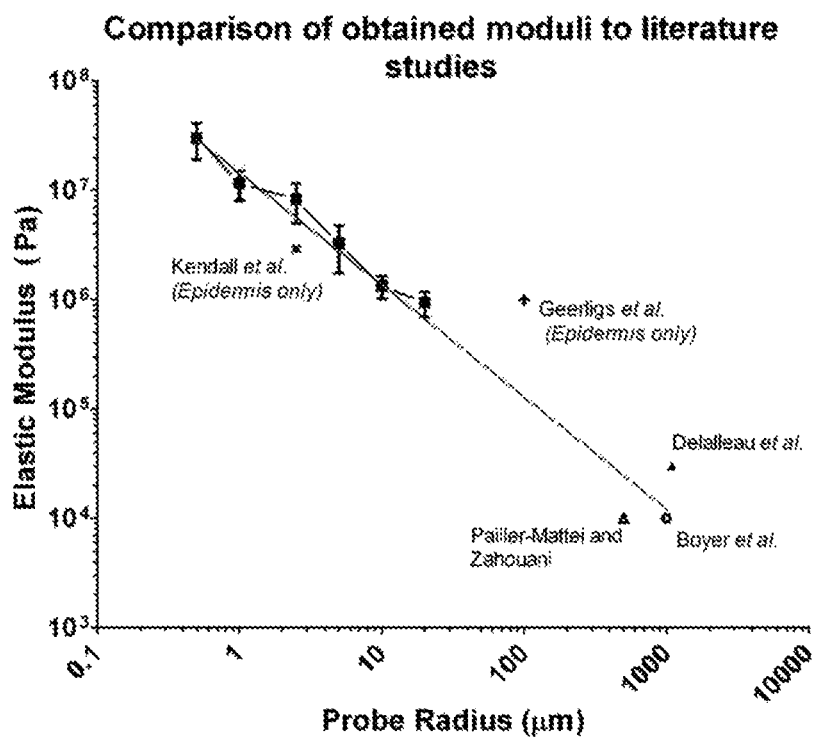

FIG. 5 illustrates a schematic cross section of an example of a projection taken at a step transition between a support section 513 and end section 512. The hatched area indicates the cross section of the end section 512 extending from step. The end section has a "cruciform" geometry provided by bridges 516 radiating from an otherwise conical end section profile of the type generally shown in FIG. 1G. It will be appreciated that bridges 516 will taper with a generally conical profile extending from an outer rim of the step to terminate at the tip along with the main conical profile of the end section.

The step involves a transition in diameter from the support section to the conical part of the end section, where a coating may accumulate with increased thickness as shown in FIG. 4. Moreover, the bridges 516 promote even thicker coatings in the step region, because the bridges 516 define further structure upon which the coating can attach, and may therefore result in the coating effectively filling the volumes defined between the bridges 516 under desirable coating application parameters.

Persons skilled in the art will understand that projection geometries as shown in FIG. 5 may be fabricated using known techniques. For example, projections may be formed using etching techniques using different mask shapes to control the resulting cross section geometry.

As will be appreciated, such techniques can result in significant increases in the quantity of coating provided upon the end section of the projections, to allow more targeted delivery of materials to desired depths within the subject.

It will be appreciated that coating of the projections can be performed using a variety of techniques, including gas jet coating and dip coating, as described, for example, in WO/2010/042996 and WO2009/079712. It will be appreciated from these disclosures that controlling the thickness of the coating solution, and hence the effective profile of the projection can be achieved by controlling coating parameters, including the volume of coating material applied, the viscosity of the coating solution, the hydrophobicity of the projections, the rate of drying of the coating, or the like.

For example, the coating parameters used to prepare the coated effective profiles in the projections of FIG. 4 were as follows. The projections were formed using a two step fabrication process, i.e. forming the end section geometry then extending the length, on a 4 mm×4 mm patch, and surfaces of the projections were coated with gold. A coating solution of 1% Methylcellulose and 67.5 μg/mL Fluvax 2011 (maximum possible) was prepared and 8 μL of this solution was applied to the patch. The coating was applied using a gas jet coating technique as described in WO/2009/079712, where the gas jet was applied initially at an 80° angle then at a 20° degree angle to dry the coating.

As mentioned in the above example, a gas jet coating process may be used to deposit liquid vaccine material in the coating solution onto the projection array. The process parameters (i.e. jet angle, jet velocity, solution viscosity, etc.) of the coating method can affect the degree to which the coating material is localized towards the tips of the projections, rather than the base. In addition to these process parameters, coating of the liquid material to the projections can be further enhanced by modifying the surface properties of the projections relative to the liquid coating material.

In the following example, we assume that the liquid coating material is aqueous, but it is recognized that other coating solutions are possible, and that the surface properties of the projection would need to be altered accordingly. For an aqueous coating solution, the patch surface can be modified to be "hydrophobic" in nature. A perfectly hydrophilic surface will cause an aqueous solution to completely wet it (assuming low viscosity). This would result in a large fraction of the liquid coating material being wicked onto the base of the projection array, which will not be delivered to the skin.

Increasing the solution viscosity slows down the wicking (or surface wetting) process. If the dry coating process is accomplished rapidly in comparison to the surface wetting, a larger fraction of the liquid coating material can be localized to the projections.

By changing the contact angle of the projection surface (by chemically modifying it), the liquid coating solution wetting properties may also be altered. In making the surface more "hydrophobic", an aqueous coating solution will be inhibited from wetting the projection surface down to the base.

Furthermore, a surfactant can be added to an aqueous coating solution which is placed on a "hydrophobic" projection. The surfactant may assist in wetting the hydrophobic surface by orienting the polar and non-polar groups of the surfactant at the surface, thus facilitating the wetting. If appropriate drying conditions (either with or without surfactant) are achieved, the result is that a significant portion of the coating material is retained near the projection tips.

Striking a balance between the surface wetting properties (i.e. contact angle), solution viscosity, and the presence or absence of a surfactant (among other solution properties) can change the degree and uniformity with which the coating solution is localized to the projection tips.

In a further embodiment, the projection surface may be altered such that the tips are hydrophilic and the lower portion of the shaft and base are hydrophobic. This can be accomplished using bulk lithographic processes. In this embodiment, the hydrophilic tip surface is easily wet, while the lower portion of the projection inhibits liquid travel towards the base due to its hydrophobic nature.

In this manner, localization of dry-coated material towards the projection tip can be further enhanced.

Tip Sharpness

The tip of a projection is required to penetrate the surface of the biological subject in use, and this penetration is typically achieved by urging the patch against the surface, at a predetermined force or velocity. Although the patches described above can be adapted for application to many different surfaces of biological subjects, it will be appreciated that it is particularly desirable to configure the patches for application to the skin.

As schematically shown in FIG. 1C, projections can penetrate through a plurality of layers of the skin, but in order to penetrate underlying layers, the outermost skin layer of the stratum corneum must first be penetrated. The stratum corneum provides a protective barrier to protect underlying tissues, and presents a substantial obstruction to penetration.

In practice, it has been found that effective penetration the stratum corneum is highly dependent on the size of the tip of the projections. Generally speaking, a sharper tip (i.e. a tip having a smaller radius of curvature) will allow the stratum corneum to be more easily penetrated.

In order to better quantify the tip sharpness requirements for penetrating the stratum corneum, penetration studies have been performed using custom fabricated tungsten micro-probes of various sizes. Data from these studies can be seen in FIG. 6A. The data shows that 1 μm and 2 μm diameter probes require similar forces to penetrate skin. However, it can be seen that very few data points exist at probe radii >2.5 μm, which is due to the fact that probes of larger diameters predominantly failed to penetrate the stratum corneum. These studies highlight the importance of sharp tips, i.e. projections having a small tip radius.

Experimental studies have also been conducted into the mechanical properties of the skin at different scales, and these mechanical properties have been found to be highly scale-dependant. FIG. 6B illustrates results of these studies. Essentially, as the size of a probe for penetrating the skin is decreased, the effective elastic modulus of the skin is increased. In other words, the skin behaves with a higher stiffness as the tip radius is decreased. This increased stiffness can be shown to be desirable, as it causes the skin to behave more plastically (and less elastically). Accordingly, the projections are able to "puncture" into the skin, uniformly. In contrast, when the skin behaves more elastically, there is greater deformation of the skin around the projections, making it harder for the projections to penetrate uniformly.

Accordingly, for fine positioning of a projection within the skin, stiffer material properties in the skin enable better control over the actual depth of penetration. The overall skin stiffness can play an important role in where projections will deliver vaccine. In the data of FIG. 6B, it can be seen that a projection with a tip radius of 0.5 μm will experience a material over twice the stiffness experienced by projection with a tip radius a 1 μm. This means that the skin will undergo reduced deflections during penetration for sharper tips, which can help to control variations in penetration depth due to skin deflection.

However, this phenomenon of increasing skin stiffness as projection sharpness decreases also causes competing projection strength considerations, given that smaller projections must withstand higher loads during penetration.

Table 1 below shows the failure stress requirements for probes of different radii to penetrate the skin without breaking, calculated using Hertzian flat cylinder maximum stress calculation. As can be seen, the failure stress generally increases with decreasing probe radius.

TABLE 1

| Probe Radius (μm) | Failure stress (MPa ± SD) |
|---|---|
| 0.5 | 34.97 ± 20.64 (n = 19) |
| 1.0 | 8.03 ± 4.74 (n = 36) |
| 2.5 | 9.84 ± 7.16 (n = 3) |
| 5.0 | 1.20 ± 0.94 (n = 7) |
| 10.0 | 0.18 ± 0.05 (n = 2) |
| 20.0 | — |

It will be appreciated that the use of a convex effective profile at the tip of a projection can help to allow a sharp tip to be provided without necessitating a narrow tapering end section as would be the case with a conical effective profile.

In any event, it will be appreciated that the selection of tip radius and design of the projection effective profile near the tip are important considerations in the design of projections. Whilst the tip radius should be sufficiently small to allow controlled, consistent penetration of the stratum corneum, there are also fabrication constraints and other projection design considerations which place limitations on the practically achievable tip sharpness. In any event, preferred tip radii for human applications will be discussed in further detail below.

Modelling of Geometry Parameters for Human Applications

Experimental data obtained in studies of skin mechanics have allowed an improved understanding of how projection geometry parameters can significantly change the ability of projections to enter the skin. This has allowed models to be generated which extrapolate the penetration behaviour of projections when individual parameters are varied, and hence allow preferred projection geometries to be determined.

FIGS. 7 and 8 are plots which have been prepared using a human skin penetration model.

Figure 7:
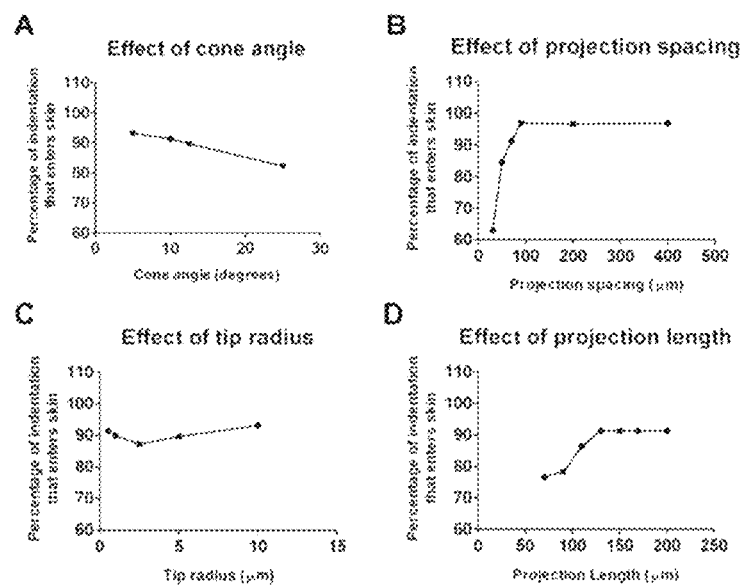
FIG. 7 shows graphs correlating geometric parameters of projections to a percentage of indentation into the skin, using a human skin penetration model.

Specifically, the plots of FIG. 7 correlate geometric parameters of projections to a percentage of indentation into the skin. In this figure, a value approaching 100% is desirable as this signifies the most efficient penetration into the skin. In view of the above discussion of skin stiffness, it will be appreciated that these plots can also be considered to illustrate the amount that skin deflection may reduce the degree of penetration.

Figure 8:
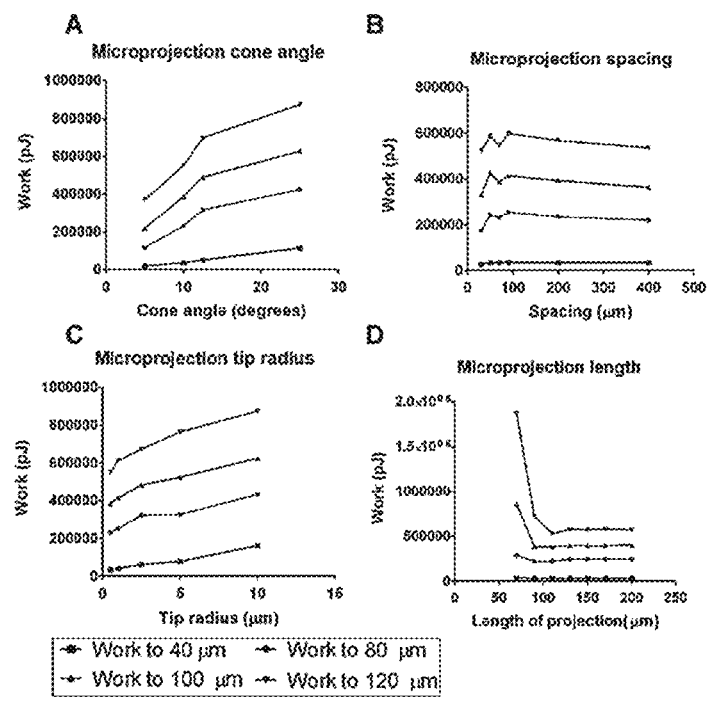
FIG. 8 shows graphs correlating geometric parameters of projections to an energy required to penetrate the skin, using a human skin penetration model.

FIG. 8 shows the energy required to push a projection into skin. In this figure, a low energy value is preferable for penetration.

The modelling results of FIGS. 7 and 8 can be used to support specific geometrical requirements for the projections.

The "A" panels show that as the cone angle is increased, then the amount of projection that enters the skin will decrease, and the required energy to penetrate the skin will increase significantly.

The "B" panels show that an inter-projection spacing less than 100 μm will substantially reduce the depth to which a projection will reach, but also show that the projection spacing will not substantially impact on the work to cause the projections to penetrate the skin.

The "C" panels show that smaller tip radii facilitate penetration, in support of the discussion above regarding tip radius.

The "D" panels show that projection length must ensure that the patch base does not contact the skin. Thus it is desirable to select the length of the projections to prevent such contact between the base and the skin surface during application, such that projections having additional length beyond the desired penetration depth.

An important observation from the modelling results is that the cone angle is a significant variable in the ability of projections to penetrate skin. Tips having a small cone angle are particularly desirable for human applications, although this needs to be balanced with a cone angle required to maintain a desired strength of the projections. In view of these results, a cone angle of less than 25°, less than 20°; and less than 15° can also be used. Similarly, the tip radius is typically, less than 5 μm, less than 2.5 μm, less than 1 μm or less than 0.5 μm can be used. More typically a cone angle is used that is between 10° and 30°, between 15° and 25°, or between 18° and 22°. In one particular example, a cone angle of 20° can be used.

Penetration Performance with Convex or Stepped Configurations

The modelling results of FIGS. 7 and 8 have demonstrated how the basic geometric parameters of cone angle, projection spacing, tip radius and projection length contribute to penetration performance. However, as mentioned above, the particular effective profile of a projection may also have a significant impact on penetration performance.

It has been found that projections having a convex effective profile have several distinct advantages in regard to facilitating improved penetration of the skin, and that stepped profiles demonstrate other penetration mechanisms which can be exploited to desirable effect.

Figure 9A:
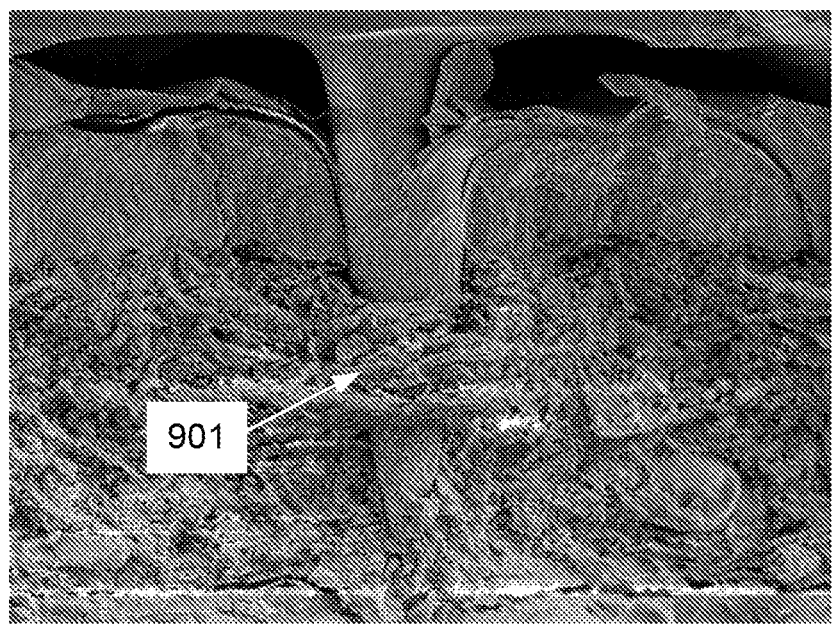
FIGS. 9A and 9B are in-situ scanning electron microscope images of patches which have been inserted into skin.
Figure 9B:
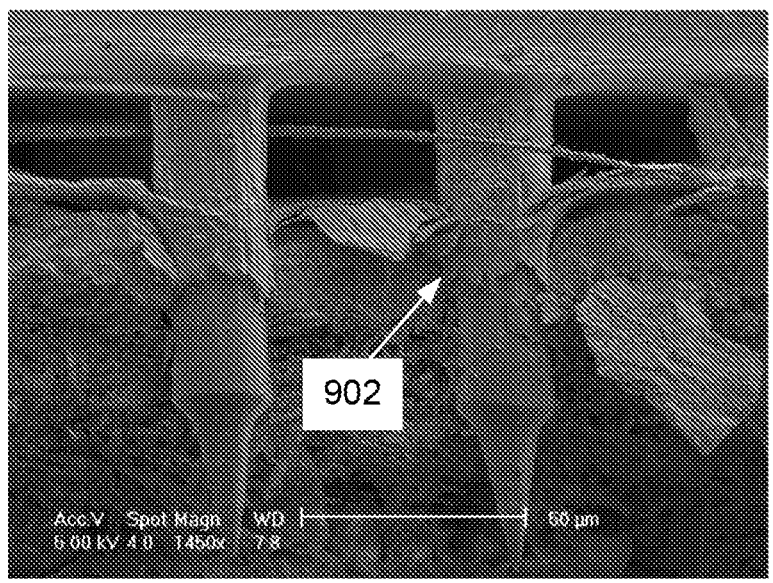

FIGS. 9A and 9B show in-situ SEM images of patches which have been inserted into the skin of mice. The patches were applied to the skin and subsequently fractured after application, to allow in situ imaging of the projections within the skin. Such images can be used to gain a better appreciation of the interactions of different projection geometries with the skin layers, and also indicate the tissue regions to which vaccine or other coating materials may be delivered in use.

The projections of FIG. 9A have a slightly convex effective profile, whilst the projections of FIG. 9B have a stepped effective profile. These figures allow better comparison of these two geometry types. Several features of penetration are visible under such a comparison.

With regard to FIG. 9A, it can be seen that the convex profile has entered the skin with minimal disruption of the internal skin structure, as indicated, for example, by arrow 901. The projection has successfully penetrated the three external layers of the stratum corneum, viable epidermis and dermis. There is some surface layer deflection but this is not substantial.

On the other hand, the stepped projections shown in FIG. 9B have caused more significant disruption to the surface skin layers upon penetration. As can be seen, the fabrication of the projections of FIG. 9B has in fact resulted in a second step closer to the base, having a less defined step surface compared to the step near the tip. The skin surface has been noticeably pulled into the skin due to the second step, as indicated by arrow 902. In this case the penetration of the stepped projections would have involved the first step starting the process of surface deflection with the second step furthering this, with the discontinuities in the effective profile due to both steps acting to limiting penetration. In this example, it is noted that the steps are not so severe as to completely inhibit penetration, but other step configuration could provide this option if desired.

By comparison of the images it can be seen that the surface of the skin has been pulled further into the skin with the stepped projections in FIG. 9B, than for with convex projections of FIG. 9A. It has been determined that the convex projections penetrate the skin with an initial puncturing action where a hole of a relatively large diameter initially formed in the stratum corneum, after which the progressive penetration gradually dilates the hole. On the other hand, stepped projections will initially form a small hole as the end section punctures the stratum corneum, and when the step passes through the stratum corneum this causes a sudden additional disruption of the stratum corneum, resulting in the observed effect of the skin surface being pulled inwardly by the support section.

Furthermore, the step in the projection in FIG. 9B has stopped penetrating when the step has reached the basal layer of the skin which defines the boundary between the tissues of the viable epidermis and the dermis. In contrast, the convex projection in FIG. 9A has penetrated to a greater depth into the skin. This indicates that penetration may be restricted with a stepped effective profile.

These differences in penetration depth are likely to be a result of the step hitting the skin and slowing penetration when there is a discontinuity in the surface geometry. For example, passing through the hard outer layer of the stratum corneum will slow penetration significantly as the step contacts this layer. The viable epidermis will result in less resistance. When the projection enters the dermis its sharp tip will spread collagen fibres to penetrate, however, when the step reaches this layer the collagen fibres will not spread as easily and resistance will significantly increase—slowing penetration. A convex geometry will not impede penetration in the same manner.

Figure 10:
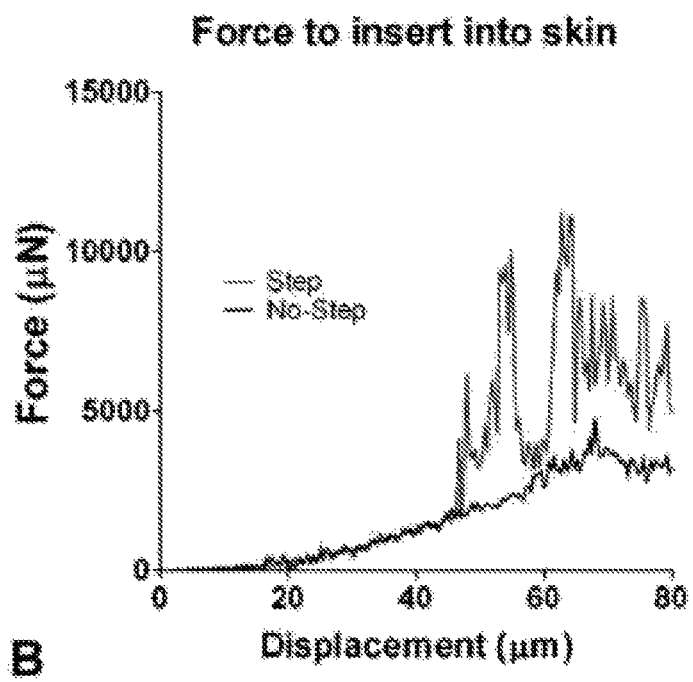
FIG. 10 shows respective graphs of force and work required to insert projections into the skin.
Figure 10:
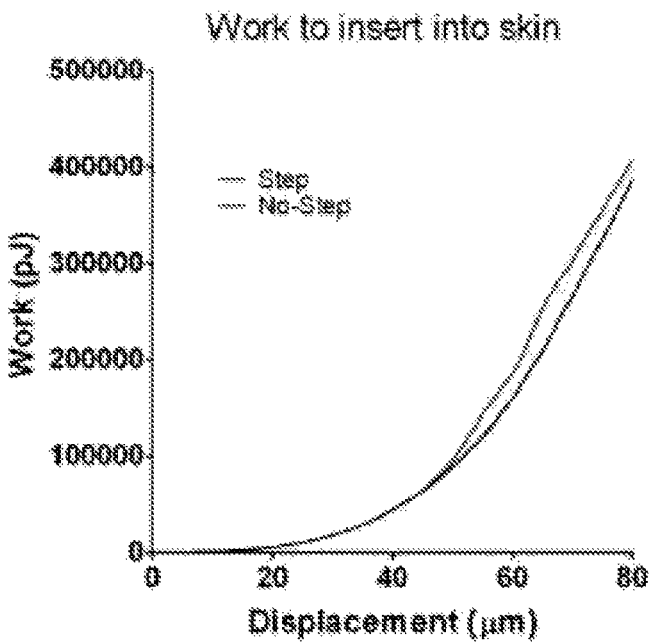

FIG. 10 shows modelling results illustrating how the force and work to insert a projection into the skin differ when there is the presence of a geometrical step in the effective profile of the projection.

As can be seen in FIG. 10A, the force-displacement relationship for a projection having no step demonstrates a relatively gradual increase in the force as penetration increases. On the other hand, a stepped configuration encounters significant spikes of force at particular displacements. These transient forces have been found to correspond with the step impacting the stiffer dermis layer in the skin, and this impact coincides with the generation of pressure waves with emanate through the skin. This behaviour will be expanded upon further below.

This is reflected in the work plot of FIG. 10B, where the work for inserting a stepped projection is offset from the work for a projection without a step, at the displacements where the aforementioned spikes of force were encountered.

In general, once the surface of the skin is penetrated with a projection's sharp tip, the projection will be able to continue to penetrate deeper into the skin as the lower layers are mechanically weaker (in terms of penetration, not elasticity). However, the collagen and elastin meshwork of the dermis serves to restrict penetration if there is a significant geometrical change, such as in a step, as confirmed by fluctuating force profile for stepped configuration. In either case, the work to penetrate into the dermal layer increases as shown by the upward inflection in the work curve for each of the stepped and unstepped projections. Nevertheless, a projection having a convex shape can spread the collagen more effectively than a projection having a step, allowing for improved penetration performance.

It is noted that the penetration of a convex projection into the skin may be slightly reduced given that convex effective profiles will typically have a tip with a larger cone angle than a conical profile. However, the overall projection of a convex shape becomes more efficient once the surface is penetrated. An increasing cross-section of a conical probe will progressively push more stratum corneum into the skin during penetration. However, a convex projection will have an initial large puncture and surface deflection, but then the subsequent change in cross-section is minimal.

Whilst a stepped projection restricts penetration into the dermis, this is not necessarily an undesirable result. In fact, this restriction on penetration can be exploited in circumstances where it is desirable to finely control the degree of penetration into the dermis. For example, projection geometries can be provided which provide an end section having a length corresponding to a desired depth of penetration within the dermis, with a pronounced step intended to not penetrate through the basal layer in use.

A pronounced step may also cause significant stress concentrations at the outer limits of the dermis where the step is forced against the stiffer dermal tissues, which can trigger cell damage in the surrounding tissues. As will be described in further detail below, cell damage has been found to promote improved immunological responses.

As will be explained below, the patch may be desirably applied to the skin with a predetermined application velocity. When, during penetration, a projection with a stepped configuration penetrates encounters the stiffer tissue structures within the dermis at speed, the step's impact with the stiffer dermal tissues may cause the generation of pressure waves which propagate from the step into the surrounding dermal and neighbouring skin tissues. Under certain application conditions, these pressure waves can also contribute to cell damage and thus promote further physical adjuvant effects due to cell damage mechanisms as will be described further below.

It will be appreciated that the size of the step feature in a stepped effective profile can vary depending on the desired penetration behaviour, and other considerations such as the overall size of the projection, the material delivery requirements, and the like. A step offset x in the range of 1 μm to 10 μm may be suitable for projections configured for human use, where preferred base diameters may lie in the range of 30 μm to 50 μm.

In any event, it will be seen that different projection geometries can be selected depending on the desired penetration requirements.

Strength of Projections

It will be appreciated that particular effective profiles can have advantages with regard to the strength of the projections.

The mechanical strength of projections having different geometries has been examined using Nanoindentation, where a single projection is broken using a sharp tip probe. These results are shown in FIGS. 11A and 11B.

Three types of projection were measured—100 μm convex projections, 260 μm projections of a conventional conical profile (designated as "long" projections) and 110 μm long stepped projections.

Figure 11A:
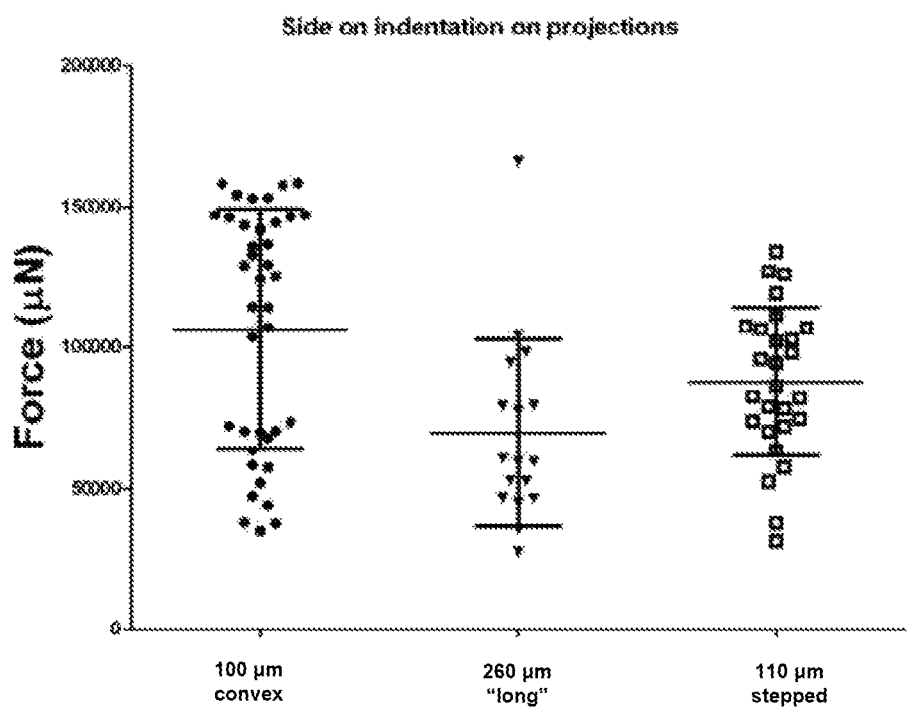
FIGS. 11A and 11B are graphs of force to break projections of different configurations, using side on and top down applications of force, respectively.
Figure 11B:
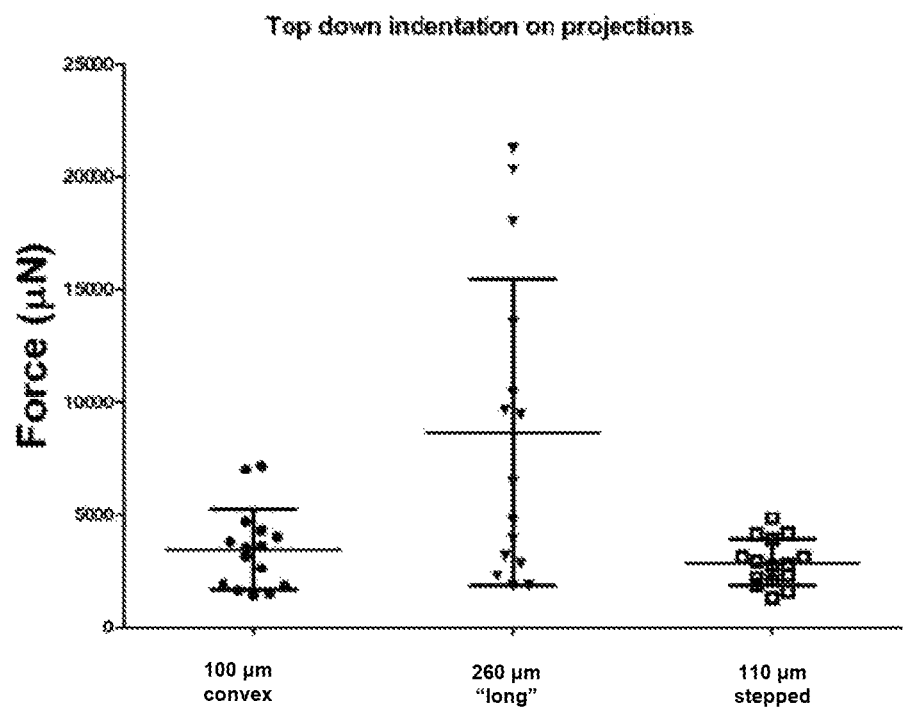

Side on indentation results are shown in FIG. 11A for each of the above mentioned projections, which indicate the lateral force required to break the projections. These results showed that the convex shape has a greater lateral breaking strength than the stepped projections.

The long projections were not much weaker than the stepped projections, supporting that the stepped shape gives a projection substantial strength over a pure conical shape, due to the increased diameter of the stepped projection between the base and the step.

The top down indentation are shown in FIG. 11B, which indicate the compressive force required to break the projection. In general, the most common failure point will be in the vicinity of the projection tips, wherein the projections have the lowest diameter. The convex shape has, slightly higher strength than a stepped shape here.

Compared to a projection having a purely conical profile, the strength of a projection having a convex effective profile will typically be substantially higher. This is due to the higher cross-sectional area of material that facilitates stress distribution. Specifically, nearer the tip of the projection, a small cross-sectional area could cause the tip break off in the skin (which has been observed in known purely conical projections). However, convex projections provide improved resistance to tip break off. If breakage of a convex projection does occur during use, it will be more likely to occur at the base, which would facilitate broken projections being removed from the skin during the natural process of desquamation of the skin (removal of tip breakages through desquamation would take significantly longer).

Although each of the projections discussed above is likely to be sufficiently strong to enter skin, it will be appreciated that these strength performance results demonstrate that variations to the effective profile of a projection can result in significant variations in strength, which can allow even further optimisation of projection geometries.

Figure 11C:
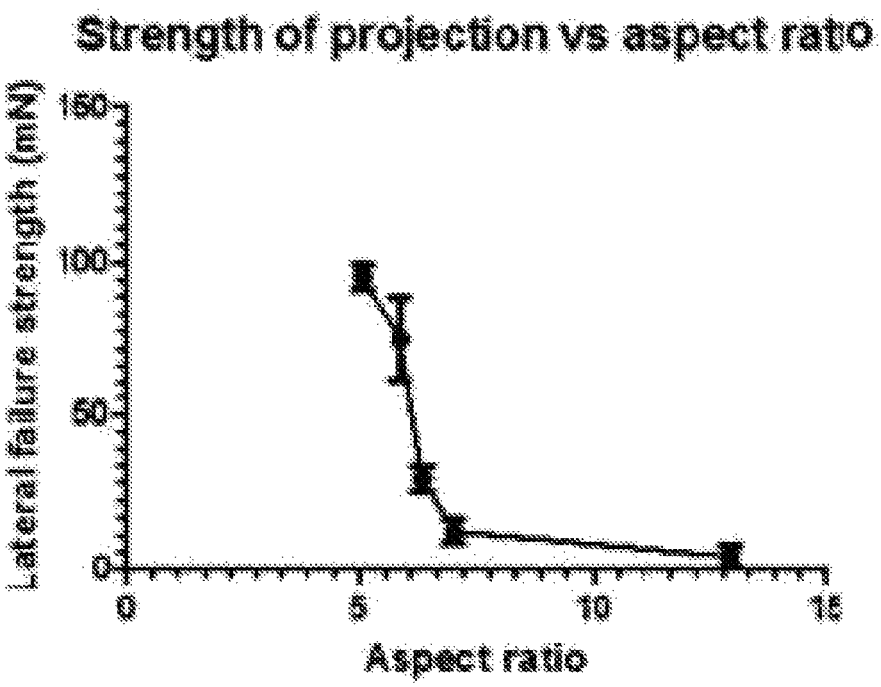
FIGS. 11C and 11D are graphs of force to break projections of different aspect ratios, using side on and top down applications of force, respectively.
Figure 11D:
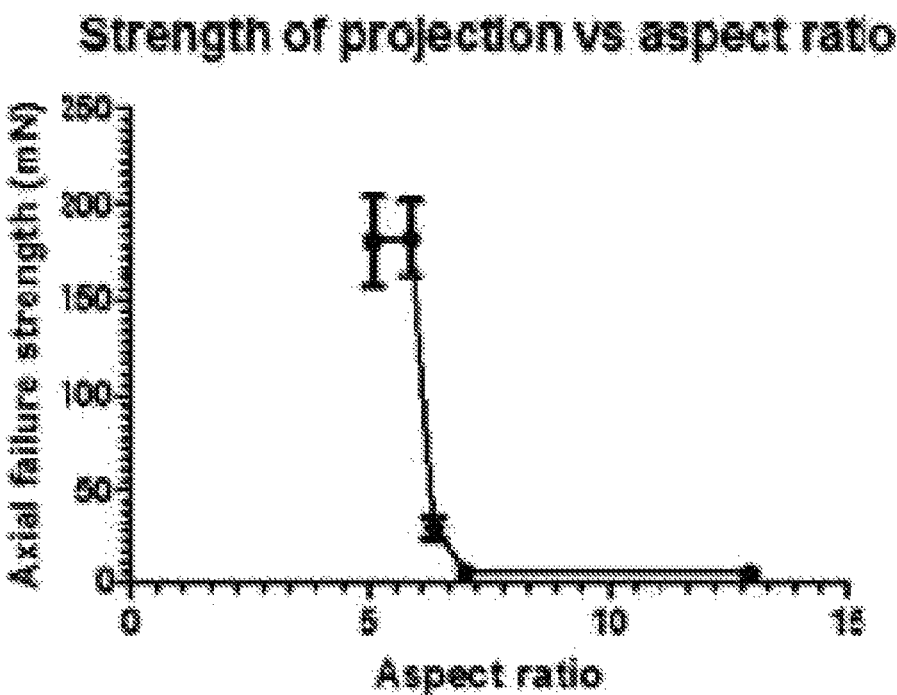

The strength of the projections will also depend on the aspect ratio, namely the ratio of the projection length to the base width. Example measured strengths in lateral (side on) and axial (top down) directions are shown for example projections having different aspect ratios in Table 2 and in FIGS. 11C and 11D.

TABLE 2

| Aspect Ratio | Experimental failure force in the lateral direction (mN) | Experimental failure force in the axial direction (mN) |
| --- | --- | --- |
| 12.94 | 7.89 | 5.35 |
|  | 1.20 | 4.93 |
|  | 8.29 | 4.24 |
|  | 1.42 | 5.51 |
|  | 2.46 | 6.26 |
| 7.00 | 8.41 | 3.35 |
|  | 8.41 | 8.35 |
|  | 8.59 | 6.31 |
|  | 17.0 | 5.23 |
|  | 11.8 | 5.46 |
| 6.35 | 25.0 | 33.42 |
|  | 26.9 | 33.42 |
|  | 27.5 | 33.42 |
|  | 27.5 | 33.42 |
|  | 35.1 | 23.49 |
|  |  | 24.73 |
|  |  | 31.94 |
| 5.86 | 73.8 | 188.11 |
|  | 62.4 | 190.80 |
|  | 89.3 | 209.60 |
|  |  | 183.63 |
|  |  | 153.22 |
|  |  | 168.15 |
| 5.07 | 99.7 | 206.54 |
|  | 92.1 | 180.36 |
|  | 94.0 | 202.66 |
|  |  | 158.02 |
|  |  | 156.40 |

Based on the above data, in one example it is typical to use a projection having an aspect ratio of <6 to ensure the projection has sufficient strength to withstand insertion into a subject, so for a projection having a length of 240 µm, the projection base would have a width of at least 40 µm.

It is also noted that the use of a solid coating to modify the effective profile of the projection may also result in improved projection strength qualities as described above. This will particularly be the case where the coating is configured to have a stiffness that is comparable with the material from which the projection is formed. Some suitable coating formulations can significantly contribute to the overall strength of the projection.

As mentioned above, projection geometry can be formed from dissolving material including a material for delivery. It will be appreciated that suitably formulated dissolving material can be used to form the actual structure of the projections and provide the desired effective profile, rather than having to be provided as a coating. In particular embodiments, the patch may include fully dissolvable projections having sufficient strength to allow penetration, formed to have an effective profile of interest.

It will also be appreciated that not all of the projections in an array need to have the same effective profile, and thus different regions of the array may have projections configured for different outcomes. Similarly, not all of the projections in an array need to be coated. Accordingly, in some embodiments, an array of projections on a patch may include some projections configured for delivery of material, and other projections configured for providing other useful results. For instance, uncoated projections having an effective profile selected for increased mechanical strength can be provided on an array to assist the overall penetration of the projection array.

Preferred Penetration into the Dermis

As will be described in further detail below, it has been found that material can be effectively delivered to the dermis, where the delivered material is desirably distributed to cells by diffusion mechanisms.

Testing on mice has demonstrated that desirable immunological responses may be obtained through the delivery of vaccines and the like to the dermis, and these tests have indicated that penetration into the dermis by a depth that is of a similar order to the thickness of the viable epidermis may be beneficial.

Accordingly, examples of patches suitable for providing desired immunological responses may have geometries that result a depth of penetration in the dermis that is approximately equal to the thickness of the viable epidermis.

For humans, a dermal penetration depth of around 50 µm is considered desirable, given typical skin layer thicknesses. A total penetration depth of approximately 100-130 µm would be required to account for the depths of the stratum corneum and viable epidermis.

Penetration depths of these approximate magnitudes are considered desirable for several reasons. Penetration into the dermis by a limited depth (compared to the overall thickness of the dermis) will generally avoid reaching nerve endings in lower portions of the dermis, allowing pain free application. Preferably the length of the projections will be selected to ensure that stimulation of nerve endings during penetration is substantially prevented. In any event, by penetrating the viable epidermis and dermis by approximately equal amounts, this will allow material to be delivered to a substantial amount of immune cells in both the viable epidermis and the dermis.

In general, it has been found that practical applications of patches having desirable geometries as discussed above will penetrate the skin by about 50% of the overall projection length. Accordingly, projection lengths falling between 150-500 µm and more particularly between 200-300 µm are considered particularly suitable for penetrating the dermis at such a desired depth.

When the relative mechanical properties of the layers of the skin are taken into consideration (discussed in further detail below), the stratum corneum provides the first barrier to skin penetration. As penetration progresses, the viable epidermis is reached which is a cellular layer of low strength. The dermis is then penetrated which, with its collagen mesh, provides a stiffer material into which to penetrate.

Figure 12:
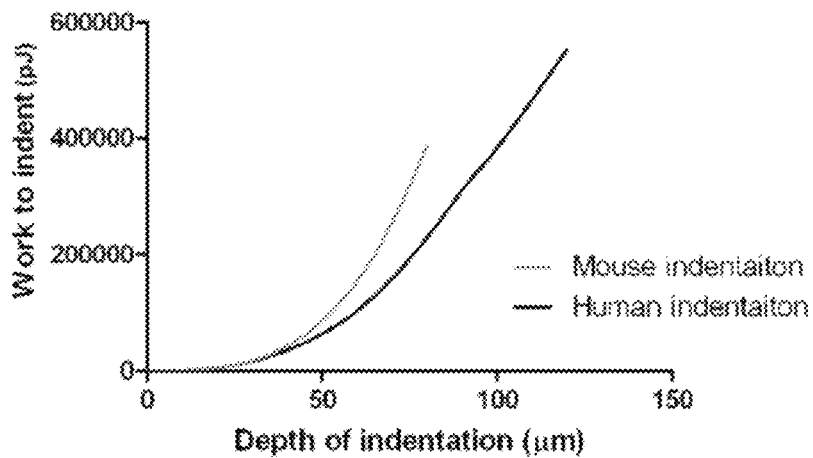
FIG. 12 is a graph comparing the work required to insert projections into mouse and human skin.

It has already been shown with reference to FIGS. 9A and 9B that projections can penetrate substantially into the mouse dermis through this collagen meshwork. Accordingly, penetration into the dermis in humans is expected to be similarly obtainable, as the viable epidermis will provide little resistance to penetration. Therefore a penetration depth of 50 µm into the dermis is considered feasible by extrapolation from the successful testing on mice. To support this, models of penetration energy for mouse and human skin were compared, and the results of these comparisons can be seen in FIG. 12. These results show that penetrating to a total depth of 120 µm in a human takes little more energy than penetrating to 70 µm in a mouse. Each of these depths corresponds to a depth of penetration into the dermis that is similar to the epidermis thickness.

As discussed above, the dermis can present an increased resistance to penetration of a projection due to the variation of mechanical layer properties within the dermis compared to the viable epidermis.

Figure 13:
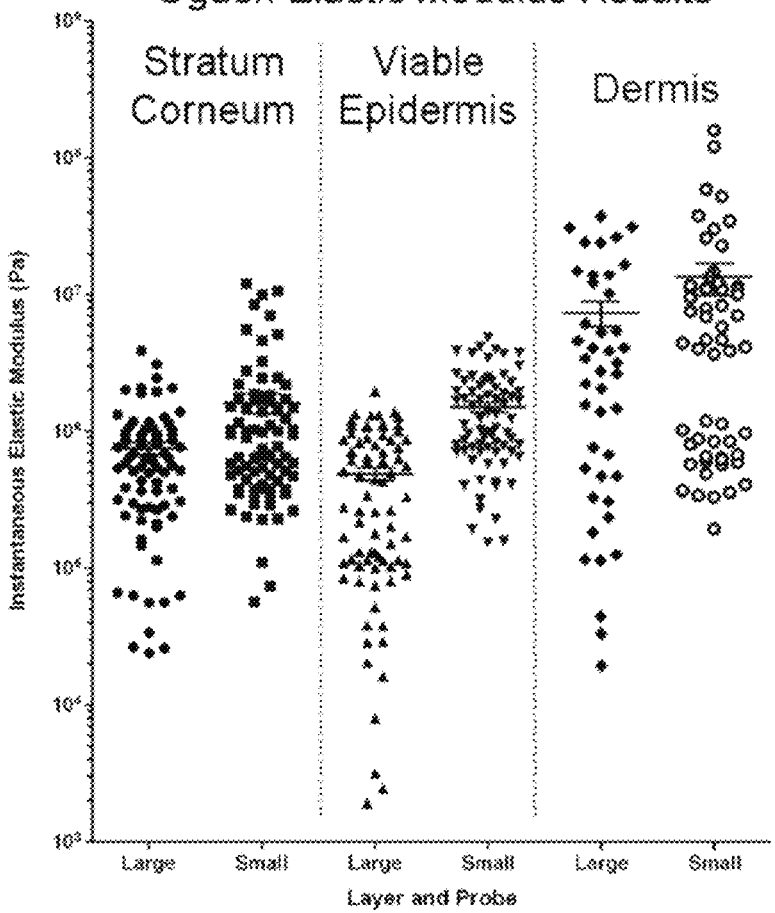
FIG. 13 is a graph of elastic modulus results for the stratum corneum, viable epidermis and dermis of the skin.

Mechanical properties of the skin layers have been measured by atomic force microscopy indentation as described in Crichton et al. (Biomaterials, 2011), and results of these measurements can be seen if FIG. 13. These results highlight that the dermis is about 1 order of magnitude stiffer than the viable epidermis. These experimental results are for two scales of probe—a "small" probe which is around 2 μm diameter and a "large" probe which is around 6.5 μm diameter.

In view of these results, it will be appreciated that a projection entering the skin will initially experience the deflection of the stratum corneum which will fracture/puncture after a relatively small deflection (which may be around 10-15 μm). Subsequently, the projection will pass through the viable epidermis, with little restriction from this layer. However, depending on the projection effective profile, at this point the hole in the stratum corneum may be increasing in size, such that some energy may still be required for continued penetration through the viable epidermis. When the projection reaches the dermis it will have to enter this stiffer layer by spreading or breaking collagen fibres which will require substantial energy. This increase in energy will be the factor that slows and stops penetration ultimately.

This effect can be beneficially used to regulate the penetration depth of a projection. A convex effective profile allows for an abrupt puncture, with little increase in force through the viable epidermis, whilst maintaining the ability to spread fibres (e.g. collagen and elastin) in the dermis. However, the dermal fibres will nevertheless regulate the depth of penetration into the dermis to some extent. Suitable application parameters may be determined in view of this effect to allow a more controlled penetration depth into the dermis, even when convex effective profiles are used.

As mentioned above, a stepped effective profile can be used where a very specific projection location is desirable. In particular, a stepped projection may cause the penetration to halt when the step encounters the dermis during penetration, so that the tip enters the dermal layer by a required amount.

In any event, the dermis can be effectively used as a "regulator" to help to ensure that the projections reach a desirable location in the skin of the subject.

Applicator Effects

Due to the small size of projections, it is desirable to have a method for reproducibly introducing them into skin to a defined depth. The depth of penetration affects which cells are targeted by the material, and may also affect the delivered dose.

In particular, the patch is typically configured to deliver a specific amount of material to predetermined depth within the subject, to thereby induce a predetermined response. As tissue can vary significantly between different individuals, it is desirable to provide a method of application that ensures consistent penetration of the patch projections.

The outer skin layer, known as the Stratum Corneum, forms a barrier to fluid transport and also acts as to impede projection penetration. To effectively breach the Stratum Corneum and ensure the projections penetrate a sufficient distance into the skin, an impact applicator can be employed allowing the patch to be applied at a set velocity, typically between 1 $ms^{-1}$ and 10 $ms^{-1}$. This helps exploit the viscoelastic properties of the subject's skin, and thereby maintain a consistent penetration of the projections.

By having the projections strike the skin at high speeds (and therefore, high strain rates), the skin behaves as an instantaneously stiffer medium and the skin penetration stress at each projection contact site is reached after a smaller strain, meaning that penetration is achieved with less skin deflection. This can help prevent large deflections of the skin before penetration, which can result in a reduced capacity to penetrate as there is only a limited distance the projections can travel before the skin surface contacts the base of the patch.

In addition to the effectiveness of the Stratum Corneum as a barrier to particle transport, the tissue beneath the skin layers of interest is highly compressible. This compressibility of the underlying tissue presents a challenge to projection penetration as a large portion of the energy intended for penetration will be used up in compressing the tissue beneath the skin. For this reason, pre-compression of the tissue can be used to compresses the underlying tissue before the patch is applied. In this manner, the projections can contact a more solid medium and penetrate more effectively.

Accordingly, in one example, the patch application process includes two phases, namely applying a preload force to the tissue to at least partially compress a subcutaneous tissue layer prior to application of the patch, and then applying the patch with a predetermined application velocity to thereby maintain tissue stiffness and help ensure that the projections penetrate to a predetermined depth.

During compression, the effective mechanical properties of the tissue are altered, temporarily making the tissue behave as a much more mechanically rigid material. By compressing tissues using a pre-load force, the effective mechanical properties of thicker tissues, or weaker tissues, are altered more significantly than thinner or stiffer tissues. The net result is that tissues of widely varying thickness and mechanical properties are temporarily made to behave in a more similar manner than tissue that is uncompressed.

In this regard, if a patch is applied to a mechanically weak substrate, the imparted energy is split between the processes of compressing the tissue, and causing needle penetration. In the case of a mechanically stiff material, the energy imparted goes primarily towards causing projection penetration. Thus the act of compressing the tissue before impacting the projection array onto the skin surface causes tissue of varying initial mechanical properties to exhibit similar penetration depth for a given impact energy.

A second effect of compressing the tissue prior to projection insertion is that the tissue layer thicknesses become physically smaller (mainly the viable epidermis), effectively bringing the dermal tissue closer to the stratum corneum. The net result is that shorter needles are able to penetrate to the dermis in compressed tissue than in uncompressed tissue.

An example of an applicator for applying a patch will now be described with reference to FIGS. 14A to 14C.

In this example, the applicator 1400 includes an elongate and typically cylindrical hollow body 1410, having a generally annular applicator ring 1420 mounted on one end thereof. The apparatus also includes a support 1430 for supporting a patch 1440 in use. The support 1430 is typically positioned radially inwardly of the applicator ring 1420, with the support 1430 being held in place relative to the applicator ring 1420 using a friction fit, interference fit or the like.

As shown in FIG. 14C, the support 1430 may include a profiled portion 1431, such as a ridge, for extending around inner region 1432, which in use receives the patch 1440, as shown. The ridge can be used so that edges of the patch substrate are shielded from the skin, thereby reducing the stress on projections at the edge of the patch to reduce breakage during insertion, and also to make the application more tolerable to the skin.

The support 1430 can also be made of, or contain, a compliant or semi-compliant material to ensure that there is some cushioning in the support 1430 to avoid patch breakage, during insertion. The support 1430 can be formed from a polymer or other similar material, although it will be appreciated that other materials can be used.

In use, the patch can be coupled to the support 1430 using a variety of techniques. In one example, this can be achieved by a friction or interference fit with the ridge 1431, although alternatively the patch could be attached using an adhesive or other similar technique.

Figure 14A:
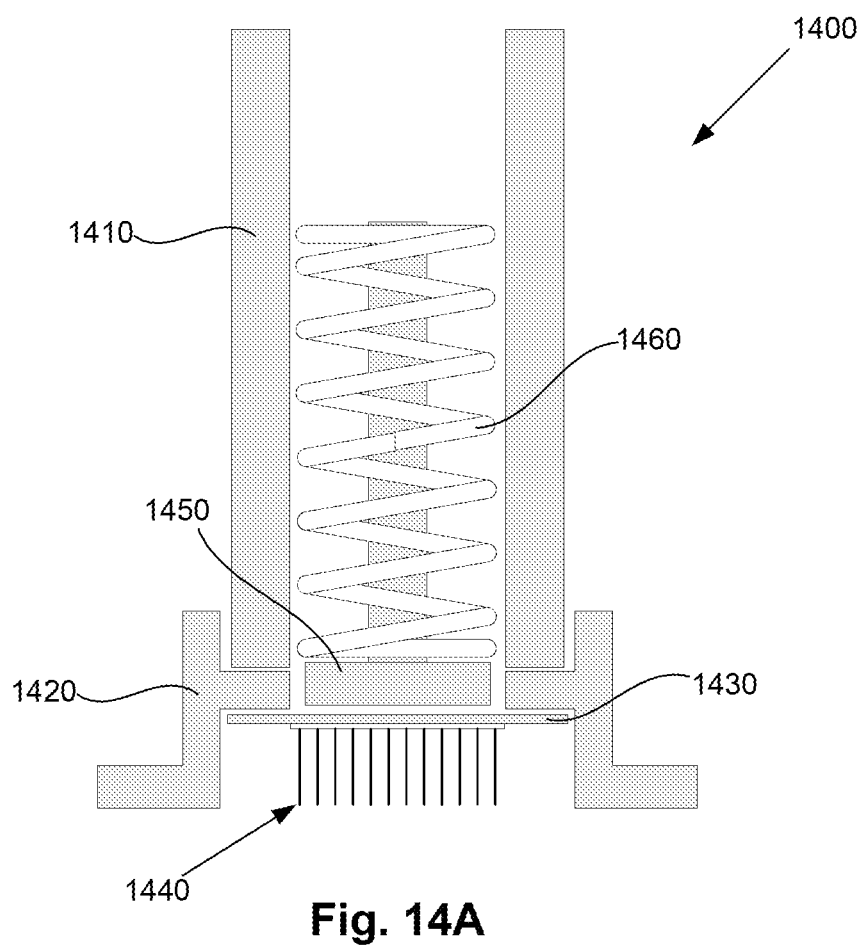
FIGS. 14A and 14B are schematic side and plan views of an example of an applicator for applying a projection patch.
Figure 14B:
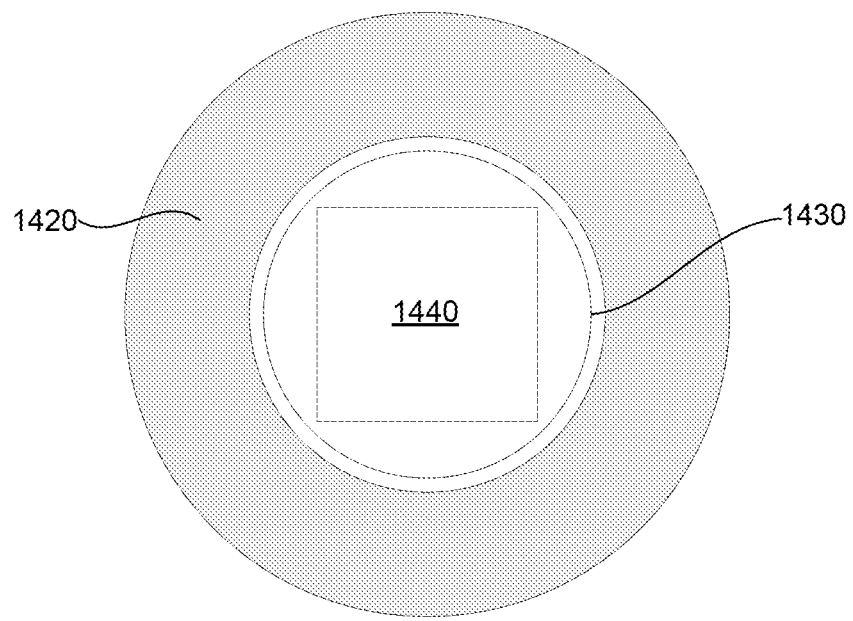
Figure 14C:
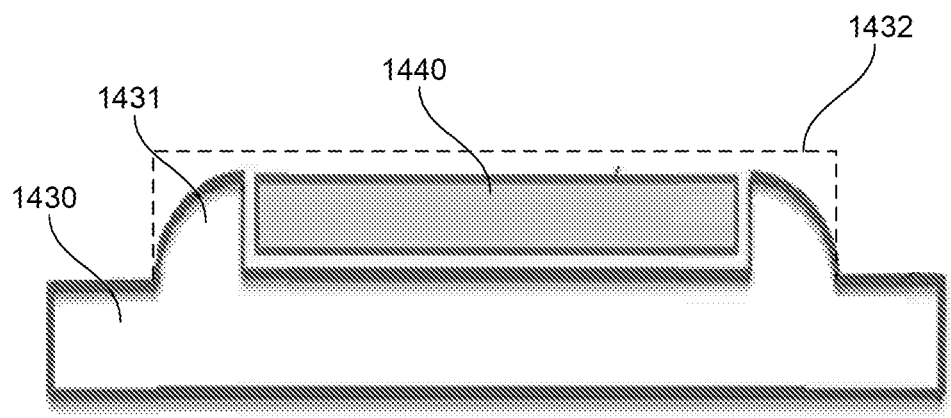
FIG. 14C is a schematic side view of an example support.

The support 1430 may also include two parts with an outer and an inner part such as that shown in FIG. 14A. The inner disk may attach to the outer using one or a combination of: adhesive, click fits, interference fits, luer fits, mechanical restraint, pressure different, glue, or the like. This allows the patch to be mounted to the inner part, whilst the outer part is permanently affixed to the applicator. This allows the patch to be mounted on the applicator by attaching the inner part to the outer part.

A piston 1450 is mounted in the housing, so as to allow movement of the piston along the body 1410. In one example, a spring 1460 may be provided to cause movement of the piston 1450, and in particular to control application parameters, such as the application velocity. The piston 1450 may also have a predetermined mass, such as between 5 grams to 100 grams, to maintain a consistent application momentum or energy, to assist with successful application, as will be discussed in more detail below. It will be noted that the mass of the piston 1450 may be scaled according to the size of the patch and number of projections. In this case, the mass range of between 10 grams and 60 grams has been selected for a 10×10 mm patch, and larger patches may require piston masses to be scaled accordingly. In one example, the piston has a mass of between 0.003 grams to 0.0625 grams per projection.

Figure 15A:
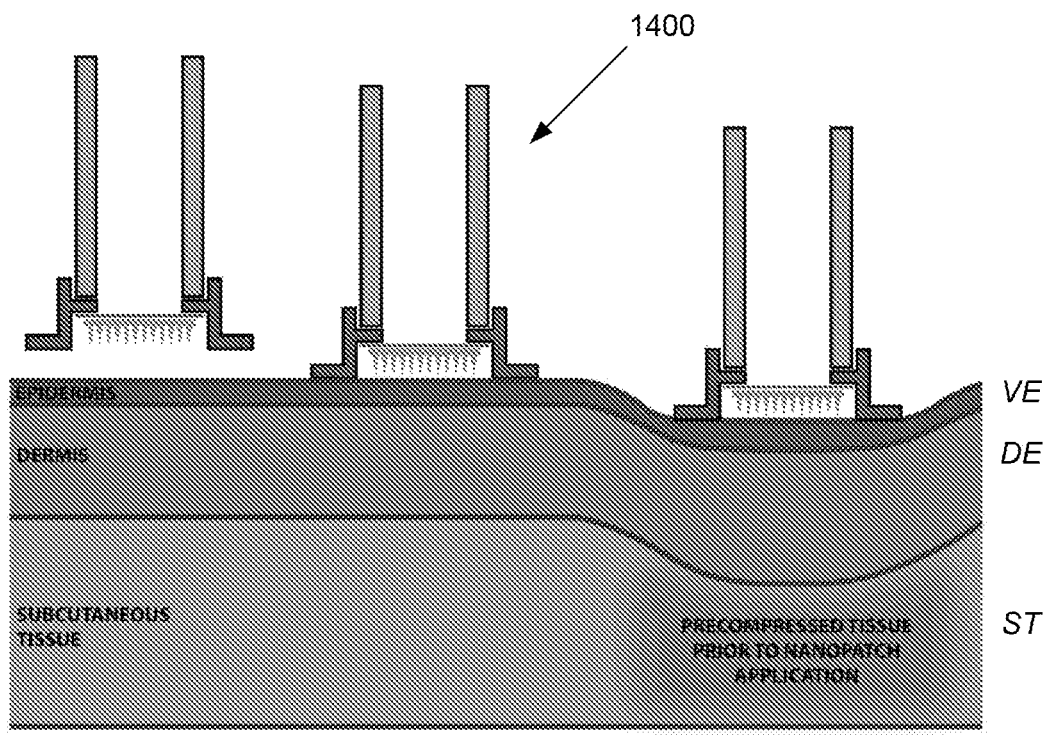
FIGS. 15A and 15B are schematic diagrams showing the effect of a preload force on the subcutaneous and epidermal tissue layers respectively, using the applicator of FIGS. 14*a* and 14B.

Operation of the applicator will now be described with reference to FIGS. 15A and 15B.

In use, the patch is initially attached to the patch support 1430. This can be achieved either by mounting the patch to the patch support 1430, whilst this is in situ on the device, or with the support removed from the device. Once the support is attached, the piston 1450 can be retracted using a handle, before the applicator is aligned with a desired application location. Throughout this process, it will be appreciated that the patch and in particular the projections, should be retained off the skin of both the subject and any operator. This ensures that coating does not dissolve prior to application, and ensures that projections do not break before application.

In one example, to assist with this, the patch can be supplied pre-coupled to all or part of the support, for example the inner part of the support 1430, and may also include a removable cap, for example coupled to the ridge 1431, as shown by the dotted lines 1432. This allows the support to be coupled to the applicator, before the cap is removed, thereby helping prevent inadvertent contact with the projections.

In use, the applicator ring 1420 is urged against the stratum corneum of the subject to thereby provide a preload force. As shown in FIG. 15A, the preload force causes compression of the subcutaneous tissue ST prior to the patch being applied.

It is notable that the dermis deflects but does not compress to the same extent as the epidermis, largely due to the properties of the dense collagen network that inhabits the dermis.

Specifically, the compression of the underlying subcutaneous tissue ST causes that layer to behave as a mechanically stiffer material against subsequent penetration of the projections. This increase in effective stiffness allows more consistent penetration into the upper layers of the skin, as depression of the subcutaneous tissue ST in response to the application of the patch will be reduced and thus have less of an impact on penetration of the projections.

Figure 15B:
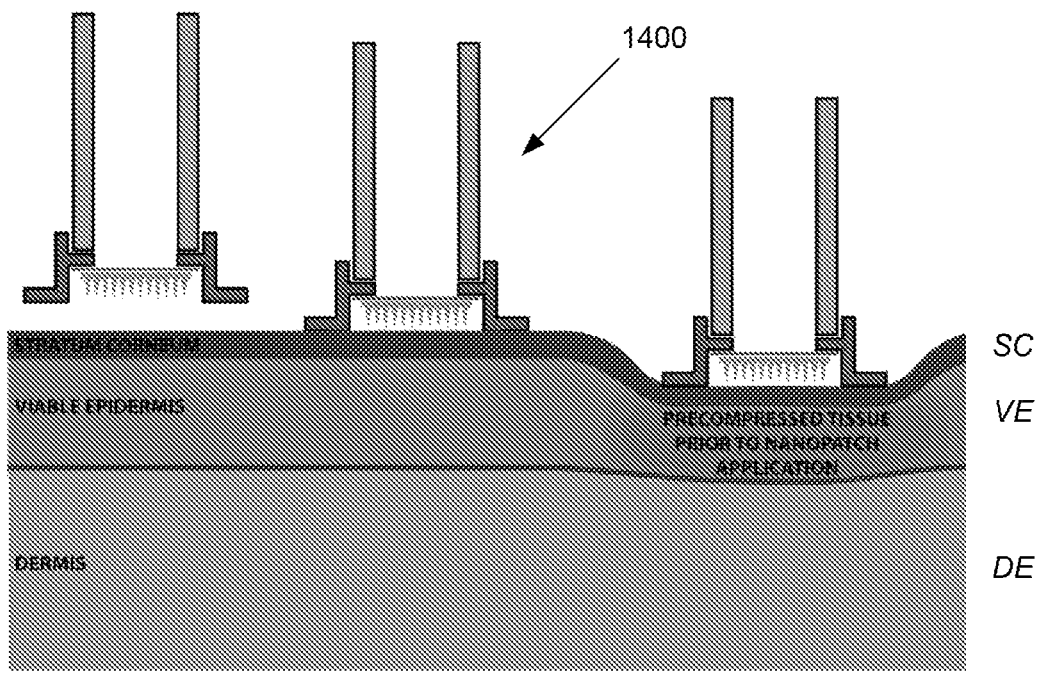

As further shown, in FIG. 15B, the preload force also serves to compress the viable epidermis VE. With the viable epidermis compressed and therefore thinner, the projections on the patch can penetrate through this layer more easily and into the dermis where the most immunologically sensitive cells are to be targeted.

Figure 16A:
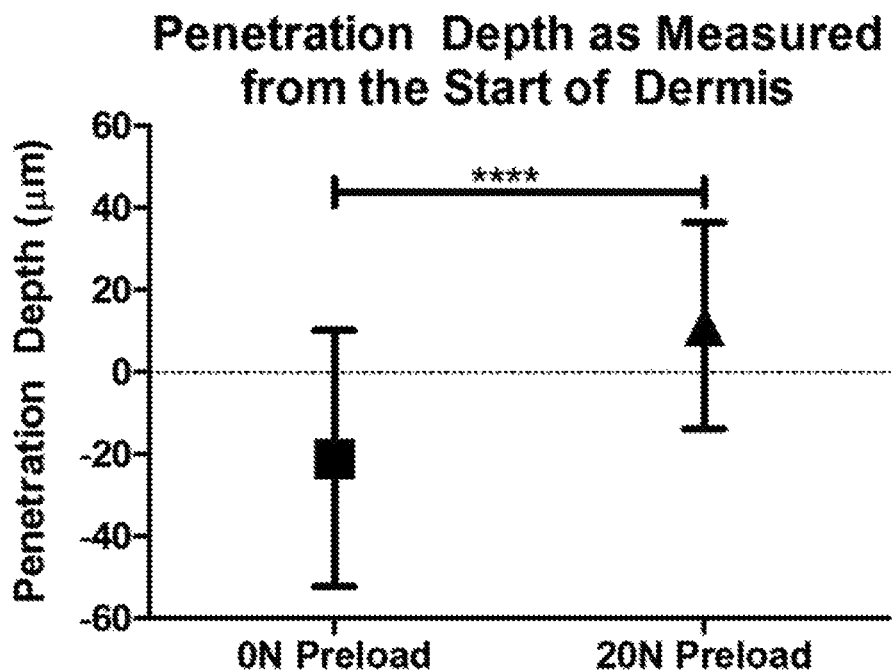
FIGS. 16A and 16B are graphs of examples of variation in penetration depth with different preload forces.
Figure 16B:
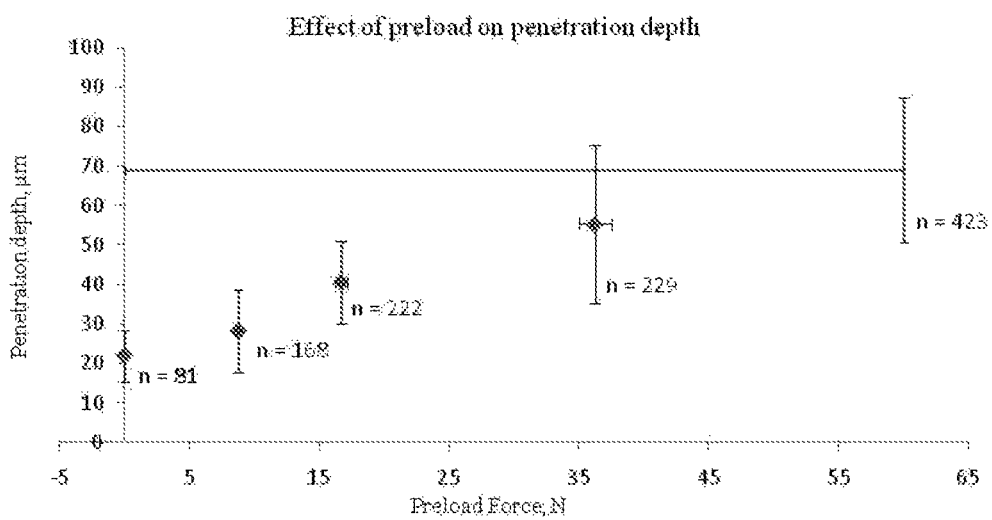
Figure 16C:
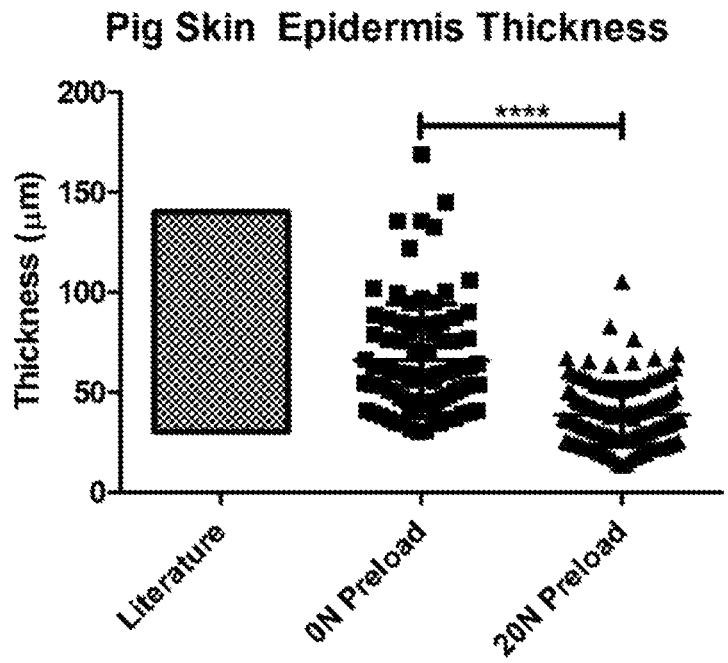
FIG. 16C is a graph of the effect of preload on pig skin epidermal thickness.

Penetration tests have been performed in pig skin to illustrate the benefit of precompressing the skin prior to impact. Results of the testing are shown in FIG. 16A, which highlight that with 20N of preload force prior to impact, the average penetration depth of projections can be increased from approximately 20 μm shy of the dermis to 10 μm into the dermis. Further experimental results shown in FIG. 16B highlight that further increasing the preload force can further increase the depth of penetration of the projections. Measurements of epidermis thickness in pig skin are shown in FIG. 16C, which highlight that the epidermis thickness is reduced under preload, thereby assisting penetration into the dermal layer.

Test on a human cadaver with 110 μm projections coated with MC, FV 2010, and Fluospheres, applied for two minutes under conditions of strong preload showed similar penetration at different locations. In particular, penetration in the forearm and deltoid were: 52.72±14.42 μm and 62.40±18.29 μm, respectively.

Thus, the use of a preload force can significantly improve penetration of the projections, primarily by causing tissues within the skin to behave as mechanically stiffer materials so that the tissues undergo reduced deflection during penetration. This is particularly the case for the relatively compliant tissues within the subcutaneous tissue ST layer, and the stiffening of this layer helps to reduce variability in penetration depth. The compression of intermediate layers within the skin can also help reduce variability in penetration depth between different individuals.

In one particular embodiment of the applicator 1400, the application includes an actuator configured to cause the patch 1440 to be automatically applied once a predetermined preload force has been provided by the user by the urging of the applicator ring 1420 against the skin. Alternatively, the actuator may be configured to require further manual input to cause the patch 1440 to be applied, and in one example the actuator will only cause the patch 1440 to be applied in response to manual input after a predetermined preload force has been provided by the user.

Figure 17A:
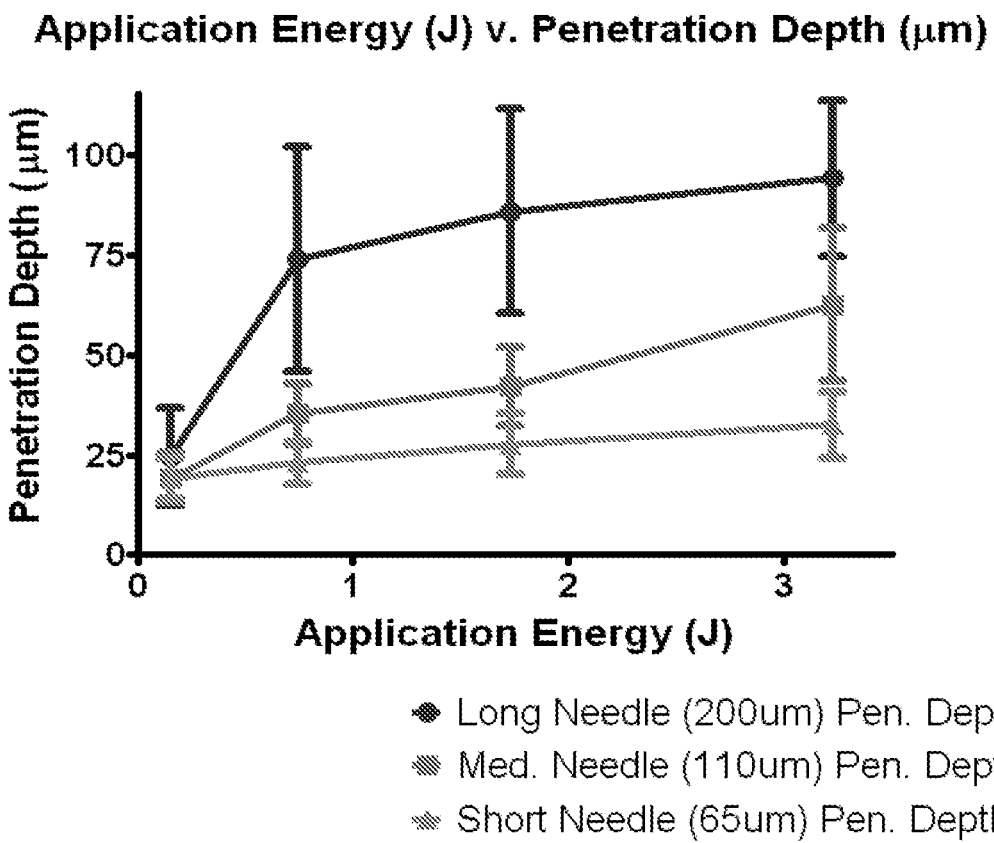
FIGS. 17A and 17B are graphs of examples of variation in penetration depth of mouse skin with application energy.
Figure 17B:
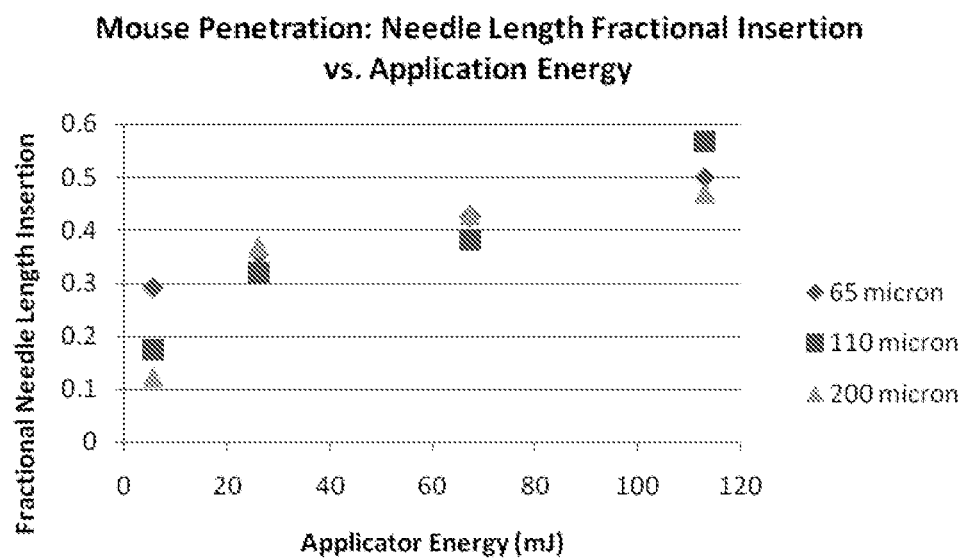

In addition to the use of pre-compression, application energy, and hence velocity, can also have an impact on projection penetration. Example measurements of penetration depth of projections in mouse skin, for different application energies, are shown in FIG. 17A and in Table 3 below, with the fraction of each projection that penetrates the skin being shown in FIG. 17B.

TABLE 3

| Application | 65 μm Projection penetration depth (μm) | | 110 μm Projection penetration depth (μm) | | 200 μm Projection penetration depth (μm) | |
|---|---|---|---|---|---|---|
| Energy | Avg. | Std. Dev. | Avg. | Std. Dev. | Avg. | Std. Dev. |
| Hole 2 | 19.00 | 5.02 | 19.22 | 6.34 | 24.49 | 12.27 |
| Hole 3 | 23.07 | 5.26 | 35.21 | 7.68 | 73.80 | 28.05 |
| Hole 4 | 27.70 | 7.69 | 42.06 | 9.86 | 85.87 | 25.52 |
| Hole 5 | 32.48 | 8.18 | 62.53 | 19.15 | 94.05 | 19.36 |

Figure 17C:
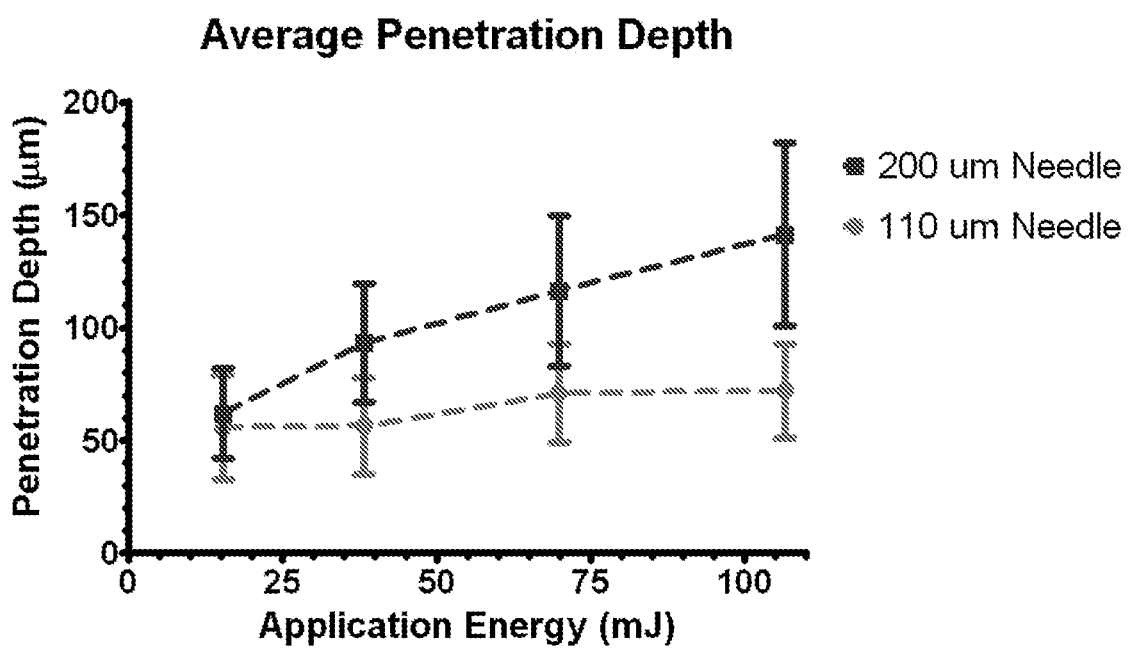
FIG. 17C is a graph of examples of variation in penetration depth of pig skin with application energy.
Figure 17D:
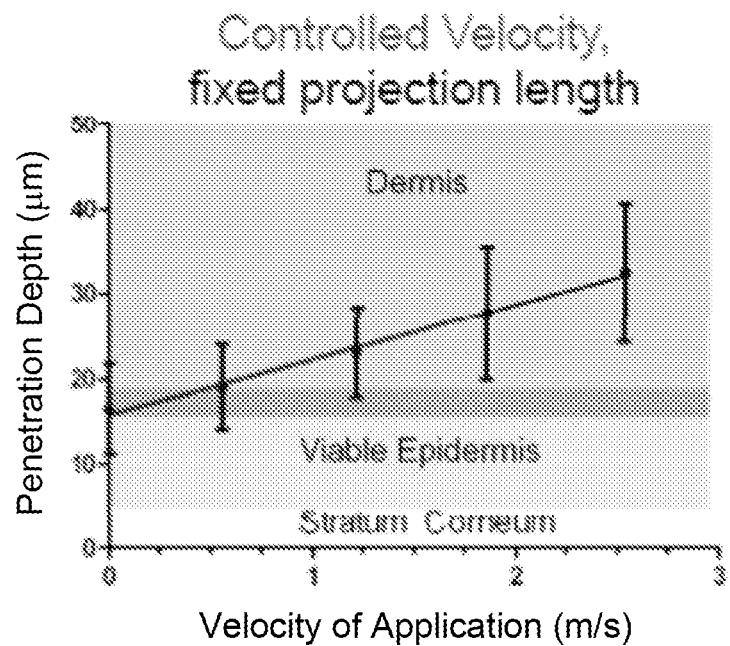
FIGS. 17D and 17E are graphs of examples of variation in penetration depth of mouse skin with application velocity and projection length, respectively.
Figure 17E:
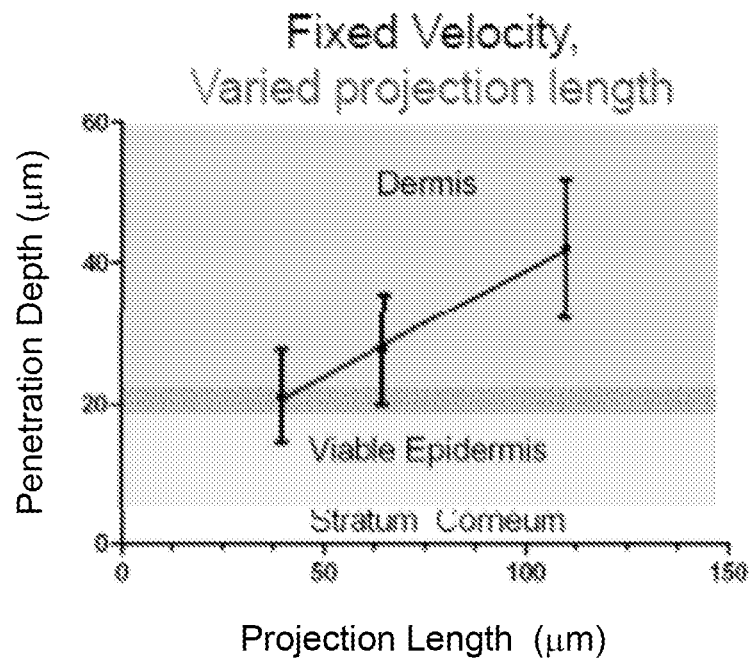

Similar data for application to pig skin is shown in FIG. 17C, with comparison of the penetration depth of mouse skin for application velocity and different projection lengths being shown in FIGS. 17D and 17E.

Figure 17F:
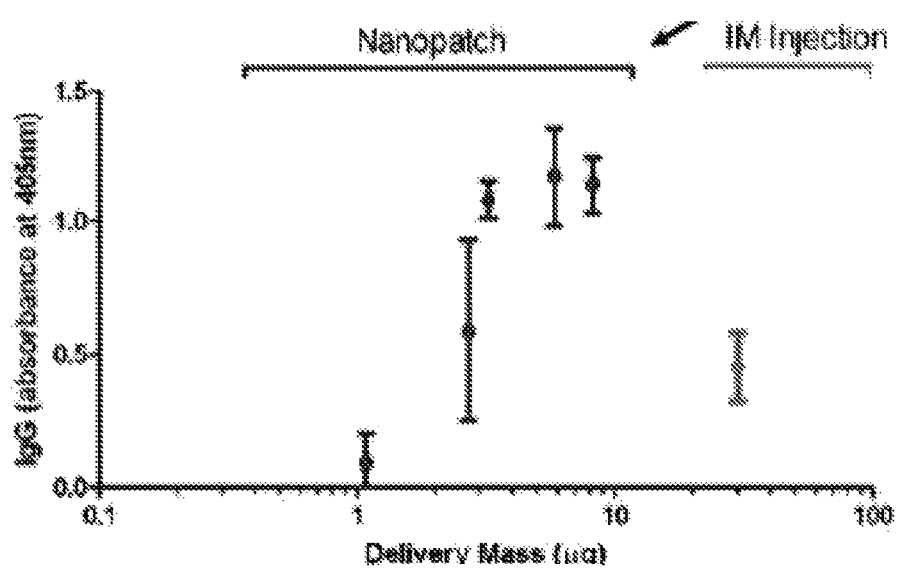
FIG. 17F is a graph of results of penetration depth test with ovalbumin protein, using the application velocities shown in FIG. 17D.

Controlling the depth of penetration is important as this can effect two factors, namely the quantity of material delivered, and the particular layer of the skin to which the material is delivered. This was tested with ovalbumin protein, using the application velocities shown in FIG. 17D, with the results being shown in FIG. 17F. This highlights that as the velocity of application, and hence the penetration depth increases, so does the response induced. It is also notable that for delivery velocities the response induced is greater than for a needle and syringe injection. These results highlight that both the depth and proportion of each projection that penetrates the subject depends on the application energy supplied by the applicator. It will be appreciated that the application energy provides the kinetic energy of the patch for impacting the skin, and is therefore related to the velocity of impact of the patch. By increasing the impact velocity, the strain rate of penetration is increased, and the behaviour of the skin moves to become more plastic (less elastic). This gives a more uniform controlled penetration.

Figure 18A:
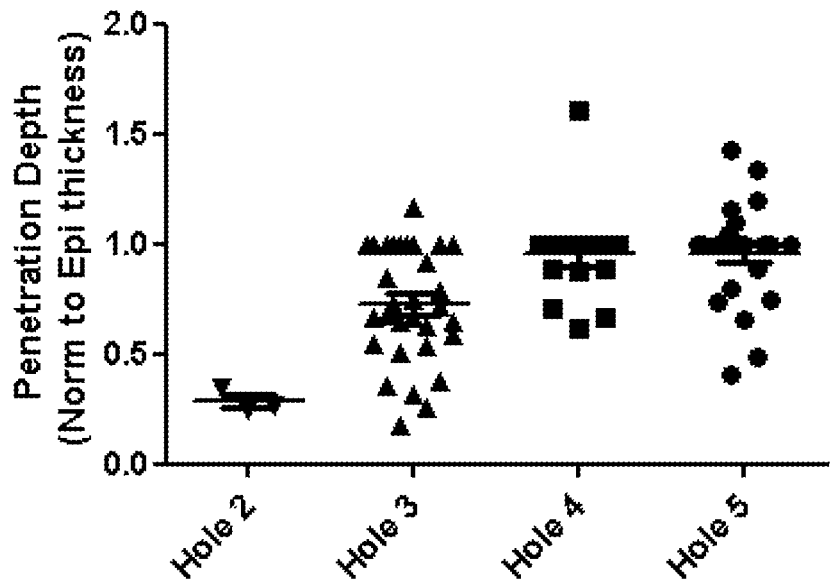
FIGS. 18A and 18B are graphs of examples of variation in penetration depth of human skin with application energy.
Figure 18B:
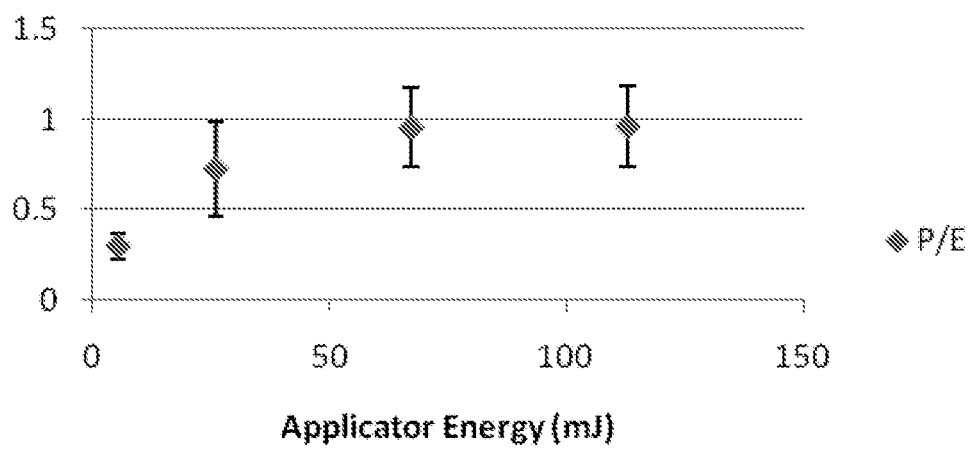
Figures 19A, 19B, 19C:
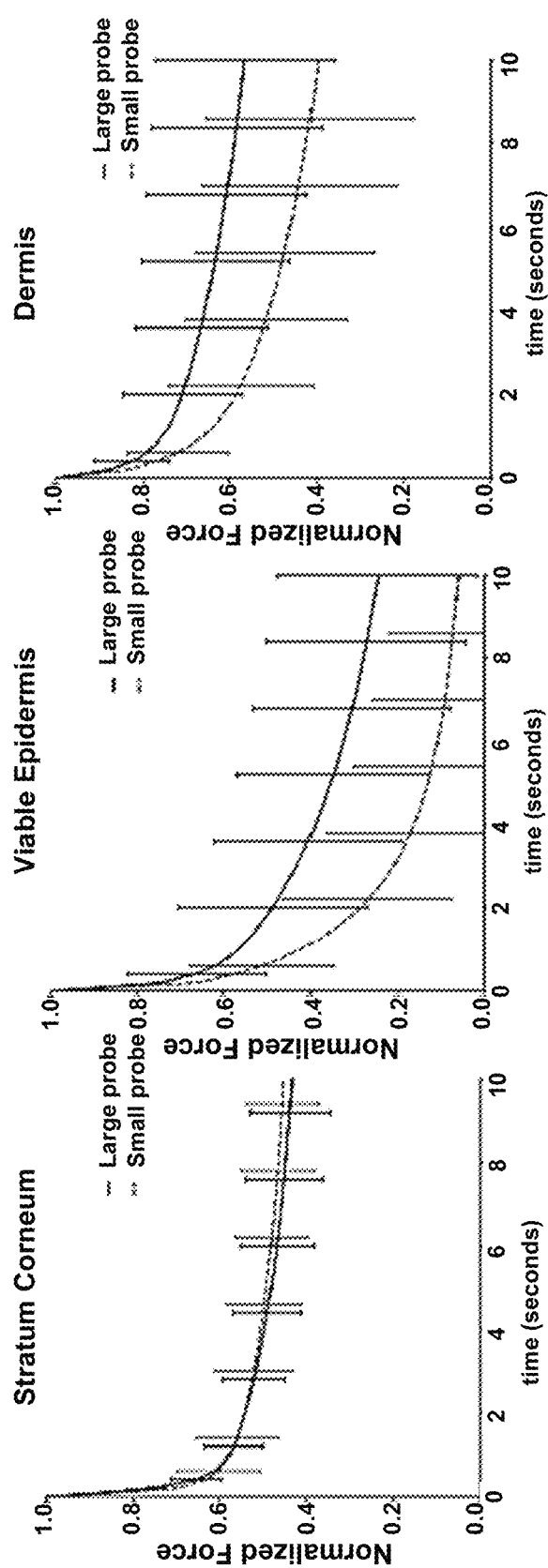
FIGS. 19A to 19C are graphs of examples of relaxation times for the stratum corneum, visible epidermis and dermis respectively.
Figure 19D:
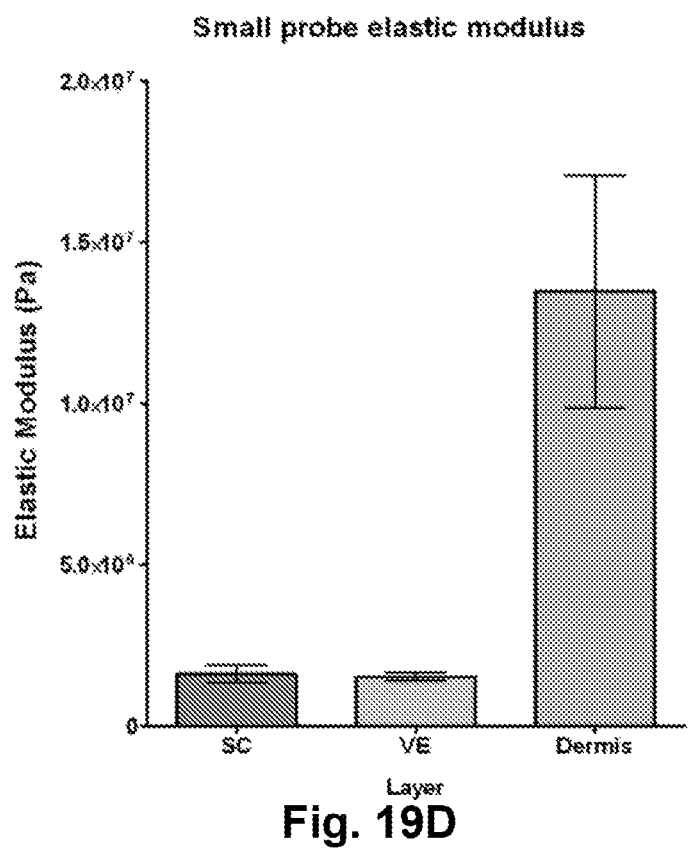
FIGS. 19D and 19E are graphs of examples of variation in layer elastic modulus for tissue layers.
Figure 19E:
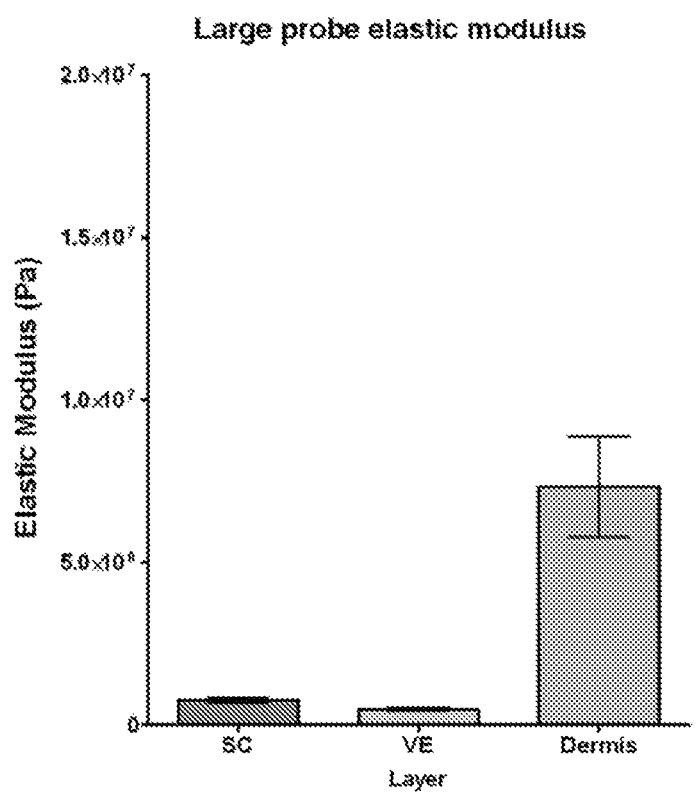

Preliminary data from human studies performed with a 100 μm long convex projection is shown in FIGS. 18A and 18B. In this example, holes 2, 3, 4, 5 are made with progressively increasing application energy. As the energy increases the depth of penetration initially increases, plateauing when the depth corresponds to the depth of the epidermal/dermal boundary. As described above, this results from the dermis presenting an effective barrier to penetration of projections, due to the collagen network of the dermis having increased modulus of elasticity than the stratum corneum and epidermal layers. Measures of relaxation of the different tissue layers for small (1.9 μm) and large (6.6 μm) diameter probes are shown in FIGS. 19A to 19C, with the corresponding modulus of elasticity being shown in FIGS. 19D and 19E.

Figure 20:
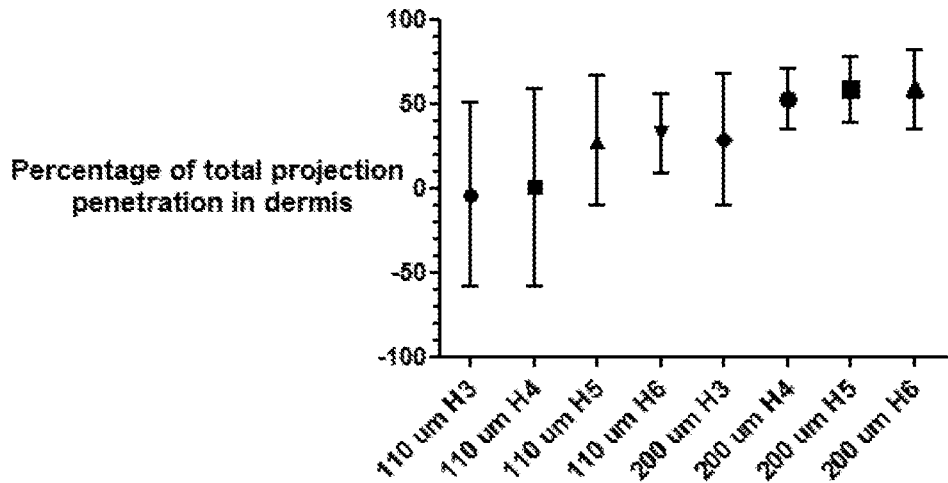
FIG. 20 is a graph of an example of the effect of projection length and application energy on dermal tissue penetration.

Further experimental results for application to excised pig skin for projection patches having 110 μm and 200 μm projections, respectively are shown in FIG. 20. The results highlight that for 110 μm projections, penetration into the dermis can only occur at high energies, and that for 200 μm, significant dermal penetrations occurs for all energies, but that penetration of 50 μm only occurs at higher energies.

Consequently, it is important to ensure that when penetration to the dermal layer is required, then the patch is applied with sufficient energy to overcome the elasticity of the dermal layer. However, if penetration into the dermis is not required, or deemed undesirable for any reason, then a lower application velocity or energy can be used in order to allow the relatively large stiffness of the dermal layer (compared to the viable epidermis) to act as a barrier to limit further penetration. Similarly, results show the length of the projection can be selected to help control the degree of penetration required.

It will be appreciated that the exact velocity or energy used will depend on factors such as the geometry of the projections, the desired penetration depth, and other factors such as the patch area, as will be described in more detail below. For the energies presented above, these correspond to application velocities greater than 1 $ms^{-1}$ and less than 50 $ms^{-1}$. More typically application velocities are less than 20 $ms^{-1}$, less than 10 $ms^{-1}$ usually between 1 $ms^{-1}$ and 5 $ms^{-1}$.

It should also be noted that experiments have demonstrated that hair has little impact of the ability of the patch to penetrate the skin, although this may depend on the extent of hair present, for example if patches are to be used to deliver material or stimulus to animals with thick hair or fur cover.

Effect of Patch Area

The patch area can also have an impact on penetration depth. To examine this variation an experiment was performed comparing penetration depths for projection patches having different areas.

Projection patches were coated individually with fluospheres before being applied to pig skin. Following this pig skin was fixed for an hour in PFA, then washed in 3 consecutive ten minute washes of 5% sucrose in PBS. Following this, the skin was refrigerated in 20% sucrose in PBS overnight. The skin was then frozen in OCT in the cryomould using dry ice before being sectioned for imaging. The imaging was performed on the Zeiss CLSM using both the argon and chameleon laser.

Figure 21:
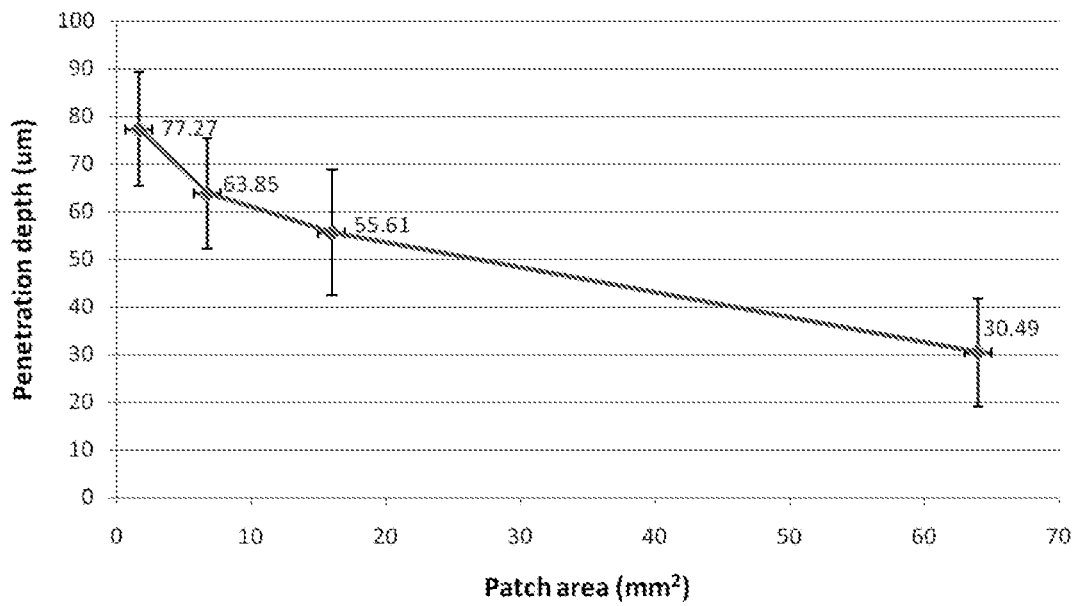
FIG. 21 is a graph of an example of penetration depth for different projection patch areas.

The results of penetration measurements for different sizes of patch are shown in FIG. 21 and in Table 4 below.

TABLE 4

| | 1.3 mm × 1.3 mm | 2.6 mm × 2.6 mm | 4 mm × 4 mm | 8 mm × 8 mm |
|---|---|---|---|---|
| Pen. Depth avg. ± S.D.(μm) | 77.27 ± 11.94 | 63.85 ± 11.59 | 55.61 ± 13.21 | 30.38 ± 11.38 |
| N(number of measurements) | 160 | 128 | 207 | 210 |
| Min.(μm) | 34.61 | 36.65 | 21.54 | 12.38 |
| Max. (μm) | 109.2 | 88.95 | 98.01 | 63.53 |

These data suggest that there is a relationship between penetration depth of microprojection arrays and the array's surface area. It can be seen that the smallest 1.3×1.3 mm patch has the greatest penetration depth, followed by the 2.6×2.6 mm, then the 4×4 mm patch, and finally the large 8×8 mm patch. With all other variables fixed, penetration depth exponentially decays as patch surface area is increased.

A further experiment was then performed to determine the impact of patch size on the immune response of a subject. This experiment used three different patch configurations, including:

Case A: a single coated 1.3×1.3 mm patch, surrounded by eight uncoated 1.3×1.3 mm patches Case B: a 4×4 mm patch Case C: a single 1.3×1 mm patch The Coating solution used for case B was made such that each patch would ideally deliver 50 ng vaccine. The coating solution for A and C were the same, both being 9 times as concentrated as case B. Using this, a C14 assay was run using these solutions. 5 mouse ears were patched for Case B, and 5 were patched for A. The coating solution was then adjusted accordingly based on the C14 results for the final coating solution. This dose matching was not confirmed due to the limited number of small patches. A C14 assay was also run for case C with 5 ears patched, but the coating solution was not adjusted for this case since this was performed after the immunogenicity experiment. For the immunogenicity experiment, cases A and C had the same solution.

Both ears on each of the 8 mice for each case were patched at H4 with the brass applicator such that 100 ng was delivered per mouse for cases A and B. Case C had ~216 ng delivered. After 21 days, retro-orbital bleeds were performed on the mice and afterwards an ELISA was performed to gather the results.

Figure 22:
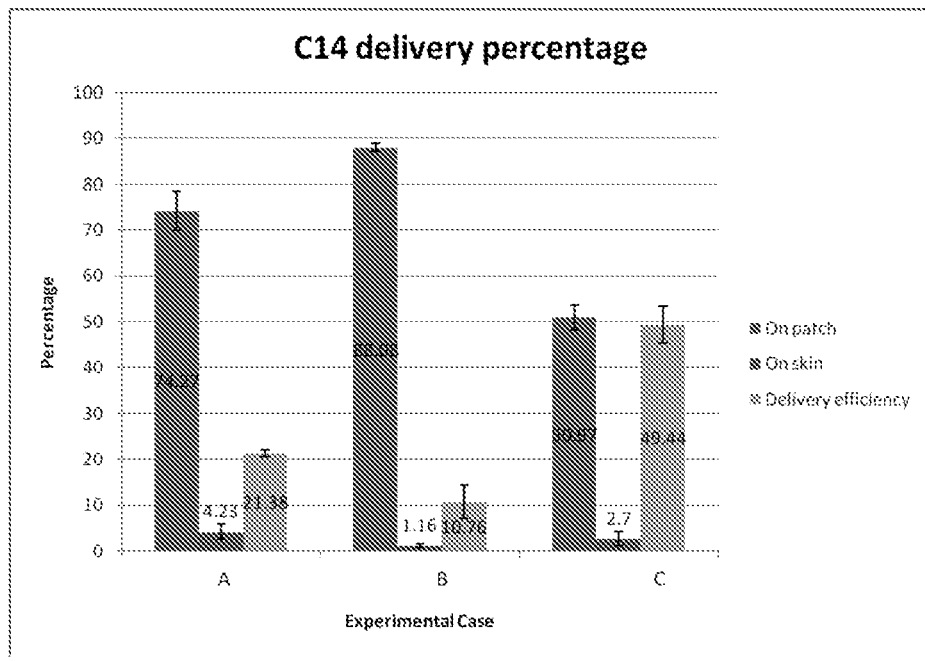
FIG. 22 is a graph of the percentage of vaccine delivered for different projection patch areas.
Figure 23:
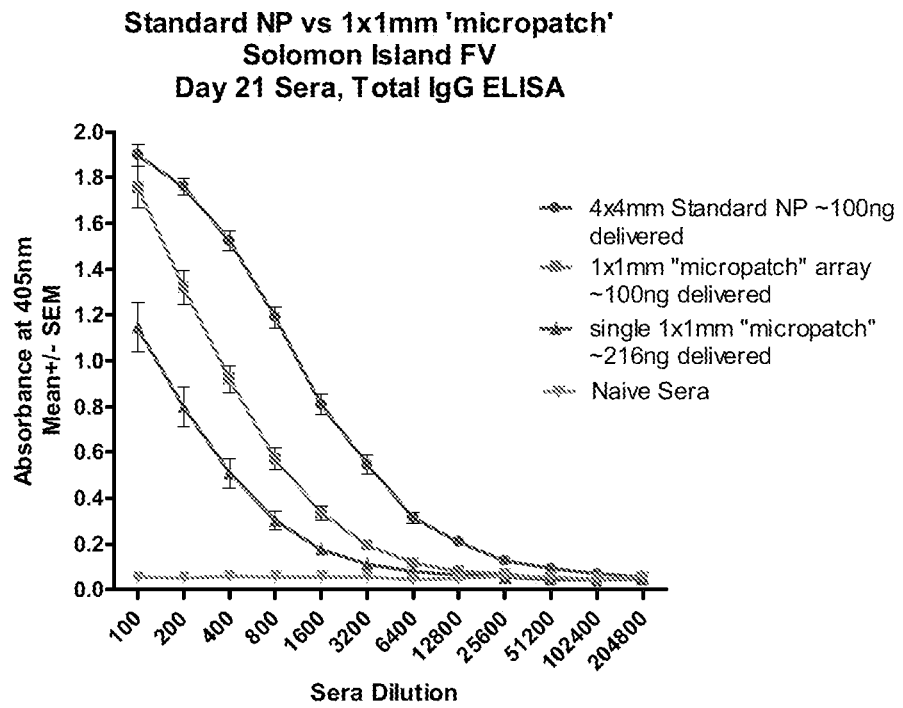
FIG. 23 is a graph indicative of the immune response induced for different projection patch areas.

Results are shown in FIGS. 22 and 23, which illustrate the percentage of C14 delivered and the resulting immune response, respectively. The ~10% delivery efficiency of the 4×4 mm patch is what was expected from the Solomon FV due to it being so concentrated because it needed to be diluted down. The results for A were used to adjust the coating solution for test cases A and C. The actual C14 for case C was not performed until after the immunogenicity experiment was under way, resulting in a much higher delivered dose for case C.

The data for the 4×4 mm patch agrees with the previous data for the Solomon FluVax strain compiled by others. The data points for case A, the 3×3 array of 1.3×1.3 mm patches where the center is coated, and the 8 surrounding patches are uncoated, mimicked the standard 4×4 mm patch in vaccine delivered, depth penetration, and cell death while reducing the targeted area.

The data shows that reducing the targeted area of the patch will reduce the antibody response. The titers of the single coated 1.3×1.3 mm patch showed reduced targeted area, increased penetration depth, less cell death, and had a much higher delivered dose, yet the single 1.3×1.3 mm patch had a significantly lower immune response than the 4×4 mm patch.

This highlights that the amount of delivered vaccine alone is not the sole factor in determining the resulting induced response. In particular, despite the delivered dose being double that of the other cases and the penetration depth being increased, the induced immunological response was reduced. From this, it is apparent that the number of projections penetrating the dermis plays an important role by inducing cell damage in the vicinity of the projections, which in turn can enhance the induced response, as will be discussed in more detail below.

Dye

It can be difficult to determine if projections are penetrating tissue, and if so, if this is to the required depth. Typical techniques for determining the extent of projection penetration typically include cryosectioning, or paraffin embedding and sectioning, which are therefore unsuitable for use with live subjects. Whilst projections can be analysed optically after application, such techniques cannot confirm that penetration to an appropriate depth has occurred, and also require the use of external measuring equipment.

To address this, projections can be coated with a coating solution including an indicator material, such as a dye. In this example, when projections penetrate the subject's tissue, dye from the coating is deposited into the tissue, thereby providing a visual indication of successful penetration.

To demonstrate the effectiveness of the technique, tests were performed using methylene blue as a suitable dye as this is clinically approved for human uses, including ingestion, injection into the blood stream, and tissue injection.

Figure 24:
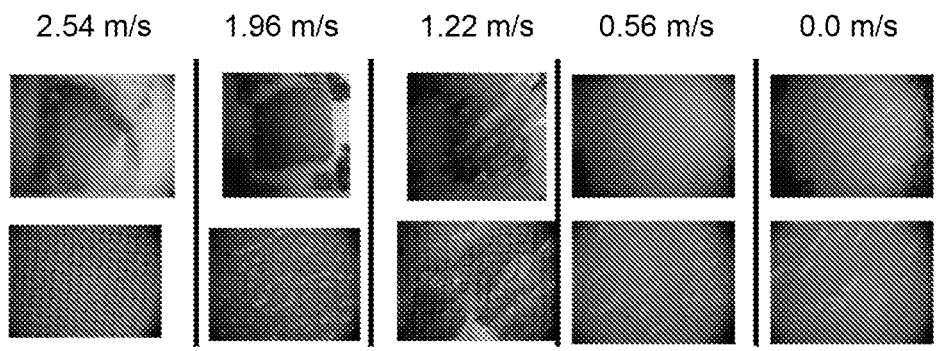
FIG. 24 shows example images of a visual indication provided by the application of dye coated projections at different velocities.

Projection patches were coated with 0.125 mg/mL methylene blue dye, and then applied onto excised pig ear skins at varying velocities. FIG. 24 shows examples of the resulting visual indication generated by the dye at low and high magnifications for each velocity. The results highlight that the dye is clearly visible at 1.96 m/s and above, only weakly visible at 1.22 m/s, and not visible at lower velocities including 0.56 m/s and below. This supports previous evidence that an application velocity of above 1 m/s is preferred to ensure penetration of projections into the tissue, and that preferably the application velocity is in the region of 1.96 m/s or above.

Figure 25:
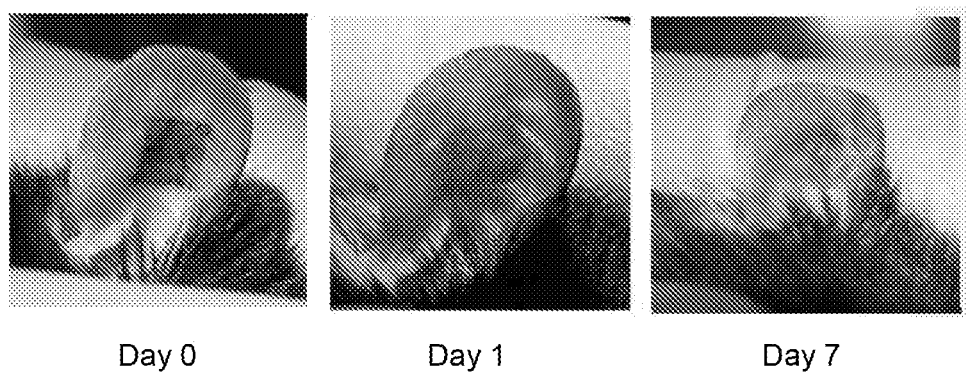
FIG. 25 shows example images of degradation of the visual indication over time after application of dye coated projections.

Following this, an experiment was performed to ascertain the impact of the dye on the ability to induce an immunological response. In this example, mice were immunized either intra-muscularly or with a projection patch using Fluvax only, methylene blue only (0.125%) or Fluvax and methylene blue (N=3 for each condition). Images of patched ears directly after patching and at day 1 and day 7 after patching, are shown in FIG. 25. This highlights that a visual indication is initially present, but that this fades over time, so no permanent marking occurs.

Figure 26:
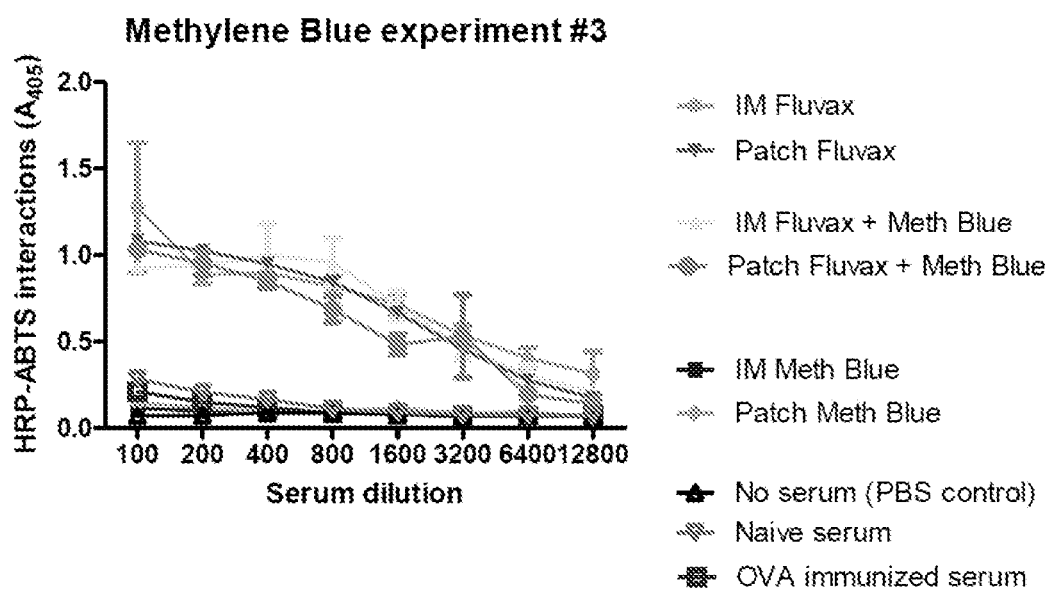
FIG. 26 is a graph showing an example of the impact of dye on the ability to induce an immunological response.

Sera were obtained 21 days after immunizations and assayed for specific antibody titers with ELISAs. Results in FIG. 26 show similar antibody counts for the groups immunized with Fluvax, regardless of methylene blue presence in the immunization solution. These data suggest methylene blue does not interfere with the standard immunization process of the commercially available flu vaccine Fluvax, highlighting that dyes can be safely utilised to provide a visual indication of successful application without interfering with the efficacy of the projection patch.

Additional data supporting the use of Methylene blue as an indicator for penetration is shown in Table 5, which highlights that there is no major difference in the delivery of material to a subject.

TABLE 5

| | | Mean Delivery | Standard Dev |
|---|---|---|---|
| 10 × 10 mm patch | With MB | 15.8 | 1.8 |
| 10 × 10 mm patch | No MB | 14.3 | 1.3 |
| 4 × 4 mm patch | With MB | 33.9 | 5.8 |
| 4 × 4 mm patch | No MB | 37.7 | 5.9 |

The above described examples therefore demonstrate that the addition of a dye to the projection coating allows the successful penetration of projections, and hence delivery of material to desired tissues, to be visually discerned.

In particular, at low penetration velocities, where the projections penetrate shallowly, very little dye is transferred to the skin. On a macroscopic scale, there is no skin coloration, while on a microscopic scale, small faint dots can be observed. At increased application velocities, where penetration is deeper, more dye is transferred to the skin. The area of projection penetration appears dark blue on a macroscopic scale, and as discrete blue dots on a microscopic scale.

Accordingly, by adjusting the dye concentration on the coated needles, the penetration depth at which a macroscopic colour change is observable can be tuned, thereby allowing the patch to be configured to only cause a visual indication to be provided if the patch has been successfully applied.

In a further example, dye could be further located on the base of the projection array. In this case, dye would only come into contact with the skin, and be transferred if the needles penetrated to such a depth that the skin could come in contact with the base region of the patch, thereby demonstrating successful penetration.

In a further example, the indicator material can be selected so that a colour of the indicator material is dependent on environmental conditions. In this case, environmental differences between the stratum corneum and epidermis/dermis can be utilized to enhance the sensitivity of the macroscopic signal. For example, the indicator material could include a pH sensitive dye. In this case, the stratum corneum is known to have a slightly acidic environment (pH=5.5) whereas the epidermis/dermis provides a neutral environment (pH=7). A pH sensitive dye can therefore undergo a discernable colour change if delivered to the stratum corneum versus delivery to the epidermis/dermis. In an alternative example, a redox sensitive dye can be used. In this example, the stratum corneum is known to be a slightly reducing environment, whereas the epidermis/dermis are slightly oxidizing. A redox sensitive dye could be chosen appropriately to clearly indicate this difference.

In a further example, a cell viability dye can be used that changes colour in the presence of living cells. In this example, this can be used to indicate a breach of the stratum corneum and delivery to the cell rich regions of the epidermis/dermis.

As a further variation, two dyes could be used simultaneously, with a first dye being used to coat the projections and a second dye being used to coat the patch base. Using two dyes, a window of penetration depths can be monitored, with shallow penetration only transferring the dye from the projections, while a deep penetration would transfer both dyes, resulting in a different visual indication. This could be used in a clinical setting to provide a visual confirmation of a successful patch application to the skin, particularly to the desired depth.

Diffusion

The skin is a highly important delivery site for vaccines. The viable epidermis, and to a lesser extent the dermis, contain an abundance of immunologically active cells that when targeted with large biomolecules have been shown to elicit strong immune responses. Using the projection patch, an immune response can be achieved with 100-fold less dose than traditional intramuscular injection (Fernando et al. (2010) PLoS ONE). As part of this process, diffusion of payload into the tissue surrounding the projections contributes to inducing the immunological response.

An example of the process of diffusion of delivered material will now be described with reference to FIGS. 27A and 27B.

Figures 27A, 27B:
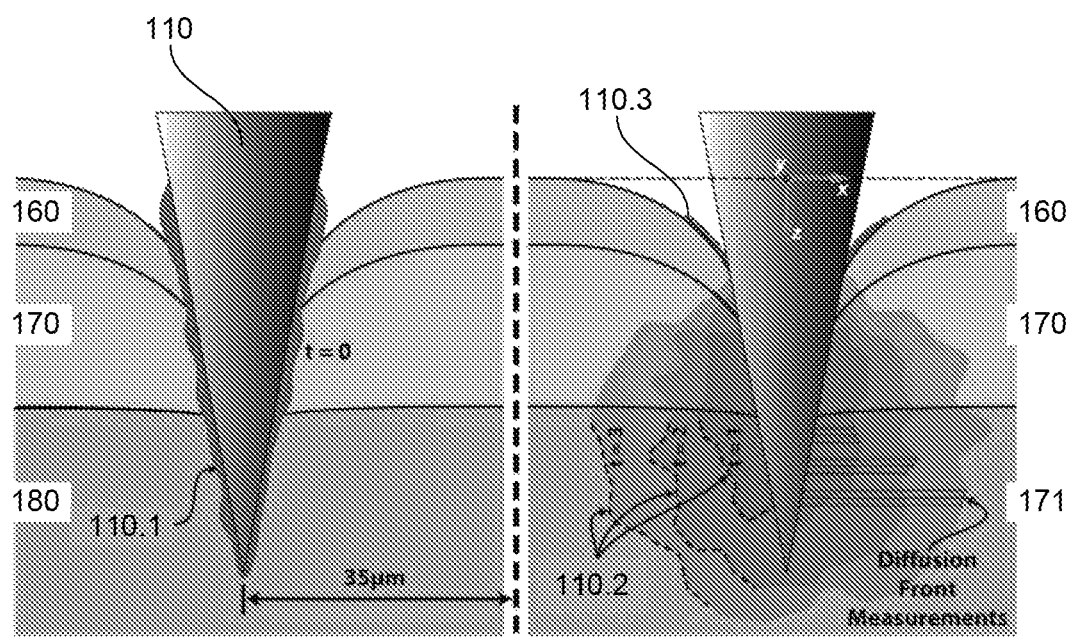
FIGS. 27A and 27B are schematic diagrams illustrating the diffusion of material payload, delivered by a projection, into the surrounding tissue.

The initial penetration of a projection 110 having a coating 111, into the stratum corneum SC, the viable epidermis VE and dermis DE is shown in FIG. 27A. As shown the projection 110 enters the tissue with the coating 110.1 substantially undisturbed and largely retained on the projection 110. As time progress, the coating material diffuses into the tissue surrounding the projection, as shown by the wave fronts 110.2 at times t=1, t=2, t=3, respectively, in FIG. 27B.

Accordingly, material coated onto the projection lateral surface that has penetrated the skin starts diffusing outwardly, whereas the material 110.3 deposited on the tissue surface cannot cross the stratum corneum. As time progresses, the material spreads (for example, due to the Brownian motion of the interstitial fluids within the tissue), so that the concentration of material moves towards a uniform distribution.

To demonstrate the impact of diffusion on payload delivery, deposits of 70 kDa and 2 MDa dextran were applied via a projection patch to in-vivo mouse skin. The diffusion properties of the payloads were analysed using a high resolution fluorescence confocal technique in three dimensions, allowing the diffusion to be mapped as a function of depth within each layer of the skin, including the stratum corneum, the viable epidermis, and the dermis.

For the purpose of this experiment, a projection patch having a 4×4 mm area and including 58×58 projections with a spacing of 70 μm between adjacent projection centres was used. The projections included a convex effective profile and had a length of approximately 100 μm and tapering to less than 1000 nm in diameter at the tips. The base diameter of the projections is 35 μm. The projections were coated with coating solution containing 10 mg/mL of methyl cellulose (MC) and either 0.1 μg/mL of 2 MDa rhodamine or 0.1 μg/mL 70 kDa rhodamine dextran using a nitrogen gas-jet coating technique.

Coated patches were applied to the inner earlobe of the ears of female BALB/c mice aged 6 to 8 weeks with a custom spring based applicator device at 2 m/s. The animals were anesthetized prior to Nanopatch administration with a solution of 60 μL of 25 mg/mL ketamine and 5 mg/mL xylazine in saline via i.p and were treated according to the protocol approved by the University of Queensland Animal Ethics Committee. Four mice were used for each time point with a single projection patch applied onto each ear (4 patches per time point). During application, each projection patch was kept in place on the skin for 2, 4, 7 and 10 minutes, respectively. Both mouse ears were patched simultaneously. Immediately after applying the patches for the specified time point, the patches were removed, the mouse was euthanized and the ear snap-frozen for imaging.

Imaging was performed using a Zeiss LSM510 Meta confocal microscope (Carl Zeiss, Inc., Germany). Rhodamine-dextran was excited using 543 nm and collected between 560-615 nm. To determine the surface of the skin, surface reflectance was used. The reflectance was excited at 780 nm and all reflected light was collected. The laser power, gain and pinhole threshold was kept constant between all samples of respective payload. Excised ears were kept in place with a cover-slip sample holder that also served to flatten the ears for imaging. No buffer solution was placed on the ear prior to imaging to prevent the possibility of further diffusion.

A 3-dimension image was produced by taking z-stack slices every 1 μm within the region of interest. To prevent enhanced diffusion bias in the lower skin layers, z-slices were imaged from the base of the dermis up towards the stratum corneum. A total of 36 deposition sites per ear were imaged, resulting in up to 144 deposition sites per time point. Representative compressed z-stacks were determined for each time point and molecular weight. These showed that an increase in time results in enhanced rhodamine-dextran fluorescence intensity in the deposition sites, demonstrating increased payload delivery. The projection remained in the skin for the entirety of each time point to prevent back diffusion of the dextran into the projection hole.

The morphology of the fluorescent signal within each deposition site differs within and between samples because of the non-uniform composite structure of the skin. Averaging the rhodamine-dextran fluorescence from 16 sites per ear and 4 ears per time-point (n=64 deposition sites per time point), was used to obtain a relatively axisymmetric fluorescence distribution around the projection centre, which was in turn used to generate a 3D representation.

Figure 28:
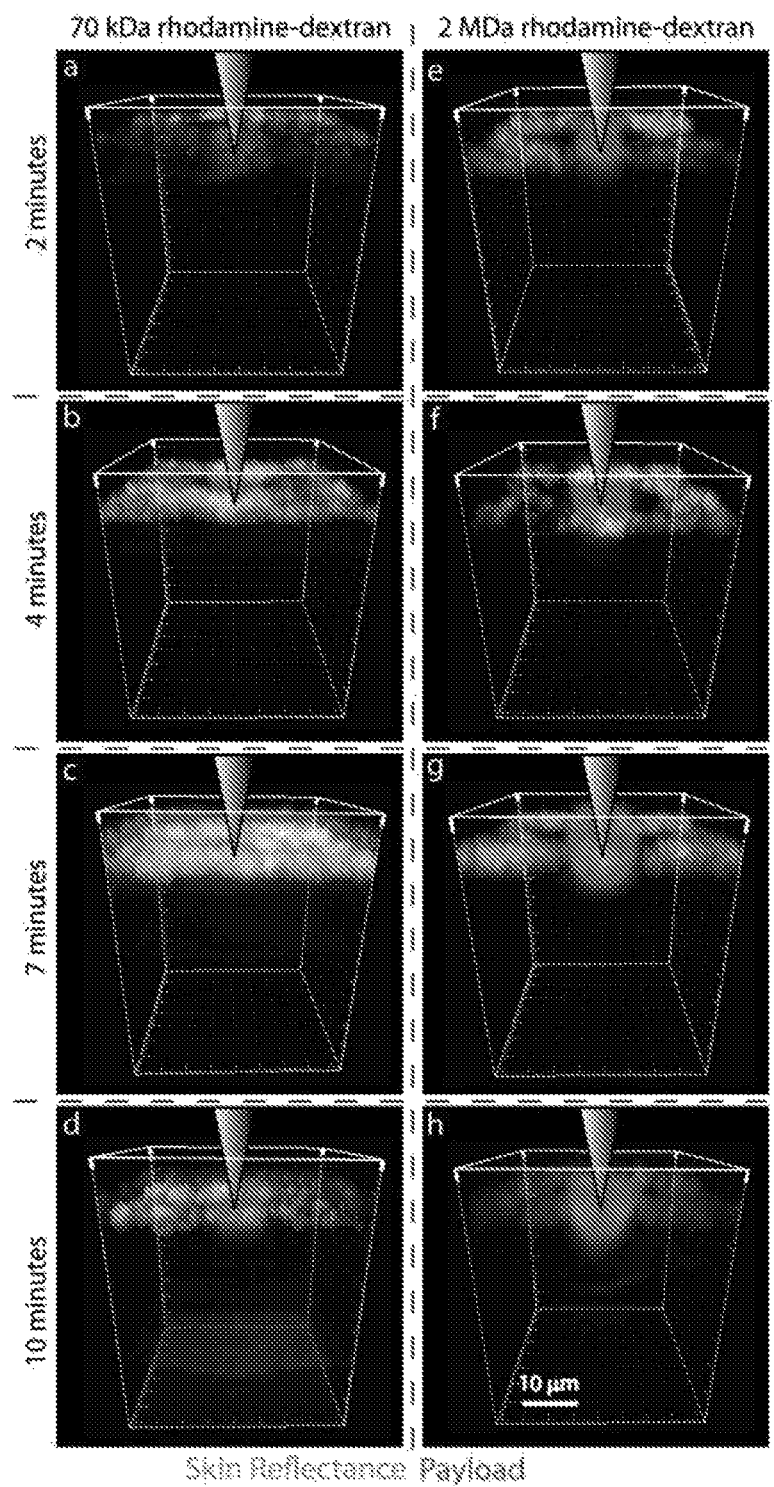
FIG. 28 shows example images illustrating a 3D representation of payload diffusion from one projection for 2, 4, 7, 10 minutes for two different sizes of rhodamine-dextran.

FIG. 28 shows the 3D representation at each time point, thereby representing the time evolution of the mean fluorescent signal around each deposition site. The volume of the 70 kDa rhodamine-dextran increased from approximately $7.3 \times 10^4$ µm$^3$ to $4.7 \times 10^5$ µm$^3$ between 2 and 10 minutes, whilst the volume of the 2 MDa rhodamine-dextran increased from approximately $2.2 \times 10^4$ µm$^3$ to $1.5 \times 10^5$ µm$^3$ between 2 and 10 minutes.

Furthermore, in 10 minutes the 70 kDa rhodamine-dextran saturated the entire deposition site (where saturation is defined as the point where signal at the specified intensity is seen in all areas of the deposition site). The 2 MDa rhodamine-dextran did not saturate the deposition site in the 10 minutes examined, however there was still a large amount of diffusion, with signal saturating the VE and at least 35 µm lateral diffusion in the upper dermis.

Figures 29A, 29B, 29C:
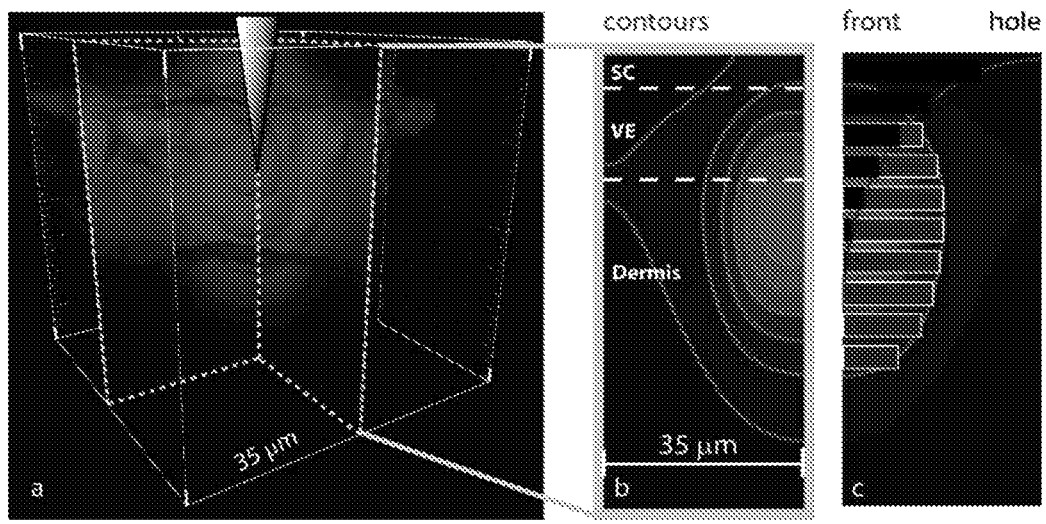
FIG. 29 is a schematic diagram illustrating the analysis steps in measuring the diffusion fronts within a deposition site.

To further quantify the diffusion and simplify the analysis without loss of generality, projected averaged 3D data of each time-point on the plane was determined by exploiting the array symmetry of the patch, as shown in FIG. 29A. The 2D concentration profile is exemplified in FIG. 29B, with a contour plot calculated by averaging the 4 plane sections along the patch projection lines. The contour plot of fluorescent intensity is then used to measure the linear distance of diffusion of the rhodamine-dextran from the hole axis along the horizontal x direction, as shown in FIG. 29C. Measurements extended up to 35 µm where the plane of symmetry marks the beginning of the next deposition site and the fronts of neighbour projections join.

Combining the morphology of rhodamine-dextran fluorescence and surface reflectance, measurements of skin deformation post patch application were achieved. Diffusion is then measured from the centre of the deposition site, although it is assumed that diffusion occurred in the regions outside of the measured projection deformation area in the skin.

Figure 30:
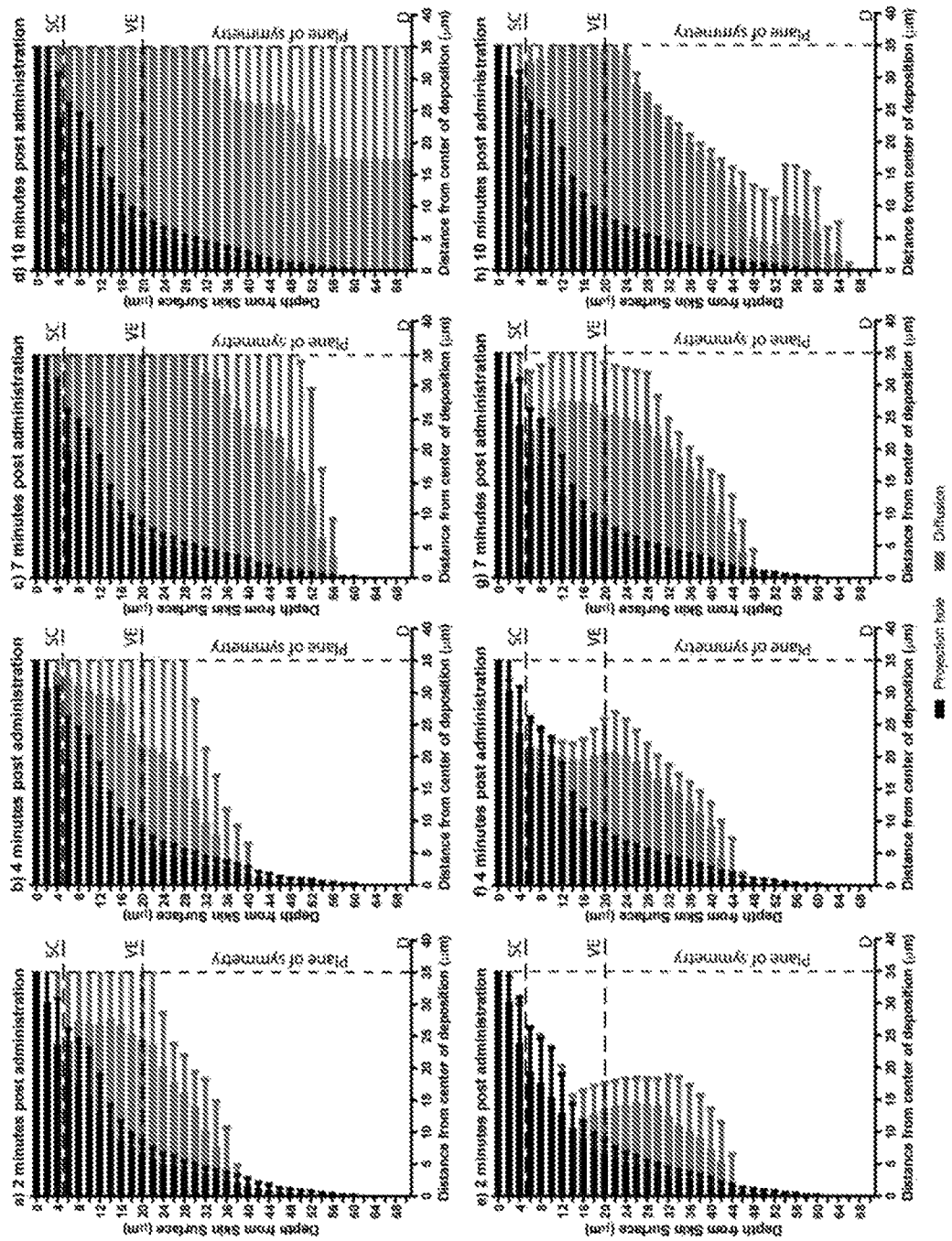
FIG. 30 shows graphs of example measurements of the diffusion fronts for the different time points in the stratum corneum (SC), viable epidermis (VE) and dermis (D)
Figure 33:
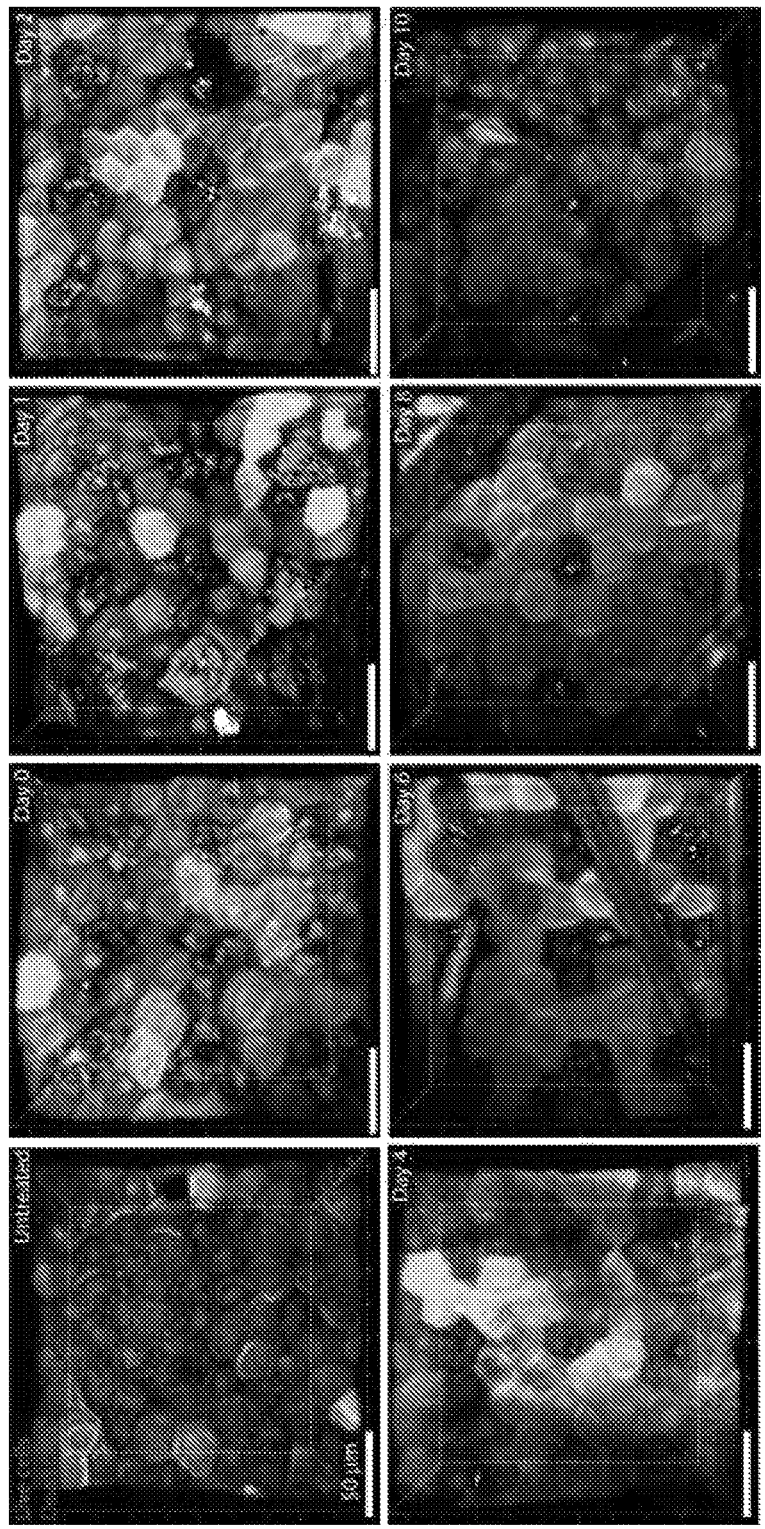
FIG. 33 shows example confocal images of murine ear skin at indicated times after application of a projection patch.

The resulting diffusion fronts are shown in FIG. 30, which together with the projection hole measurements provides an accurate representation of the quantified diffusion profiles occurring in the skin over time. This was used to determine the graphs shown in FIG. 30, which show the diffusion at 2 µm intervals from the surface into the dermis. Both 70 kDa rhodamine-dextran (FIGS. 30a-d) and 2 MDa rhodamine-dextran (FIGS. 30e-h) diffusion increased laterally and vertically as time increased.

Figure 31:
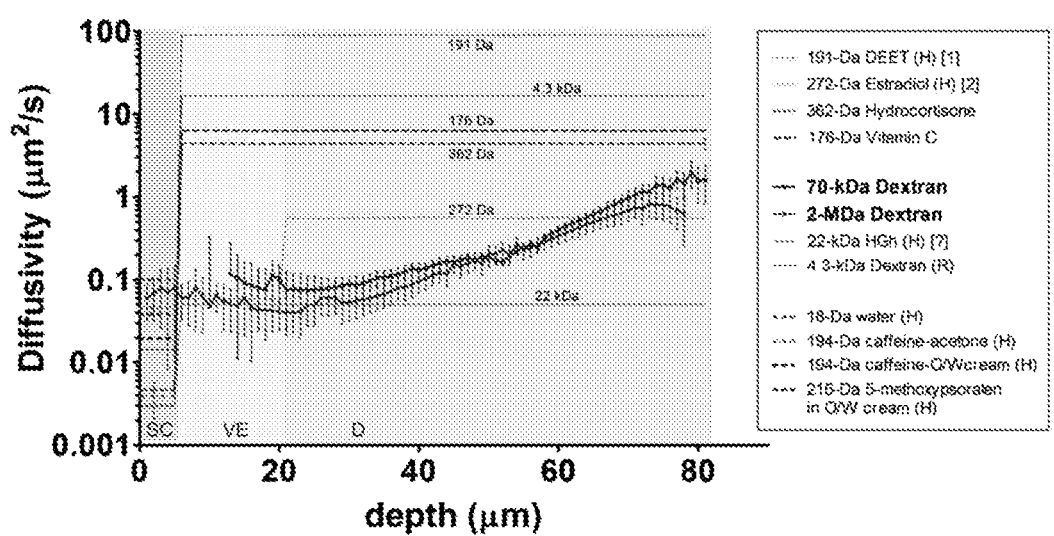
FIG. 31 is a graph showing calculated diffusivities compared to diffusivities derived in previous studies.

The diffusivity of the skin as a function of depth was calculated from the evolution of the 2D rhodamine-dextran concentration throughout the 4 time-points. The diffusivity as a function of depth for 70 kDa and 2 MDa rhodamine-dextran are shown in FIG. 31. This highlights that diffusivity increases by one order of magnitude from the top of the epidermis to the bottom of the dermis underlining the stratified heterogeneity of the material.

Thus, the poorly hydrated 'brick and mortar' structure of the SC inhibits diffusion. The aqueous VE (~70% hydration), consists of a tightly-packed cellular arrangement, also inhibiting the rate of diffusion, whereas the fibrous dermal region has an increase in diffusivity.

Furthermore, it is evident that within the dermis, there is a further increase in diffusivity, probably due to an increase in hydration and decrease in collagen packing/network from the upper papillary dermis to the lower hypodermis.

This highlights that diffusion is hindered in the SC and VE presumably due to poor hydration and by the tightly-packed cellular arrangement, whereas it increases with depth along with the pore size of the dermal collagen network. Accordingly, this highlights that improved delivery of material to cells can be achieved by ensuring delivery of material to the dermis, which in turn allows enhanced diffusion of the material, thereby ensuring that exposure of surrounding cells is maximised.

Whilst diffusion is an important mechanism for the distribution of materials to cells within the subject, it will be appreciated that material delivered by the projections may also reach target cells in other ways. For example the material may be distributed by movement of fluids within the tissue, or may be directly delivered to cells through contact between the non-liquid coating and the cells.

Cell Death

Another factor contributing to the ability of the projection patch to induce an improved immunological response compared to traditional needle and syringe, is the ability to induce localized discrete cell damage in the vicinity of the projections.

When infection, tissue damage or trauma occurs, an inflammatory cascade is triggered by the innate and adaptive immune system. However, damaged cells can also release molecules emitting danger signals—cytokines, heat shock proteins and oxidized mitochondrial DNA—all endogenous signals with known danger indicating properties. These danger signals are released by both living and dying cells, although in higher concentration by dying cells in the vicinity.

Generally, apoptosis does not cause inflammatory responses, although under certain circumstances, inflammatory signals can become an intrinsic element of apoptosis. By contrast, necrosis is known to induce inflammatory responses of the immune system due to the cellular contents being released into extracellular space.

'Physical' adjuvants in form of direct stress or signals from necrotic cells have shown that immature DCs are able to capture apoptotic and necrotic cells, but only exposure to necrotic cells induces DC maturation. In particular, necrotic but not apoptotic cells release Hsp, inducing DC maturation. Further, Hsp70 can protect cells from stressors and against several apoptotic and necrotic cell death inducers Additionally, necrotic but not apoptotic lysates induced translocation of NFkB to the nucleus activating DCs and subsequently the NFkB pathway, which is involved in organism's responses to infection, stress or injury. Danger signals from necrotic cells stimulate cytokine production and secretion, triggering a cascade of inflammatory events. Cell death has also been observed following alum administration, which subsequently led to host DNA release which acted as an endogeneous stimulatory signal mediating alum adjuvant activity. Accordingly, the ability to induce cell damage can lead to an improved immune response.

An experiment to test the level of cell damage will now be described. For this example, a 4×4 mm area projection patch containing 3364 densely packed projections, a density of >20,000 projections/cm$^2$. The diameter of the projections at their base was approximately 28 µm and the distance between the centre's of adjacent projections was 70 µm. The length of the projections used in this study was 110 µm in length.

The patch was on the inner lobes (ventral side) of anaesthetized mice by a brass piston impact applicator, delivering a brief pressure spike and kept in place for 5 minutes. The selected velocity of 1.96 m/s for projection patch application was indicative for ~95% of the projections penetrating the skin. Intradermal (i.d.) injections, were conducted into the ventral side of murine ears with a 31 G needle.

Mice were sacrificed by cervical dislocation either immediately after patch application or at different time points after projection patch application. Two mice (n=4 ears) were used per group for all experiments with one projection patch per ear unless otherwise stated. All animal experiments were conducted according to the University of Queensland animal ethics regulations.

To discriminate between live and dead cells, a mixture of metachromatic AO and EB was used. Stains were dissolved in 1 ml of 95% ethanol and 49 ml of phosphate buffered saline (PBS), aliquoted into 1 ml eppendorf tubes and were stored light protected at −20° C. (AO, AOEB) or at room temperature (EB). Working solutions were freshly prepared from stock solutions prior to the experiment in PBS with a final concentration of 3 µg/ml (AO) and 10 µg/ml (EB), respectively.

Murine ears were split into dorsal and ventral halves at the dermis-cartilage-dermis junction and the cartilage carefully removed. Single stain controls were prepared of untreated dorsal and ventral ear halves whereas only ventral sides were retained and imaged from Projection patch or i.d. treated samples. Negative controls were stained with AO, EB and AOEB whereas positive controls were pre-treated with ice-cold (−20° C.) methanol (Merck, NJ, USA) prior to staining. All tissue samples were stained for 30 min at 37° C. followed by three 10 min washes in ice-cold PBS on an orbital shaker (Xtron P/BAS-3.16L, PathTech, VIC, Australia). Live or viable cells stained with metachromatic AO fluoresced green when intercalated with DNA (emission peak 525 nm) while cells with an impaired or ruptured cell membrane internalized EB and were interpreted as non viable with red fluorescence being emitted (~635 nm). Care was taken to protect the stains and stained tissue from light at all times.

Samples were immediately observed under an upright Zeiss Axiovert LSM 510 (CLSM, Carl Zeiss AG, Jena, Germany) coupled to a multi-photon excitation source, provided by a Chameleon® titanium/sapphire NIR tuneable (690-1040 nm) laser oscillator from Coherent (Santa Clara, Calif.) and a photomultiplier tube used as a detector. The excitation light was collected from the sample through a 40× oil immersion, 20× air or 10× water objective (all Zeiss) coupled to the confocal scan head. Samples were placed SC facing up on a microscope slide in the appropriate mounting fluid (immersion oil (Zeiss) or water) and covered with a cover slip.

A total of 9 projections from 5 sites within the treated or untreated area per ear were imaged, resulting in up to 180 projection sites per time point. 3D images were produced by imaging up to 110 µm deep into the tissue taking z-stack slices every 1 µm measured from the SC to the cartilage. LSM 510 and ZEN software (both Zeiss, Germany) were used for image acquisition and analysis. Both, AO and EB were simultaneously excited using the chameleon laser at 750 nm with emissions collected with a BP500-550IR and BP650-710IR filter, respectively. The laser power and pinhole threshold was kept constant between all samples while the gain was minimally adjusted to compensate for over and undersaturation.

Tissue samples were snap frozen before being embedded in OCT (Tissue Tek, Thuringowa, QLD, Australia) and stored at −20° C. until ready for cryosectioning. Cryosections were prepared on a Hyrax C60 (Zeiss, Germany) with section thicknesses of 5, 10 and 50 µm Samples were fixed in 2% PFA prepared in PBS prior to hematoxylin (Harris hematoxylin, Sigma) and eosin (Eosin Y accustain, Sigma) staining.

Statistical analyses were performed using the student's t-test (two groups) or one way ANOVA (multiple groups) using GraphPad Prism version 5.04 for Windows (GraphPad Software, San Diego, Calif., USA). P-values of <0.05 were considered as significant. All values are expressed as mean±standard deviation (SD) unless otherwise stated.

Differentiation between live, apoptotic and necrotic cells was based on their staining: live cells have normal nuclei staining which present green chromatin with organized structures; apoptotic cells contain condensed or fragmented chromatin (green or orange); necrotic cells showed similar nuclei staining as live cells except the chromatin is orange.

Imaging results are shown in FIGS. 32A to 32D. Deep tissue imaging of up to 110 µm per sample revealed a large amount of cell damage within both, VE and dermis, thought to be caused by handling the tissue with tweezers, splitting of dorsal and ventral sides and scraping off the cartilage. An optimized handling process of the tissue included fast splitting of dorsal and ventral sides, partial cartilage removal with tweezers handling at the base of the ears resulted in reduced cell damage within the dermis and VE, allowing a clear separation of projection patch treated and untreated areas, as shown in FIG. 32B.

In addition, measurements showed that the localized cell damage corresponded to the projection sites with some individual damaged cells occurring between projections and no or low levels of cell damage outside of patch treated areas, as shown in FIG. 32C. Minimal cell damage was observed within the VE and dermis in untreated controls, showing that the established techniques caused no artefacts in the tissue samples, as shown in FIG. 32D.

Cell damage was quantified using manual and automated processes, with counts yielding 72.78%±1.466% live and 27.22%±1.466% damaged cells in a treated sample. Untreated samples showed less than 2.605%±1.165% of dead cells within the same area as a treated sample.

Since the application of the projection patch induced observable cell damage around the projection penetration holes left behind in the skin, investigations were made as to the change in cell damage within the VE and dermis over time. Time points ranged from 0 to 8 days, based upon a full tissue recovery expected between 10 to 14 days. Resulting confocal images are shown in FIGS. 33A to 33F.

Untreated samples showed negligible cell damage. Immediately after patching at t=0 h, imaging revealed localized cell damage (23.03±2.59%) around the projection sites with a radius of approximately 14.24±0.59 µm per projection site. This equates to a live-dead ratio of approximately 4:1. One day after patch application, AOEB staining indicated an increase of damaged cells, difficult to measure the increased radii around the initial insertion points. Quantification revealed an increase of damaged cell to 32.31±2.01%. This time point also represented the maximum cell damage observed with 58.01±3.99% damaged cells in the tissue. No increased cell damage was seen outside of the patch treated areas.

Figure 34A:
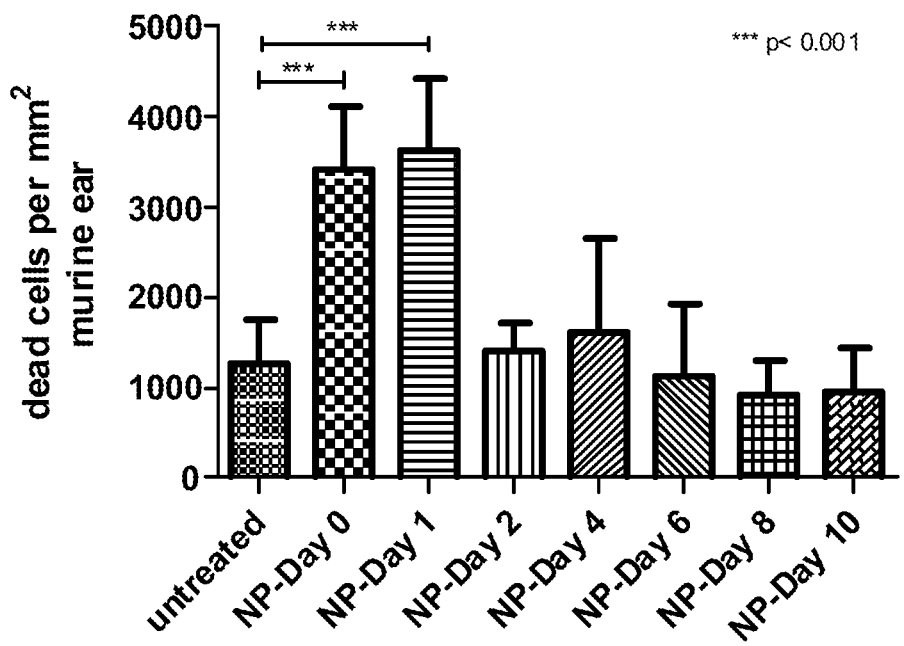
FIG. 34A is a graph of example of variations in extent of cell damage over time following application of a projection patch.

By day 2, the percentage of damaged cells dropped significantly down and represented only 15.86±1.45% and returned to normal pre-patch conditions by day 8 with 3.35±0.83%. Measured values are shown in FIG. 34A. These results provided evidence for localized cell damage caused by the Projection patch, which spread and reached its maximum 1 day following patch application but returned to pre-patch conditions by day 2 (figure).

It is known that LCs and dDCs migrate to dLN ad that that danger signals are released by damaged cells into surrounding tissue, which can in turn cause an increase in damaged cells observed 24 hours after patching, with viable cells migrating to dLN while neighbouring cells become permeabilized due to the released cell contents and thus incorporate EB. In addition to an inflammatory response evoked by attracting neutrophils and macrophages to the site of physical stimulus and an increase of cytokine and chemokine production and secretion, activating DCs that induce similar immune responses as adjuvants have can also occur.

By contrast, the sudden drop in damaged cells observed on day 2 may result from the delayed onset of the adaptive immune responses, including a large influx of phagocytic cells such as neutrophils and macrophages, phagocytising damaged and dead cells. Further, this sudden decrease may also reflect sufficiently injured cells to undergo apoptosis and thus not remain EB-stained. However, due to the natural turnover rate of keratinocytes within the skin, a fast replacement of cells was likely to be achieved.

Figure 34B:
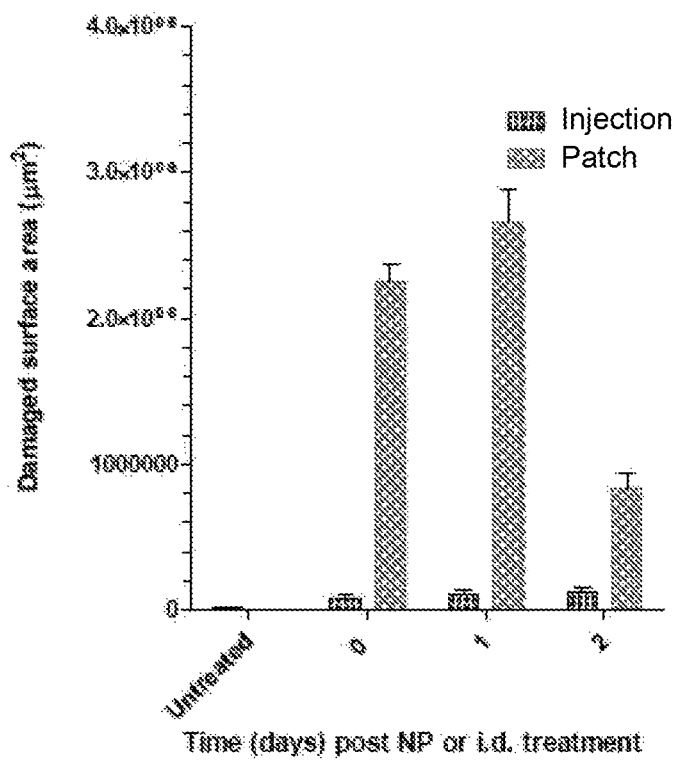
FIG. 34B is a graph of example of variations in extent of cell damage over time following application of a projection patch and intradermal needle and syringe injection.

A comparison of the extent of cell damage for a projection patch versus a needle and syringe injection is shown in FIG. 34B. Again this demonstrates an initial increase of cell damage or death following application of a patch, followed by a decrease in cell death two days after application. This experiment also highlights that the quantity of cell damage or death is significantly greater with a patch compared to a needle and syringe injection, as would be expected due to the single point of penetration with the needle as opposed to the multiple points of penetration with the patch.

Further experiments performed with different application velocities resulted in different levels of cell damage, with neither skin penetration nor cell damage observable with static patch applications, and localized cell damage noted after applications at speed. The results obtained showed that both percentage and radius of dead cells increased with increasing velocity of application. This was expected, as with deeper projection penetration, a wider diameter of the projection penetrates the skin, thus increasing the regions with higher stress contours, which leads to increasing the radius of dead cells and hence percentage of dead cells. These preliminary experiments present evidence that pressure and force have an important impact upon cell membrane damage and cell damage.

Accordingly, the results confirm that cell damage can be caused by the projection patch, around the sites where projections are inserted into the skin. The results also show a consistent ratio of 4:1 of live and damaged cells within the patch treated area immediately after its application. Subsequent skin recovery studies revealed that this ratio increased and peaked approximately 24 hours after patching with over 58% of the cells within the patch treated area being damaged. This peak was followed by a rapid decline of damaged cells and returned to pre-patching conditions by day eight with approximately 3% of damaged cells. In addition, initial cell damage studies obtained from static patch applications provided evidence that different levels of cell death were achievable, important for future experiments.

These results support that cell damage caused by the projections can provide a 'physical adjuvant' effect, which can improve vaccine antigen delivery eliciting protective immunity.

The mechanism for inducing cell damage includes both physical contact between cells and the projections, as well as stress induced within the tissue resulting from penetration of the tissue by the projections. An example of the stress induced for projections have stepped and convex effective profiles will now be described with reference to FIGS. 35A and 35B.

Figure 35A:
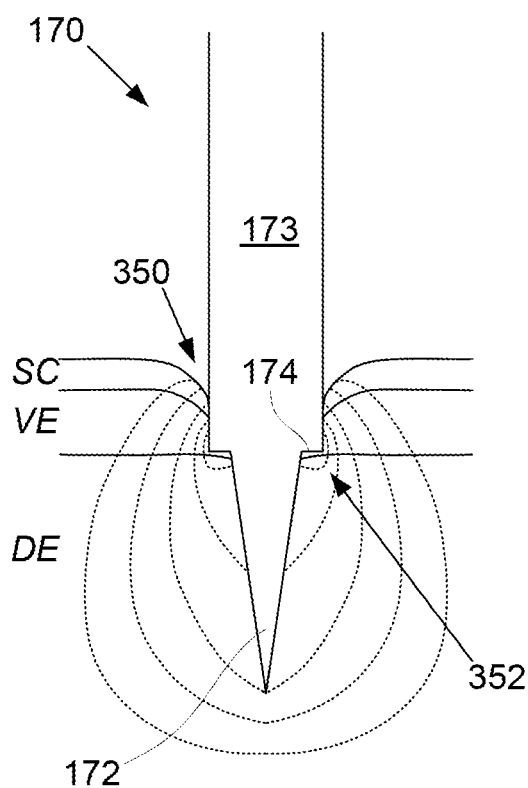
FIGS. 35A and 35B are schematic diagrams showing the resulting stresses caused by penetration of a projection having stepped and convex effective profiles, respectively.
Figure 35B:
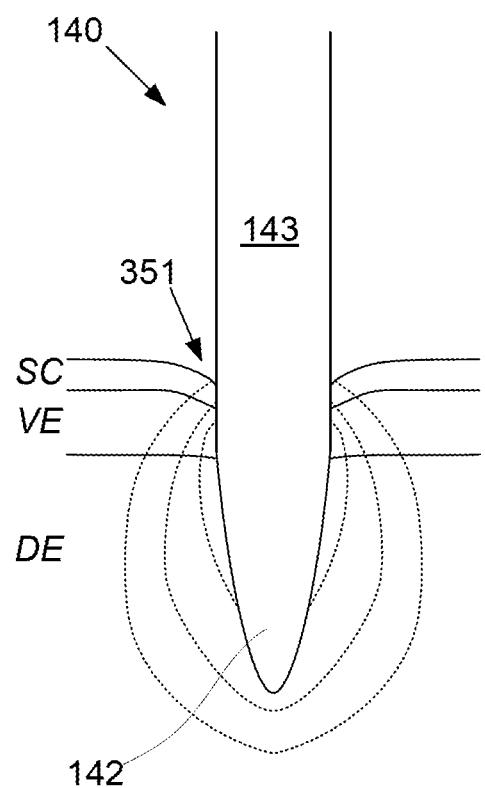

In the example of FIG. 35A, the projection is a stepped projection 170 similar to that described in FIG. 1H and therefore includes a tip 172 provided on a support section 173, with a step 174 provided where the tip 172 meets the support section 173. In contrast, in FIG. 35B the projection is similar to the projection 140 described in FIG. 1E and therefore includes a tip 142 having a convex profile provided on a support section 143. For both diagrams, stress contours representing a locus of points subject to similar stress levels are shown in dotted lines.

As the projections 140, 170 enter the skin, the convex shape of the tip 142 gradually urges the stratum corneum apart, whereas the presence of the step 174 causes a greater impact with the stratum corneum, which in turn increases stratum coreum disruption compared to the convex projection, as shown at 350, 351.

In addition to this, as previously described, as the projection penetrates the tissue, this generates a pressure wave, which in turn causes stress to the tissue. The greater number of stress contours for the stepped projection lines shown highlights that greater overall stress is generated. Additionally, as can be seen from the contour indicated generally at 352, a greater amount of stress is generated around the vicinity of the step 174.

Accordingly, it is apparent from the above that the stepped projection results in a greater degree of stress within the tissue and in particular, within the dermis DE. As such stress can cause cell damage, it will be appreciated that the use of the stepped projection can enhance the extent of cell damage and hence the "physical adjuvant" effect described above.

It will be appreciated from the above that each time a patch is applied and projections penetrate the tissue, cell damage should be caused. Accordingly an experiment was performed to determine if repeated application of patches could further increase the extent of cell damage.

For this experiment, a patch was applied to murine ear skin, with a patch being applied a single time for one sample, and a patch being applied three times to a different sample. Staining with acridine orange and ethidium bromide was used to distinguish between live and dead or damaged cells, with cell counts being determined in a manner substantially similar to that described above.

Results for the single patch application showed 16.74±4.66% dead cells (mean±SD) within the patched area. In contrast for the region where a patch was applied multiple times, 47.81±4.1% dead cells were detected, highlighting that applying a patch multiple times can induce additional cell damage or death.

Following this, a dose-matched immunogenicity study was performed using Fluvax 2009. In this example, the single patch application protocol involved applying a single patch coated to include 20 ng of Fluvax 2009. In contrast the multiple patch application protocol involved applying two uncoated patches, followed by a single patch coated to include 20 ng of Fluvax 2009, applied to the same application site.

Figure 36A:
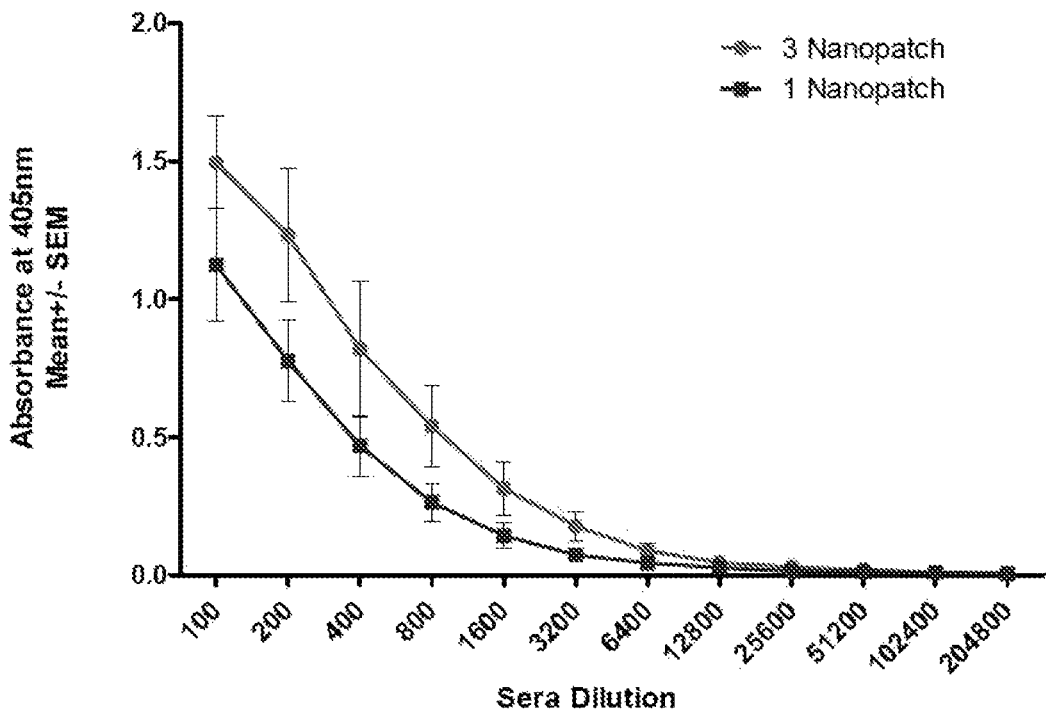
FIG. 36A is a graph of the immunological response induced by application of a single patch and application of multiple patches in sequence.
Figure 36B:
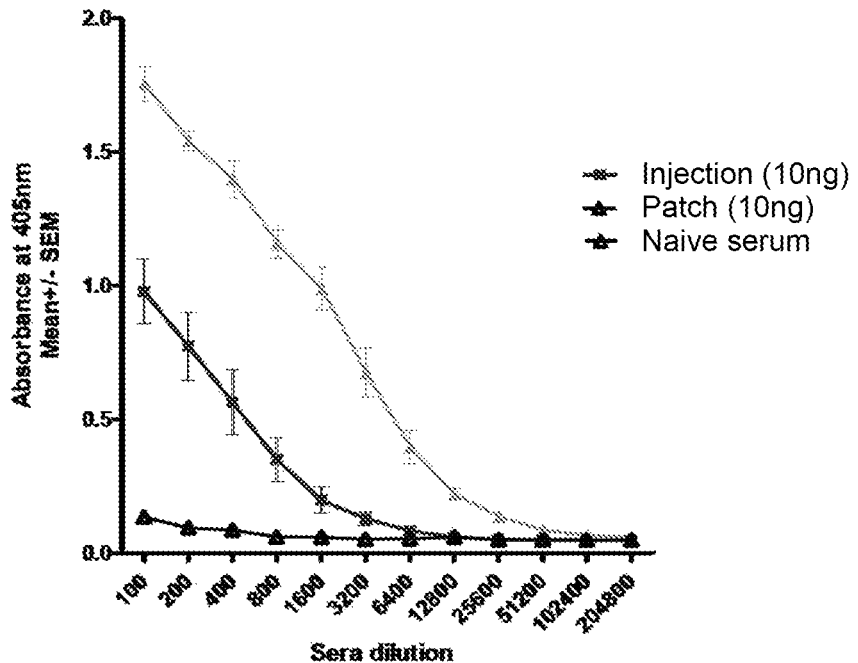
FIG. 36B is a first graph of an example of the immunological response induced by application of a single patch compared to an intra-dermal injection.
Figure 36C:
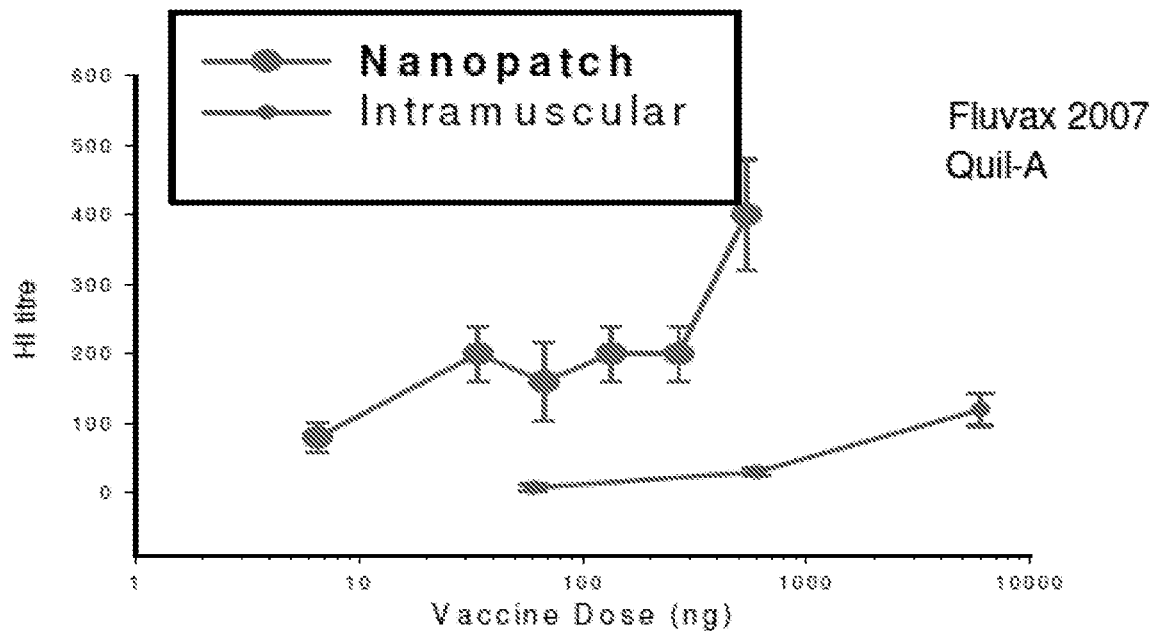
FIG. 36C is a second graph of an example of the immunological response induced by application of a single patch compared to an intra-dermal injection.
Figure 36D:
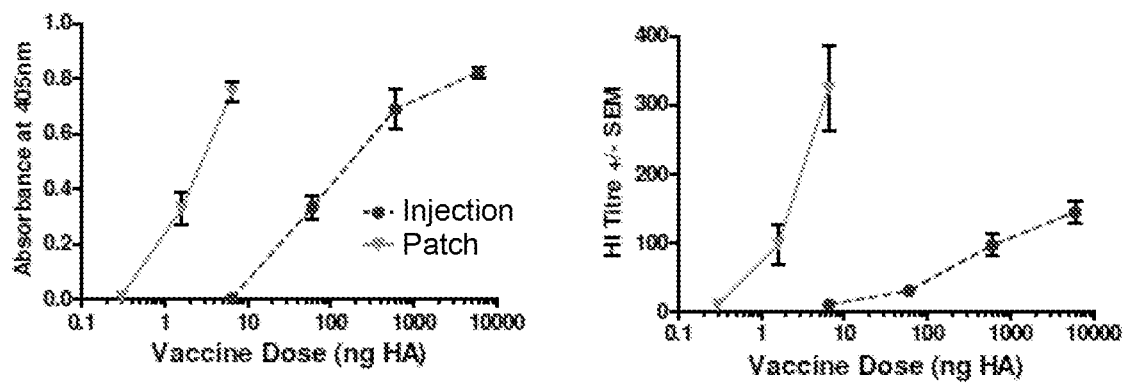
FIG. 36D is a third graph of an example of the immunological response induced by application of a single patch compared to an intra-dermal injection.

Results are shown in FIG. 36A, highlighting that even though the same amount of Fluvax was administered using identical patches, a greater immune response is induced using the multiple patch application process. As all other variables are equal, this highlights that the increase in cell death induces a greater immunological response. Further evidence is shown in FIGS. 36B to 36D, which shows results of comparisons of the immunological response obtained for a projection patch and an intradermal needle and syringe injection. In this example, a significantly greater immunological response is achieved using a patch compared to the injection, which would induce reduced cell death compared to the patch as the needle only penetrates the dermis in a single location.

The interaction between cell damage and diffusion of coating material will now be described in more detail with reference to FIGS. 37A and 37B, which show a projection 110 applied to tissue immediately after penetration and some time later, respectively.

Figures 37A, 37B:
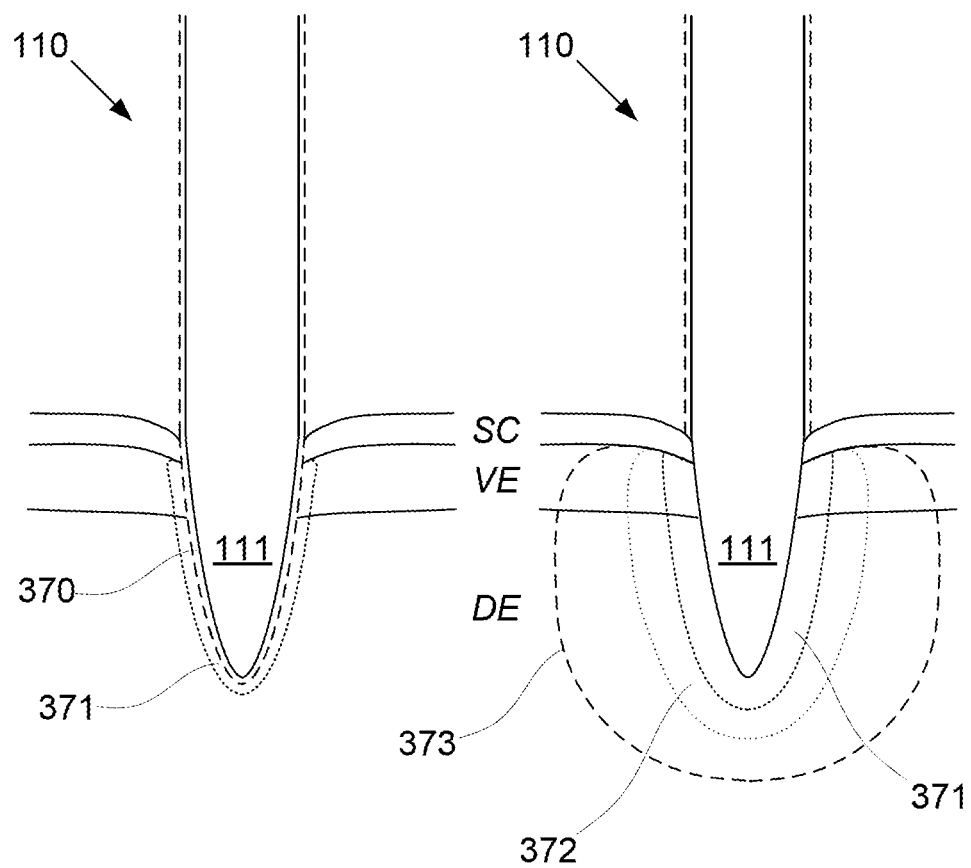
FIGS. 37A and 37B are schematic diagrams showing the combined effect of cell damage and diffusion of material into the tissue surrounding a projection.

As shown in FIG. 37A, as the projection 110 penetrates the tissue, the coating 370 initially remains in place on the tip 111, with the penetration of the projection initiating necrotic death for cells in a region 371 immediately surrounding the projection tip 111, as described above. As time passes, apoptosis of cells immediately adjacent the damaged cells, will cause the extent of the region 371 containing damaged cells to expand, as described above with respect to the explanation of cell damage, and as shown in FIG. 37B.

The damaged cells typically generate signalling agents, which propagate to cells immediately surrounding the region containing the damaged cells, thereby providing a region 372 containing live and/or undamaged cells that are subject to "danger signals" from the damaged cells. In addition, the coating provided on the tip 111 dissolves and diffuses through the tissue, as shown by the diffusion wave front 373. Critically this means that cells in the region 372 are exposed to both "danger signals" as well as being exposed to any adjuvants contained within the coating.

The "danger signals" trigger immunological response mechanisms of the cells in the region 372, which then react to the presence of the adjuvant, thereby resulting in enhanced immunogenicity.

Figure 38:
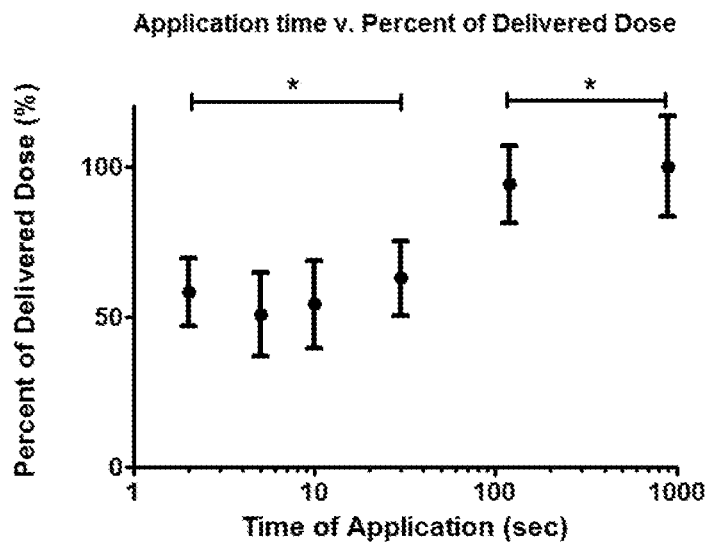
FIG. 38 is a graph of an example of the rate of release of material from a projection patch.

An example of the rate of release of coated material (e.g. vaccine with antigen and adjuvant) from the coating is shown in FIG. 38. This highlights that at least half of the total released vaccine is released in the first few seconds of penetration. As cell damage or death also occurs rapidly, it will be appreciated that this helps ensure a rapid immunological response. The rapid release of vaccine is due to the very high surface area provided by the large density of projections on the patch, meaning that a large amount of the vaccine volume is immediately exposed to the wetness of the surrounding tissue. This causes the coating to dissolve rapidly, thereby rapidly releasing the vaccine from the projections into the skin.

Following this, after about 10 seconds (as shown in FIG. 38), further vaccine is released, with the majority of vaccine being released by about 100 seconds. This occurs as wetness travels along the projection to dissolve coating not exposed to wetness immediately on penetration, for example coating in the stratum corneum (which often can be rather dry), and any coating around the projection entry site. With the remainder of the vaccine being released over time, this can be used to provide a mechanism to allow the amount of payload delivered to be controlled.

Figure 39A:
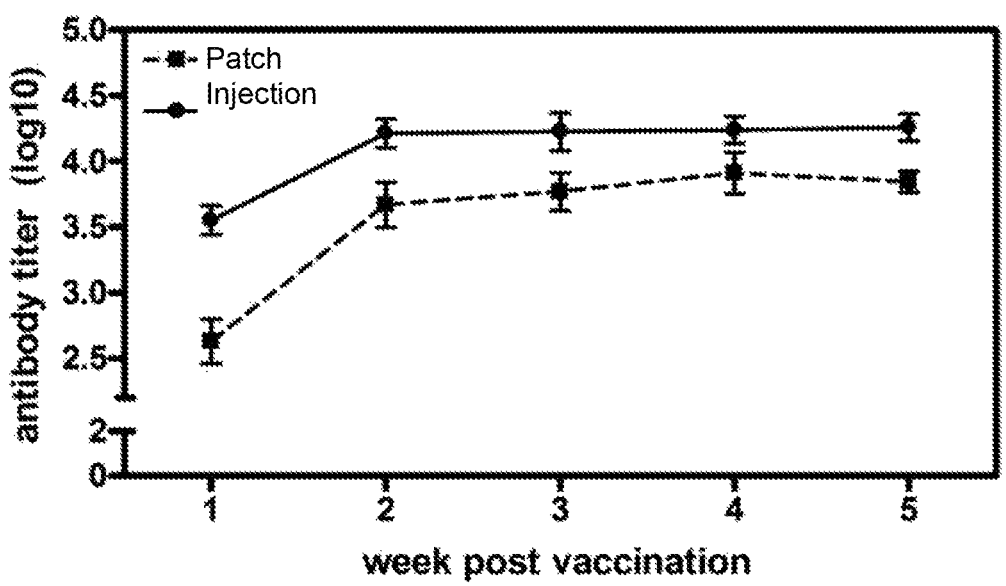
FIGS. 39A to 39C are graphs of examples of the development over time of the immunological response induced by a patch and needle and syringe following application.
Figure 39B:
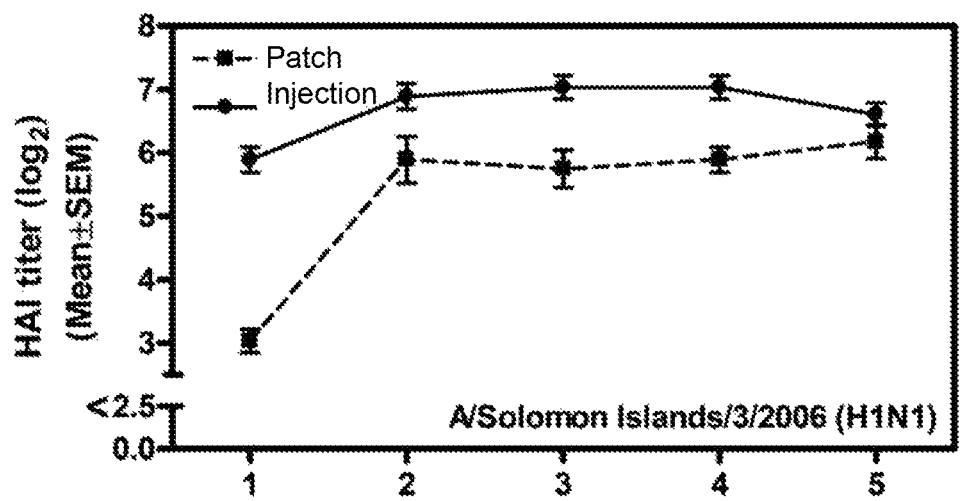
Figure 39C:
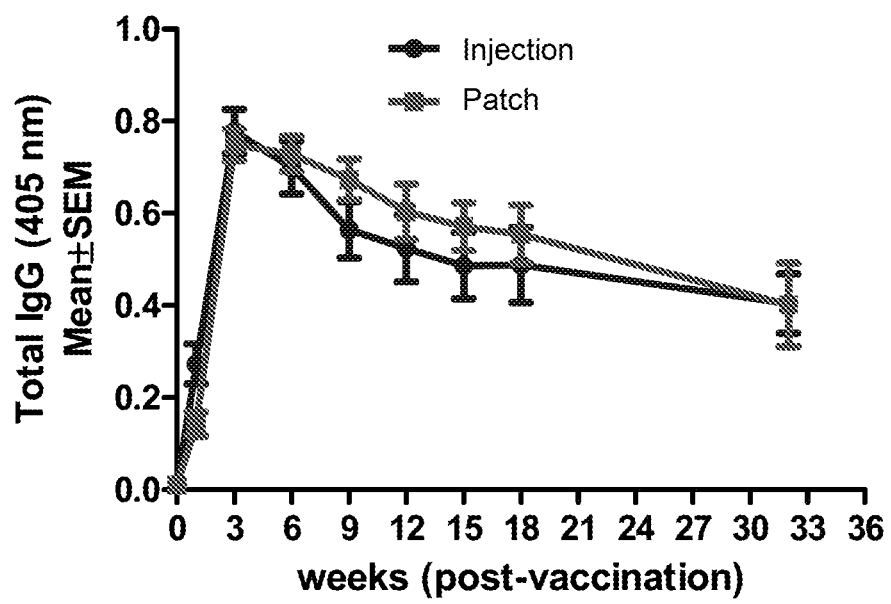
Figure 40A:
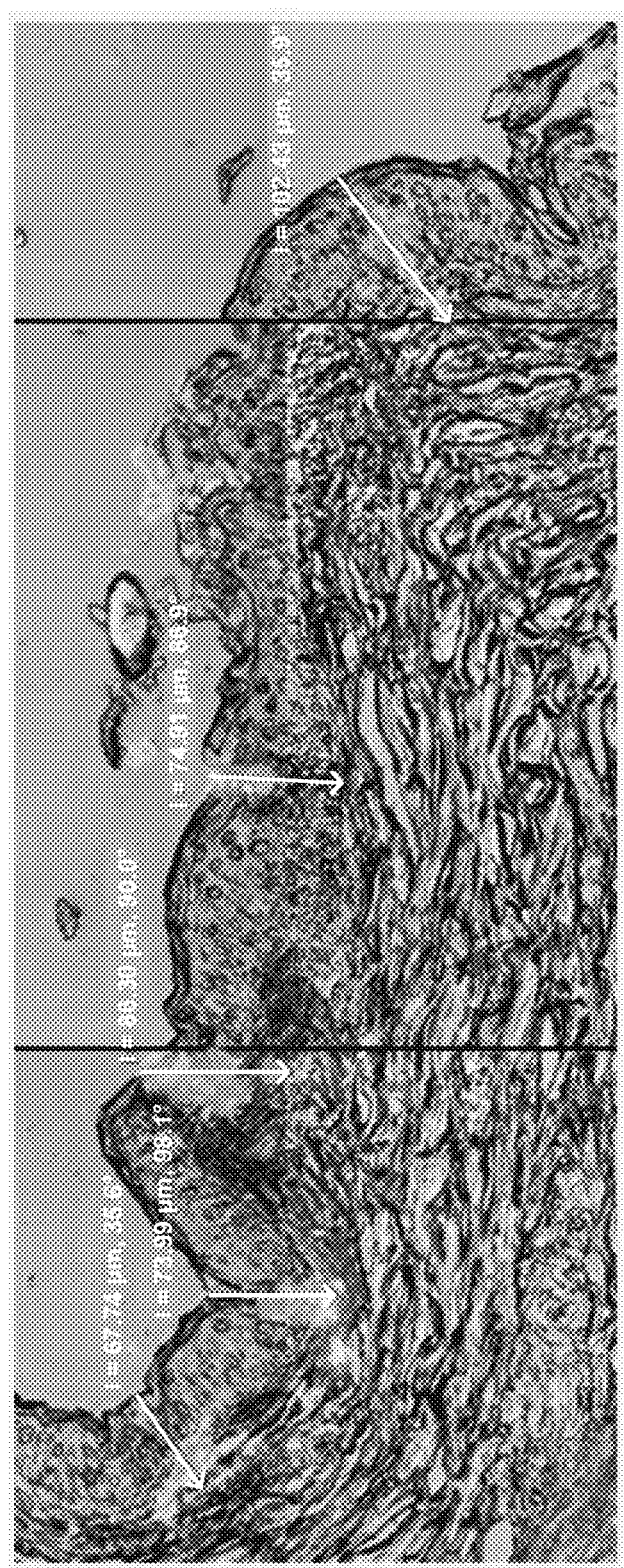
FIGS. 40A to 40C are example images showing the delivery of fluorescent dye in to the skin of longtailed macaques.
Figure 40B:
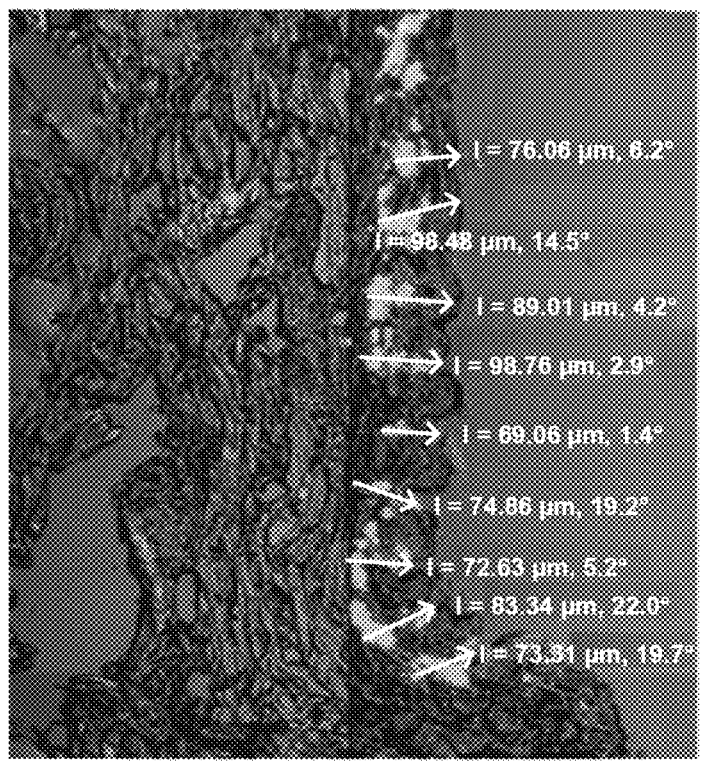
Figure 40C:
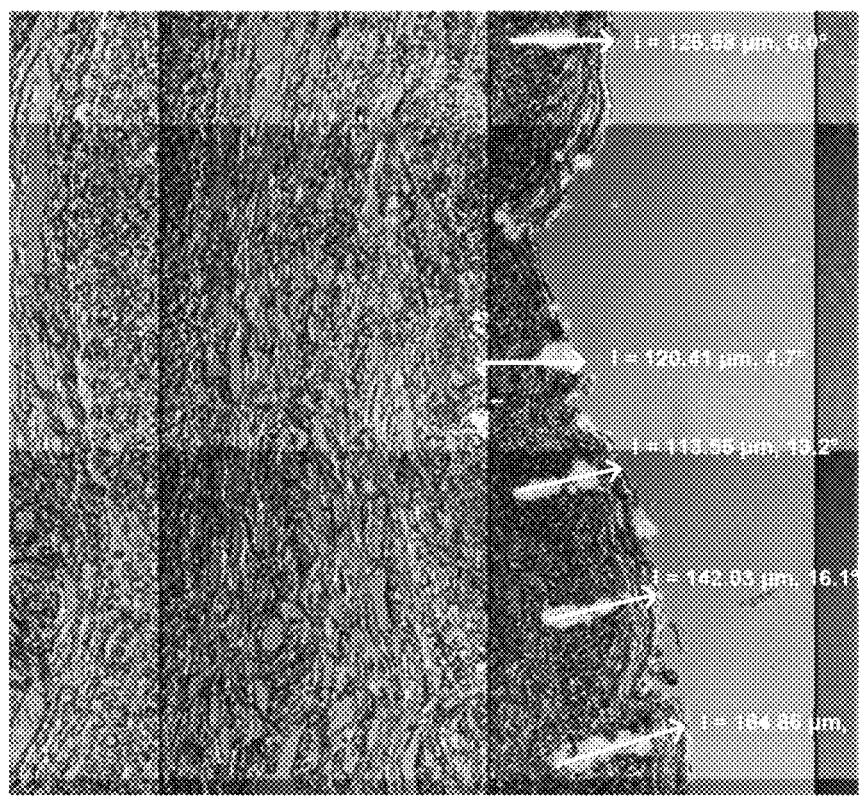

The resulting immunological response that is obtained (following the delivery of FluVax) is shown in FIGS. 39A to 39C, particularly as compared to a needle and syringe intramuscular injection. For these examples, the patch utilised a 100 fold reduction in total vaccine compared to the needle and syringe injection. In both cases, the level of response rises rapidly over time, at approximately the same rate, with the response showing a generally similar profile, albeit with the magnitude of the response initially slightly smaller for the patch. This shows not only that material is delivered from the patch rapidly, but also that the resulting kinetics of immunological response (to protection) is broadly equivalent to that of a needle and syringe intramuscular injection, whilst requiring a 100 fold reduction in vaccine.

Accordingly, it will be appreciated that the above described mechanism can result in an improved immunological response. The effect of damaged cells causing an improved response in neighbouring cells may be referred to as a "bystander response", and it will be appreciated that the perturbation of cells by projections induces bystander responses irrespective of whether projections are used to deliver material. Indeed, a patch may be provided with at least one uncoated projection with the sole intention of perturbing cells to induce bystander responses.

Further, it will be appreciated that the selection of a particular projection geometry can have a further impact on the response within the subject.

For example, whilst projections having an effective convex profile can penetrate the skin more easily, and causing less surface damage, the use of projections having a discontinuity can increase cell damage and hence improve immunogenicity. A further benefit of the use of a stepped projection is that this can typically accommodate a greater volume of coating on the tip, thereby increasing the payload of material that can be delivered to the subject.

Accordingly, it will be appreciated that the different profiles have different benefits, and may therefore be used in different circumstances. For example, a convex projection may be used if ease of penetration is required, whilst a stepped projection may be used if a greater immunological response is to be induced.

In either case, enhanced diffusion of material through the dermal layer suggests projections should be sized and applied with sufficient velocity so that at least the tip of the projection penetrates the dermal layer. Furthermore, due to the natural elasticity of the dermal layer, the tips of the projections must be sufficiently sharp to allow the dermal layer to be penetrated.

Further Experimental Data

Further supporting data regarding the application of patches to a subject will now be described. For the purpose of these examples, a patch was applied to two Longtailed macaque monkeys showing dye delivery and fluorescent dye delivery to highlight penetration of projections in to skin utilising velocity, pre-load and a patch attach. This data was achieved using a preload of 10-20 N.

Example images showing the delivery of fluorescent dye in to the skin of longtailed macaques are shown in FIGS. 40A to 40C. Images show the dermal collagen as red (dark), green (light) is delivered dye. Outer rings around patches show the impressions from pre-load on the skin.

In this example, FIG. 40A to 40C show a forearm application, deltoid application, and ear application, respectively, for a longtailed macaque. Measured penetration depths using sections such as those above on different animal sites, for two longtailed macaques are outlined below in Table 6.

TABLE 6

| | Penetration depth (μm) ± SD | |
|---|---|---|
| Application site | Macaque 1 | Macaque 2 |
| Forearm 1 | 70.10 ± 16.3 | 84.71 ± 14.99 |
| Forearm 2 | 67.22 ± 5.64 | 99.04 ± 16.66 |
| Forearm 3 | 78.53 ± 12.53 | 90.07 ± 19.69 |
| Deltoid | 79.08 ± 14.59 | 84.39 ± 25.6 |
| Ear 1 | 141.27 ± 19.79 | 135.10 ± 21.21 |
| Ear 2 | 127.09 ± 22.23 | 118.13 ± 19.28 |

In comparison, skin thickness in these different anatomical areas are set out in Table 7, highlighting the projections are able to penetrate the epidermis, if suitably configured.

TABLE 7

| | Epidermis thickness (μm) ± SD | |
|---|---|---|
| Anatomical region | Macaque 1 | Macaque 2 |
| Forearm | 41.0 ± 10.47 | 48.19 ± 11.39 |
| Deltoid | 37.68 ± 11.14 | 42.29 ± 9.75 |
| Ear | 56.43 ± 10.6 | 65.94 ± 15.18 |

Example data for different application parameters will now be described. This data was based on the application of 4 mm² patches to skin, using different masses of piston.

Figure 41A:
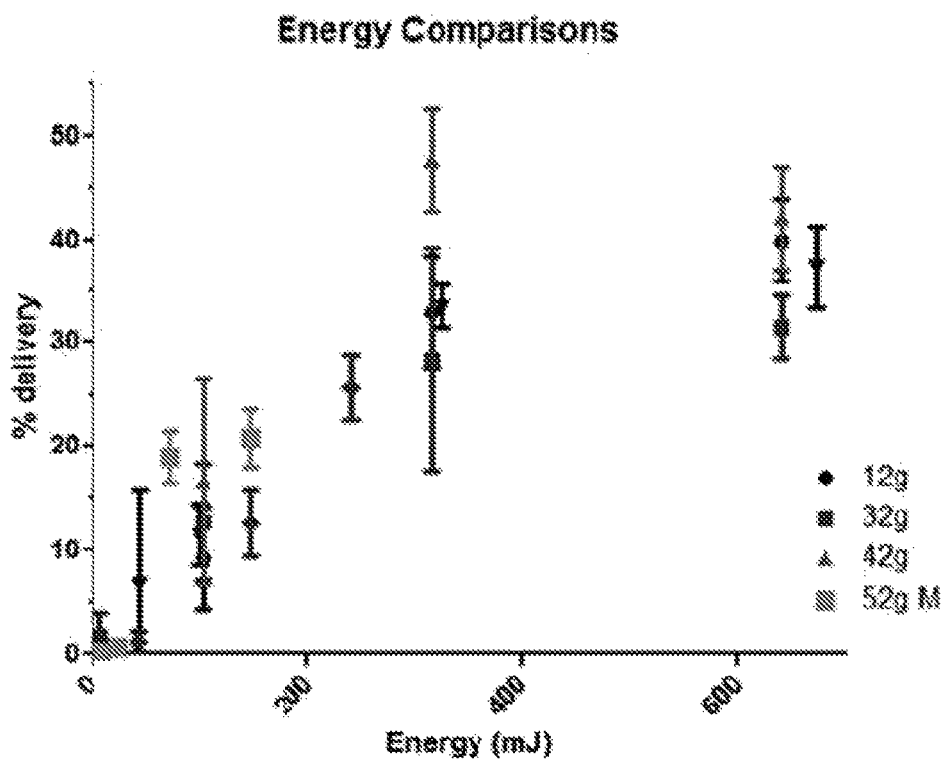
FIGS. 41A and 41B are graphs of examples of the percentage of material delivered for different application energy and momentum, respectively.
Figure 41B:
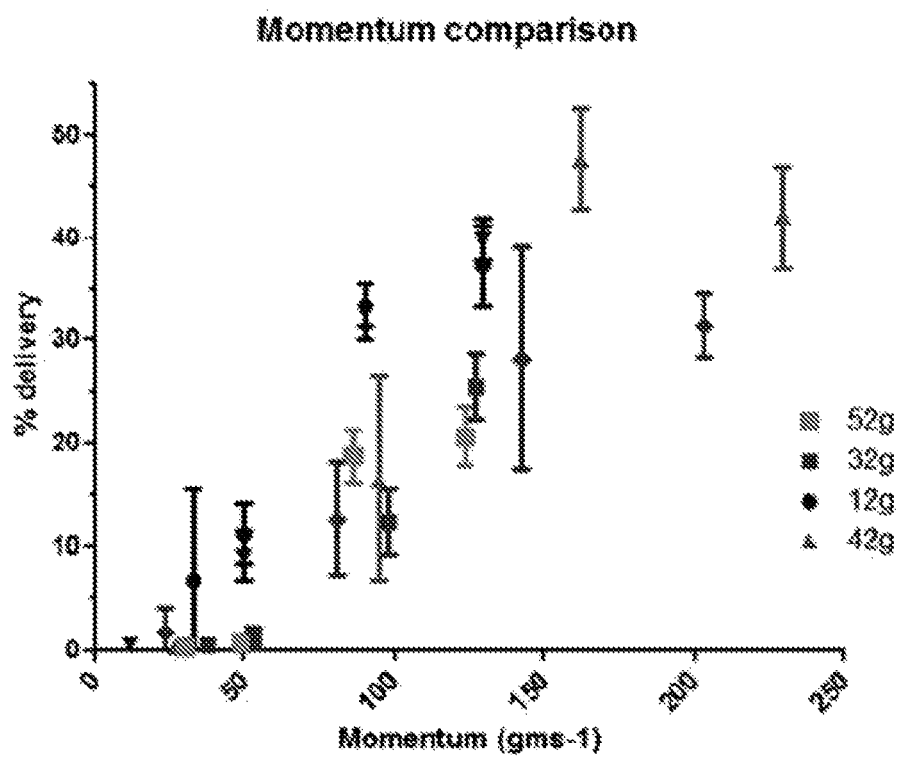

FIG. 41A shows application energy (based on the velocity and mass of the piston) versus percentage of material delivered. These highlight that generally increasing the application energy leads to increased payload delivery. However, there are generally diminishing returns at an application of around 300 mJ, even for different mass pistons. Similar momentum results in FIG. 41B show some level of correlation with delivery based on the conditions used in this study.

With regard to spacing, it has been determined that the kinetic energy per unit projection is a driver for penetration. When projections are too close to each other, then the surface area of the projection tips across a given area of the skin surface will distribute the pressure to such an extent that penetration is more difficult (i.e. a significant superposition of pressure distributions between projections will take place). A projection patch suitable for application to mouse skin preferably has a projection spacing of 70 μm (approximately 20,000 projections per cm²; length of 110 μm), whilst a projection patch suitable for application to human skin will preferably have a spacing of 100 μm (10,000 projections per cm²; length of 250 μm).

An example of the release of C14-OVA when delivered with 2 different projection spacings (CJ) will now be described.

Figure 42A:
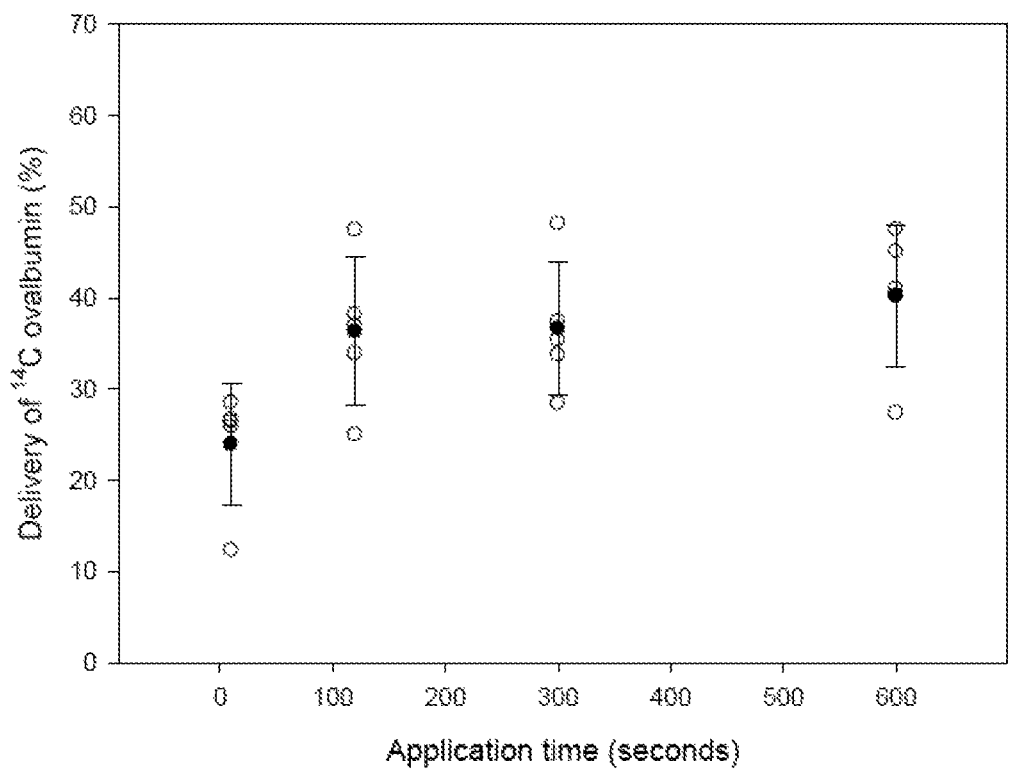
FIGS. 42A and 42B are graphs of example results for the delivery of 14C Ovalbumin into pig skin (ear) over different application times.
Figure 42B:
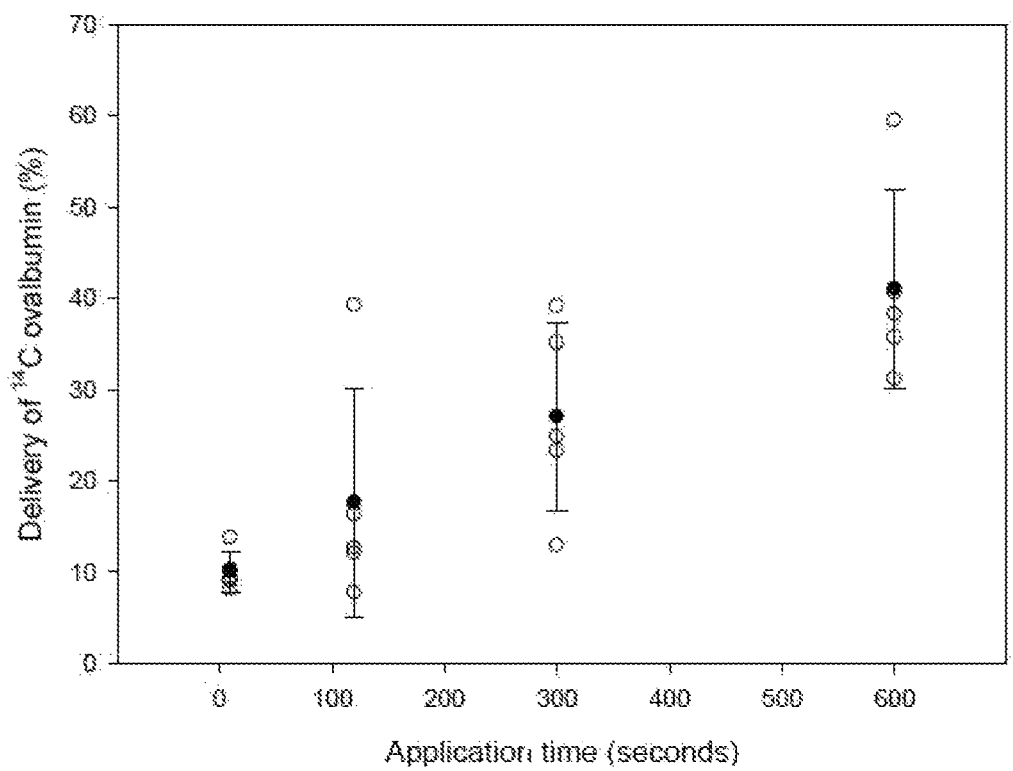

FIGS. 42A and 42B shows example results for the delivery of 14C Ovalbumin into pig skin (ear) over different application times. Open circles show the individual delivery value per Nanopatch. Closed circles show the mean per application time point (n=5). Error bars show the standard deviation. In the example of FIG. 42A, the patch includes 70 μm spacing, 260 μm needle length and an area of 4 mm², whilst in FIG. 42B, a spacing of 100 μm is used.

These results demonstrate that tighter spacing releases faster than greater spacing.

Figure 43A:
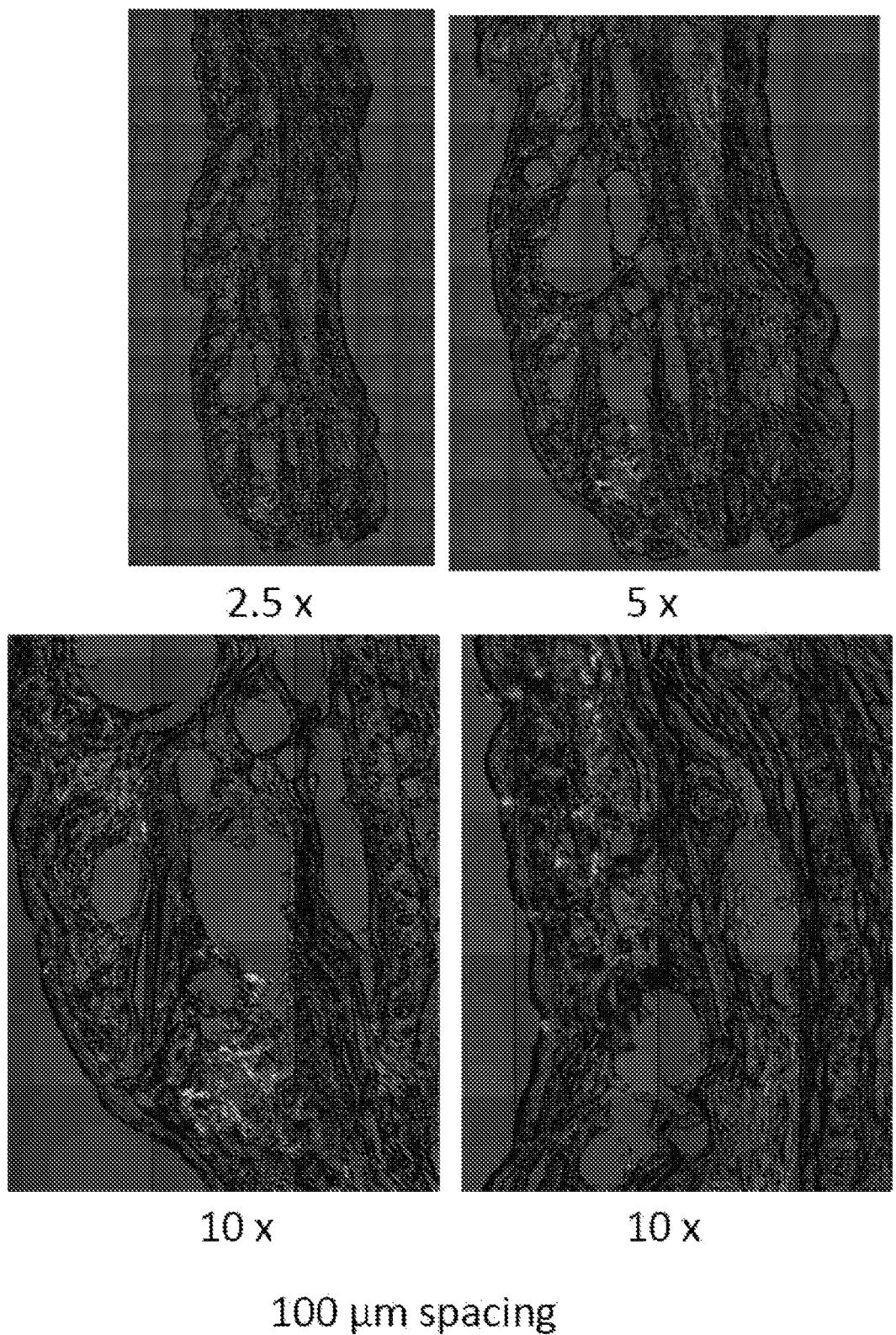
FIGS. 43A and 43B are images of a comparison of the penetration of different projection spacings with in ferret skin.
Figure 43B:
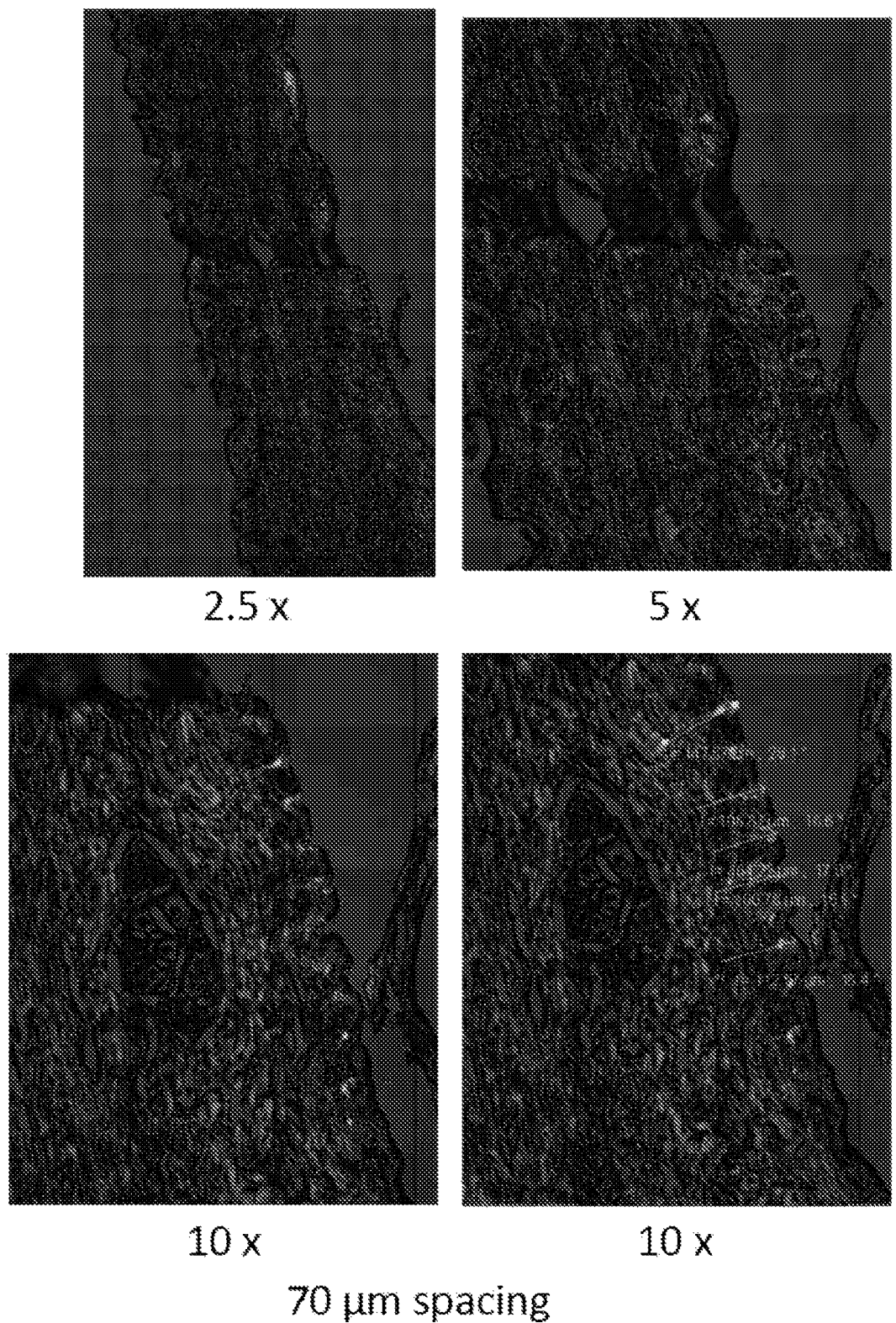

A comparison of the penetration of different projection spacings with reference delivered dose and penetration depth in to ferret skin are described in FIG. 43A and FIG. 43B, and set out in Table 8 below.

TABLE 8

| Group | Penetration depth (μm) Mean + SD* | Penetration depth range (μm) |
|---|---|---|
| 100 μm spacing | 186.74 + 30.61 | 116.82-255.33 |
| 70 μm spacing | 115.12 + 14.48 | 65.08-159.17 |

These results demonstrate that wider spacing penetrates more deeply than narrower spacing.

Figure 44:
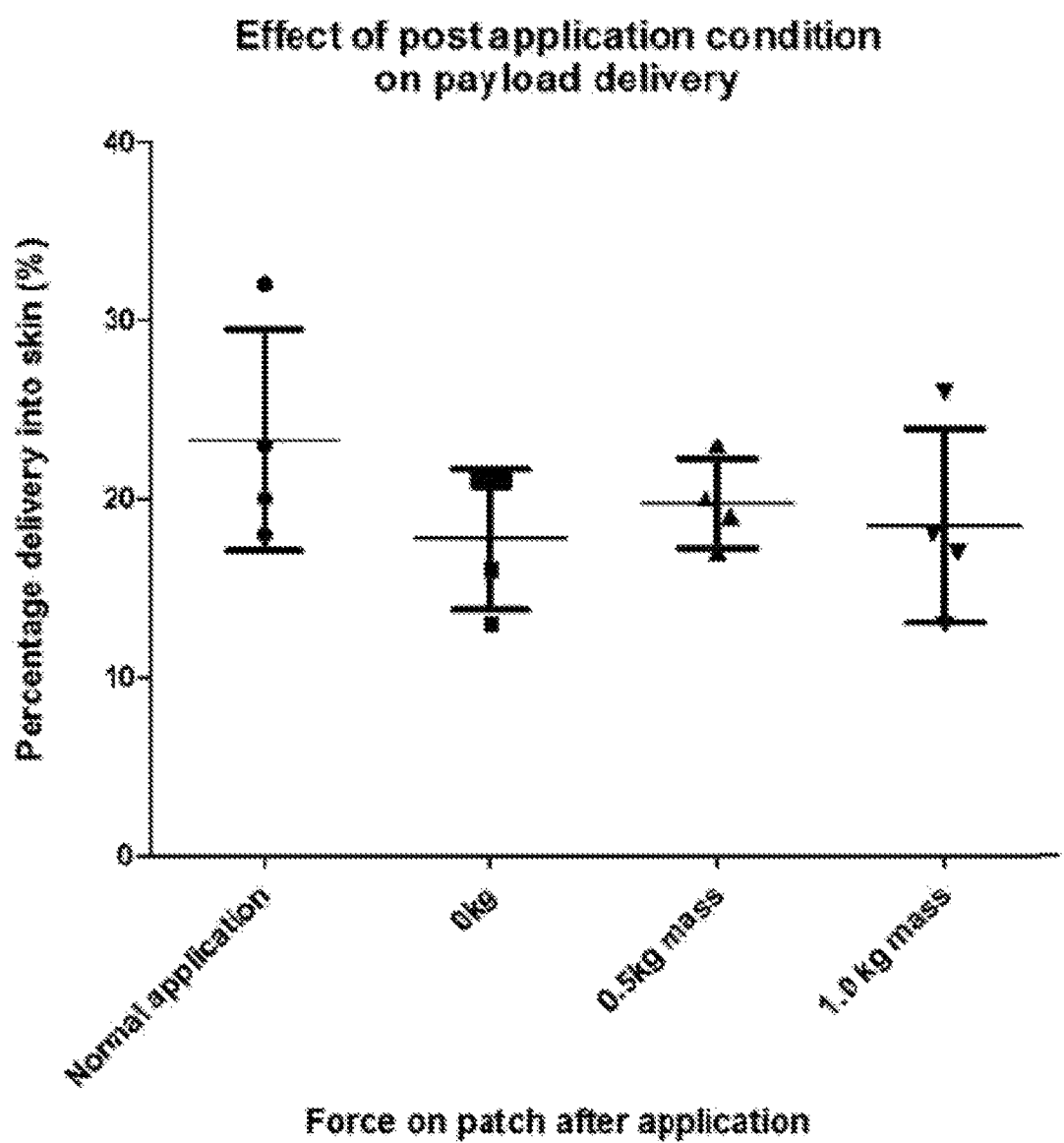
FIG. 44 is a graph of an example of the effect of the application of residual force on a patch after application.

The effect of the application of residual force on a patch after application is highlighted by data shown in FIG. 44. This indicates that overall the inclusion of post application pressure on the patch has little major impact on the overall amount of payload delivered, but can assist in maintaining a more consistent delivery amount.

Figure 45:
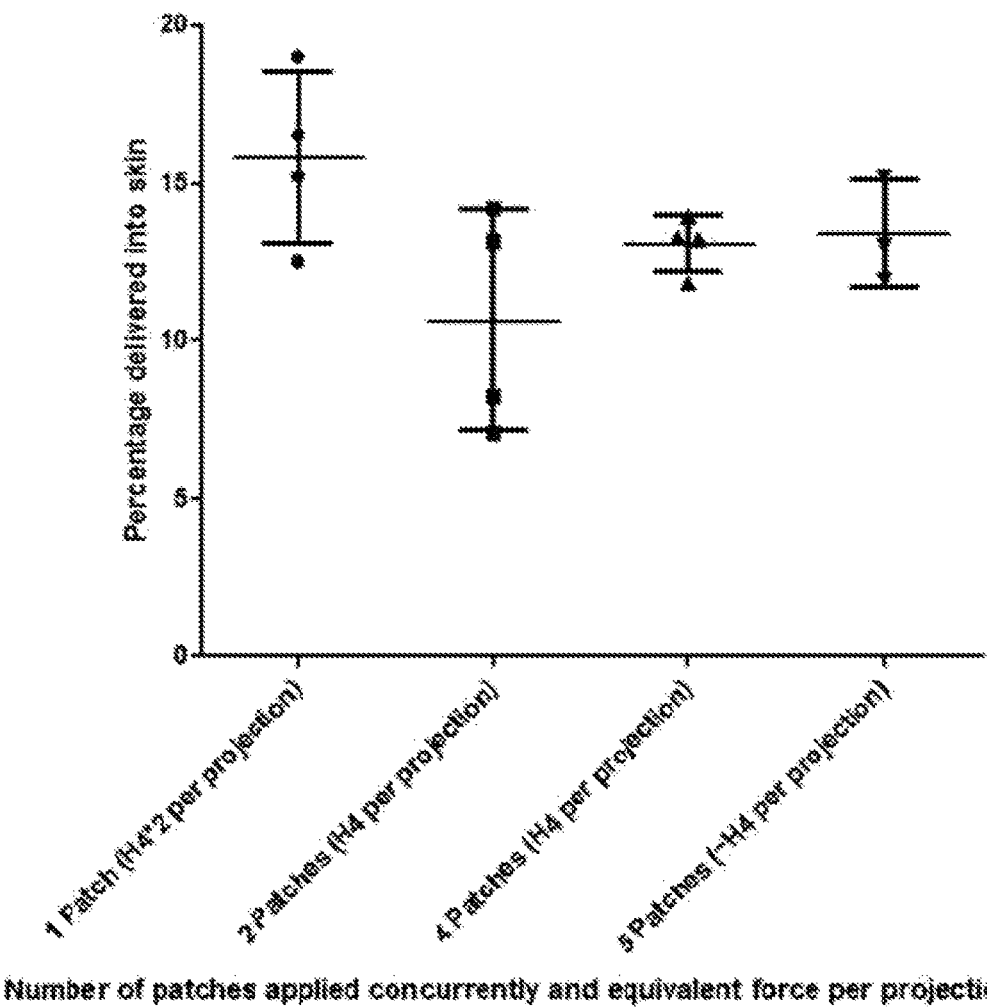
FIG. 45 is a graph of an example of the effect of maintaining a constant force per projection during application of patches to surrogate skin.

The effect of maintaining a constant force per projection during application of patches to skin is shown in FIG. 45. This demonstrates that regardless of the area of a projection array, the percentage of material delivered into the skin remains constant (for a given application energy defined as H4 for this study). Each patch in this study is 4×4 mm in size with multiple patches being used to provide different surface areas.

Figure 46:
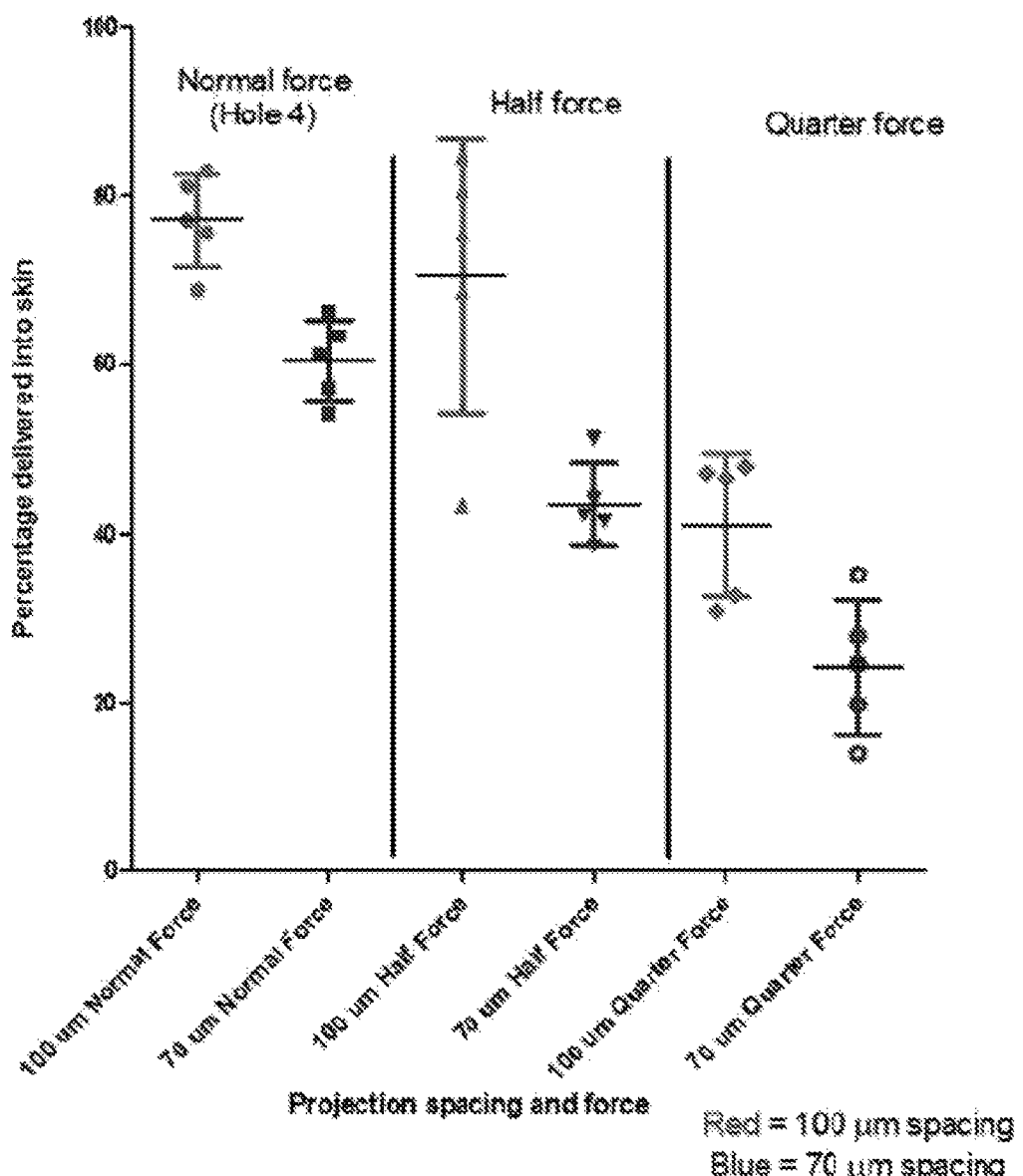
FIG. 46 is a graph of an example of a comparison of different projection spacings and their relative delivery of payload into the skin.

A comparison of using 100 μm or 70 μm spaced projections, and their relative delivery of payload into the skin, for different application forces, is shown in FIG. 46. This highlights that in general a reduction in force reduces payload delivery, whilst a greater spacing has an increased delivery, particularly at lower application forces (and hence energies). In this case, for a given condition of delivery into a skin surrogate, a 10,000 per cm² array requires half the application force of a 20,000 per cm² array.

Figure 47:
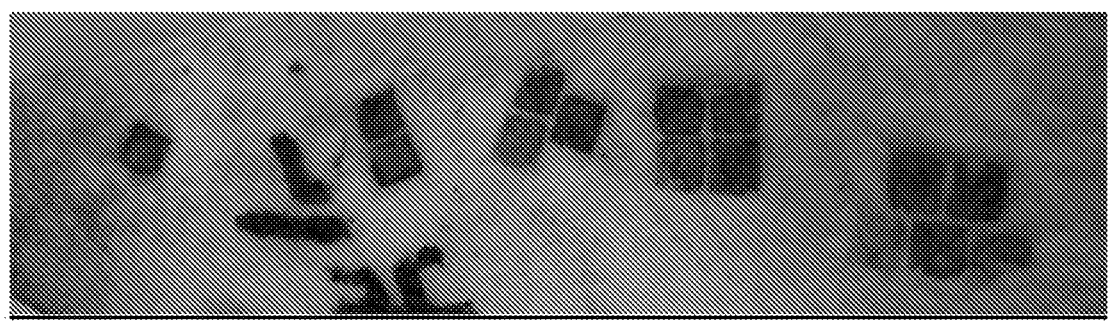
FIG. 47 shows example images of a number of patches with a projection matched application force on pig skin.

Example images of a number of patches with a projection matched application force on pig skin are shown in FIG. 47, further highlighting that larger area patches require higher application forces.

Neutrophil Infiltration

Further experiments have been conducted to characterise the local immunological interactions within skin as a result of application of the projection patch. These interactions include physical cell death and adjuvantation.

Specifically, projection patches have been applied to mouse ear skin, with coated with vaccines (such as Fluvax 2011) and/or methylcellulose (MC), and also without coatings. Intradermal (ID) delivery of vaccine was also performed as a control. Observations were made regarding the infiltration of neutrophils in to the skin in each case.

The findings of these experiments are summarized below, and further details of the experimental approach and specific observations will follow.

Cells with neutrophil-like phenotype including CD11b+ Ly6C+Ly6G+ cells have been found to infiltrate mouse ear skin after delivery of Fluvax 2011 vaccine coated on a projection patch. When an uncoated projection patch is used, it was found that a lower number of neutrophils also infiltrate.

These neutrophil cells are present at 24 hours post application in high numbers, and lower numbers at 4 hours post application (with the same trend). Preliminary experiments indicate that the peaks of neutrophil cell numbers occur at around 24 hour post application, decreasing to naive level by about 72 hours.

The combined stimulus provided by application of the patch coated with a vaccine induced more neutrophils at the 24 hour time point compared to application of the uncoated patch. However, at the 4 hour time point, the number of neutrophils for coated projection and uncoated projections was similar. This is believed to suggest that the influencing factor at the early time point was similar in both these groups, i.e. damage caused by projections.

The neutrophil numbers were boosted at 24 hours post application in cases where the projections were coated solely with a vaccine, and less so in the uncoated cases and in cases where the projections were coated with methylcellulose (MC). This is considered to support the theory that immunological response is improved by 'co-localisation' of antigen with cell death caused by a projection patch. This theory has been explored further in additional experiments discussed below.

Neutrophil infiltration has been observed 5 times using a Fluvax 2011 vaccine and once using a different vaccine, namely OVA protein. It is noted that lower numbers of neutrophils infiltrated in the latter case—this was expected as Fluvax contains highly immunostimulatory viral PAMPs and OVA does not.

No neutrophil infiltrate was observed with ID delivery of either vaccine. It is considered that this is likely to be because the vaccine is rapidly transported to the lymph node under ID delivery, and so has little direct contact with the skin environment before draining to the lymph node. However, it has been noted that neutrophils do infiltrate the skin when ID vaccine is given with Quil A adjuvant.

Since Quil A is a saponin and causes damage to cell membranes it is believed that the mechanism of adjuvant action is, or is influenced by, cell death. Accordingly, it is theorized that the projection patch and Quil A act in similar ways to provide adjuvant responses. This may be via a mechanism involving or coinciding with the infiltration of neutrophils. This theory is currently under evaluation.

It is also noted that the primary neutrophil chemo-attractant molecule CXCL1 is up-regulated in patched skin compared to naive. This means that after patch application, mediators are expressed in the skin, which allows neutrophils to enter. This could either be by skin cells that have transduced damage signals/alarmins or as a positive feedback mechanism by neutrophils that have already reached the skin.

Detailed results of these experiments, supporting the above findings, will now be outlined.

Figure 48A:
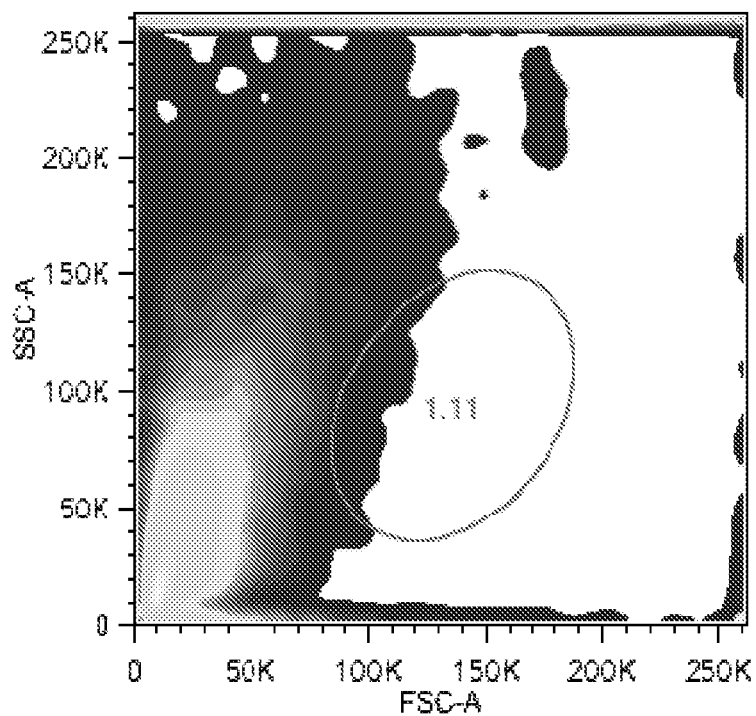
FIGS. 48A to 48C are fluorescence-activated cell sorting (FACS) plots showing side scatter versus forward scatter for cell populations present in mouse skin 24 hours after Fluvax immunisation using different methods.
Figure 48B:
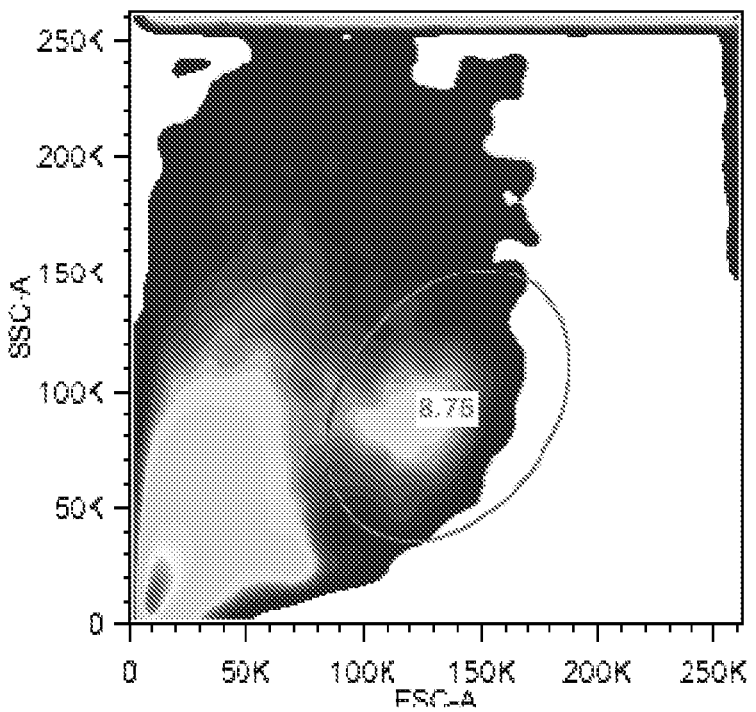
Figure 48C:
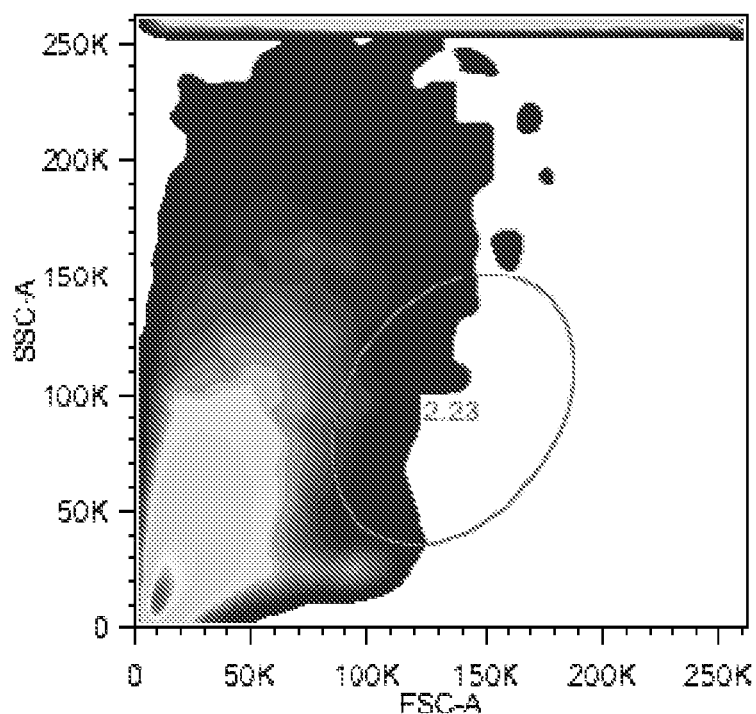

The fluorescence-activated cell sorting (FACS) plots of FIGS. 48A to 48C demonstrate the presence of an extra population of cells in the skin of mouse ears following projection patch immunisation. These plots were generated from cell distribution results of the first experiment of this kind performed. In each plot, the horizontal axis corresponds to side scatter (granularity) and the vertical axis corresponds to forward scatter (size). These results have been found to be repeatable, and have been observed a total of 5 times to date.

FIG. 48A shows the results for intradermal application to the a mouse ear, and FIG. 48B shows the results for projection patch application to a mouse ear. These results were taken 24 h after application of the projection patch with Fluvax 2011 coated projections, and a delivered dose of 162 ng per projection patch. FIG. 48C represents a naive case.

An extra population of cells in the skin after projection patch application can be observed in FIG. 48B, which is absent in naive and ID immunised skin. The population has been circled in plot 48B, and a region corresponding to this region has been circled in FIGS. 48A and 48C to facilitate comparison.

FIGS. 49A to 49D show dead cell marker negative cell plots of the above mentioned experimental results, in which the horizontal axis corresponds to CD11c and the vertical axis corresponds to CD11b.

Figure 49A:
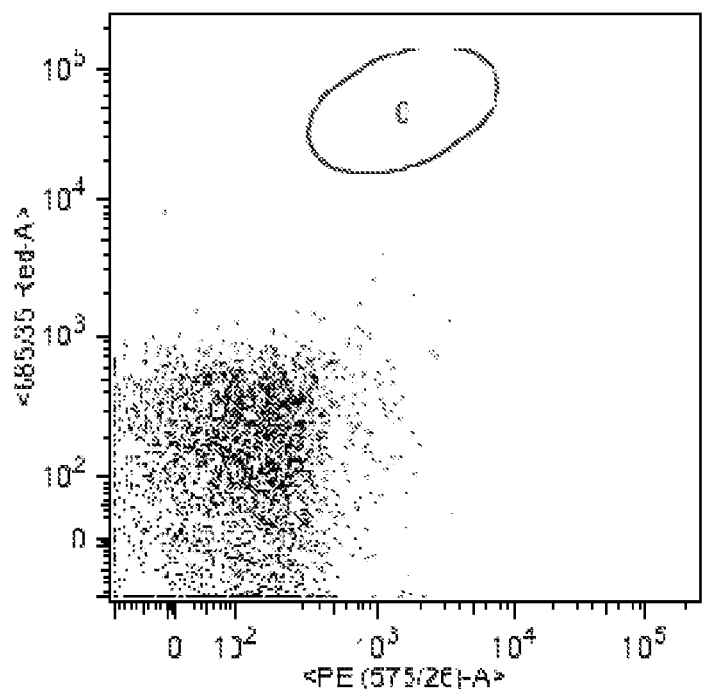
FIGS. 49A to 49D are FACS plots showing CD11c versus CD11d markers for cell populations present in mouse skin 24 hours after Fluvax immunisation using different methods.
Figure 49B:
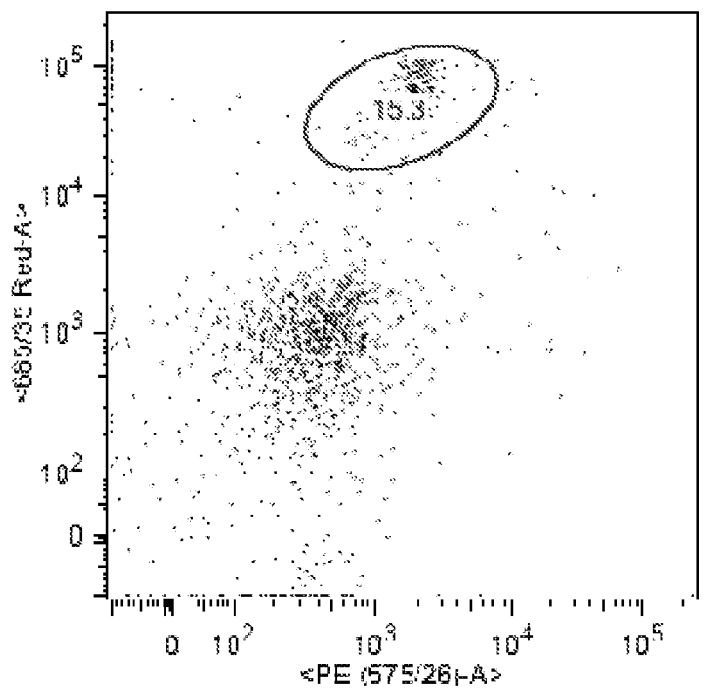

FIG. 49A shows an unstained reference case in which none of the extra population is present. FIG. 49B shows the intradermal case, FIG. 49C shows the results for projection patch application and finally, FIG. 49D illustrates the naive case.

Figure 49C:
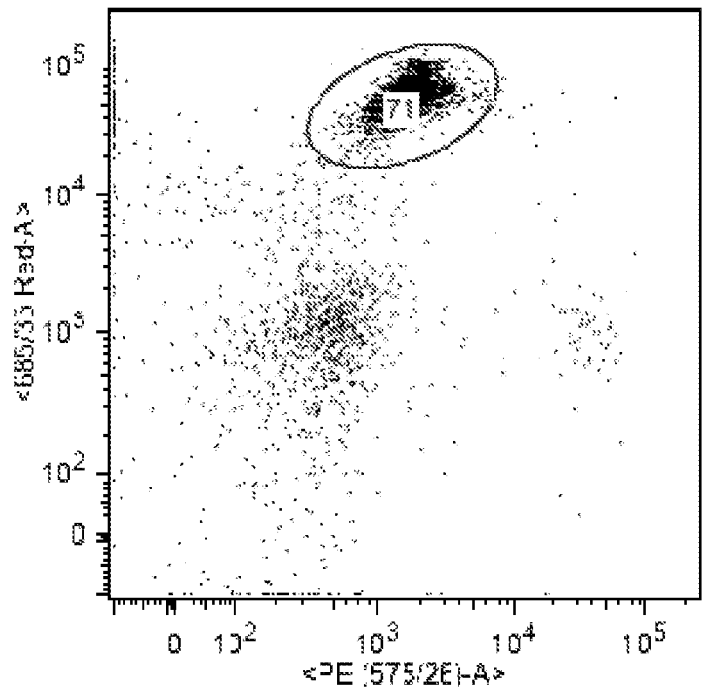
Figure 49D:
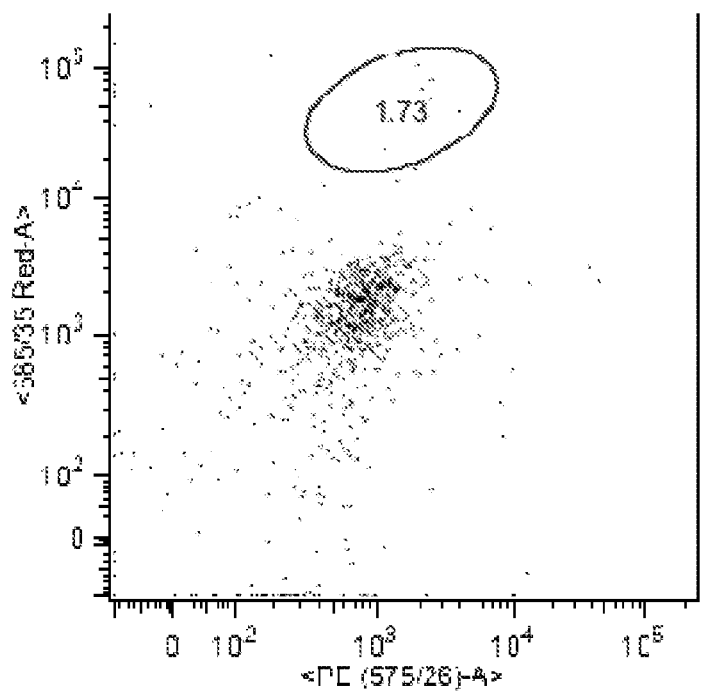

As can be seen in FIG. 49C, the extra population of cells were found to be CD11b+ and CD11c−, i.e. of myeloid origin but not DC.

Figure 50A:
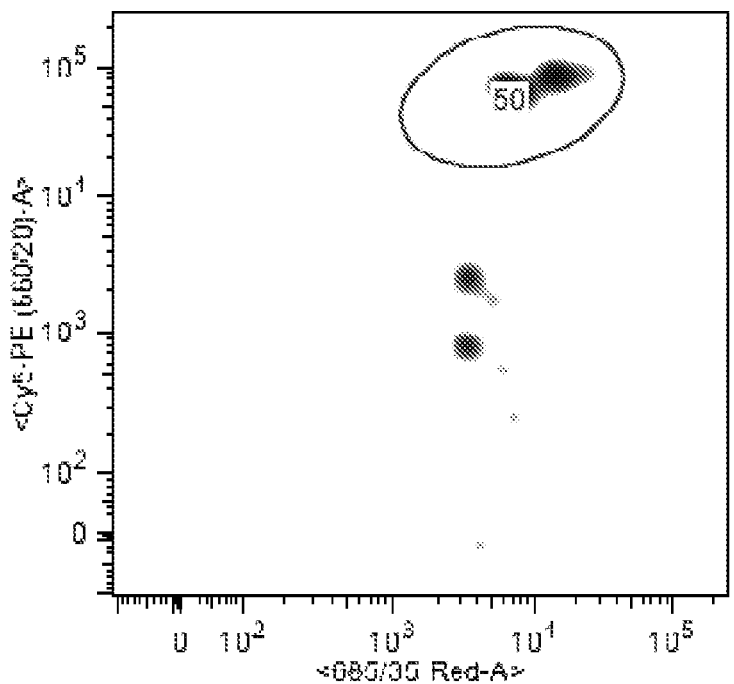
FIGS. 50A to 50C are FACS plots showing CD11b versus Ly6G markers for cell populations present in mouse skin 24 hours after Fluvax immunisation using different methods.
Figure 50B:
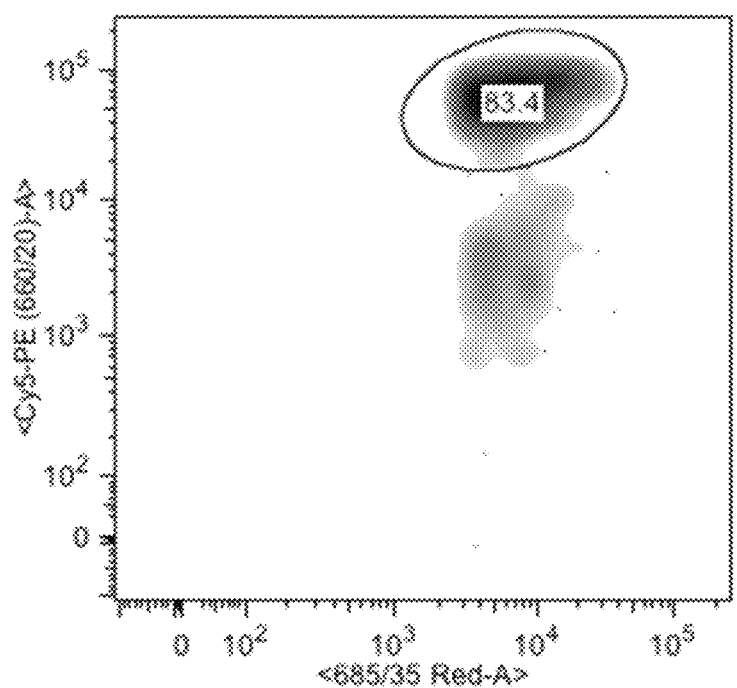
Figure 50C:
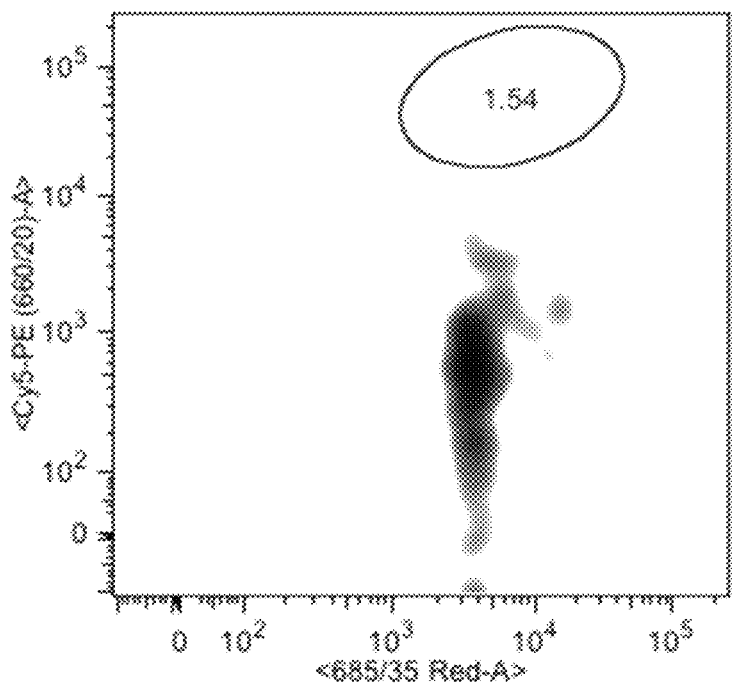

The plots of FIGS. 50A to 50C show further cell marker plots, in which the horizontal axis corresponds to CD11b and the vertical axis corresponds to Ly6G.

In this case, FIG. 50A shows the intradermal case, FIG. 50B shows the projection patch application case, and FIG. 50C illustrates the naive case. From these plots it can be seen that a majority of the extra population of the CD11b+ cells are also Ly6G+(neutrophil marker).

Figure 51:
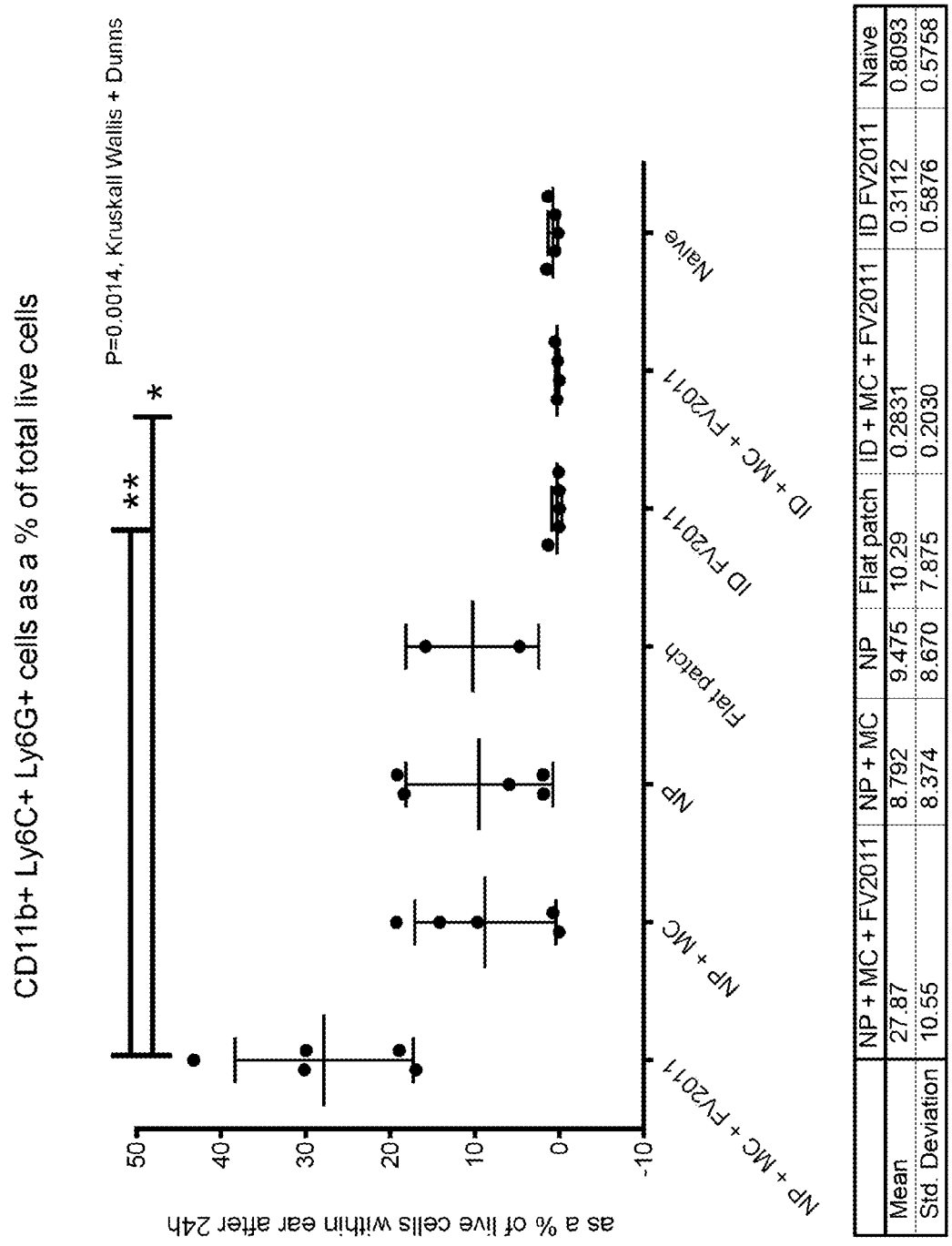
FIG. 51 shows a graph of CD11b+Ly6C+Ly6G+ cells as a percentage of total live cells within mouse ears 24 hours after Fluvax immunisation using different methods.

Repeat experiments were performed with N=5, including extra treatment groups. Two ears per mouse were pooled in this experiment, both ears being treated. FIG. 51 shows a plot of CD11b+Ly6C+Ly6G+ cells as a percentage of total live cells, within the mouse ears 24 hours after application/immunisation, whereas FIG. 52 shows the total number of CD11b+Ly6C+Ly6G+ cells per two mouse ears pooled.

Figure 52:
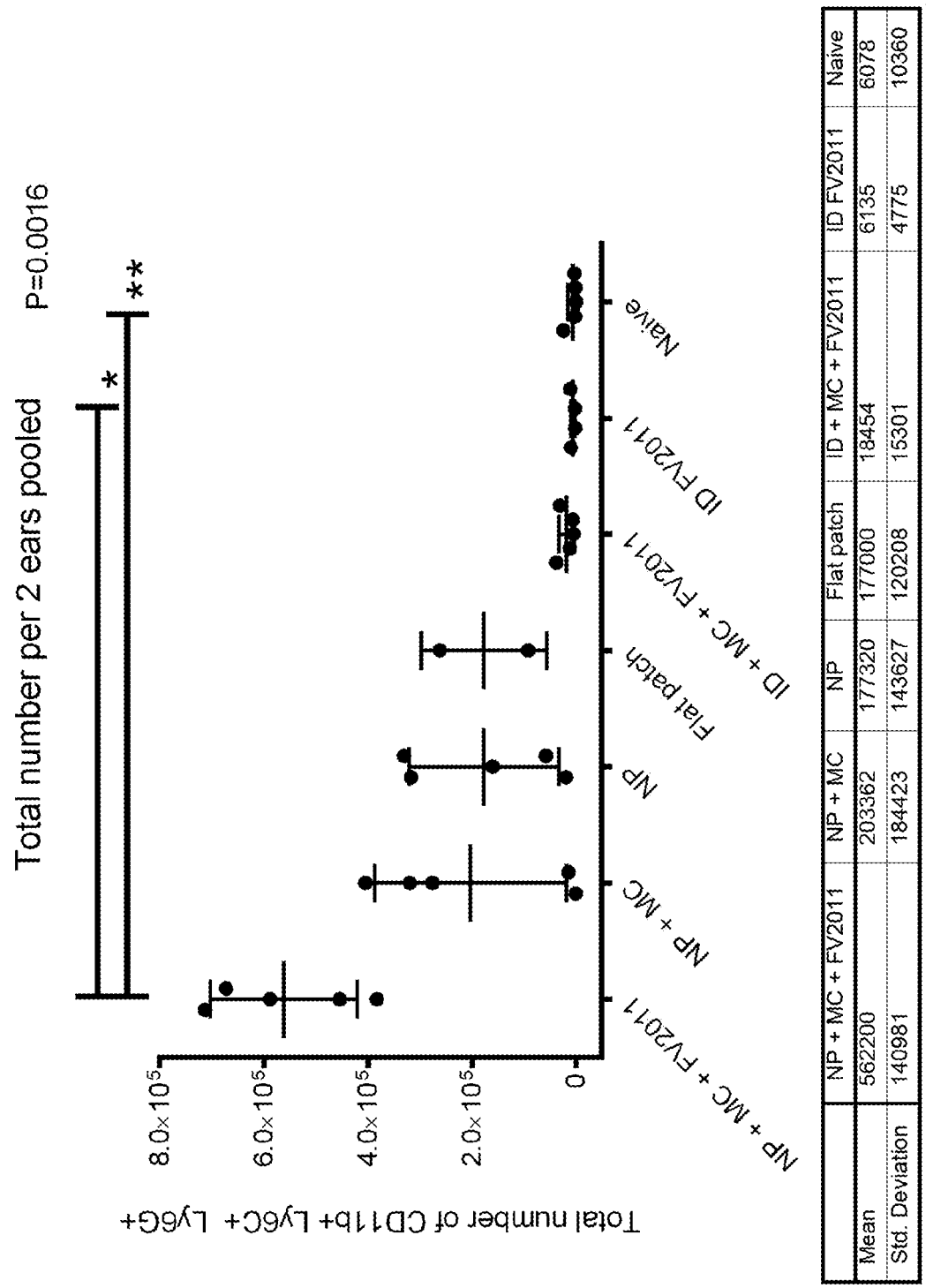
FIG. 52 shows a graph of total number of CD11b+Ly6C+Ly6G+ cells per two mouse ears pooled within 24 hours after Fluvax immunisation using different methods.

The treatment groups as indicated in FIGS. 51 and 52 were as follows:
  NP+MC+FV2011: application of projection patch coated with methylcellulose and Fluvax 2011 coating;
  NP+MC: application of projection patch coated with methylcellulose coating only;
  NP: application of uncoated projection patch;
  Flat patch: application of a flat patch, i.e. no skin-penetrating projections;
  ID FV2011: intradermal delivery of Fluvax 2011 vaccine;
  ID+MC+FV2011: intradermal delivery of methylcellulose and Fluvax 2011 vaccine; and,
  Naive: naive control cases.

It is noted that this experiment included a second neutrophil marker Ly6C. Double staining for Ly6G and Ly6C strongly distinguishes neutrophils from other CD11b+ cells in flow cytometry. The extra populations of cells were also found to be negative for markers for B cells, DCs, and macrophages.

The most significant result here is that neutrophils also migrate in to the skin in the cases where projection patches are applied without any coated vaccine, although fewer than when vaccine is delivered. It is believed that intradermally delivered vaccine does not stay in the skin long enough to generate an inflammatory response, i.e. there is no neutrophil infiltration.

Figure 53:
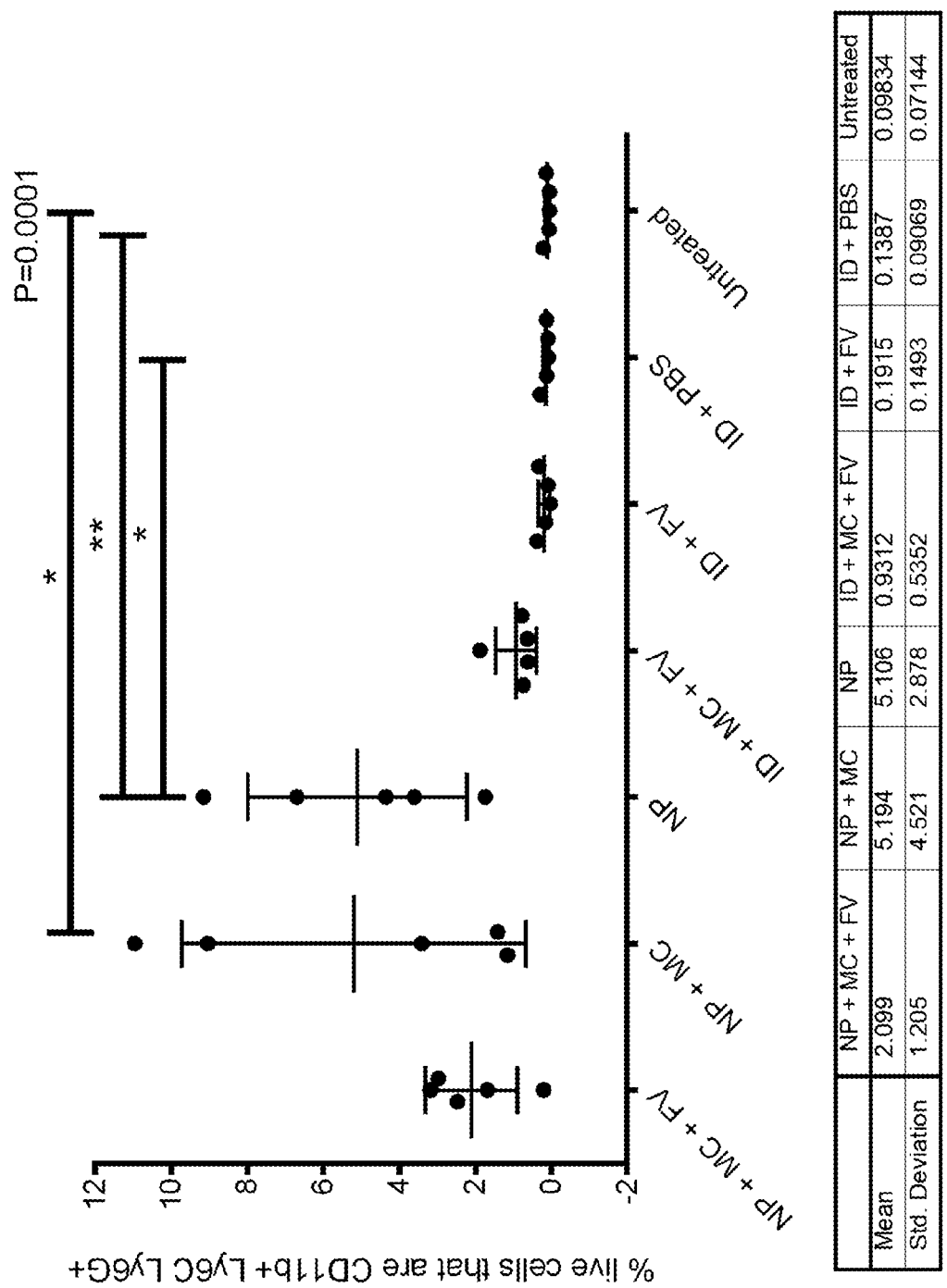
FIG. 53 shows a graph of CD11b+Ly6C+Ly6G+ cells as a percentage of total live cells within mouse ears 4 hours after Fluvax immunisation using different methods.
Figure 54:
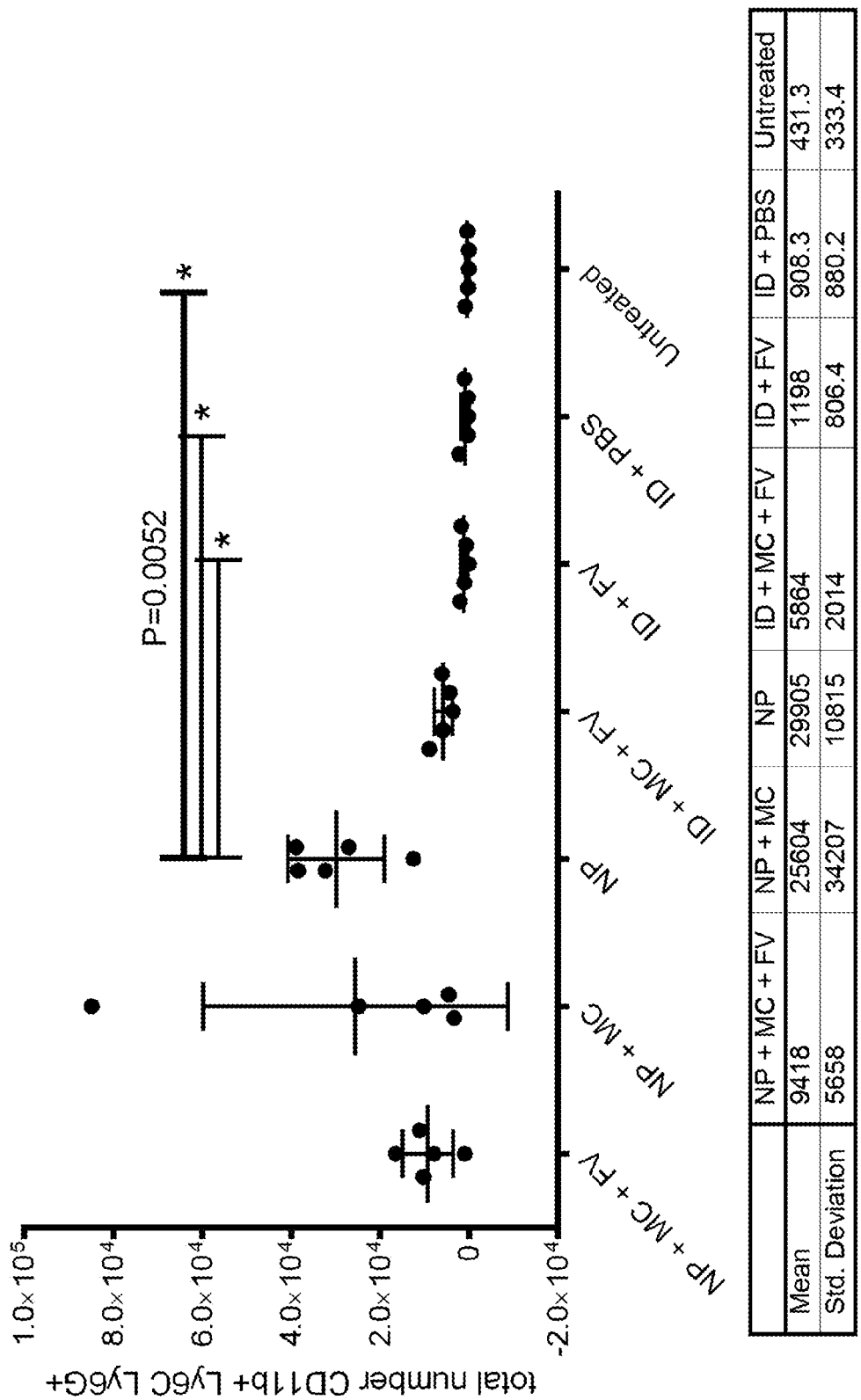
FIG. 54 shows a graph of total number of CD11b+Ly6C+Ly6G+ cells as a per two mouse ears pooled within 4 hours after Fluvax immunisation using different methods.

The above discussed FIGS. 51 and 52 show results 24 hours post application/immunisation. Similarly obtained results at only 4 hours post application/immunisation are shown in FIGS. 53 and 54. Specifically, FIG. 53 shows a plot of CD11b+Ly6C+Ly6G+ cells as a percentage of total live cells, within the mouse ears 4 hours after application/immunisation, whereas FIG. 54 shows the total number of CD11b+Ly6C+Ly6G+ cells per two mouse ears pooled at the same 4 hour time point.

The results of FIGS. 53 and 54 indicate that neutrophils are present in the skin within 4 hours of projection patch application. Accordingly, it would appear that neutrophils are infiltrating immediately.

Unlike at 24 hours post application, the number of neutrophils when vaccine is delivered by a projection patch is similar to when a projection patch is applied without a vaccine coating, at the 4 hour time point. This may suggest that the early neutrophil cell infiltration is 'damage specific' rather than 'pathogen specific' and that the increased number of neutrophils at 24 h when vaccine is coated is due to pathogen specific infiltration, seemingly occurring slightly later.

Figure 55:
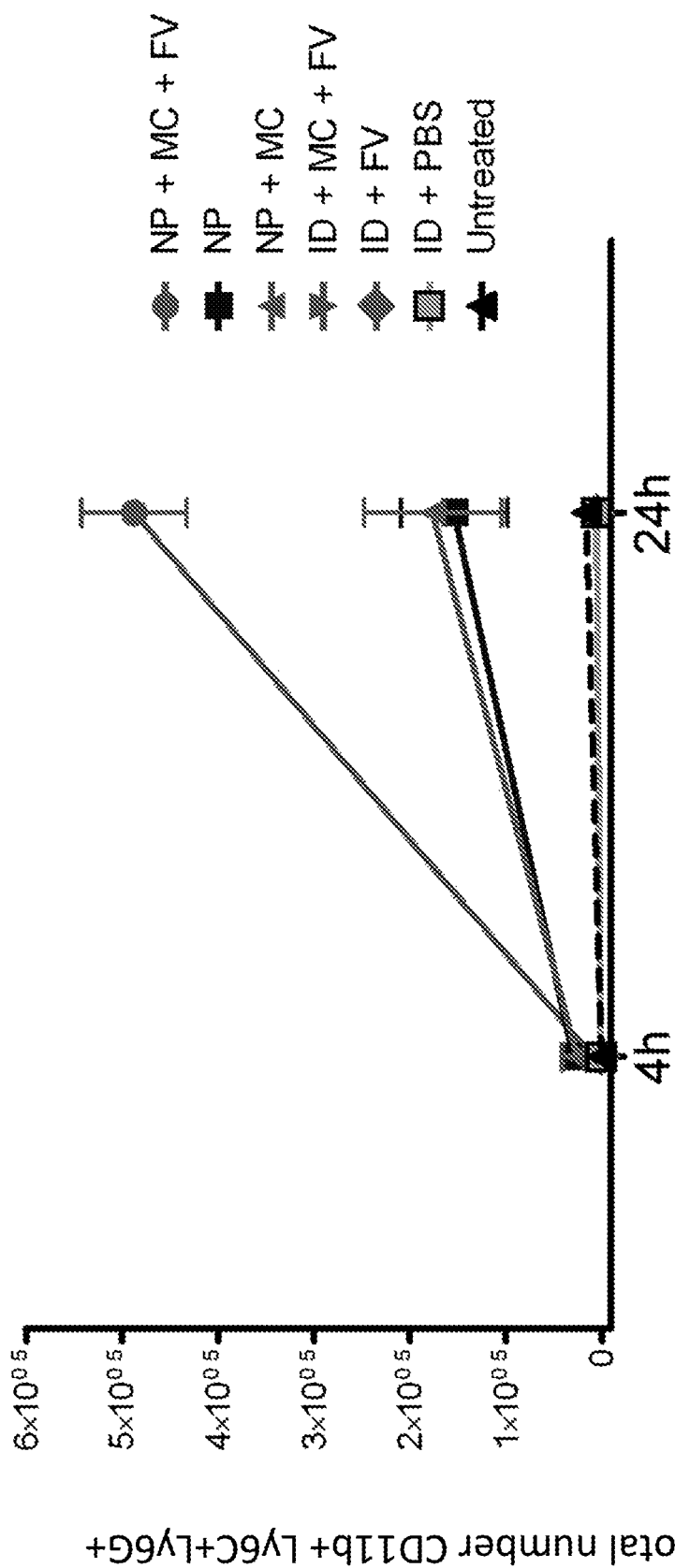
FIG. 55 shows a graph comparing the total number of CD11b+Ly6C+Ly6G+ cells within mouse ears 24 hours and 4 hours after Fluvax immunisation using different methods.

A comparison between the 24 hour and 4 hour data discussed above is shown in FIG. 55. This illustrates the scale of changes post application/immunisation.

As mentioned previously, the number of neutrophils rises more rapidly in the cases where the Fluvax vaccine is delivered with the projection patch. This is considered to be due to a "co-localisation" of immunological effects due to cell damage and the vaccine. This may promote synergy between the DAMP (damage-mediated) and PAMP (vaccine-mediated) signalling mechanisms as observed in the vaccine coated projection patch cases. In contrast, in the projection patch cases without vaccine (NP/NP+MC) the signalling mechanism may be restricted to DAMP only. PAMP influence appears to initiate later than DAMP (between 4 and 24 h), as indicated in the comparison results.

It has also been found that neutrophils infiltrate after OVA protein immunisation (using a different mouse strain). However, there are fewer extra cells than for Fluvax. Two arms of experiments have been conducted with respect to OVA protein and Fluvax to facilitate comparison, and to compare the adjuvant effect against Quil A adjuvant for each. Results are outlined below.

Representative FACS plots for the OVA arm of this body of experiments can be seen in FIGS. 56A to 56F. The horizontal axis corresponds to Ly6C and the vertical axis corresponds to Ly6G in each plot.

Figure 56A:
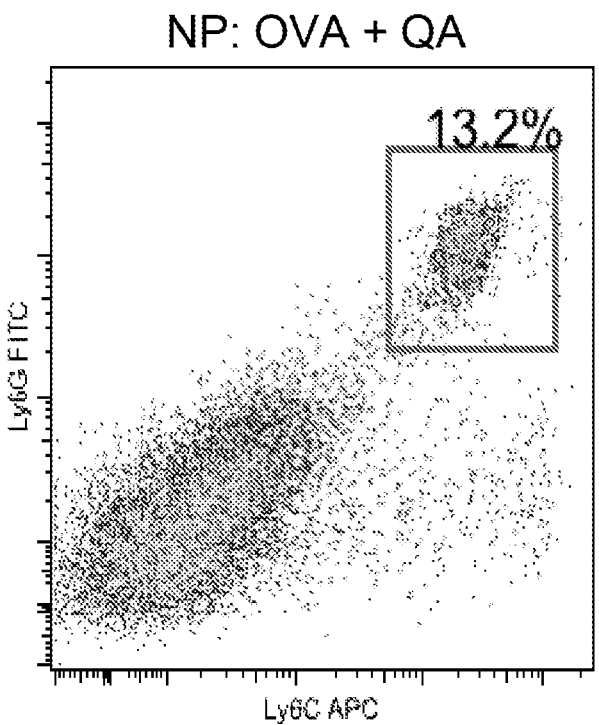
FIGS. 56A to 56F are representative FACS plots showing Ly6C versus Ly6G markers for cell populations present in mouse skin 24 hours after OVA protein immunisation using different combinations of methods and Quil A.
Figure 56B:
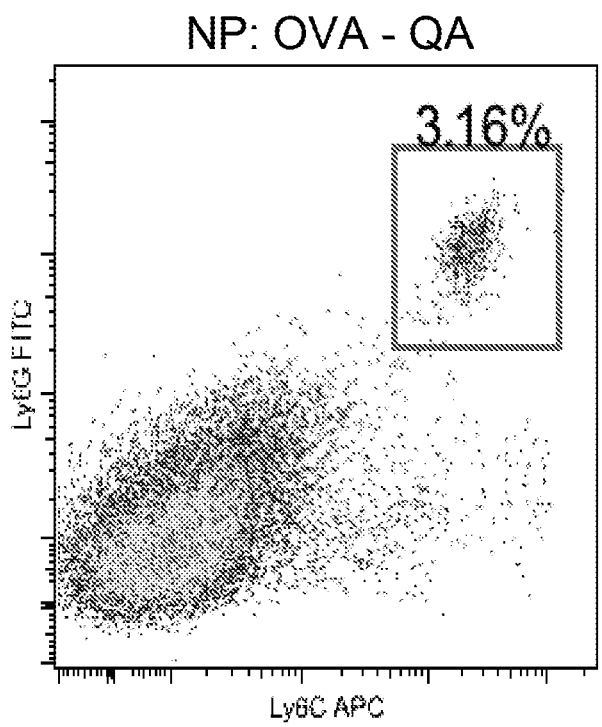
Figure 56C:
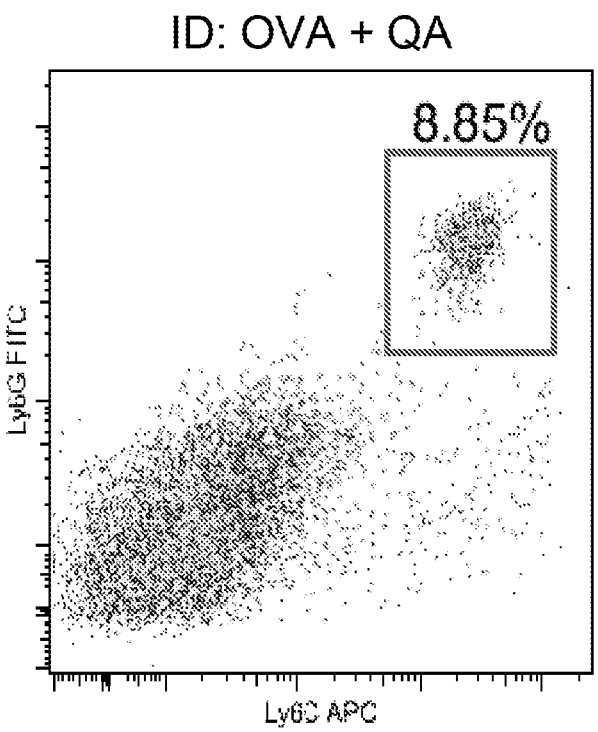
Figure 56D:
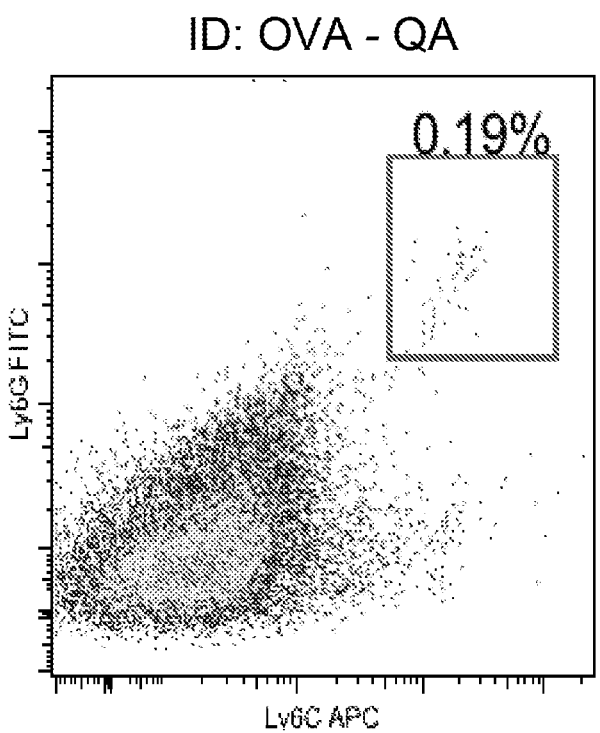
Figure 56E:
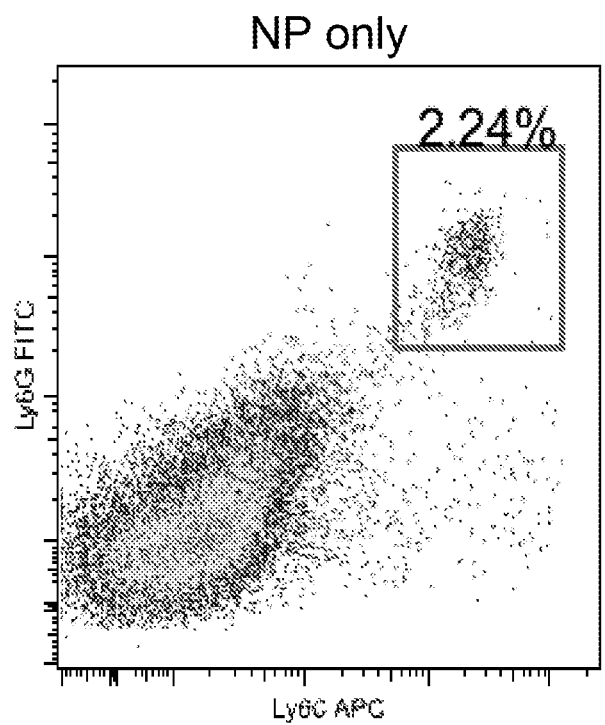
Figure 56F:
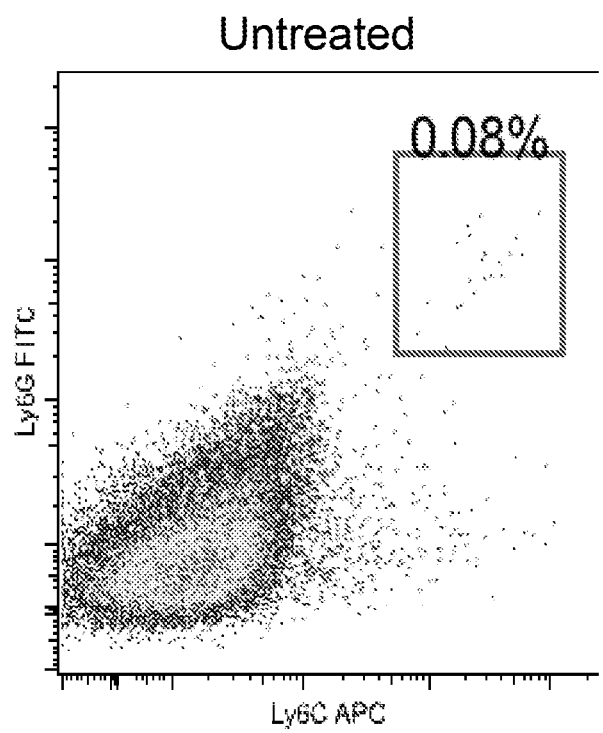

Two plots are provided for each immunisation delivery mode (projection patch or intradermal)—one for OVA protein immunisation with Quil A adjuvant, and one without. FIGS. 56A and 56B relate to projection patch OVA protein immunisation, with and without Quil A, respectively. FIG. 56C and FIG. 56D relate to intradermal delivery of OVA protein with and without Quil A, respectively. FIG. 56E relates to application of an uncoated projection patch, and FIG. 56F is for the untreated case.

Figure 57A:
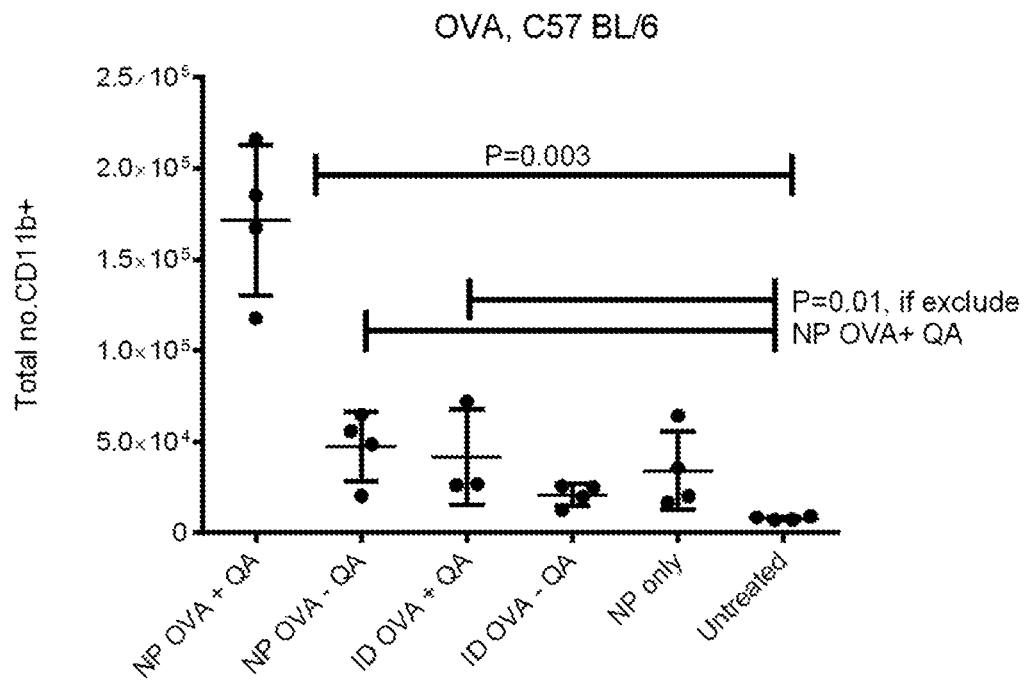
FIGS. 57A and 57B are respective graphs of the total number of CD11b+ cells, and the total number of Ly6C+Ly6G+ cells as a percentage of the total number of live cells within mouse ears 24 hours after OVA protein immunisation using different combinations of methods and Quil A.
Figure 57B:
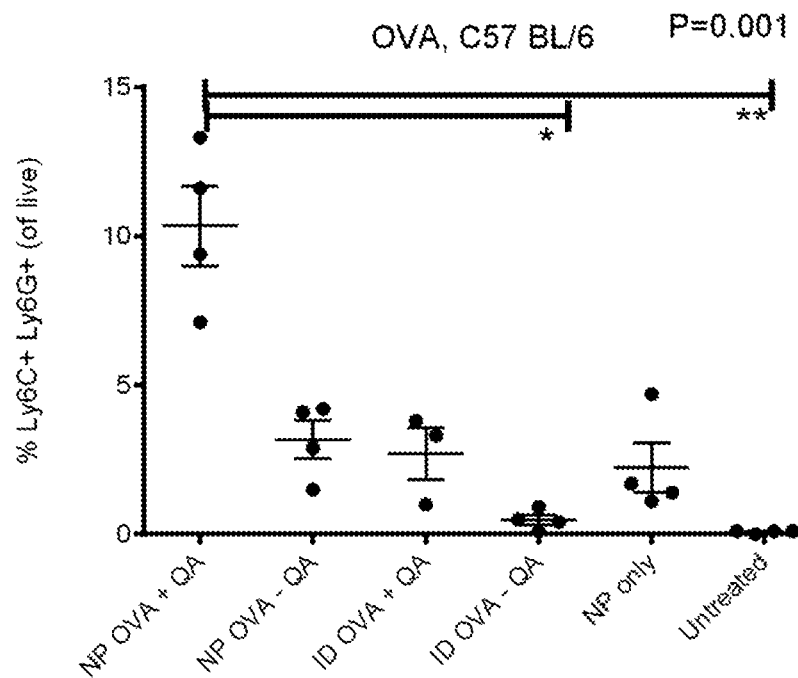

Repeat experiments with N=4 were performed for the above discussed OVA protein immunisation scenarios, and the results are collated in FIGS. 57A to 57B. FIG. 57A shows a plot of the total number of CD11b+ cells after immunisation, whereas FIG. 57B shows the total number of Ly6C+ Ly6G+ cells as a percentage of the total number of live cells.

As can be seen in these results, neutrophils do not infiltrate after intradermal immunisation unless Quil A is added. In general, the number of neutrophils increases when Quil A is added. However, it is also observed that projection patch results without Quil A exhibit neutrophil infiltration of a similar scale to the intradermal injection with Quil A. It is thus theorized that the projection patch adjuvantation may have a similar mode of action to that of Quil A.

It is noted that Quil A is a saponin and is likely to cause damage to cell membranes—stimulating the release of alarmins, damage associated danger signals, etc. Previous research has suggested that the mechanism of adjuvantation of alum and iscomatrix (which also induces neutrophils) is by cellular damage and activation of the NALP3 signalling pathway. It is believed that similar signalling mechanism may be activated by the projection patch, but with physical rather than chemical adjuvantation.

Representative FACS plots of the Fluvax arm of this experiment are shown in FIGS. 58A to 58F, similar to those shown in FIGS. 56A to 56F. The horizontal axis corresponds to Ly6C and the vertical axis corresponds to Ly6G.

Figure 58A:
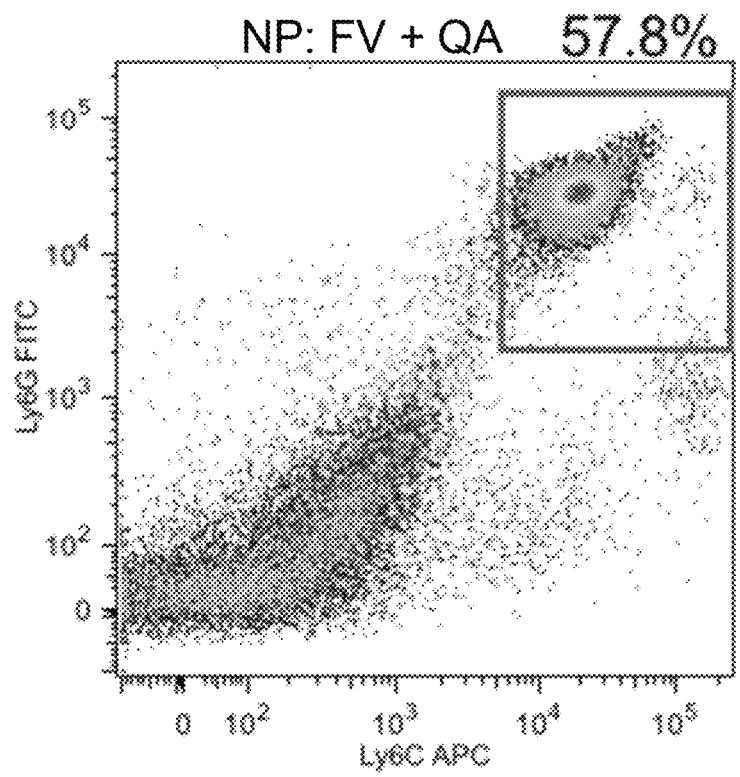
FIGS. 58A to 58F are representative FACS plots showing Ly6C versus Ly6G markers for cell populations present in mouse skin 24 hours after Fluvax protein immunisation using different combinations of methods and Quil A.
Figure 58B:
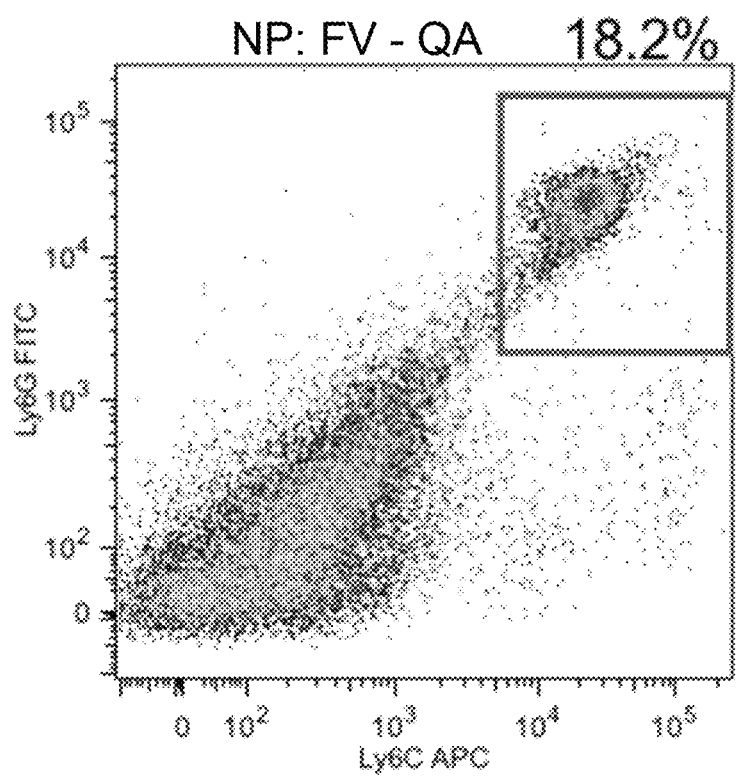
Figure 58C:
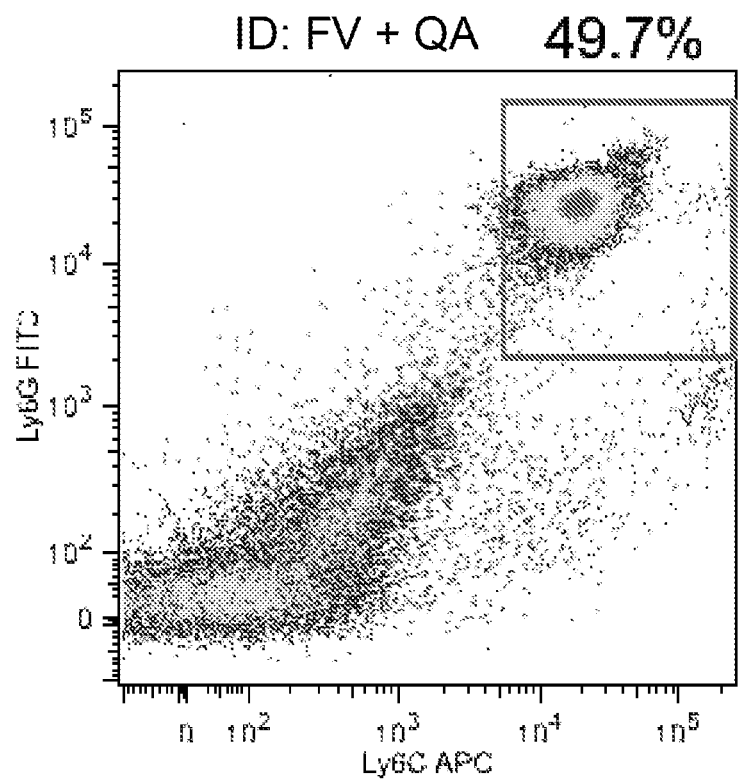
Figure 58D:
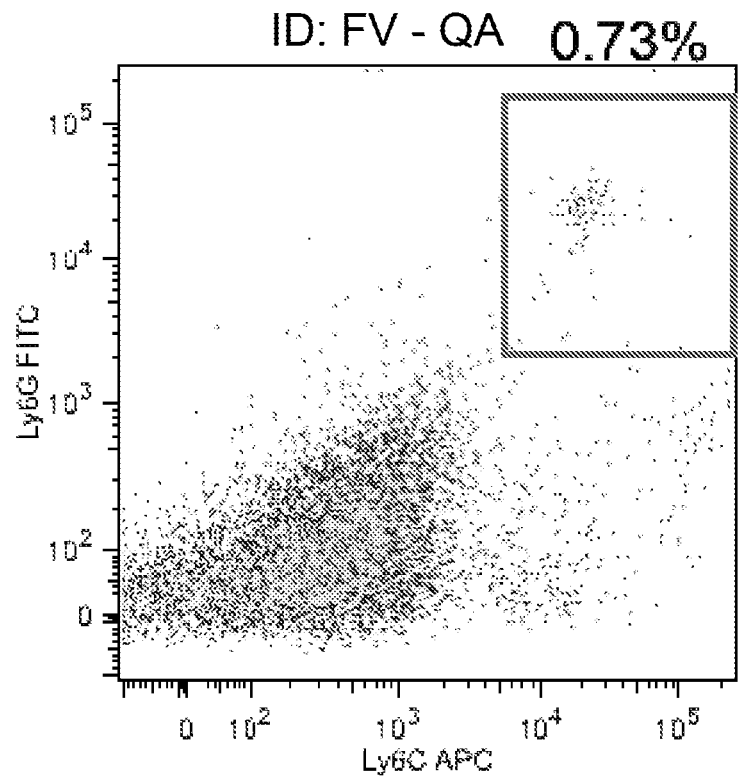
Figure 58E:
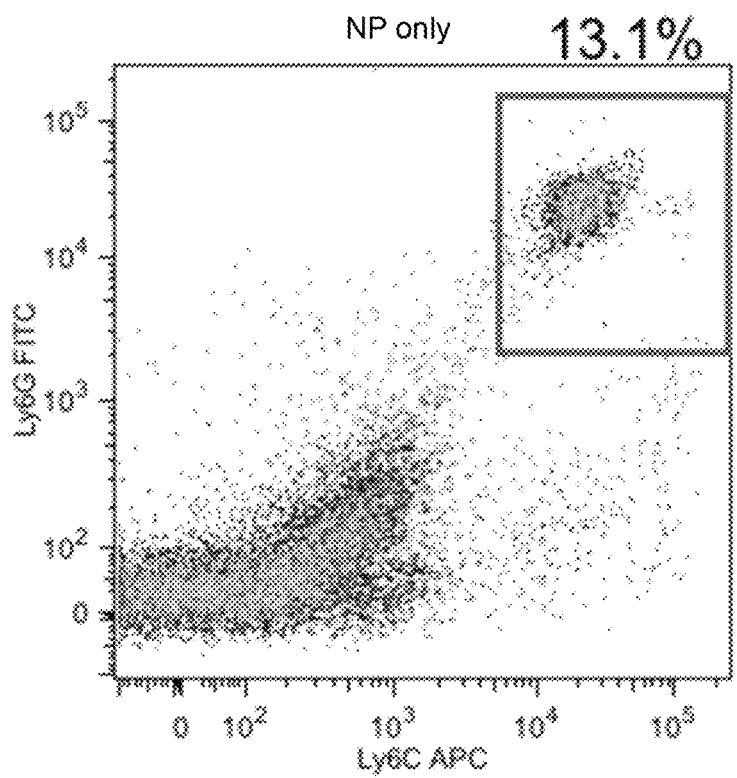
Figure 58F:
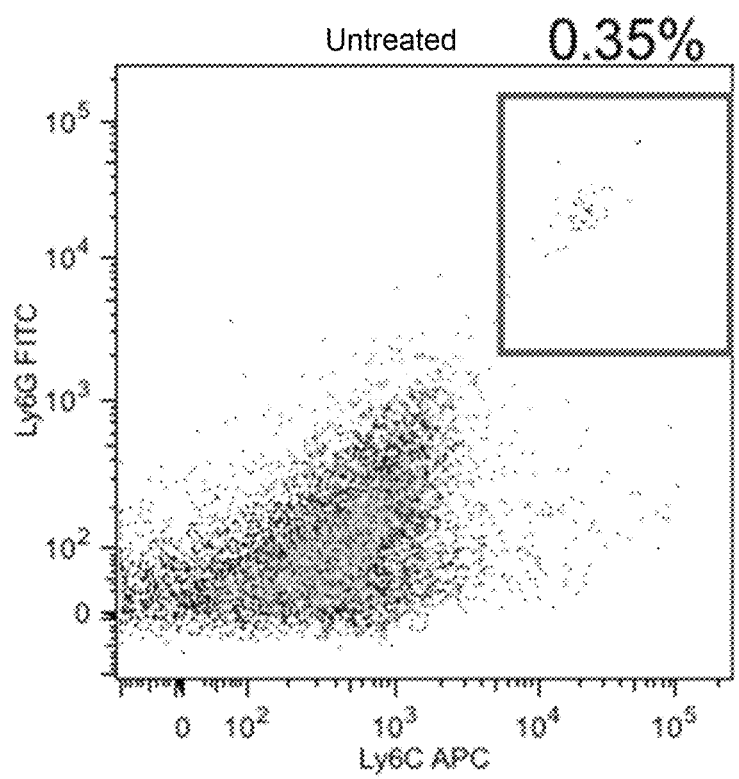

FIGS. 58A and 58B relate to projection patch Fluvax, with and without Quil A, respectively. FIG. 58C and FIG. 58D relate to intradermal delivery of Fluvax vaccine with and without Quil A, respectively. FIG. 58E relates to application of an uncoated projection patch, and FIG. 58F is for the untreated case.

Figure 59A:
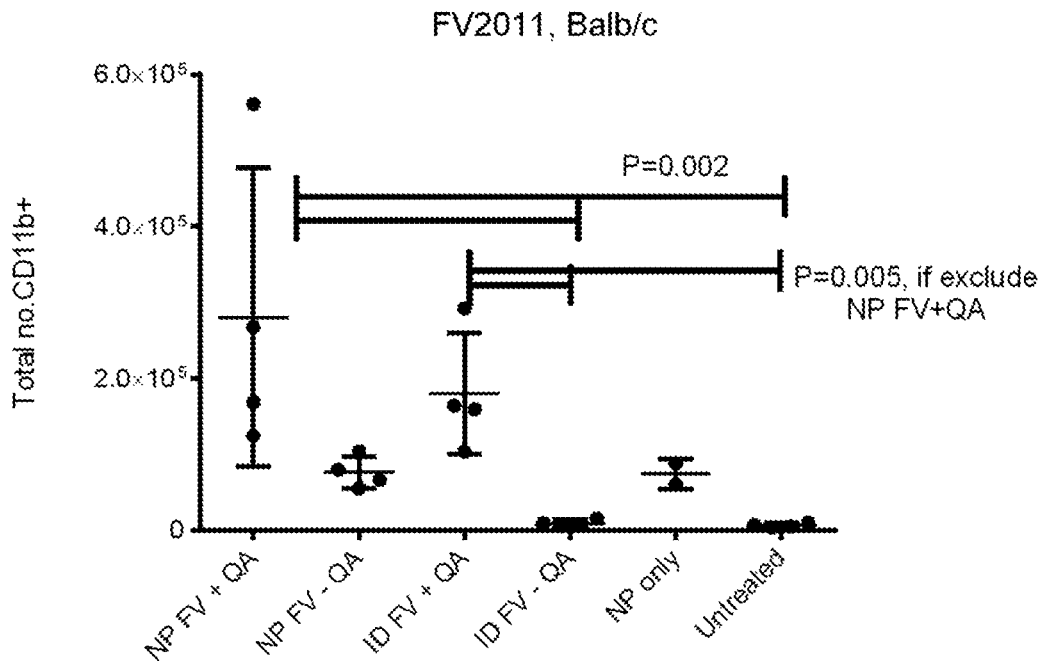
FIGS. 59A and 59B are respective graphs of the total number of CD11b+ cells, and the total number of Ly6C+Ly6G+ cells as a percentage of the total number of live cells within mouse ears 24 hours after Fluvax immunisation using different combinations of methods and Quil A.
Figure 59B:
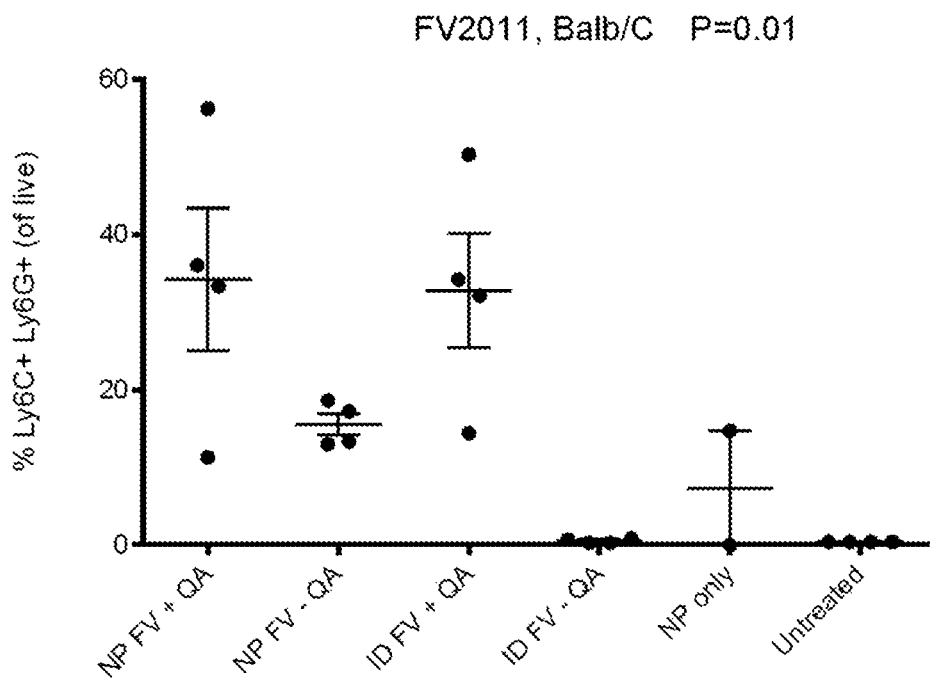

Similar observations have also been made for Fluvax immunisation scenarios, as supported by FIGS. 59A to 59B. FIG. 59A shows a plot of the total number of CD11b+ cells after immunisation with Fluvax 2011, whereas FIG. 59B shows the total number of Ly6C+Ly6G+ cells as a percentage of the total number of live cells. Generally similar treatment groups have been used, i.e. Fluvax 2011 with or without Quil A using projection patches or intradermal delivery, alongside cases using uncoated projection patches and untreated.

Again, it can be seen that the projection patch treatments induce a level of neutrophil infiltration that is not seen in the intradermal treatments unless Quil A is present.

It is also noted that the data from these further Fluvax experiments supports the data collated from the earlier experiments described with reference to FIGS. 51 and 52, showing that the results are repeatedly observed. In fact, the findings have been repeated a total of 5 times to date (6 times including the 4 hour time point).

Further experiments were performed to determine the time course of neutrophils from 24 hours to 72 hours post application of a projection patch coated with Quil A versus a naive case. In particular, changes in the total number of Ly6C+ and Ly6G+ were observed post application. It was found that neutrophils were present not only at 24 hours, but also at 48 hours and 72 hours after application of the projection patch. The results indicated that neutrophil numbers peaked at 24 hours and decreased down to naive level by 72 hours.

Figure 60:
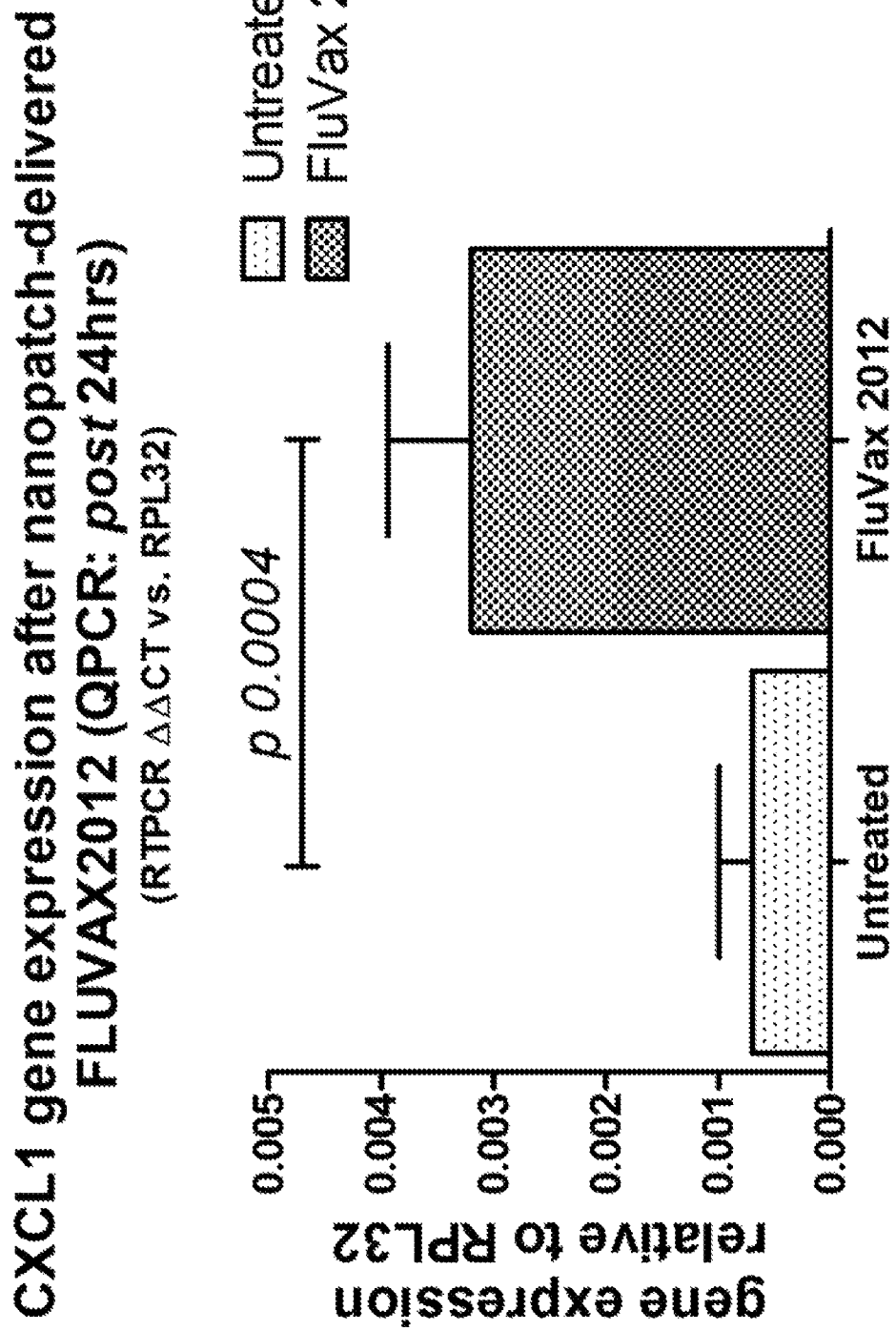
FIG. 60 shows a graph of CXCL1 gene expression 24 hours after Fluvax protein immunisation using a projection patch.

Additional experiments have been conducted to determine CXCL1 gene expression 24 hours after the application of a projection patch coated with Fluvax 2012 vaccine, and these results are shown in FIG. 60. In this regard, it is noted that CXCL1 is a chemokine involved in the attraction of neutrophils from the circulation into inflamed tissues. It has been found that CXCL1 mRNA is significantly up-regulated in the skin after vaccination using a projection patch (relative to a housekeeping gene constitutively expressed), compared to the naive case.

Correlation Between Tissue Stress and Cell Death

As discussed above, it has been found that localised cell death in the vicinity of projections penetrating tissues may induce an improved immunological response compared to traditional intradermal needle and syringe injections.

It is hypothesized that excessive stress within the tissue causes cell death. Further experiments have been performed to allow correlations between tissue stress and cell death to be determined. General findings of these experiments will be outlined, followed by a detailed discussion of the specific experimental results.

A series of experiments involving the static application of a flat punch have been conducted to controllably induce stress in the surrounding tissues. Cell death was seen to occur at the edges of the punch only, where cells experience high stress levels. It was observed that negligible cell death took place at a 0.15 kg static load but the extent of cell death increased above this load. Accordingly, a "threshold stress causing cell death" was determined, as the stress caused by the 0.15 kg load, which was about ~1 MPa.

A mean radial distribution of dead cells was then calculated averaging the distribution from radial sections. Comparison between the dead cell distribution (mean dead cell distribution as function of distance from punch centre for different loads) and induced compressive stress (hydrostatic stress in Pa as function of distance from punch centre for different loads) was then performed. It was confirmed that the dead cell distribution correlates with stress distribution.

Using the determined 1 MPa threshold stress causing cell death, the region of dead cells caused by application of a projection patch was predicted from a simulated stress distribution caused by a projection penetrating the skin. The predicted region of dead cells was then validated using multi-photon microscopy (MPM) images of cell death following a practical application of a projection patch.

Detailed results of the above mentioned experiments will now be discussed.

The static load experiments were conducted by application of a 3 mm flat punch onto mouse ears, in which the static loads were provided by different weights applied to the punch. The murine ear tissue stained with viability stains (acridine orange for viable cells and ethidium bromide for dead cells), and images were obtained in which red indicates dead cells and green indicates viable cells. The results for four different weights can be seen in FIGS. 61A to 61D, each Figure showing negative and positive images in upper and lower portions, respectively.

Figure 61A:
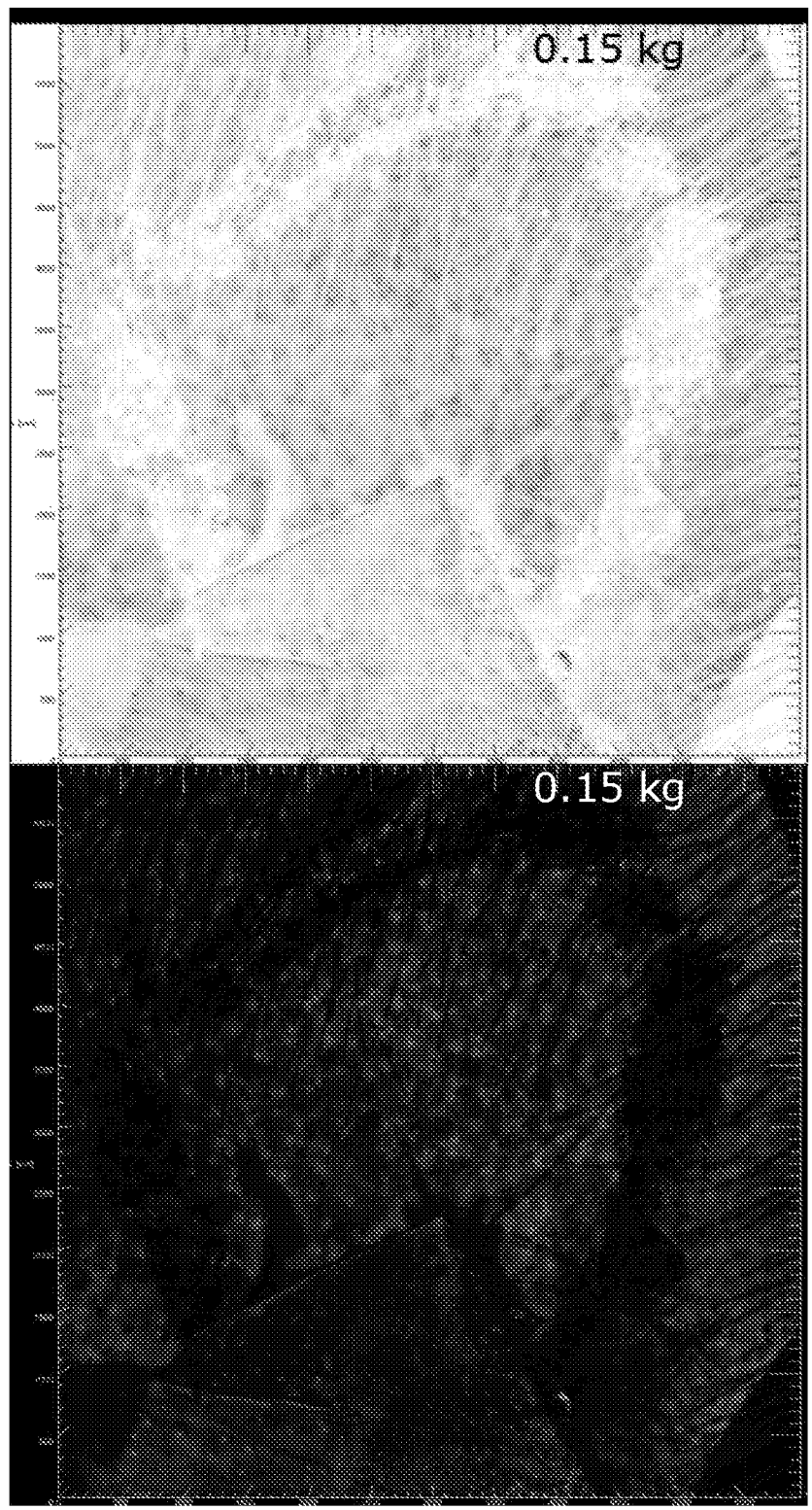
FIGS. 61A to 61D are negative and positive stained images indicating dead and viable cells after application of a 3 mm flat punch onto mouse ears under different static loads.
Figure 61B:
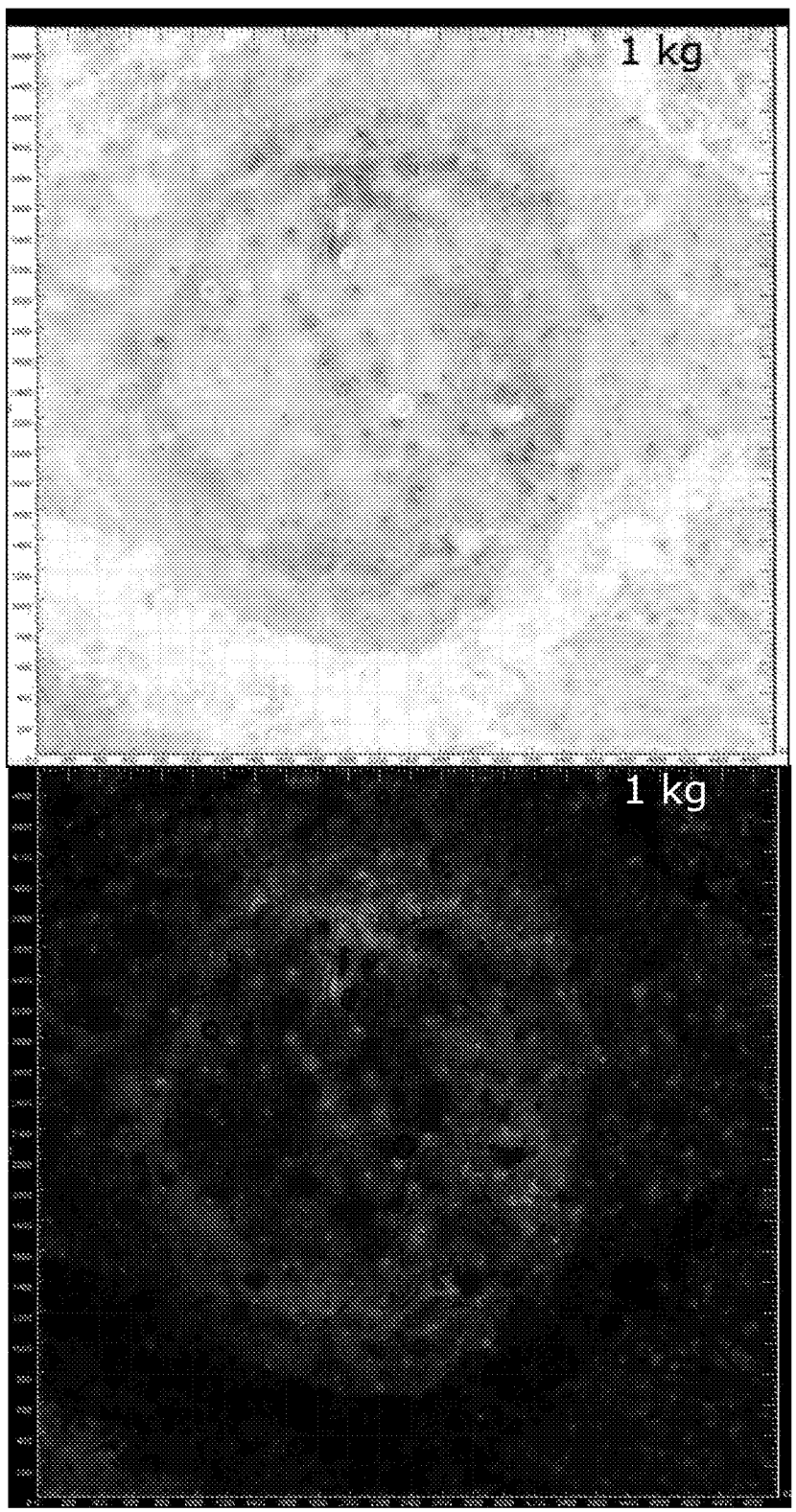

FIG. 61A represents the results of applying 0.15 kg of weight to the flat punch. A barely perceptible region cell death was observed around the perimeter of the flat punch. Turning to FIG. 61B, which represents the results for a 1 kg weight, a more distinct region of cell death can now be observed around the perimeter of the flat punch. In both of these cases, cell death was located only around the edges of the flat patch but not in the middle of the flat punch or outside of this area.

Figure 61C:
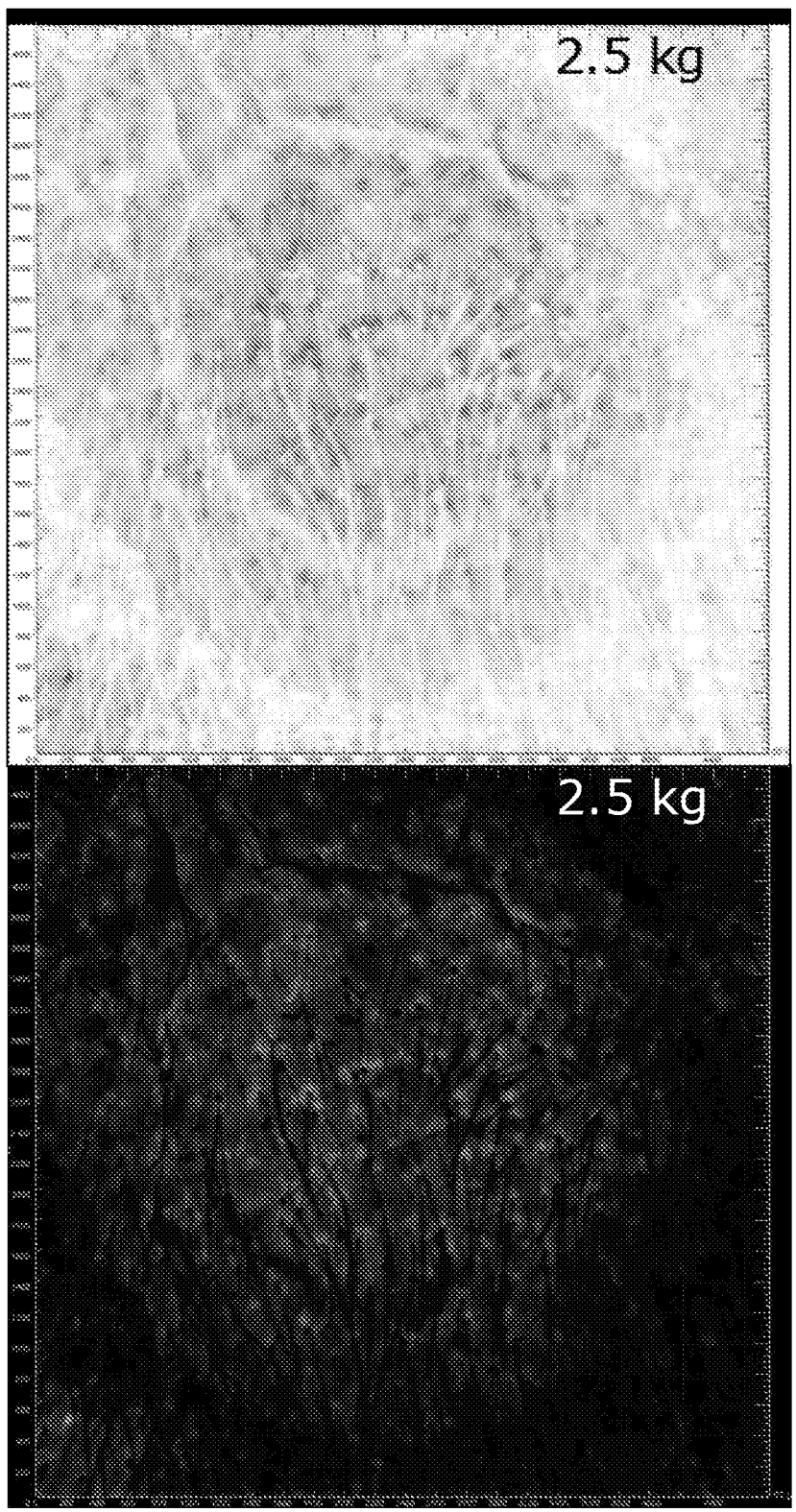
Figure 61D:
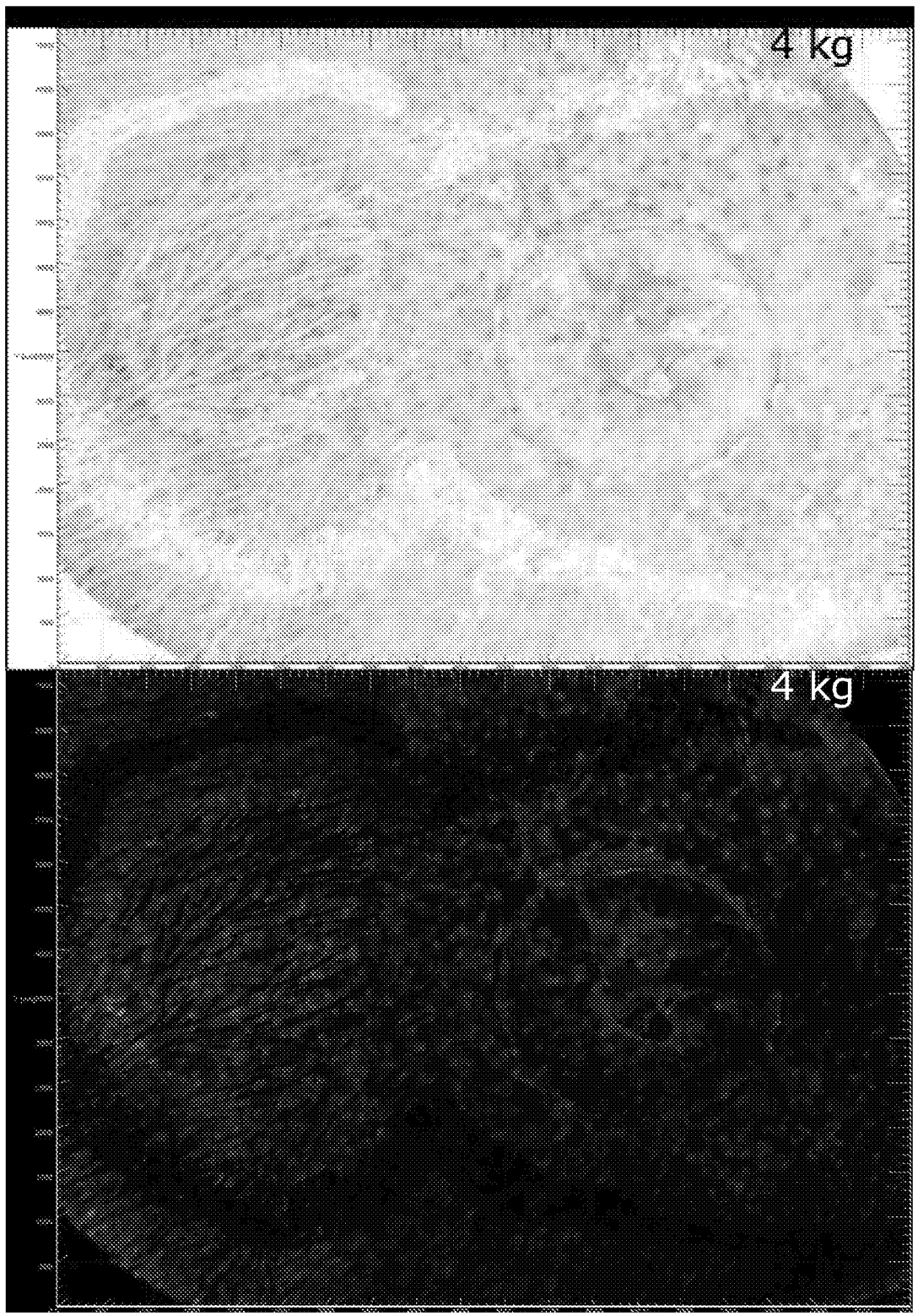

A weight of 2.5 kg was applied to the flat punch to generate the results of FIG. 61C, and a weight of 4 kg was applied for FIG. 61D. Significantly more cell death was observed in these higher static load cases, primarily located at the edges of the flat punch coming into contact with the skin cells. These results are indicative of high levels of stress that the cells are exposed to in those positions.

Figure 62A:
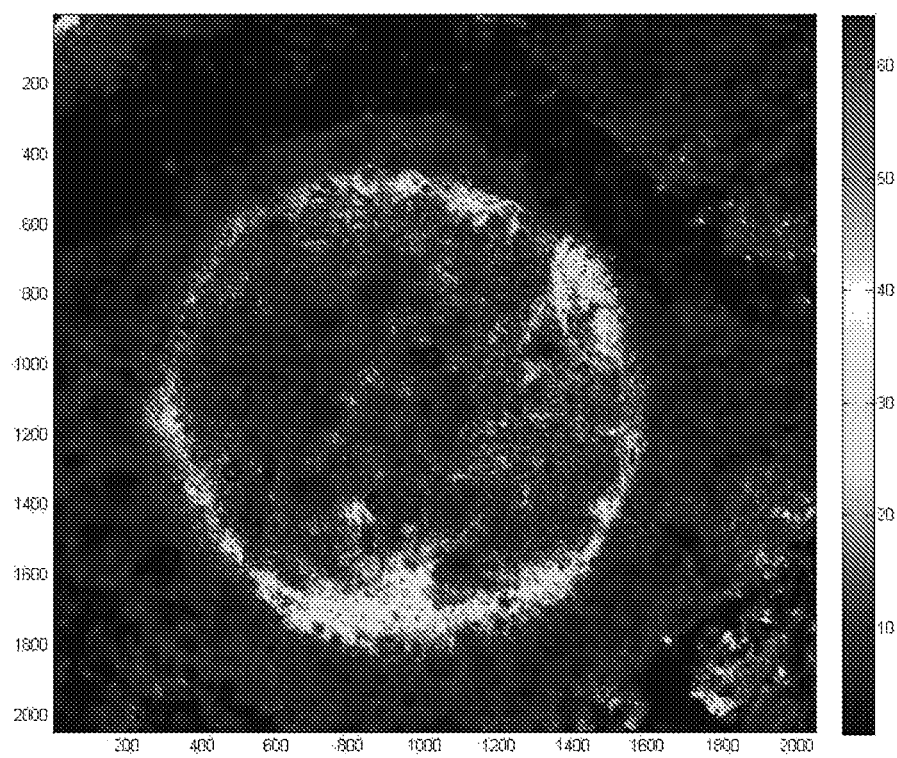
FIGS. 62A and 62B are example stained images after application of a 3 mm flat punch onto mouse ears under different static loads, before and after processing to acquire a red intensity distribution indicative of cell death.
Figure 62B:
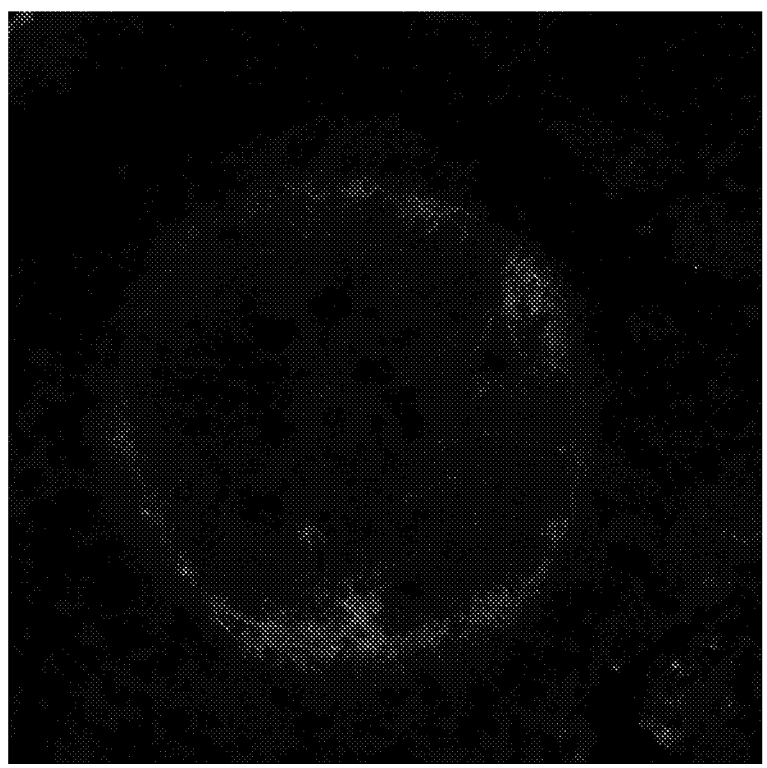

Image data from these static load experiments was processed with MATLAB to acquire a red image, whereby the distribution of dead cells could be derived from the red intensity distribution. FIG. 62A shows an example of an original unprocessed image and FIG. 62B shows an acquired red image using this technique.

The mean radial distribution of dead cells was then calculated by averaging the distribution along N=80 radial sections through the red image. This averaging process can be visualized through the following example set of images in FIGS. 63 to 65 which illustrate the averaging process for a simplified case including N=4 radial sections.

Figure 63:
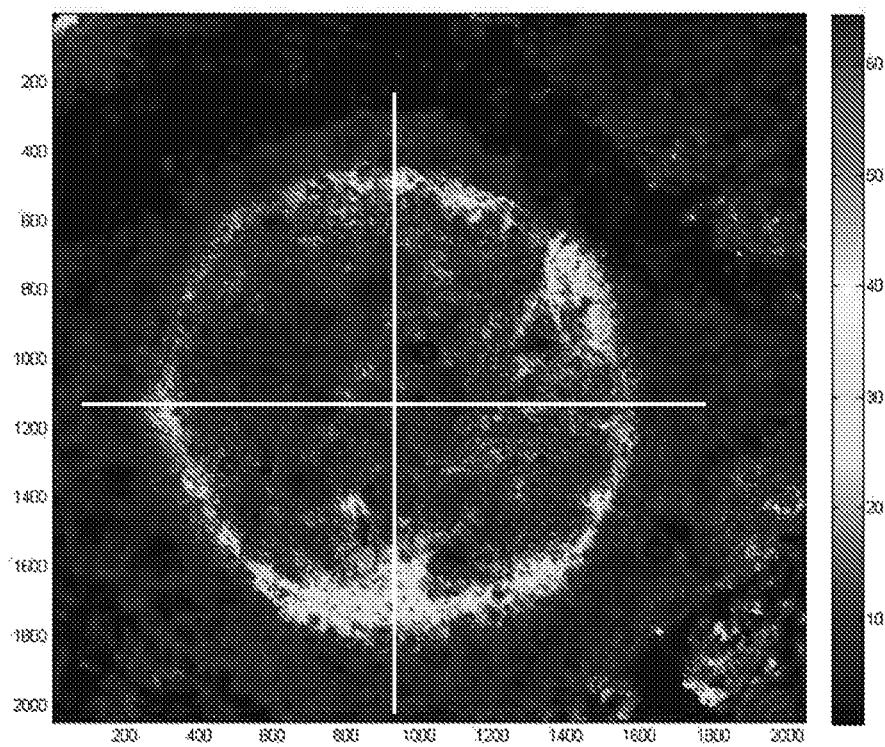
FIG. 63 shows an example of an unprocessed stained image, indicating 4 radial sections.
Figure 64:
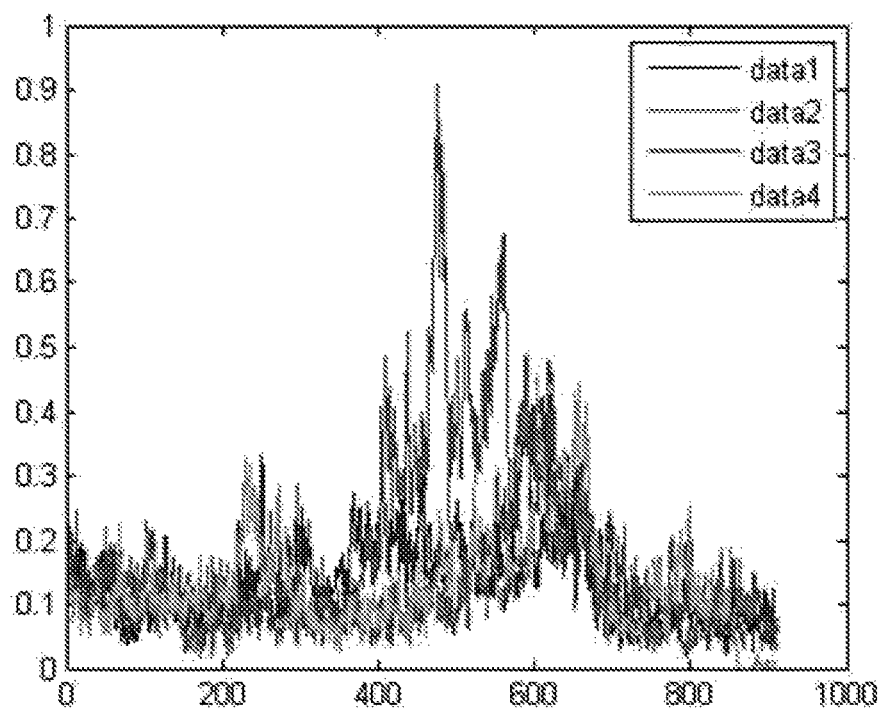
FIG. 64 shows an example of a graph of radial red intensity distribution data for the 4 radial sections of FIG. 63.
Figure 65:
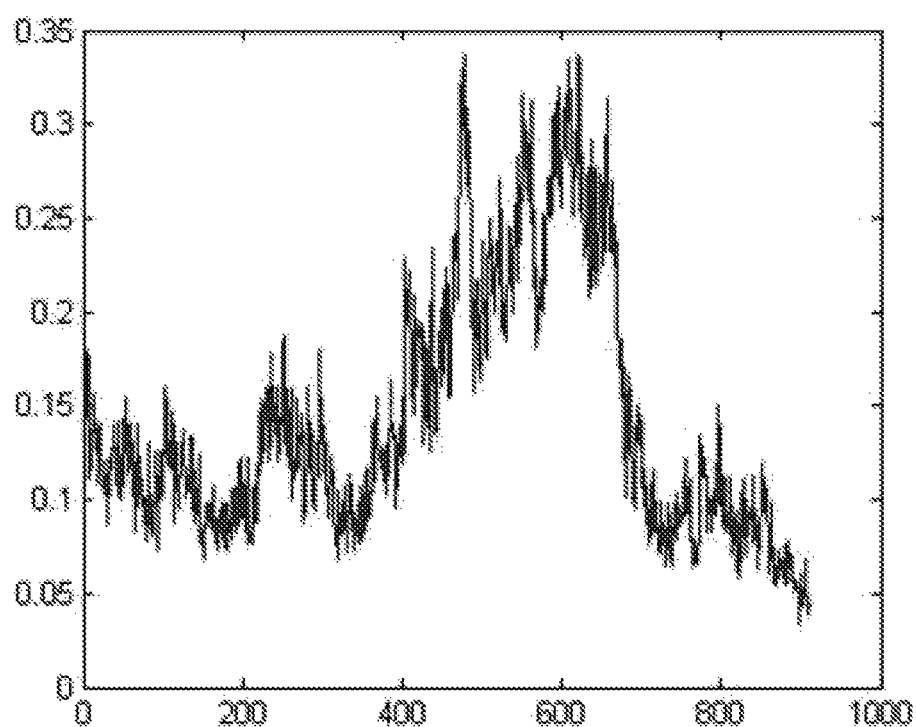
FIG. 65 shows an example of a mean radial distribution of dead cells for the 4 radial sections of FIG. 63.

With reference to FIG. 63, an original image is shown split into four radial sections. The radial red intensity distribution is analyzed for each section and this is plotted in FIG. 64. A mean radial distribution of dead cells is then determined, as shown in FIG. 65. It will be appreciated that a similar process will be used to obtain results for 80 radial sections.

Figure 66:
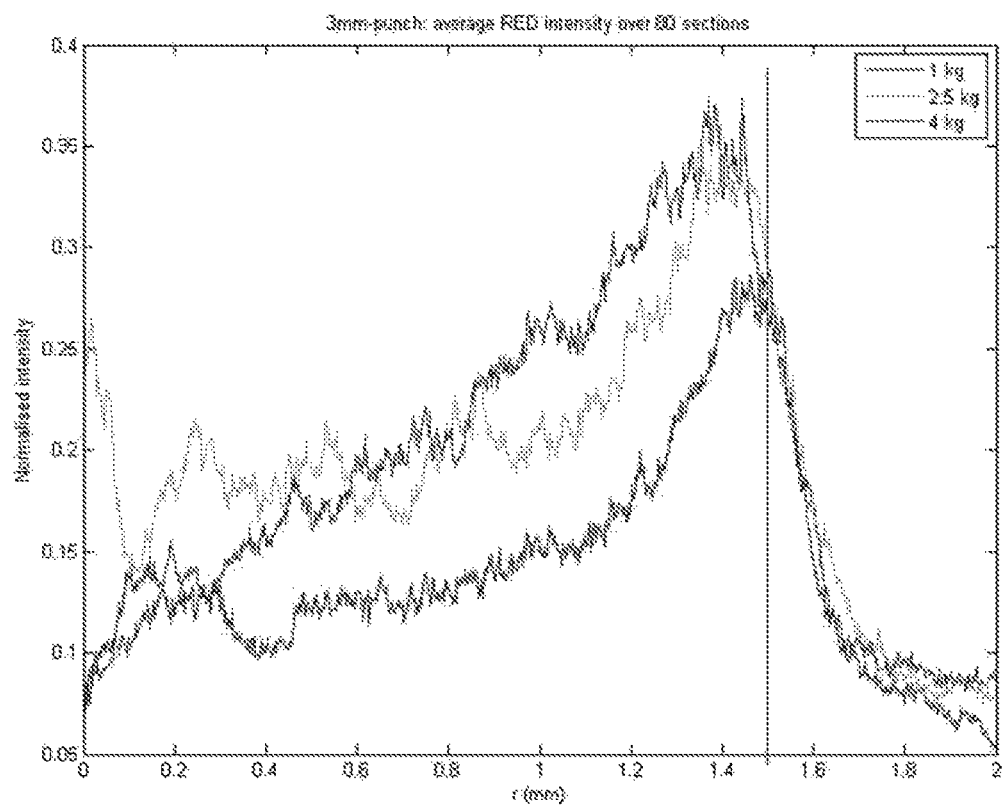
FIG. 66 is a graph of dead cell distribution as a function of distance from punch centre, under static loads of 1 kg, 2.5 kg and 5 kg.

The average red intensity where N=80 was determined for each of the static load experiments. FIG. 66 shows the dead cell distribution as a function of distance from punch centre for the 1 kg, 2.5 kg and 5 kg load cases (as per FIGS. 61B to 61D). The 0.15 kg results were omitted because the red intensity in this case was negligible in comparison to the heavier load cases.

Figure 67:
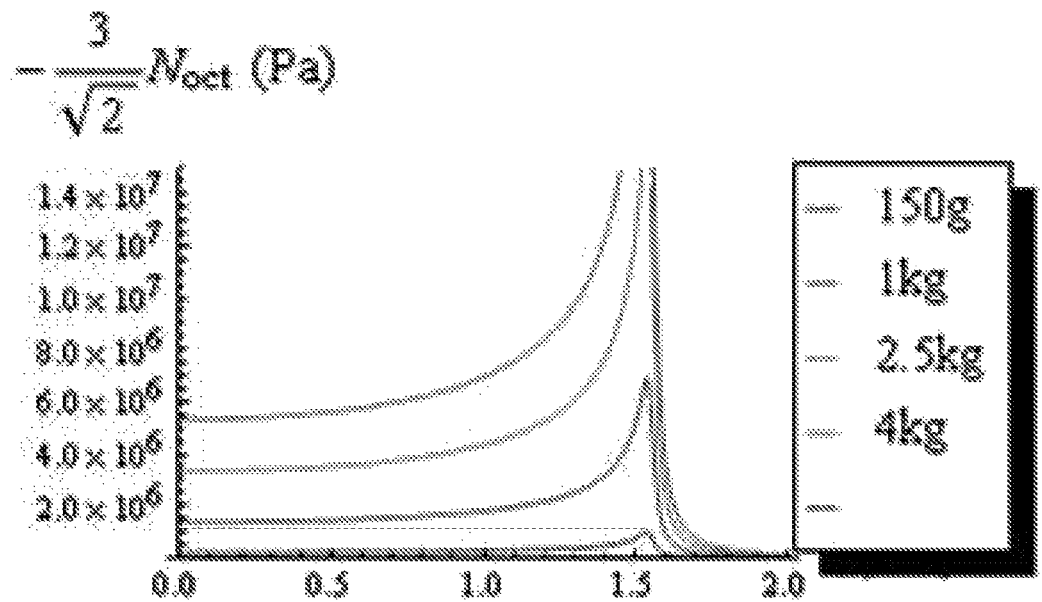
FIG. 67 is a graph of theoretical induced hydrostatic (compressive) stress due to the application of a flat cylindrical body as a function of distance from punch centre, under static loads of 0.15 kg, 1 kg, 2.5 kg and 5 kg.

The dead cell distribution plot of FIG. 66 can be compared with the theoretical induced hydrostatic (compressive) stress (in Pa) due to the application of a flat cylindrical body under the weights used in the experiments as shown in FIG. 67, as a function of distance from punch centre.

As can be seen from the comparison, the cell death results correlate with the hydrostatic (compression) stress. It is therefore hypothesized that excessive stress causes cell death. Since the 0.15 kg load caused negligible cell death (see FIG. 61A), the "threshold stress causing cell death" has been defined as the theoretical stress caused by the 0.15 kg load. From FIG. 67, this is approximately 1 MPa.

Figure 68:
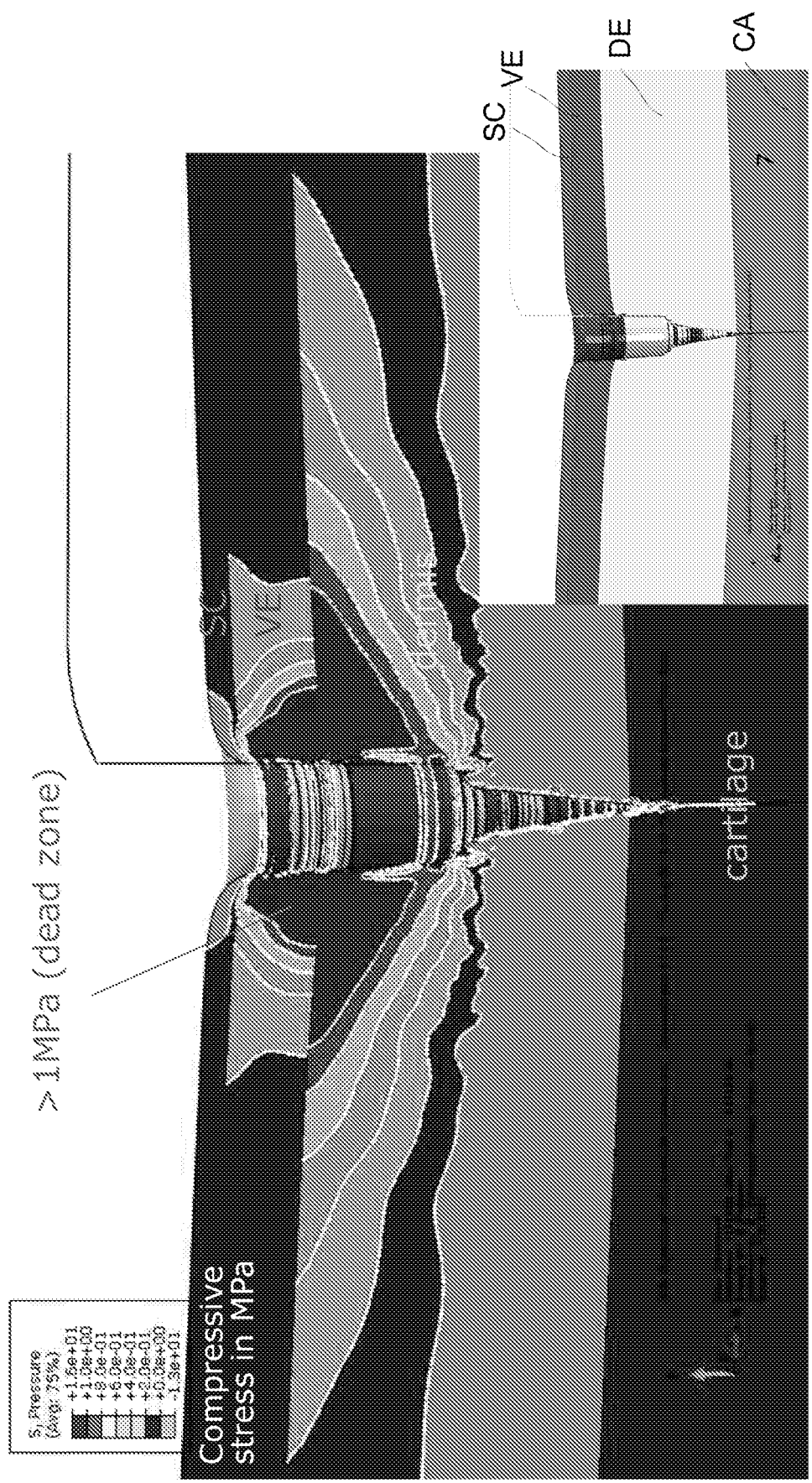
FIG. 68 is an example of simulated stress contours obtained from a finite element model of a projection penetrating layers of skin.

A finite element model has been prepared to simulate the stress distribution caused by a microprojection penetrating the skin. FIG. 68 shows results obtained from a simulation in which compressive stress in MPa is indicated as shaded contours. As can be best seen in the lower right inset image which does, the finite element model includes distinct skin layers of the stratum corneum (SC), viable epidermis (VE), dermis (DE) and cartilage (CA) and properties of these layers have been modelled accordingly. The differences in properties at the boundaries between layers can be distinctly observed as discontinuities in the stress contours.

The stress contours have been selected such that the highest stress contour bracket corresponds to stresses greater than the "threshold stress causing cell death" of 1 MPa, thus depicting a "dead zone" in the simulation results in the vicinity of the projection (as indicated on FIG. 68), particularly in the viable epidermis and upper portion of the dermis.

Accordingly, in view of the results of the simulated stress due to projection penetration into skin depicted in FIG. 68, and using the predetermined threshold of 1 MPa, the region of dead cells caused by application of the projection patch can be extrapolated.

Furthermore, this predicted dead zone can be validated using multiphoton microscopy (MPM) images of cell death following application of the projection patch.

Figure 69A:
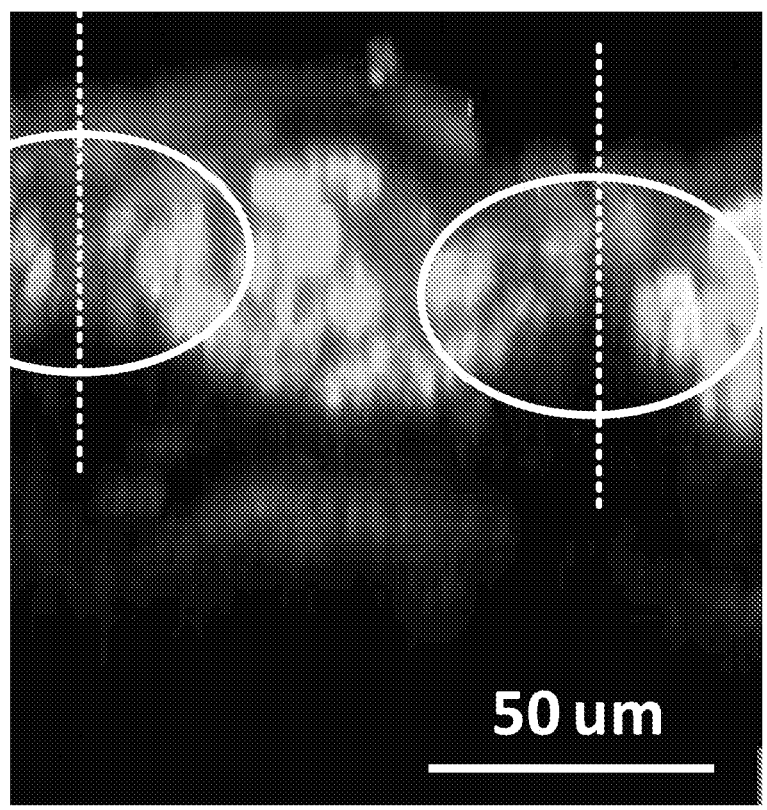
FIGS. 69A and 69B show sample profiles of ex vivo stained mouse ears following application of a projection patch.
Figure 69B:
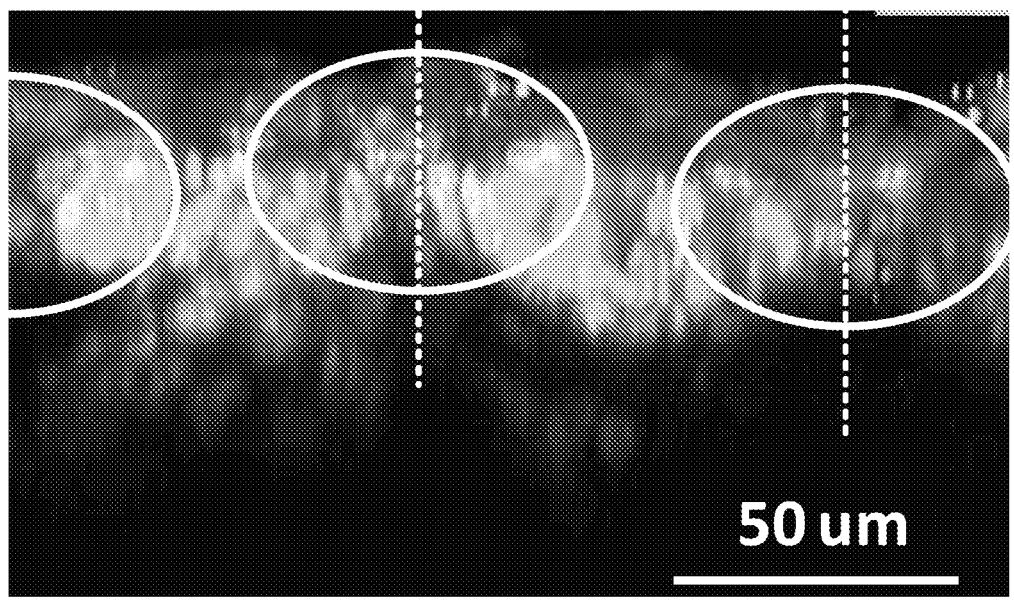

FIGS. 69A and 69B each show sample profiles of ex vivo stained mouse ears following application of a projection patch. Tissue was excised and stained immediately post treatment with viability stains (acridine orange and ethidium bromide). The projection patch used in these experiments had projections 110 μm in length, spaced apart by 70 μm, with 3364 projections per patch. The profiles of FIGS. 69A and 69B can be compared with the simulated profile of predicted cell death stress in FIG. 68.

Each of FIGS. 69A and 69B show an approximately 10 μm thick section. Dead cells (circled) can be observed in the vicinity of each projection penetration point (as indicated by vertical dotted lines), surrounded by viable cells between the projection penetration points. A darker layer of collagen can be seen below the dead cell sections. It is noted that the distribution of dead cells within 69A and 69B is consistent with that predicted by the simulation.

Figure 71:
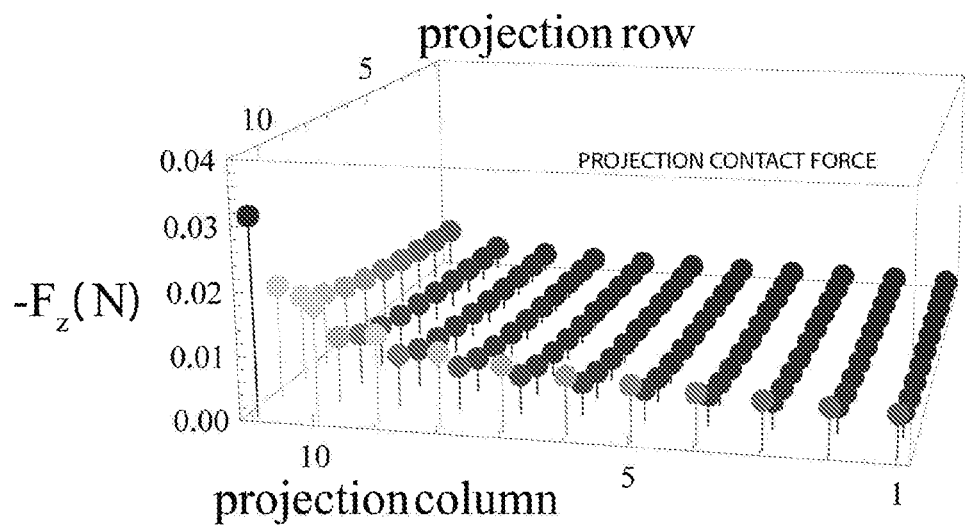
FIG. 71 is a graph of predicted projection contact force due to application of a projection patch, for different projection positions.
Figure 72:
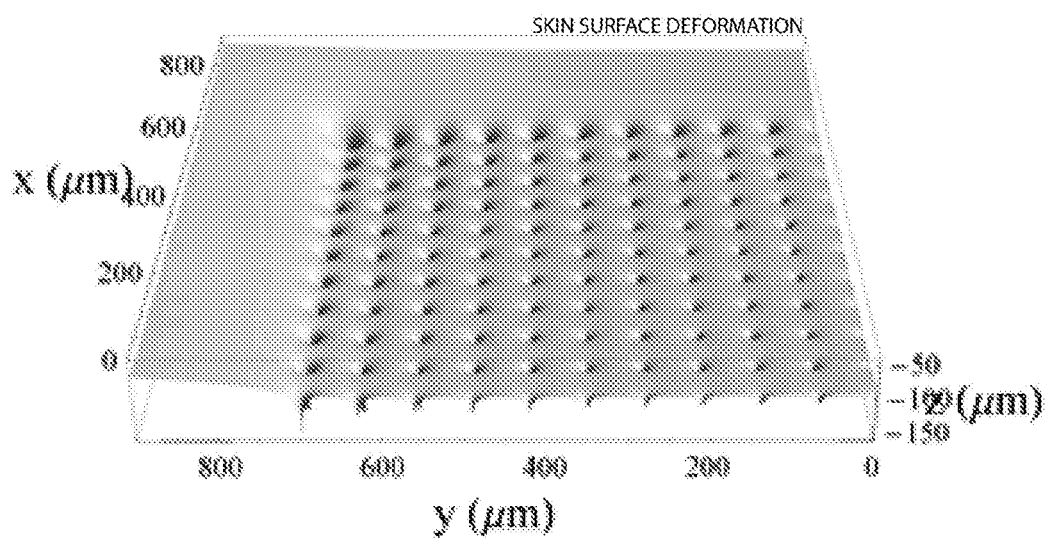
FIG. 72 is a graph of predicted skin surface deformation due to application of a projection patch, for different projection positions.

Further evidence of correlation between stress and cell death can be observed by comparing images obtained by viability staining of murine tissue following application of a projection patch (FIGS. 70A and 70B) with models of the respective contact forces (FIG. 71), skin surface deformations (FIG. 72) and stresses (FIG. 73) predicted for tat projection patch.

Figure 70A:
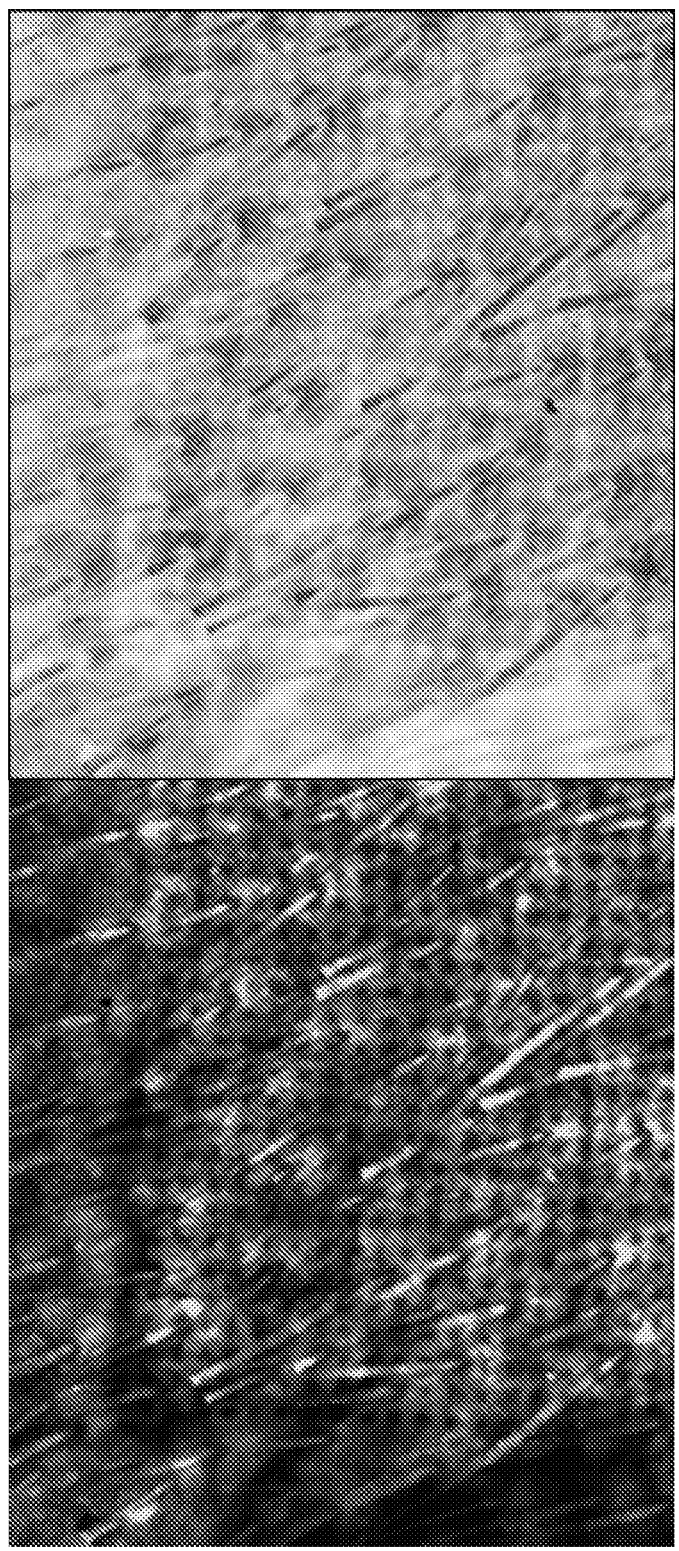
FIGS. 70A and 70B are negative and positive stained images indicating dead and viable cells after application of a projection patch onto a mouse ear, at different magnification scales.
Figure 70B:
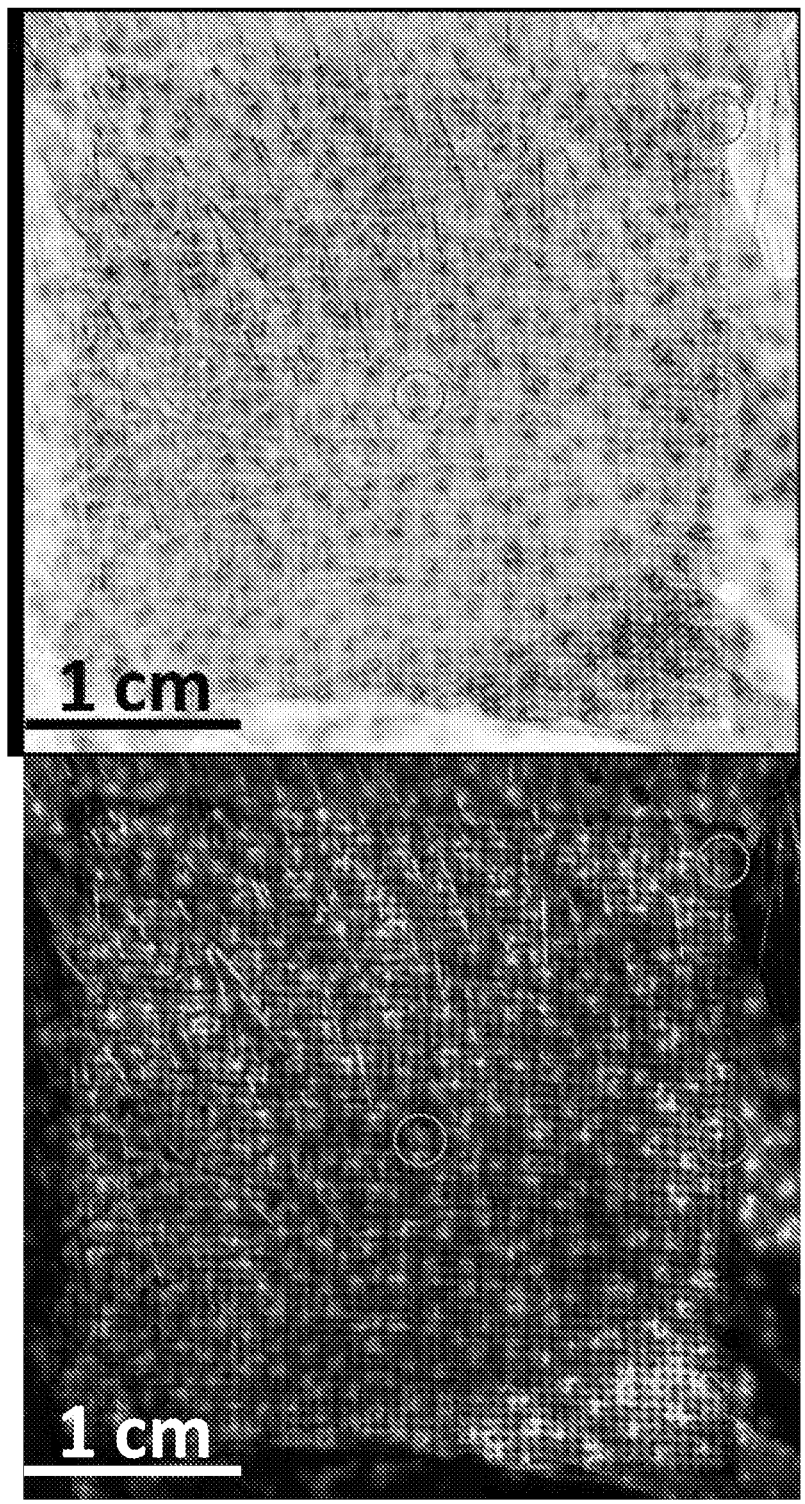

In particular, the contact force that the projections of a projection patch exert onto the skin is smaller at the centre of the array and increases towards the edges. The stained images of FIGS. 70A and 70B depict higher levels of cell death in the corners of the patch, supporting the force, deformation and stress model results of FIGS. 71, 72 and 73.

Figure 73:
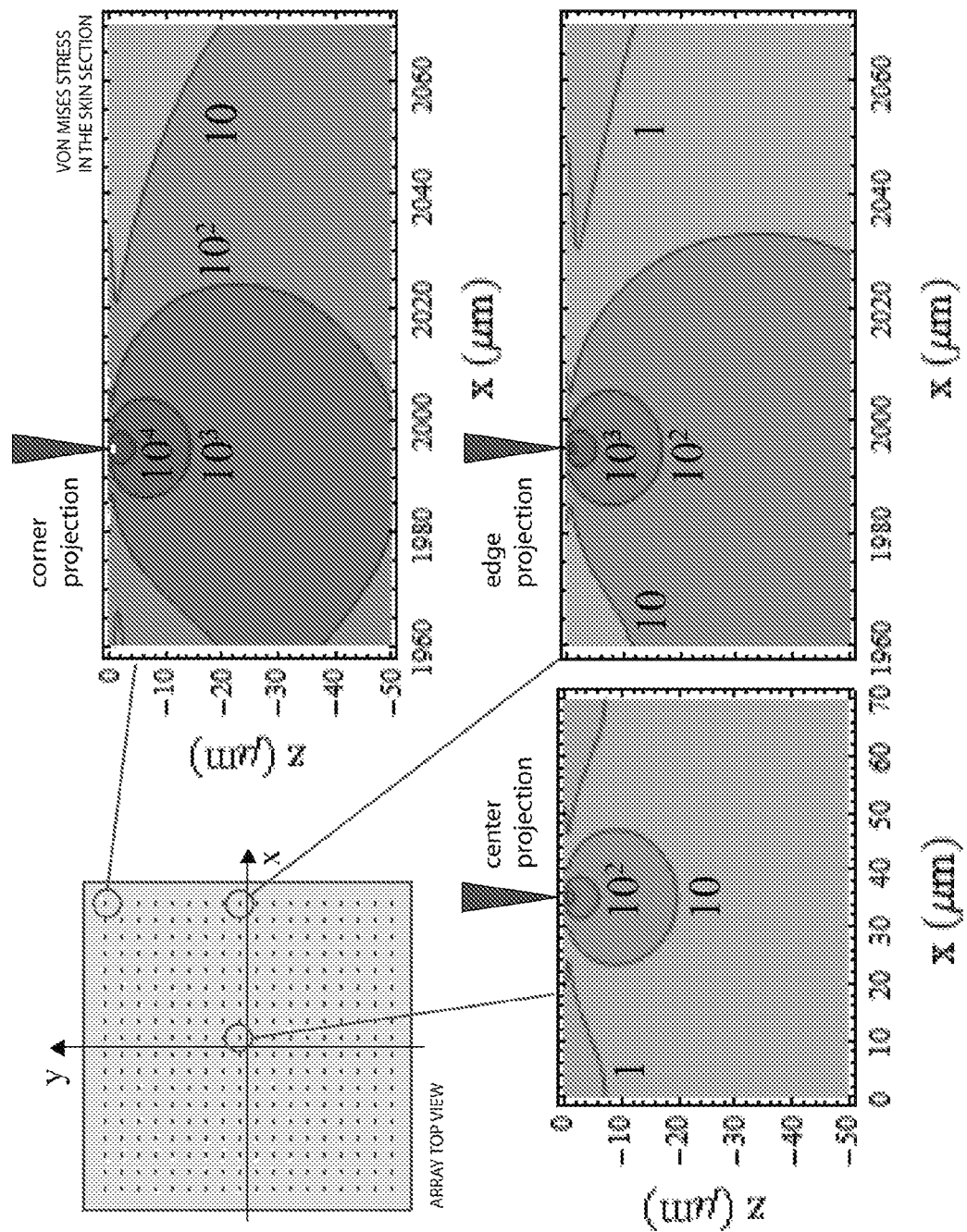
FIG. 73 is a graph of predicted von mises stress in skin due to application of a projection patch, for different projection positions.

The stress caused in the skin will smaller in the array centre and increases towards the corners. This principle is illustrated in FIG. 73, in which relative stress magnitudes are shown for centre, edge and corner projections. This is well correlated with the dead cell distribution in FIG. 70B, which is relatively low at the centre, greater at the edges, and greatest at the corners of the applied projection patch area.

Correlation Between Cell Death and Immunogenicity

It is hypothesized that co-localisation of cell death with antigen enhances immune responses. It has been found that the application of a projection patch induces highly localised cell death within the skin (mainly in the viable epidermis layer). In contrast intradermal injections (ID) induce only cell death at the needle insertion site.

Experiments have demonstrated that projection patches induce significantly higher levels of cell death than intradermal injections, despite the fact that intradermal delivery affects a significantly larger area than a projection patch. Immunogenicity experiments have also shown that the projection patch always performs better and more consistently than the intradermal injection comparison group.

Different levels of cell death induced by multiple projection patches are indicative that there is a threshold of cell death which is beneficial. Cell death in excess of this threshold can be detrimental to the immune system. Accordingly a balance must be struck to ensure the level of cell death does not become excessive.

Further immunogenicity investigation has shown that enhanced immune responses were primarily only achieved when cell death is co-localised with antigen deposition. Furthermore, the administration of adjuvant was shown to induce significantly higher levels of cell death than control groups without adjuvant. Accordingly, the immune response was found to be significantly higher with adjuvant than without.

Experimental data supporting the above findings will now be discussed in detail below.

Figure 74A:
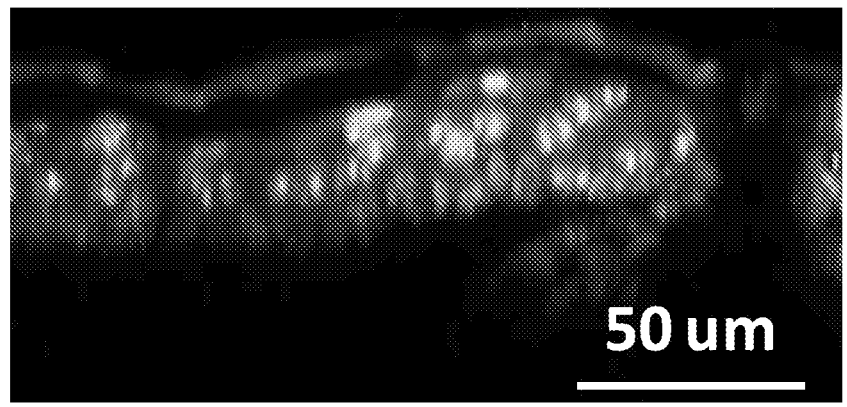
FIGS. 74A to 74E show side view profiles of ex vivo stained mouse ears, for an untreated sample and four samples following application of a projection patch.
Figure 74B:
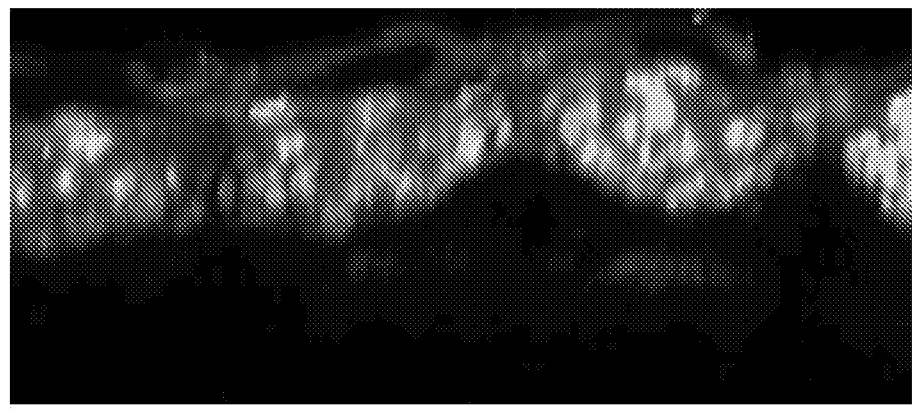
Figure 74C:
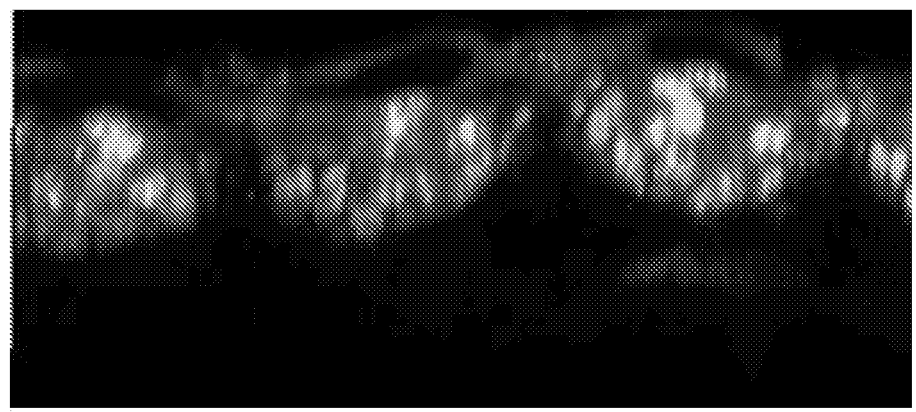
Figure 74D:
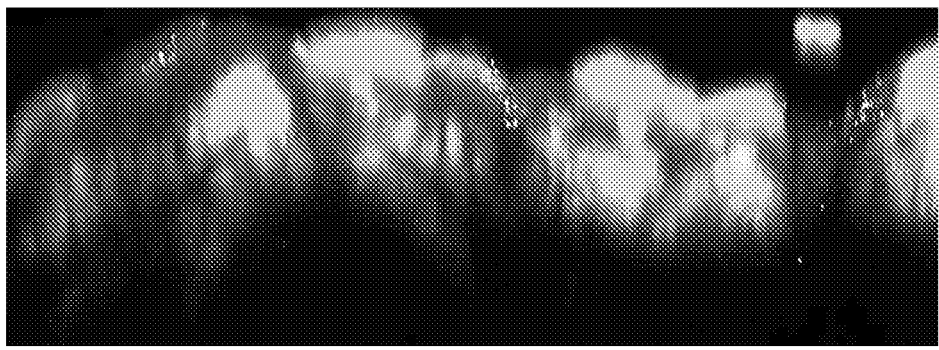
Figure 74E:
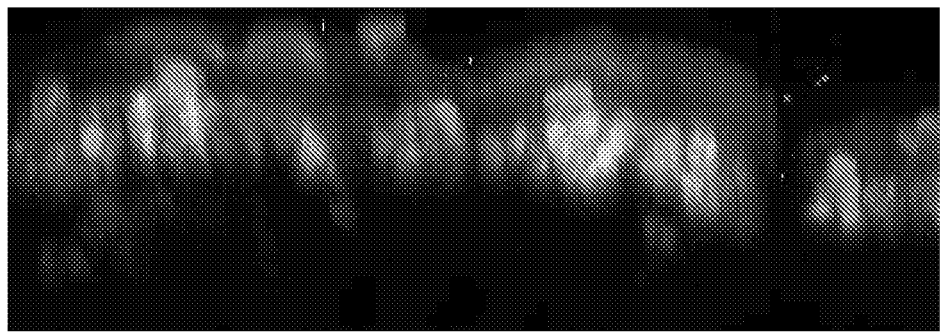

FIGS. 74A to 74E each show sample side view profiles of ex vivo stained mouse ears, in which FIG. 74A depicts an untreated profile and FIGS. 74B to 74E depict profiles following application of a projection patch. Tissue was excised and stained immediately post treatment with viability stains (acridine orange and ethidium bromide).

From FIGS. 74B to 74E, cell death is predominantly visible around the projections penetration regions, within the viable epidermis. Only few dead cells within the dermis are visible presumably due to relatively low cell density within the dermis and the relatively narrower profile of the projection penetrating into this layer.

Figure 75:
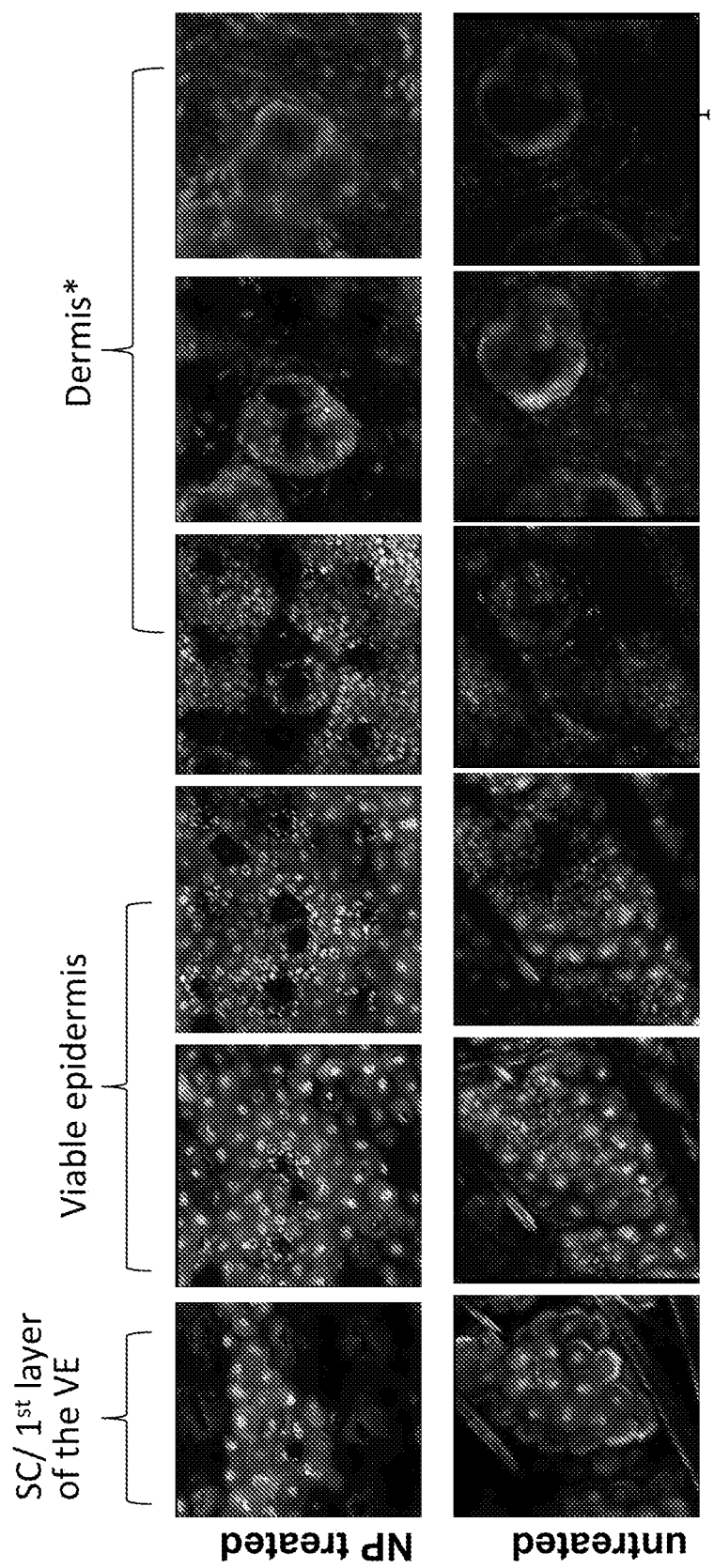
FIG. 75 shows a matrix of horizontal views of different layers of stained mouse skin after treatment with a projection patch (upper row) and in an untreated state (lower row)

Horizontal views of stained mouse ears are shown in the matrix of images of FIG. 75. The upper row of images corresponds to different layers of murine skin which has been treated with a projection patch. In contrast, the lower row of images corresponds to the same layers in an untreated state.

In FIG. 75, cell death is again predominantly visible around the projection penetration points (appearing as a regularly spaced array of dark holes) within the viable epidermis. Only few dead cells within the dermis, presumably for the reasons mentioned above.

Figure 76:
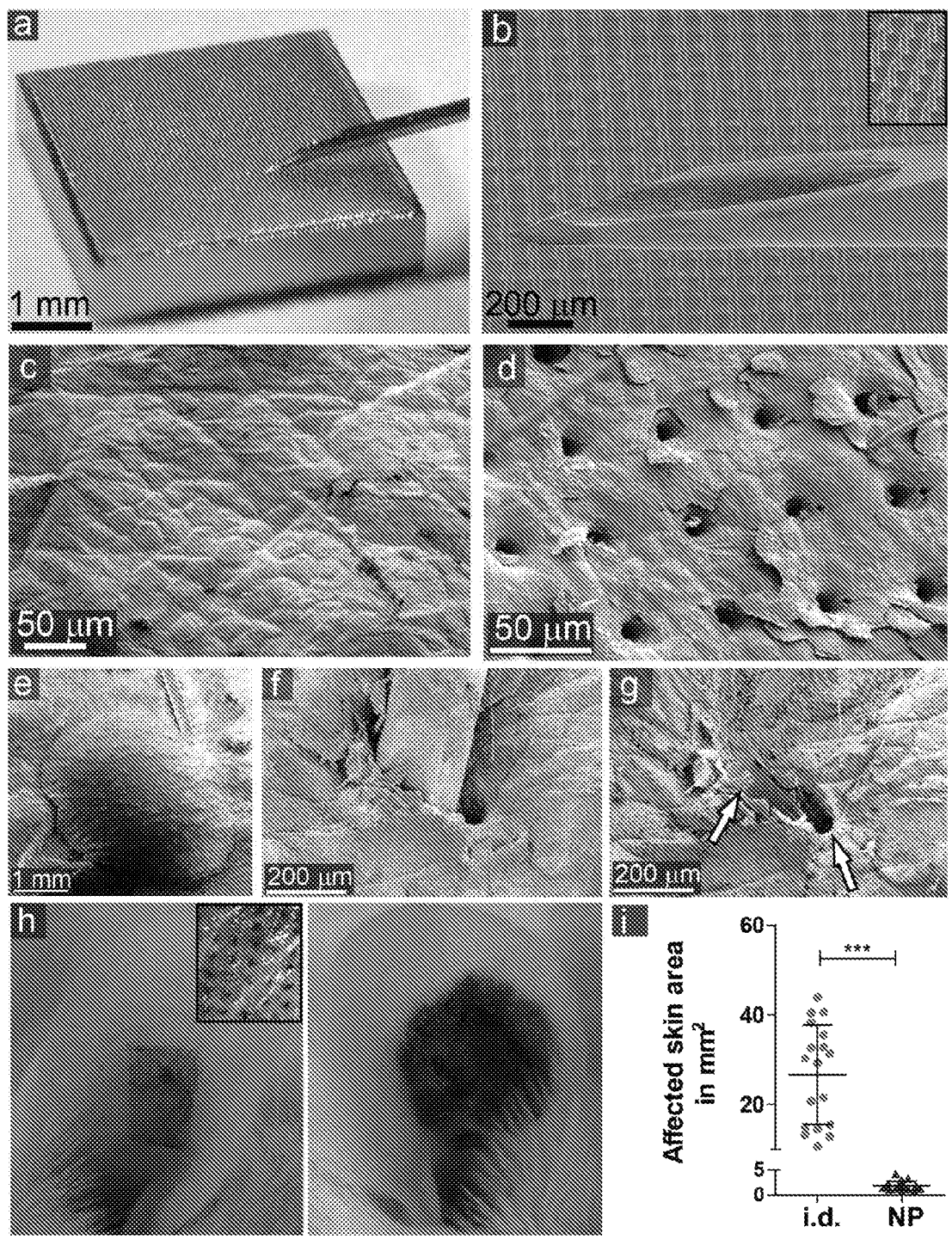
FIG. 76 is a collection of images comparing the area of affect following application of a projection patch to skin and intradermal injection by hypodermic needle.

FIG. 76 provides a comparison of the area of affect following application of a projection patch to skin and intradermal injection by hypodermic needle. A 4×4 mm projection patch was used, having 3364 projections at 110 µm in length, spaced apart by 70 µm. Panel (a) depicts a photographic size comparison of the projection patch alongside a 31G needle. Panel (b) shows a scanning electron microscopy image of a 31G needle tip over an array of projections (a further magnified view of the projections is inset).

Cryo-SEM images of murine skin are shown in panels (c) to (g) of FIG. 76. In particular, panel (c) shows an untreated mouse ear, panel (d) shows mouse ear skin following application of a projection patch, panels (e) and (f) show a 31G needle intradermal needle in situ at different magnification scales. Panel (g) shows mouse ear skin after 31G needle removal following delivery of 20 µm saline, in which arrows depict ruptured skin around the needle insertion site.

Panel (h) of FIG. 76 shows Coomassie Blue dye administered into mouse ears by either projection patch (left) or intradermal injection (right). Finally, panel (h) shows a plot of affected skin surfaces by Coomassie Blue measured in panel (h), with a sample size of 18, and (i.d.: intradermal; NP: projection patch). Error bars show means±SD (*** $p<0.001$).

In the comparisons, the calculated projection patch contact surface area was $17.7 \text{ mm}^2 \pm 2.3 \text{ mm}^2$ while the area of the bevelled tip of a 31G needle was $1.60 \pm 0.12 \text{ mm}^2$—an area comparable to approximately 310 (of a total of 3364) projections. This corresponds to approximately 1/10th of the 4×4 mm array. These data suggest that the area of skin affected by application of the projection patch to skin will be about 11-fold greater than that of a 31G intradermal needle.

This comparative data highlights a striking physical difference in the way a payload is delivered to the skin by each device. Fluid delivered using a 31G needle displaced skin by the formation of a liquid reservoir trapped within the skin, as shown in panel (e) of FIG. 76. In contrast, the individual projections are dry coated with a payload, and each projection punctures the skin delivering its payload within a respective puncture hole.

Figure 77A:
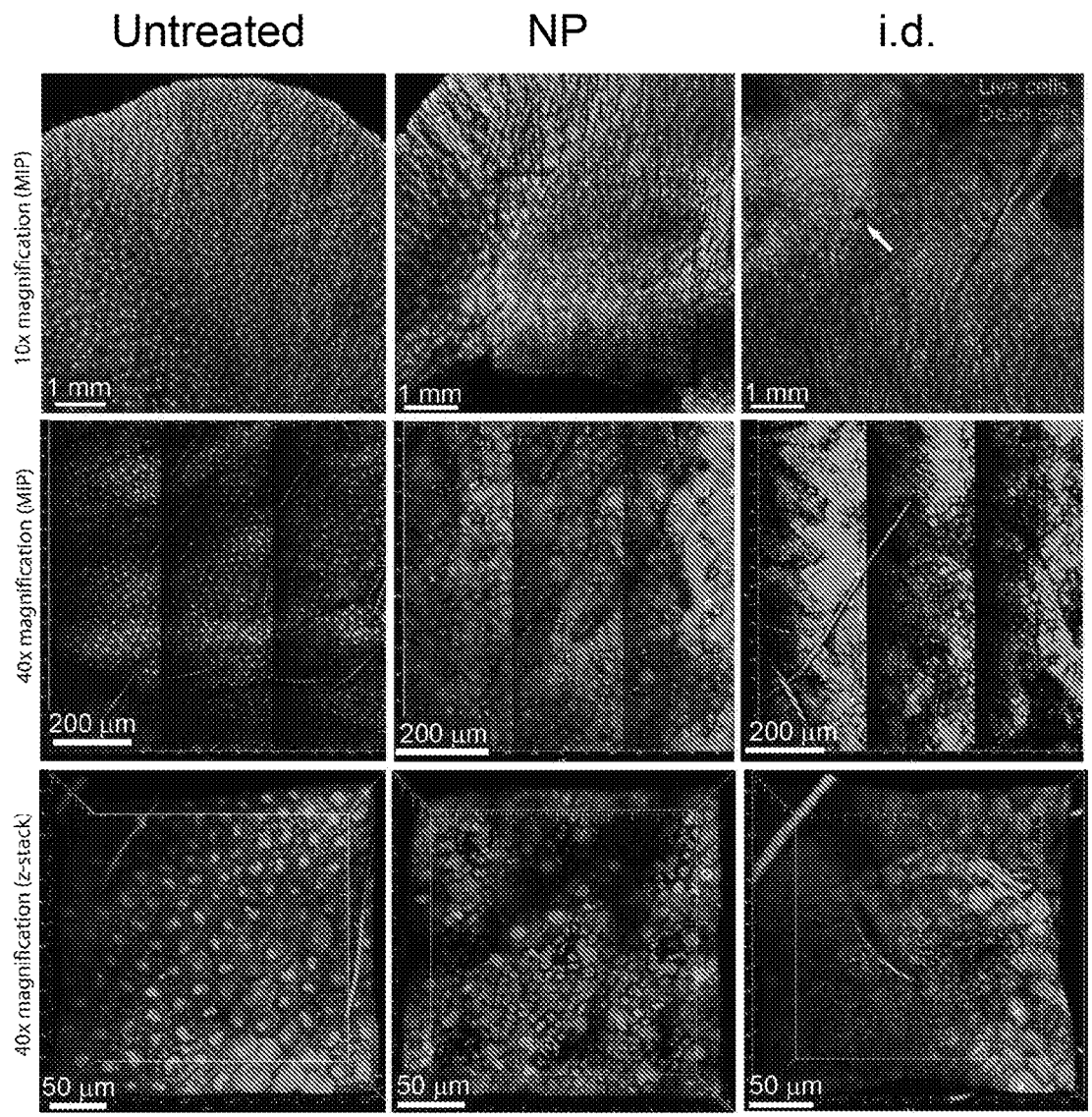
FIGS. 77A and 77B show cell viability stain images in untreated, uncoated projection patch-treated and intradermal (i.d.) saline injected murine skin.
Figure 77B:
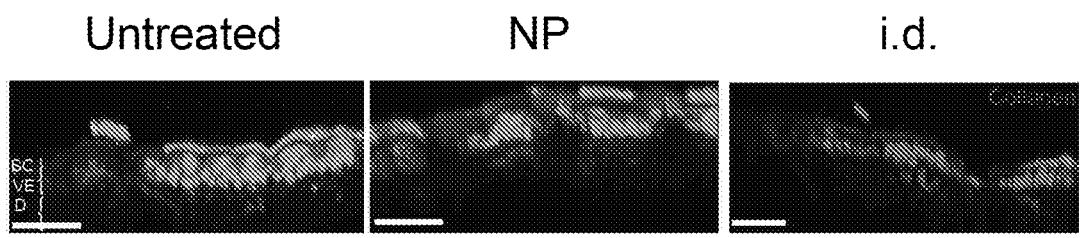

Cell death can be more readily visualised in FIGS. 77A and 77B, which shows cell viability stains in untreated, uncoated projection patch-treated and intradermal (i.d.) saline injected murine skin. Acridine orange (AO) and ethidium bromide (EB) were used to differentiate between viable (AO, green) and non viable (EB, magenta) cells.

In particular, FIG. 77A shows multiphoton microscopy images of stained murine; untreated (left column), uncoated projection patch-treated (centre column) and intradermally injected (right column). Original images are magnified 10× and 40× across the upper two horizontal rows, respectively, whilst the lowest row is a z-stack image at the 40× magnification level). The white arrow in the right column, upper row, depicts the intradermal injection site.

In FIG. 77B, representative side views of untreated, NP-treated or intradermally injected samples are shown, in which an underlying dark layer of collagen can be seen. The section thickness in FIG. 77B is 9.88 µm.

Figure 79:
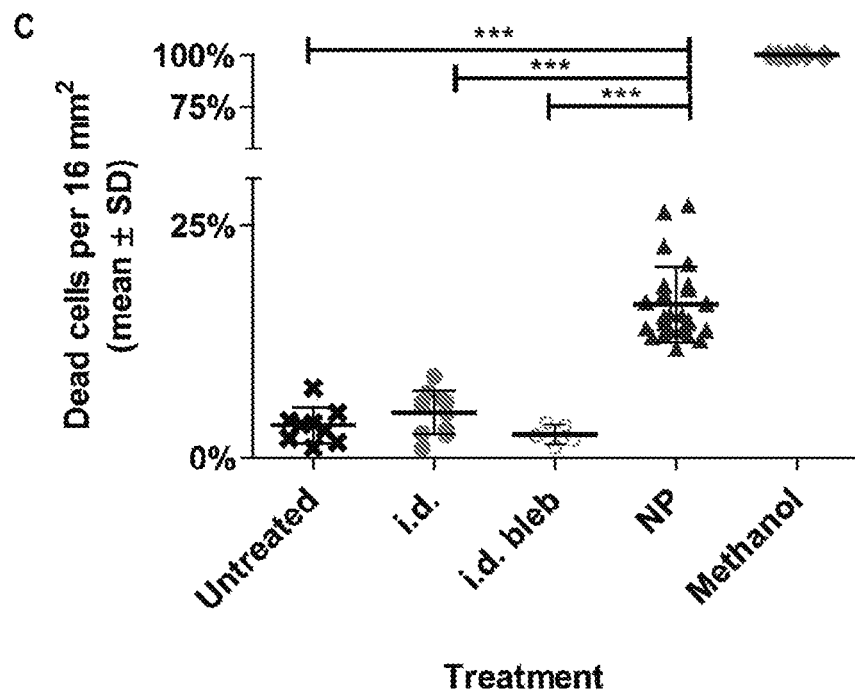
FIG. 79 is a graph of percentage of dead cells per 16 mm$^2$ following different treatments in murine skin.

The images of FIGS. 77A and 77B are representative of three independent experiments with n=5 or 6 replicates. FIG. 79 shows a plot corresponding to these repeated experiments, with quantification of cell viability per 16 mm², for each of untreated skin (untreated), an intradermal injection site (i.d.), a bleb formed following intradermal injection (i.d. bleb), a projection patch site (NP) and a control case wherein methanol was applied to cause 100% cell death. In this plot, error bars represent means±SD (*** $p<0.001$).

The data collated in FIG. 79 demonstrates that treatment of skin with a projection patch caused a greater area of damaged tissue than intradermal delivery of liquid by a 31G needle. This data supports the notion that payload delivery to the skin by projection patch causes focused cell death around individual projections of the projection patch, which serve as the payload reservoir delivery points. This is in striking contrast to cell death caused by the 31G needle, which is restricted to the skin puncture point, and is distal to the bleb that serves as the payload reservoir.

Figure 78A:
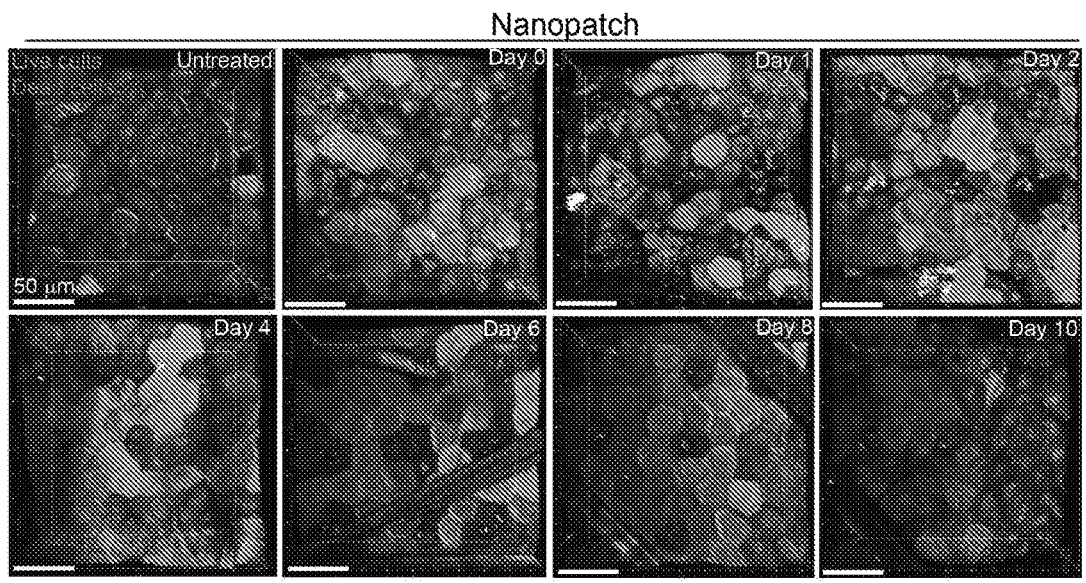
FIGS. 78A and 78B show representative cell viability stain images over time, after respective projection patch-treatments and intradermal (i.d.) treatments in murine skin.
Figure 78B:
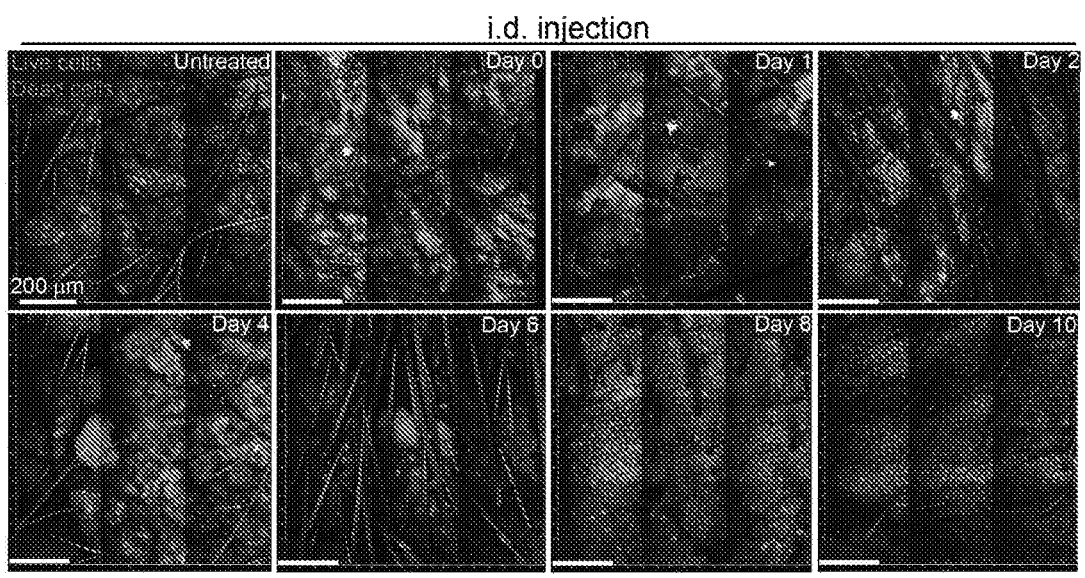

Localised cell death over time can be visualised in FIG. 78A and FIG. 78B for the projection patch and intradermal delivery scenarios respectively.

FIGS. 78A and 78B show representative images of projection patch-treatments and intradermal (i.d.) treatments in murine skin over time. Murine ears were subjected to projection patch application or intradermal injection (20 µl saline), excised at indicated time points post treatment, stained with AOEB prior to imaging by MPM and quantified from Maximum Intensity Projections (MIPs) by measuring EB-stained area per 16 mm$^2$.

In the upper left panel of each of FIGS. 78 A and 78B, an untreated reference image is shown for the treated area, and then images are shown for 0, 1 and 2 days following treatment across the upper row, and 4, 6, 8 and 10 days following treatment across the lower row.

Figure 80:
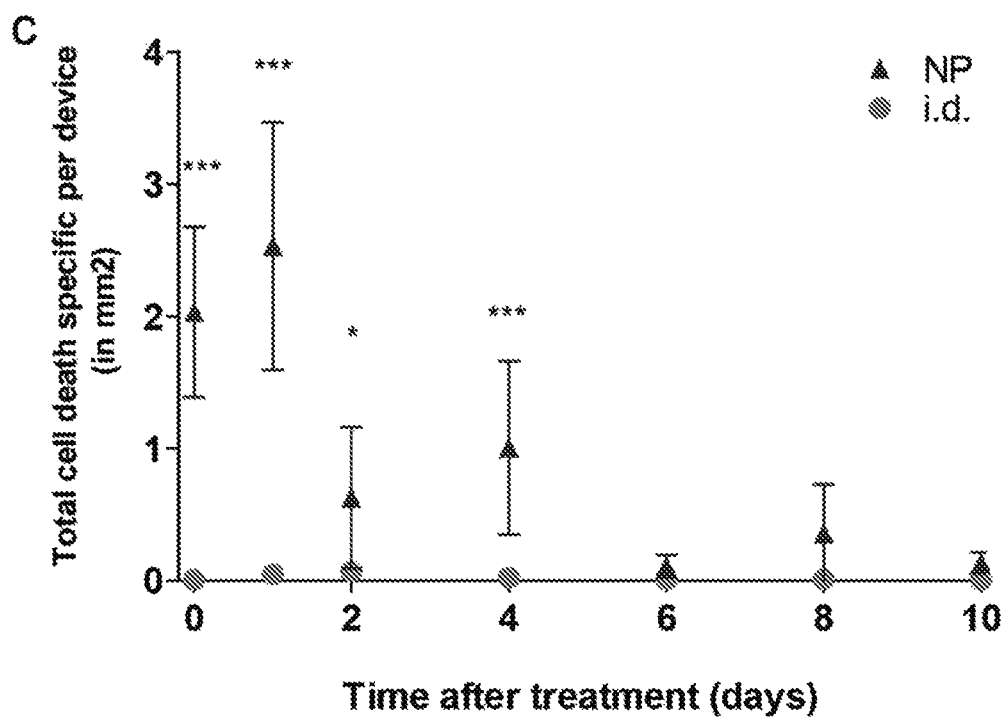
FIG. 80 is a graph of total cell death over time after projection patch and intradermal treatments in murine skin.

Results from these images are collated in the plot of FIG. 80, showing quantification of cell death per device (background removed), pooled from two independent experiments with a minimum of n=25 (projection patch) and n=4 (intradermal delivery) per time point. In this plot, error bars show means±SD (* $p<0.05$, *** $p<0.001$).

Further comparisons of intradermal delivery versus delivery by application of a projection patch can be performed using dose response curves. In particular, increased dose-sensitivity to antigen has been observed in projection patch-treated samples compared to intradermally injected samples, as supported by FIGS. 81A and 81B. To prepare these Figures, endpoint titers of influenza vaccine (Fluvax) were administered by projection patch or intradermal injections at various doses (0.1, 1, 5, 10, 20, 50 and 100 ng) and analyzed by ELISA 21 days post immunization. An intramuscular injection was also included for comparison.

Figure 81A:
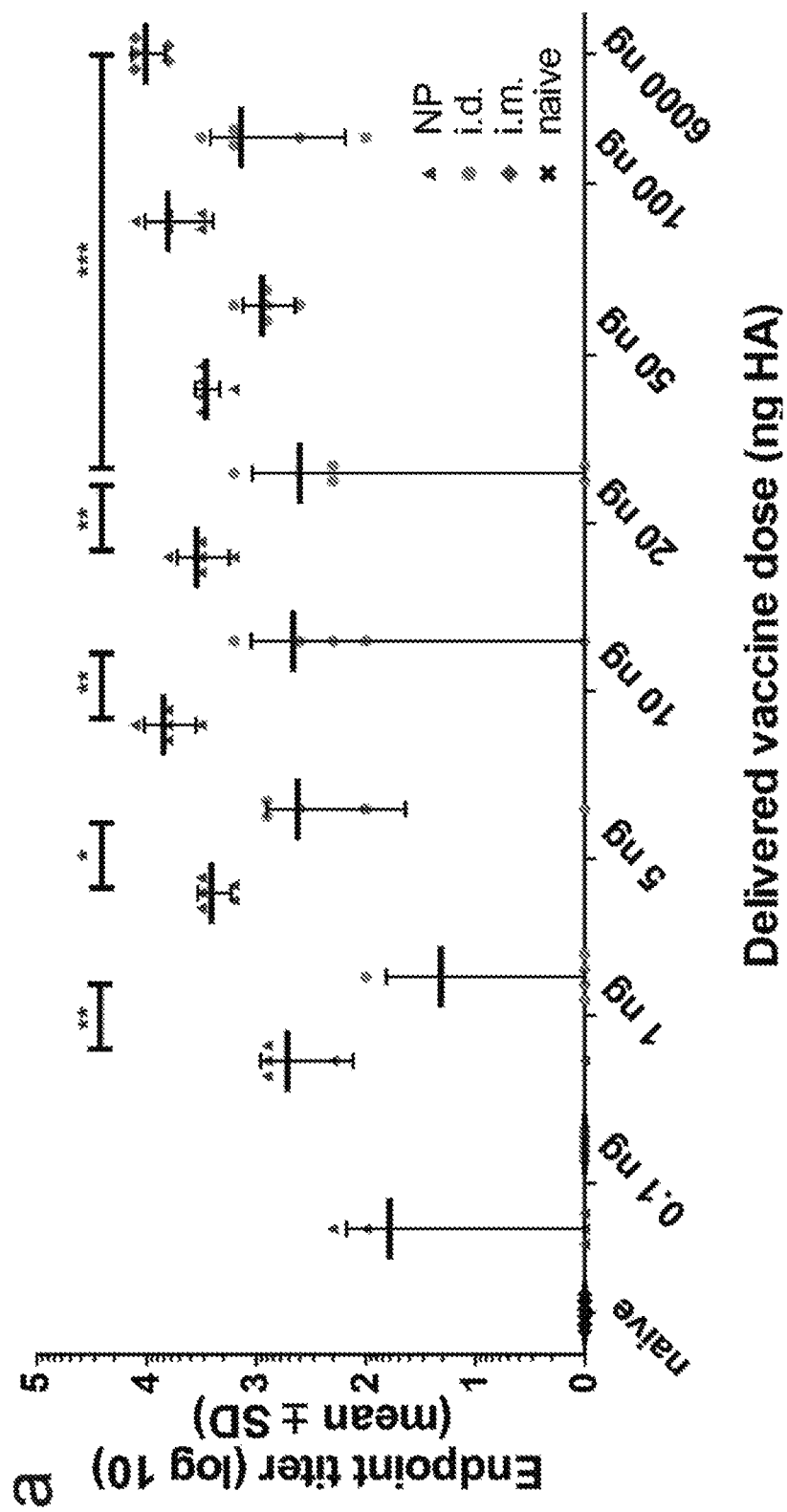
FIGS. 81A and 81B are graphs of dose response curves from endpoint titers of Fluvax in murine skin, using different delivery methods.
Figure 81B:
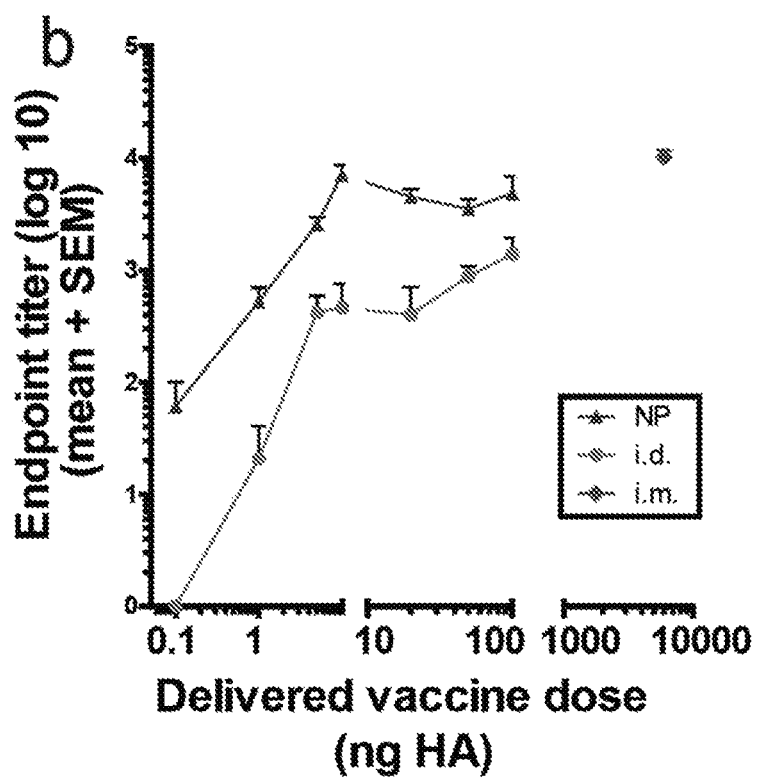

FIG. 81A plots the dose response titration with outliers, whilst FIG. 81B plots the dose response curve on log scale depicting the dose differences between intradermal (i.d), projection patch (NP) intramuscular (i.m.) and naive cases. Error bars show means±SD (*$p<0.05$,  $p<0.01$, * $p<0.001$).

From these results it can be shown that projection patch delivery consistently performs higher than intradermal delivery, with more consistent responders.

Further investigations into immune responses to Fluvax following different levels of induced cell death were performed, to determine whether there is a cell death threshold which, if exceeded, would no longer exhibit beneficial effects on immune response.

Fluvax was delivered by coated projection patches or intradermal injections into murine ears, at 1 ng and 10 ng doses, respectively. Samples were analyzed by ELISA on day 21 post-immunization with endpoint titers plotted. Different numbers of projections were applied for different cases, to scale the level of cell death when using the projection patches.

Figure 82:
FIG. 82 shows cell viability stained images following projection patch applications with different numbers of projections in murine skin.

FIG. 82 shows representative MPM images of AOEB-stained ventral ear halves following projection patch applications with 1682 (½ NP—a single projection patch having half the number of projections on the standard patch having 3364 projections), 3364 (1 NP—a single standard projection patch) or 10,092 projections (3 NP—achieved by two applications of an uncoated standard patch in the same area, followed by one coated standard patch).

Figure 83:
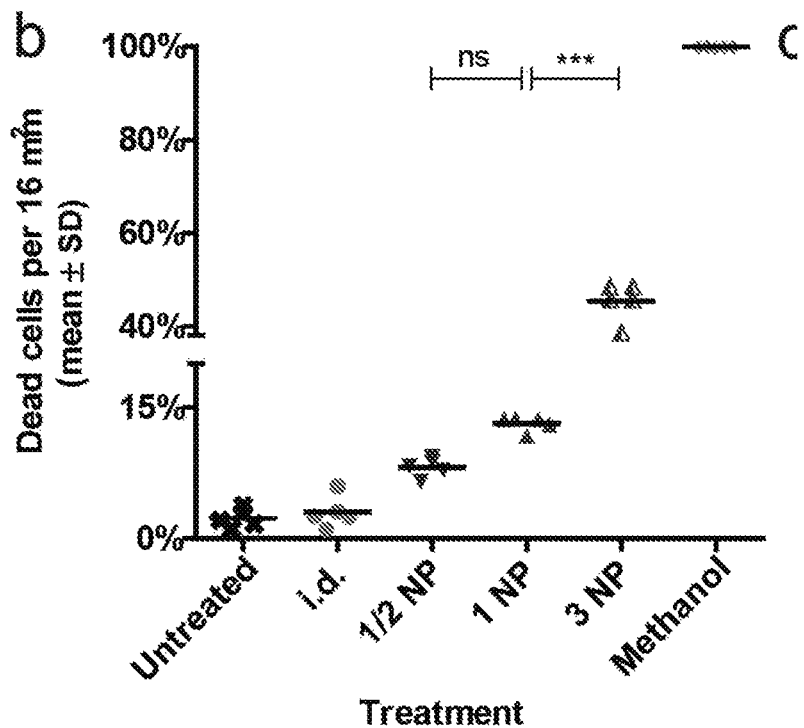
FIG. 83 is a graph of percentage of dead cells per 16 mm$^2$ following projection patch applications with different numbers of projections in murine skin.
Figure 84:
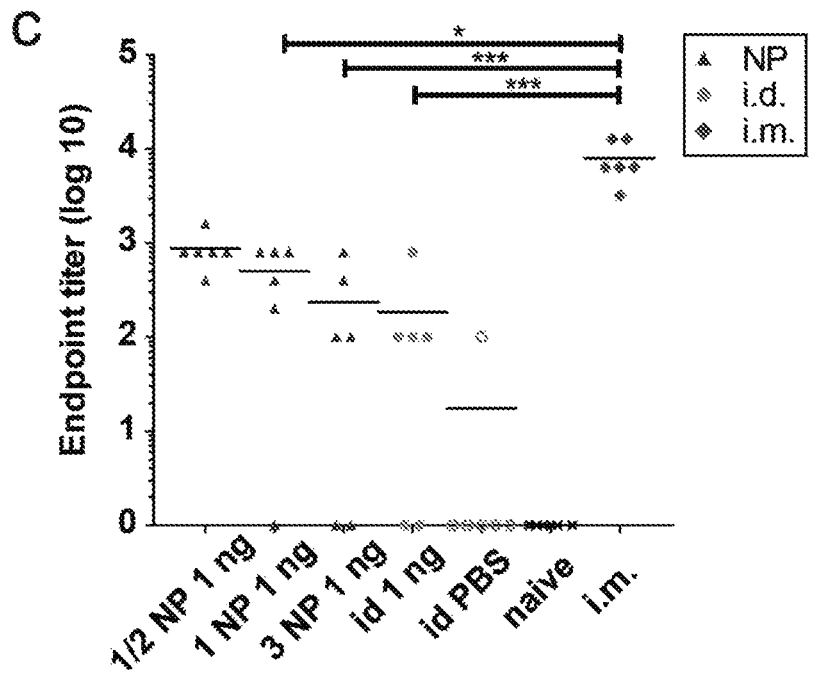
FIG. 84 is a graph of endpoint titers following delivery of 1 ng Fluvax to murine skin with different numbers of projections.

The results of these investigations can be seen in the plots of FIG. 83, which shows quantification of cell death for each application calculated in Imaris from MPM images such as those shown in FIG. 82, and FIG. 84, which shows endpoint titers of multiple treatments following 1 ng Fluvax 2010 delivery. In these plots, ½ NP: single Nanopatch containing 1682 projections; 1 NP: single Nanopatch containing 3364 projections; 3 NP: two plain followed by one coated Nanopatch, totaling 10,092 projections; FP: flat patch; i.d., intradermal: i.m., intramuscular. Error bars show means±SD with n=6 or n=5 (d); ( $p<0.01$, * $p<0.001$).

The projection patch case having the lowest cell death is ½ NP, and this correlates well with a slightly lower immune response as can be seen in FIG. 82C. Increased cell death enhances the immune response.

However, this data implies that there is a threshold of cell death. It is hypothesized that there is a specific cell death threshold that is beneficial (i.e. enhances the immune response) before becoming detrimental to the whole immune system. The endpoint titres appear to reach an upper limit for the 1 NP and 3 NP groups, indicating a cell death threshold may have been reached. In the ½ NP (with 100 µm spacing between projections), only 1682 projections penetrate and deliver vaccine. The resulting endpoint titres based on ELISA assays are lower in the ½ NP groups, although not significantly.

In view of the above findings, it has been hypothesized that co-localization of antigen with cell increased immunogenicity. Accordingly, the impacts of co-localisation have been investigated further. The specific aim of this investigation is to compare the projection patch with intradermal delivery at ultra-low doses of 1 ng Fluvax 2010.

It has been revealed that projection patches yield higher immune response than intradermal delivery. Experiments to test the co-localisation hypothesis involving combining the application of an uncoated projection patch with subsequent intradermal vaccine delivery saw no improved immune response.

Figure 85A:
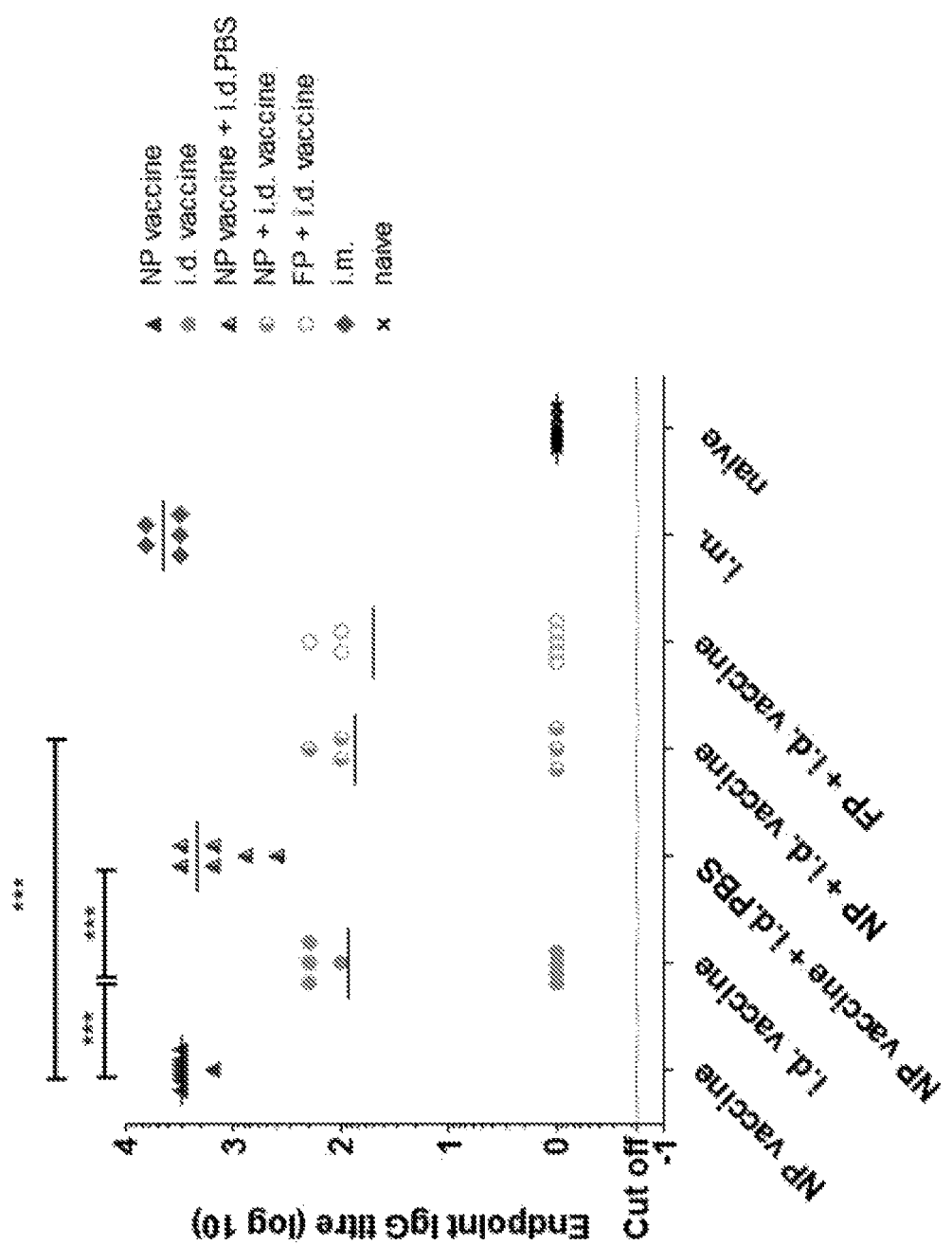
FIGS. 85A and 85B are respective graphs of endpoint titers and absorbance curves following delivery of 10 ng Fluvax to murine skin, for different treatments types.
Figure 85B:
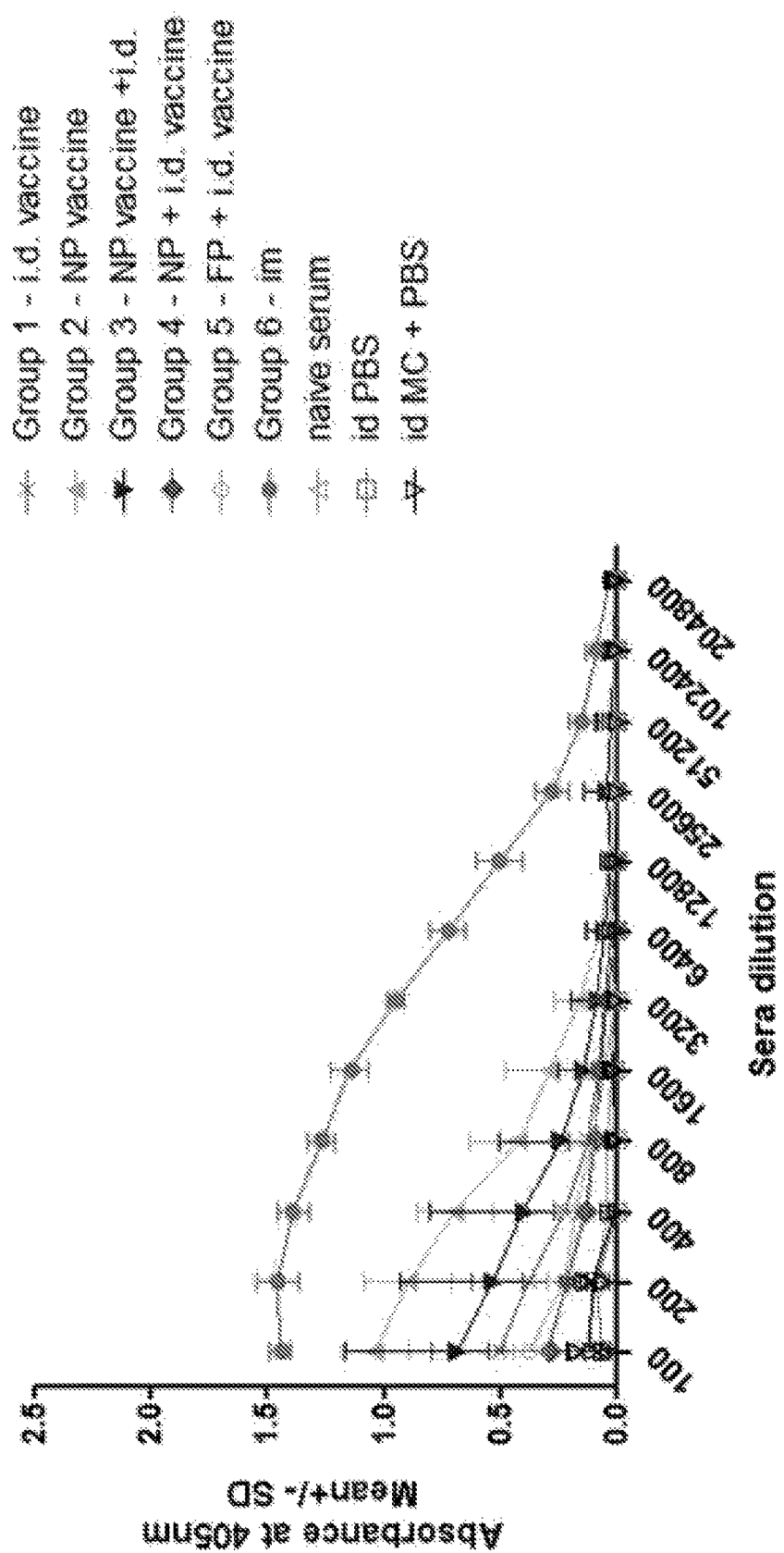

FIG. 85A shows endpoint titers of multiple combinations of immunisation treatments with a 10 ng dose of Fluvax 2010. In this plot, "NP vaccine" indicates the application of a projection patch coated with vaccine; "i.d. vaccine" indicates intradermal vaccine injection; "NP vaccine+i.d. PBS" indicates application of a vaccine-coated projection patch followed by intradermal injection of phosphate buffered saline (PBS); "NP+i.d. vaccine", indicates application of an uncoated coated projection patch followed by intradermal injection of vaccine; "FP+i.d. vaccine" indicates application of a flat patch followed by intradermal injection of vaccine; "i.m." indicates intramuscular injection and "naive" indicated the naive untreated case. FIG. 85B shows the same data as FIG. 85A, only as an absorbance curve (raw data) instead of the endpoint titre data.

The results of these experiments will now be discussed. Vaccine administered by NP alone results in a high endpoint titre, as expected from previously obtained results. In contrast, vaccine administered intradermally is significantly lower than the projection patch groups.

By combining vaccine delivery via projection patch, followed by an intradermal injection of PBS, no significant change in endpoint titre occurs. However, it was noted that the spread within this group was larger than the projection patch group along, suggesting that the intradermal PBS injection 'washes' away the vaccine (antigen).

When vaccine was delivered intradermally after a plain projection patch application, no significant increase in immune response was observed. When the projection patch was substituted by a flat patch (FP), the immune response was not different to the intradermal vaccine or the combined intradermal vaccine and projection patch groups. This is believed to be due to there not being any cell death co-localised with the antigen delivery point.

Figure 86:
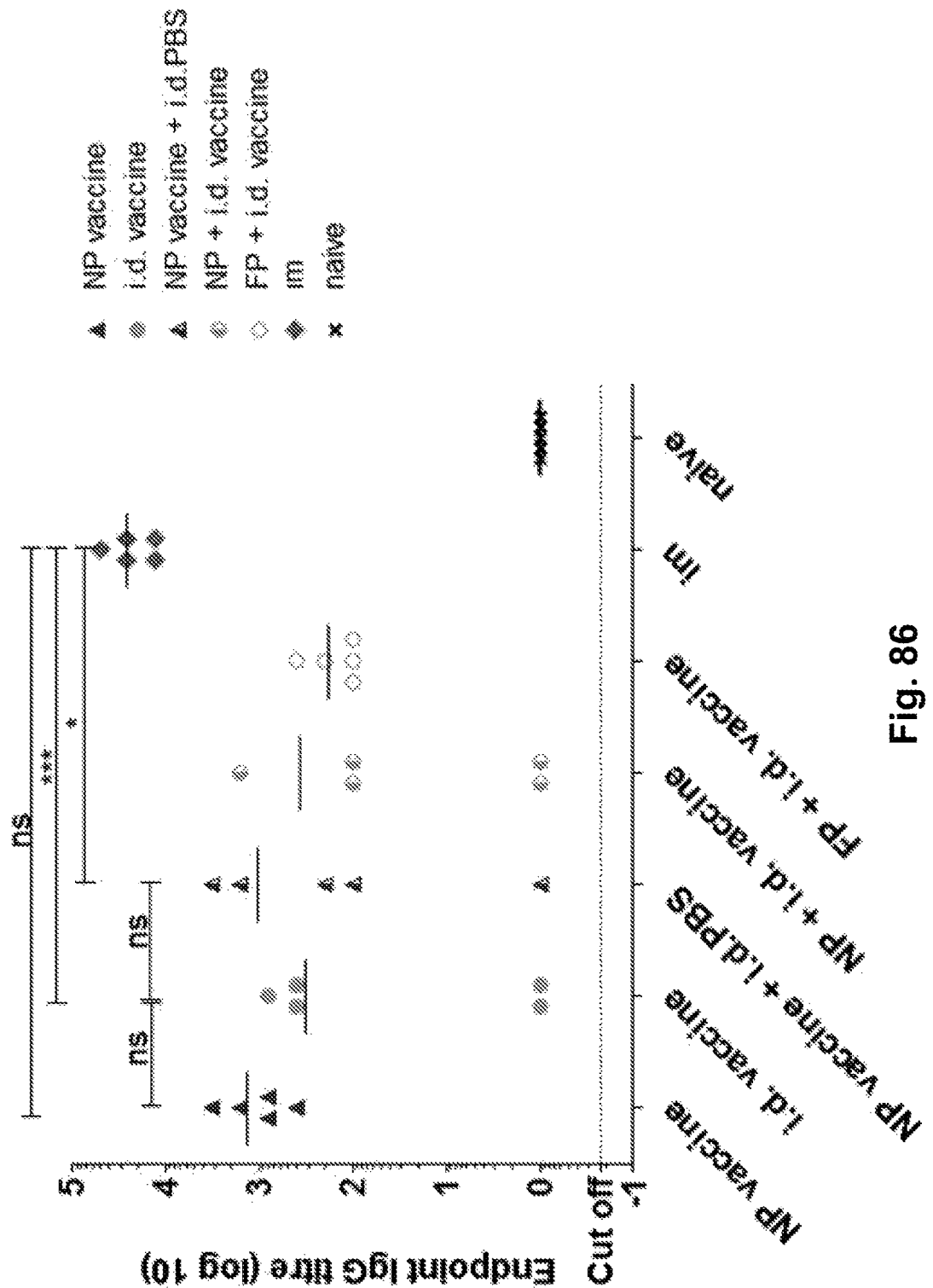
FIG. 86 is a graph of endpoint titers following delivery of 1 ng Fluvax to murine skin, for different treatments types.

FIG. 86 shows endpoint titers of the combinations of immunisation treatments seen in FIG. 85A, now with a 1 ng dose of Fluvax 2010. The 1 ng dose data shows similar trends to the previously discussed 10 ng does data. However it is noted that the statistical distributions of results are slightly different (potentially due to outliers in the intradermal delivery groups).

Brief findings from the 1 ng data are as follows. If intradermal PBS is given following projection patch (NP) application, a larger spread of the group is observed. The application of a projection patch followed by intradermal vaccine administration does not result in increased immune responses, similar to the corresponding 10 ng cases.

In view of the above experiments, it is theorized that vaccine delivered intradermally travels more rapidly to the lymph nodes than projection patch delivered vaccine.

Figure 87:
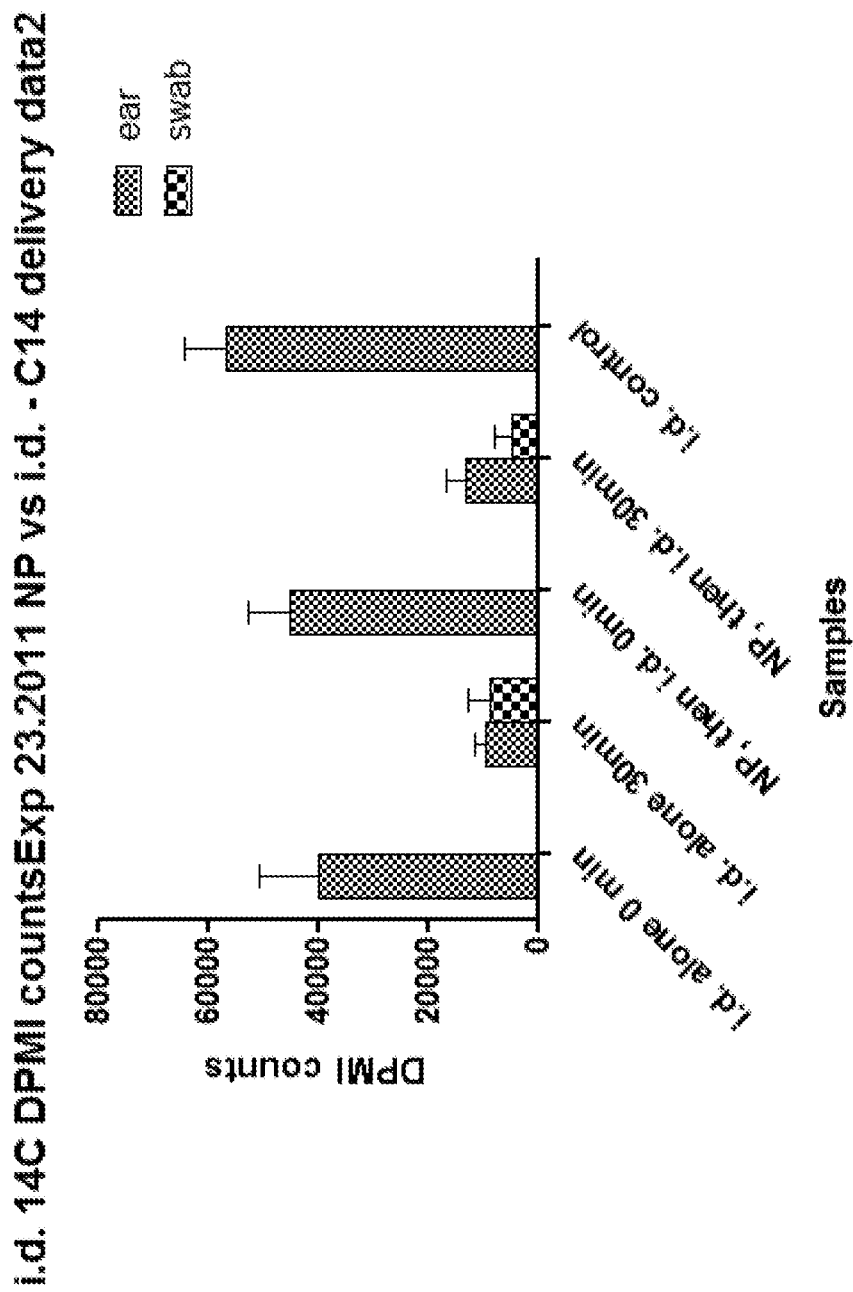
FIG. 87 is a graph of DPMI count over time following delivery of a radioactive labelled ova protein, for different delivery methods.

A radioactive labelled ova protein (C14) was administered and DPMI counts were assayed over time for the cases of intradermal delivery alone and application of a projection patch followed by intradermal delivery, and results are shown in FIG. 87. From this data, we observed that a significant amount of C14 'migrated' to the lymph nodes in less than 30 min.

Concurring visual results were also determined after intradermally injecting methylene blue and coomassie blue into mouse ears followed by excision of lymph nodes of the mice. It was found that within approximately 5 minutes, dyes had reached the lymph nodes.

Further experiments were conducted to study the effects of Quil-A addition to projection patch coatings, particularly with regard to cell death, and to visualize cell death and conduct immunogenicity data. A primary aim of these experiments Was to determine whether Quil-A+Fluvax would induce different levels of cell death compared to a Fluvax vaccine alone. Quil-A is a saponin which creates non reversible pores in cell membranes, and provides an adjuvant effect.

In these experiments, the sample size was n=1 (2 ears) per group, with the following groups being studied:
NP+MC: projection patch coated with methylcellulose;
NP+MC+FV: projection patch coated with methylcellulose and Fluvax; and,
NP+MC+FV+QA: projection patch coated with methylcellulose, Fluvax and Quil-A.

Imaging and analyses were performed by MPM. Results from immediately after application (0 hours) are shown in FIGS. 88A to 88C and results from approximately 15 hours after application are shown in FIGS. 89A to 89C.

Figure 88A:
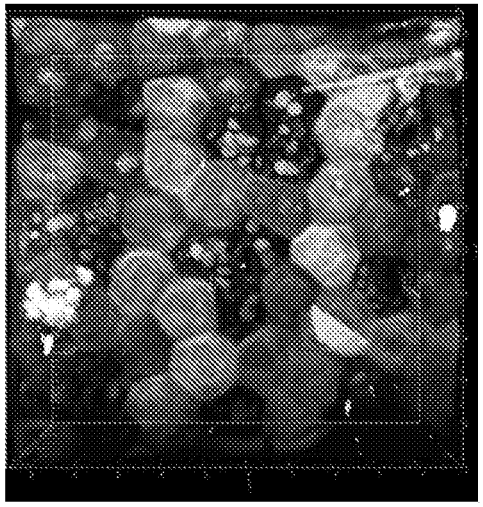
FIGS. 88A to 88C are cell viability stain images for different projection patch treatments upon application.
Figure 88B:
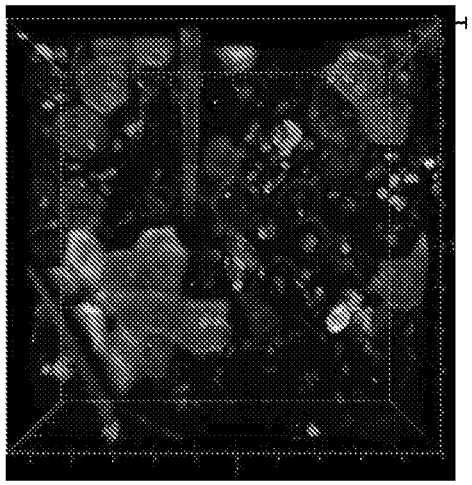
Figure 88C:
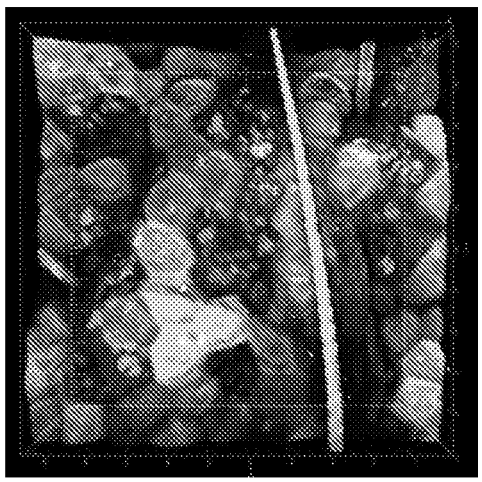
Figure 89A:
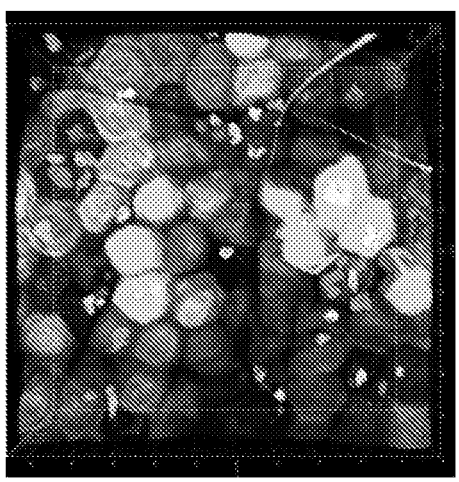
FIG. 89A to 89C are cell viability stain images for the different projection patch treatments shown in FIGS. 88A to 88C, 15 hours following application.
Figure 89B:
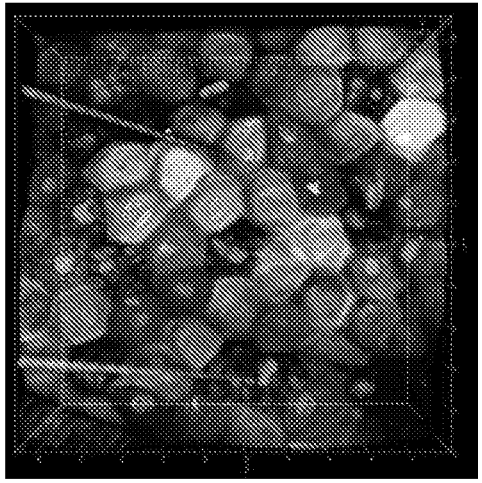
Figure 89C:
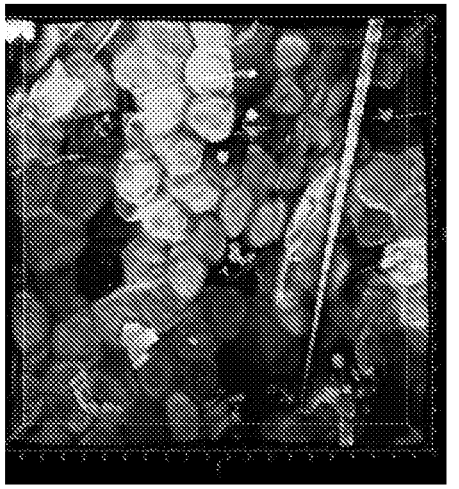

In particular, FIG. 88A shows the NP+MC case at 0 hours whilst FIG. 89A shows the same case after about 15 hours. FIG. 88B shows the NP+MC+FV case at 0 hours whilst FIG. 89B shows the same case after about 15 hours. FIG. 88C shows the NP+MC+FV+QA case at 0 hours whilst FIG. 89C shows the same case after about 15 hours.

In the results of the NP+MC+FV+QA, it was found that the Quil-A induces cell death upon application/delivery (depending upon the dose, high levels of inflammation, fibroblasts and necrosis have been reported). It is hypothesized that the cell death is initially necrosis based on images at 15 h, followed by apoptosis.

Coating Morphology

As discussed above, the effective profile of projections on a projection patch can be defined by the combined profile of the uncoated projection and the coating.

Experiments have been conducted to investigate the morphology of projection coatings and the associated dose delivery efficiency into skin at different concentrations. Standard projection patch geometries were used, having projections with lengths of about 100 μm, 70 μm spacing, and with 3364 projections per patch.

Figure 90A:
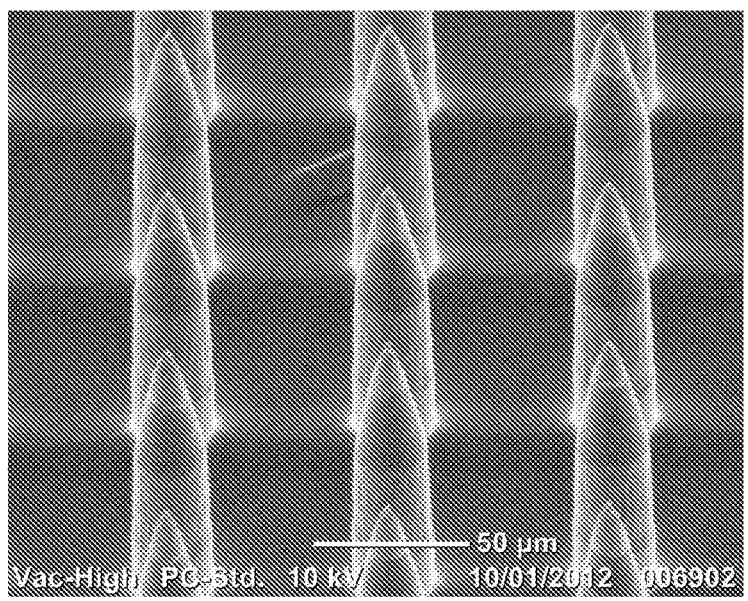
FIGS. 90A to 90E are SEM images of an uncoated projection patch and coated projection patches with 10, 20, 50 and 100 ng doses, respectively.
Figure 90B:
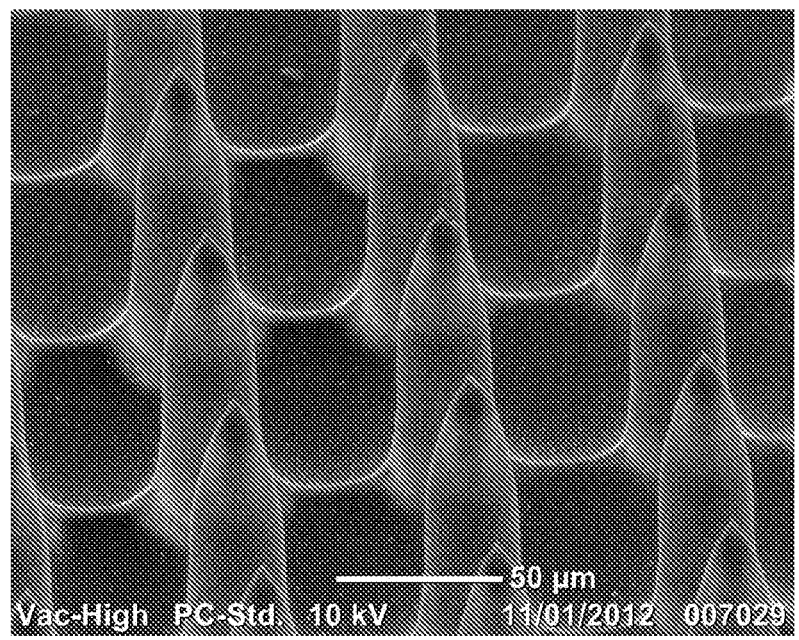
Figure 90C:
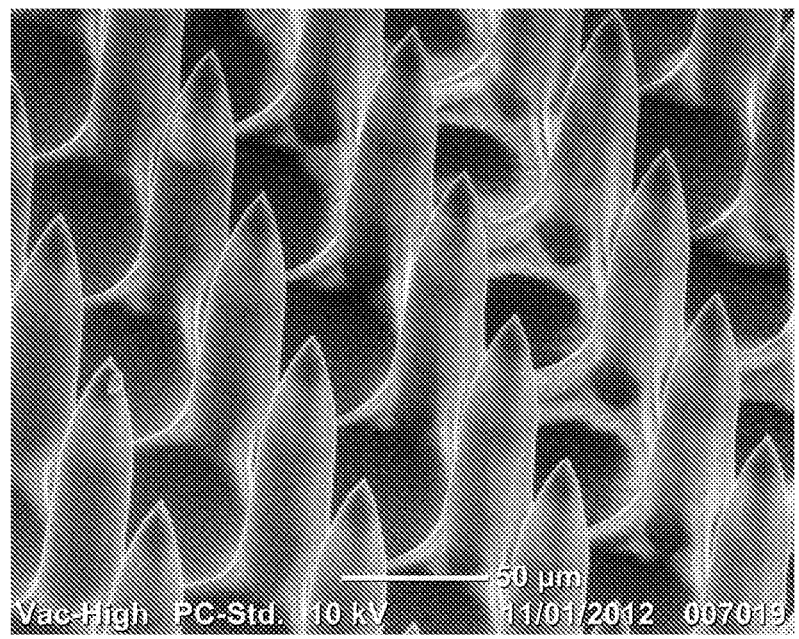
Figure 90D:
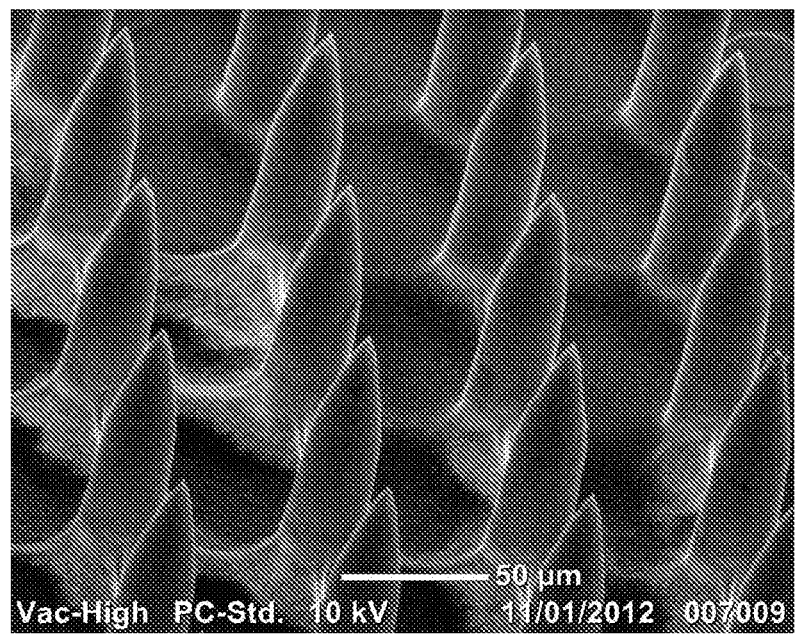
Figure 90E:
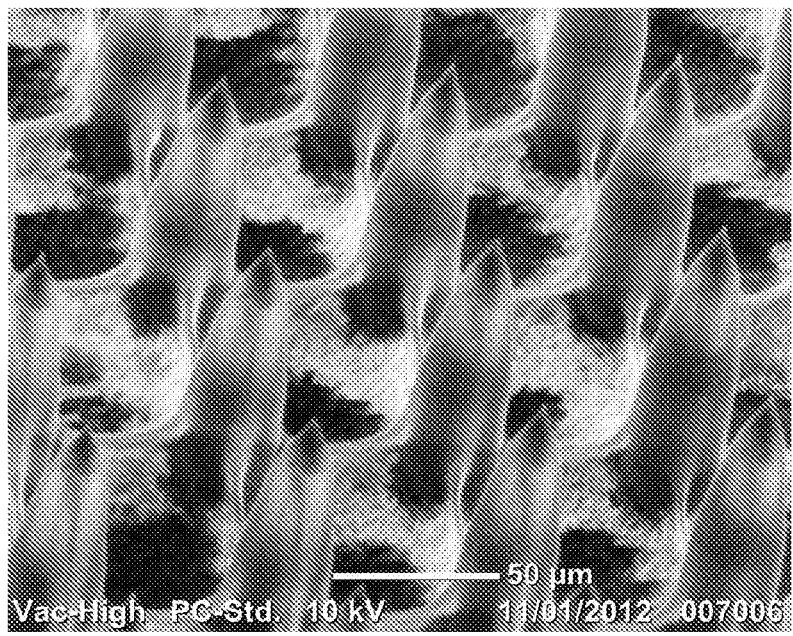
Figure 91A:
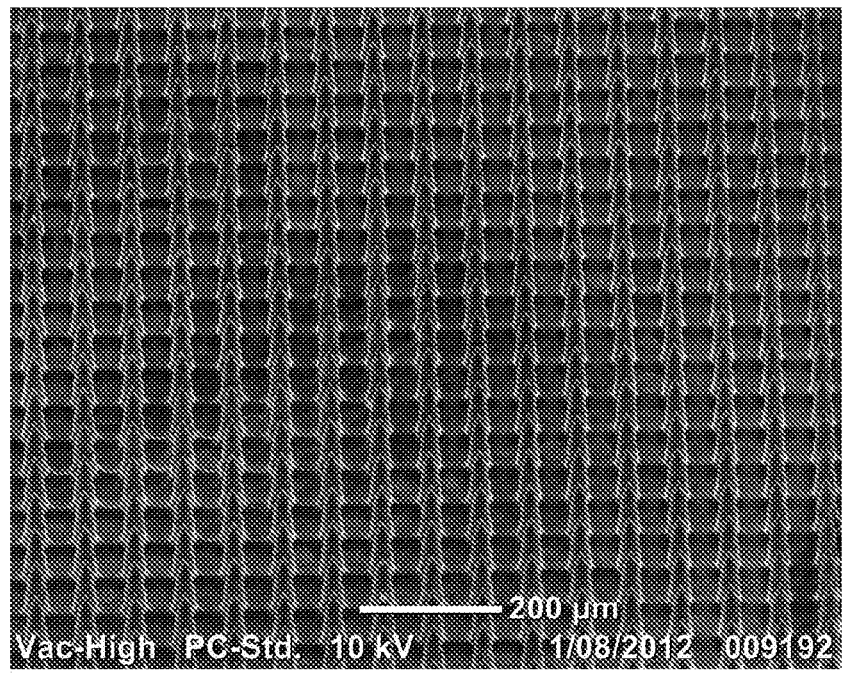
FIGS. 91A to 91E are SEM images of a coated projection patch having 70 μm projection spacing with a 1 ng Fluvax coating, at different magnification scales.
Figure 91B:
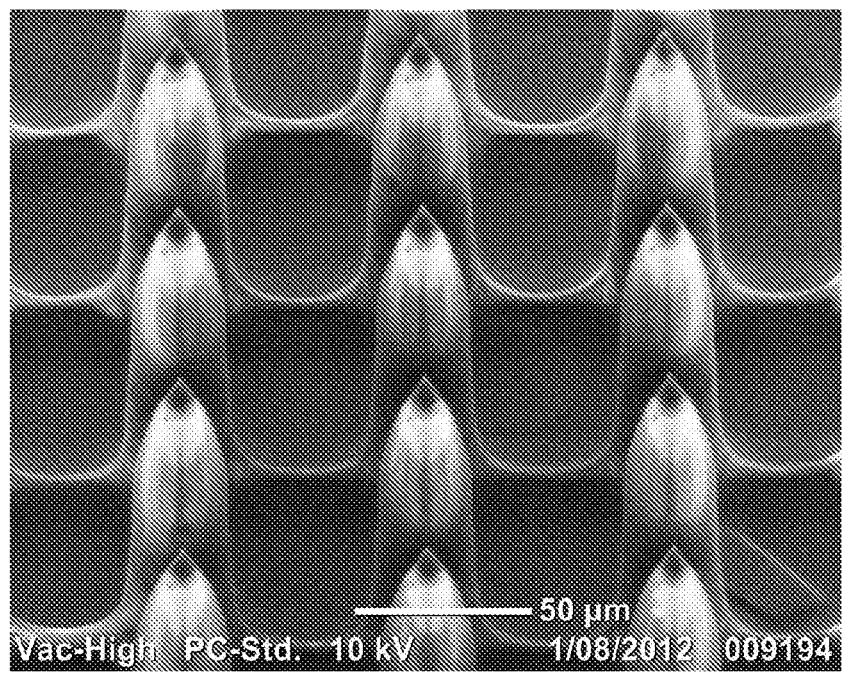
Figure 91C:
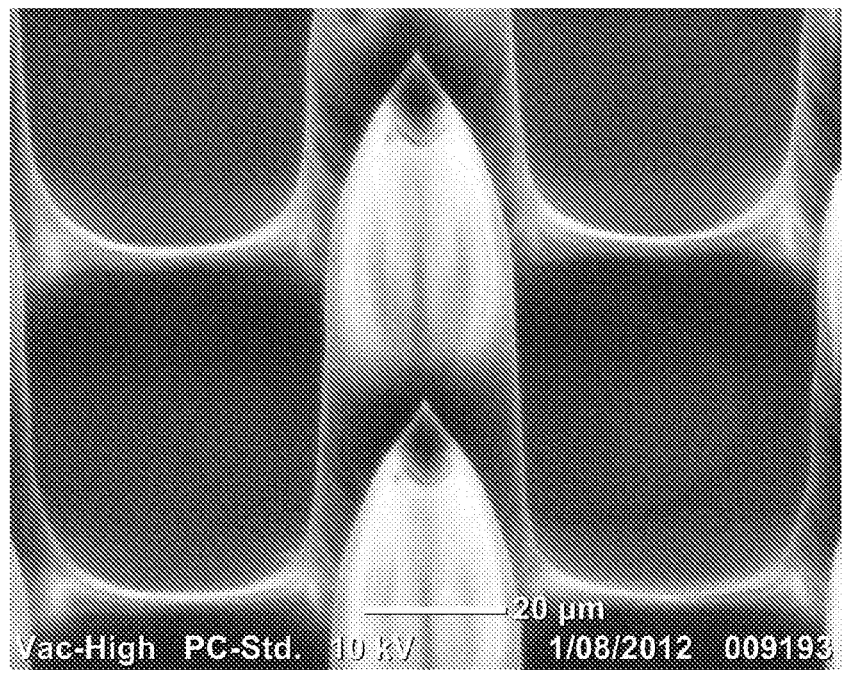
Figure 91D:
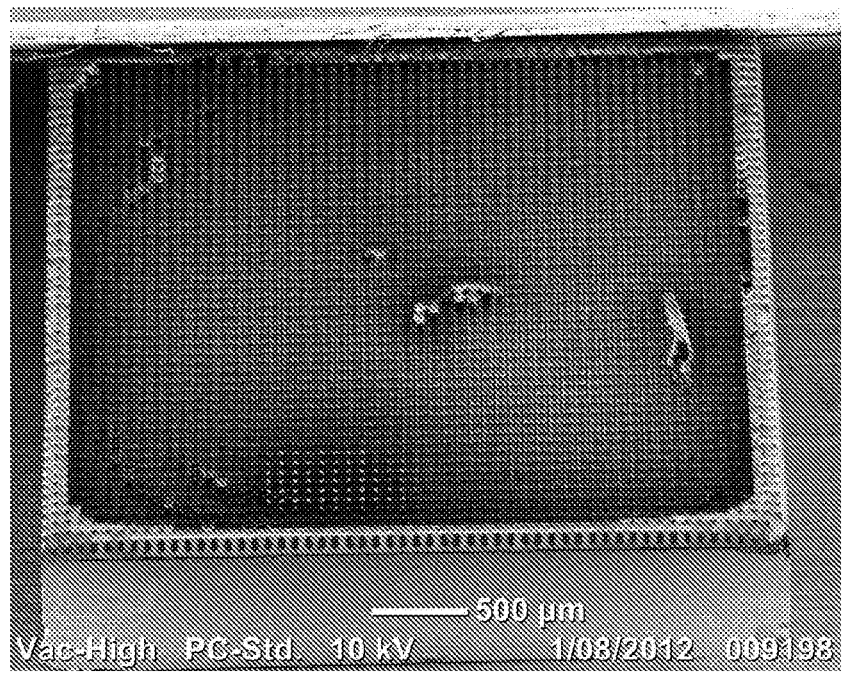
Figure 91E:
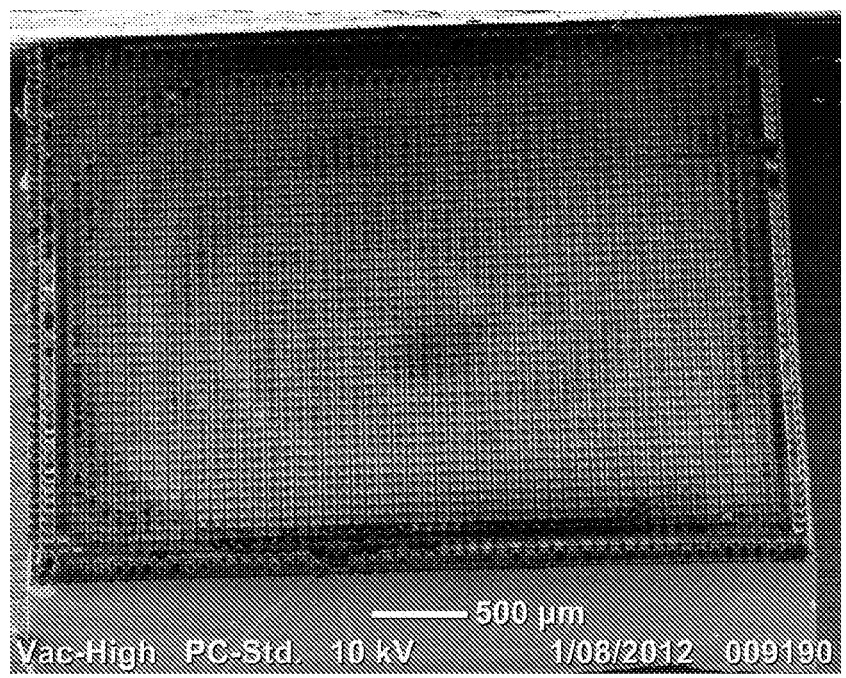
Figure 92A:
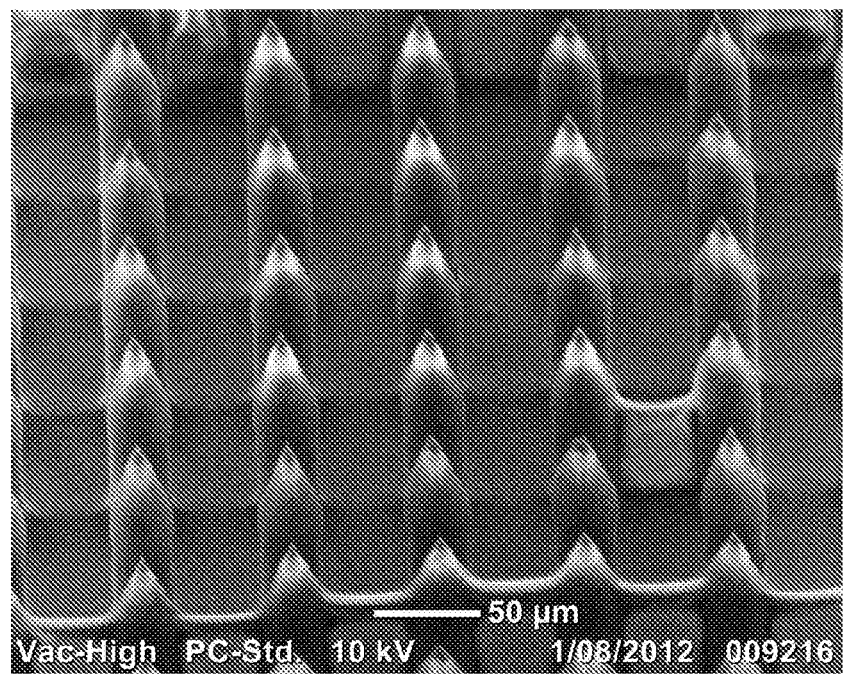
FIGS. 92A to 92D are SEM images of a coated projection patch having 70 μm projection spacing, in which 1 ng Fluvax coating was distributed across three patches, at different magnification scales.
Figure 92B:
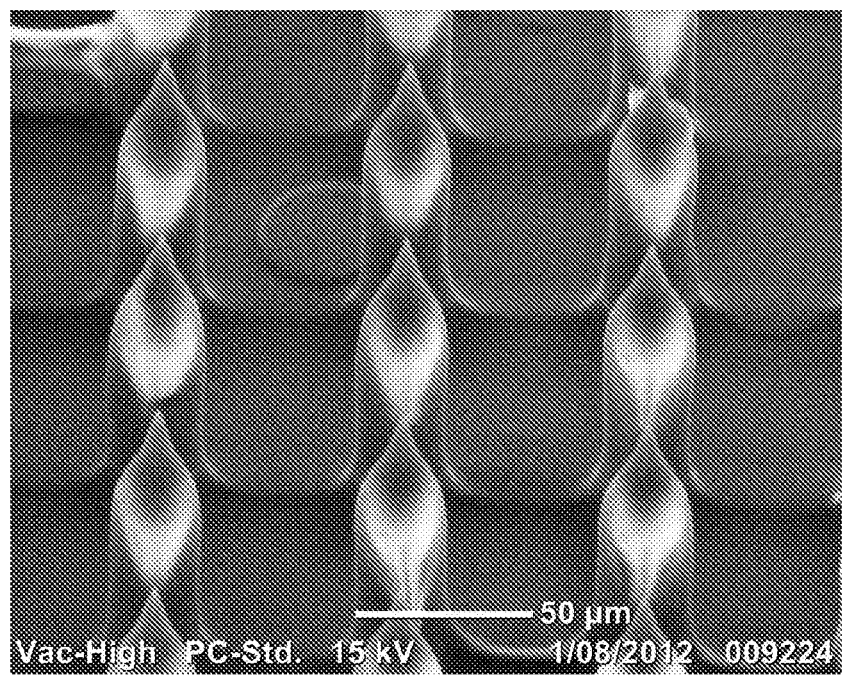
Figure 92C:
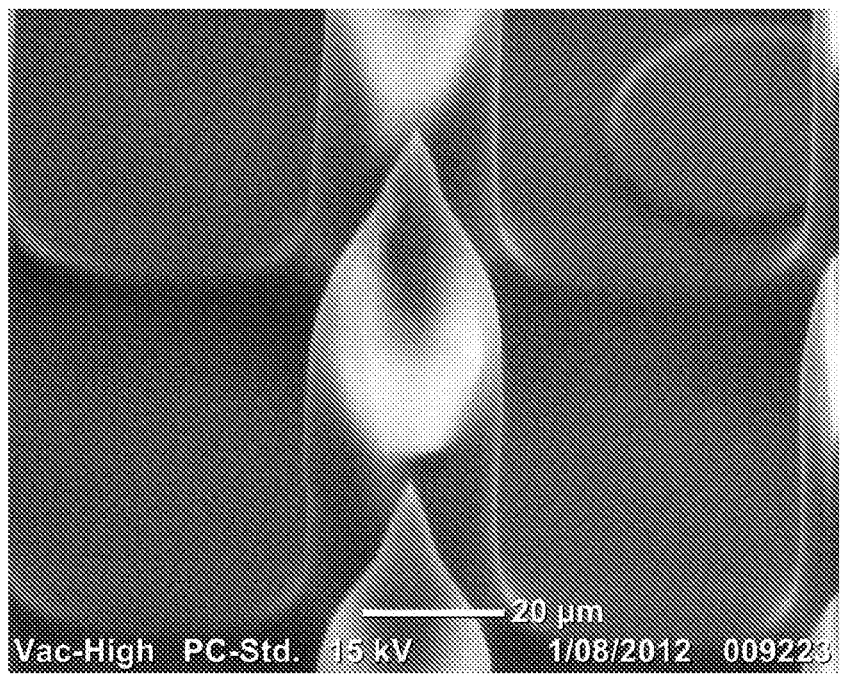
Figure 92D:
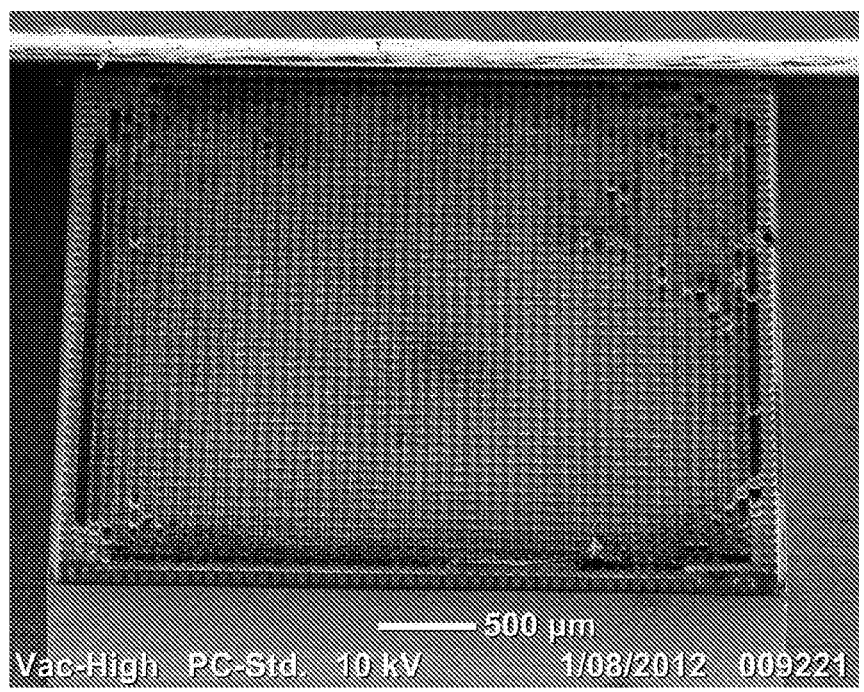

SEM images were obtained of Fluvax coated projection patches with 10, 20, 50 and 100 ng Fluvax doses prior to delivery into murine ear skin. FIG. 90A shows an uncoated projection patch. The further FIGS. 90B, 90C, 90D and 90E show effective profiles of the projections when the projection patch is coated with 10, 20, 50 and 100 ng of Fluvax vaccine, respectively. The coating morphology in these Figures depicts consistent coating (representative SEM of n=4).

FIGS. 91A to 91E show projection patches of the standard geometry discussed above with a 1 ng Fluvax coating, at different magnification scales, prior to delivery into murine ear skin.

FIGS. 92A to 92D show projection patches having the same standard geometry as FIGS. 91A to 91E, only this time coated with effectively ⅓ of the dose in FIGS. 91A to 91E. This was achieved by delivering 1 ng Fluvax coating across three projection patches. Comparison of images at like magnification scales clearly reveals that the resulting effective profile for the reduced dose (92A to 92D) exhibits a sharper tip, indicating a smaller contribution to the effective profile due to the coating.

Figure 93A:
FIGS. 93A and 93B are SEM images of a coated projection and projection patch having 100 μm projection spacing with a 0.1 ng Fluvax coating.
Figure 93B:
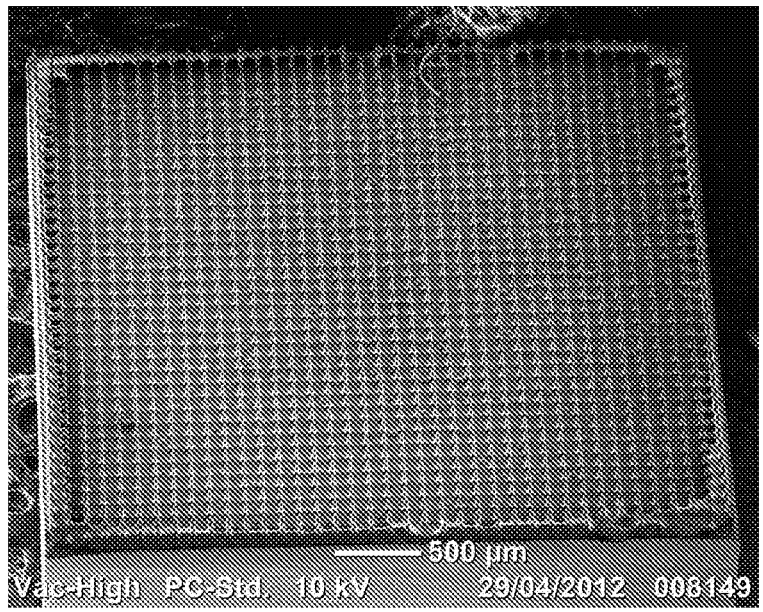
Figure 94A:
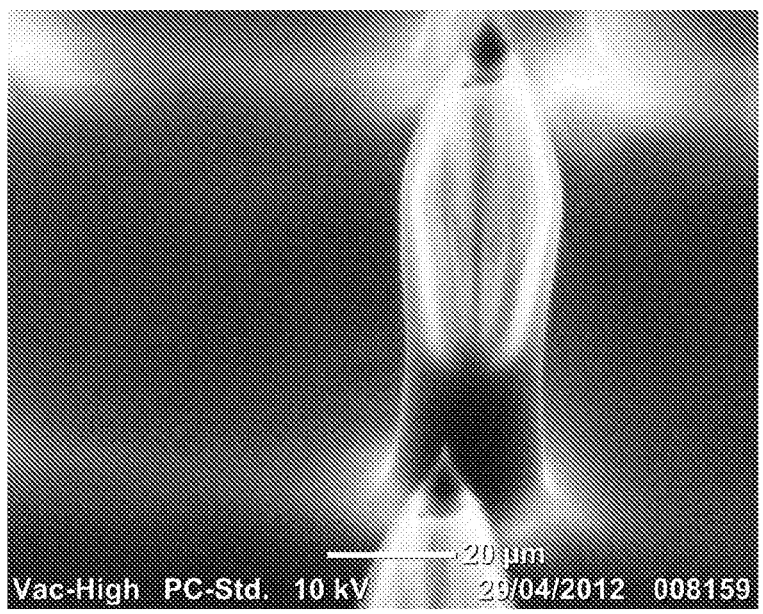
FIGS. 94A and 94B are SEM images of a coated projection and projection patch having 100 μm projection spacing with a 1 ng Fluvax coating; and, FIGS. 95A to 95E are SEM images of a coated projection patch having 100 μm projection spacing with a 1 ng Fluvax coating, at different magnification scales.
Figure 94B:
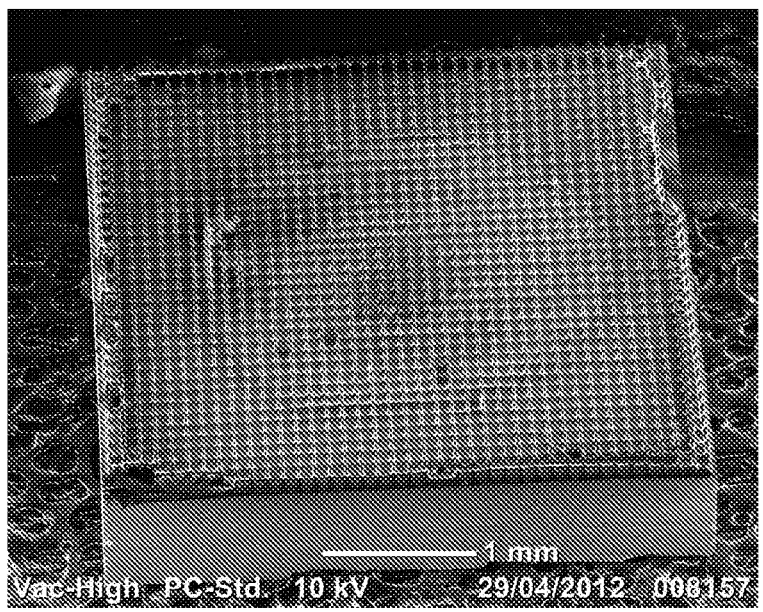
Figure 95A:
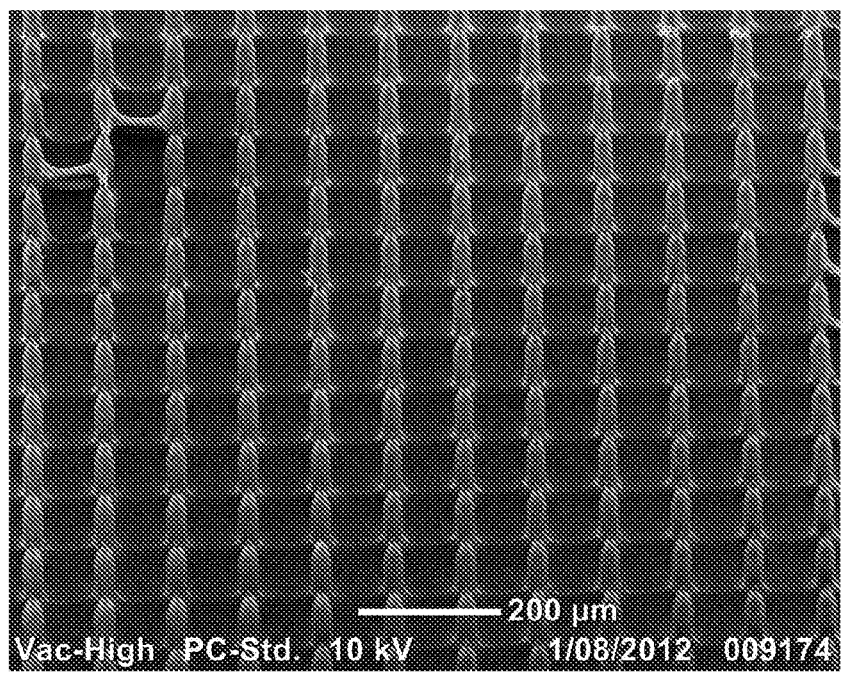
Figure 95B:
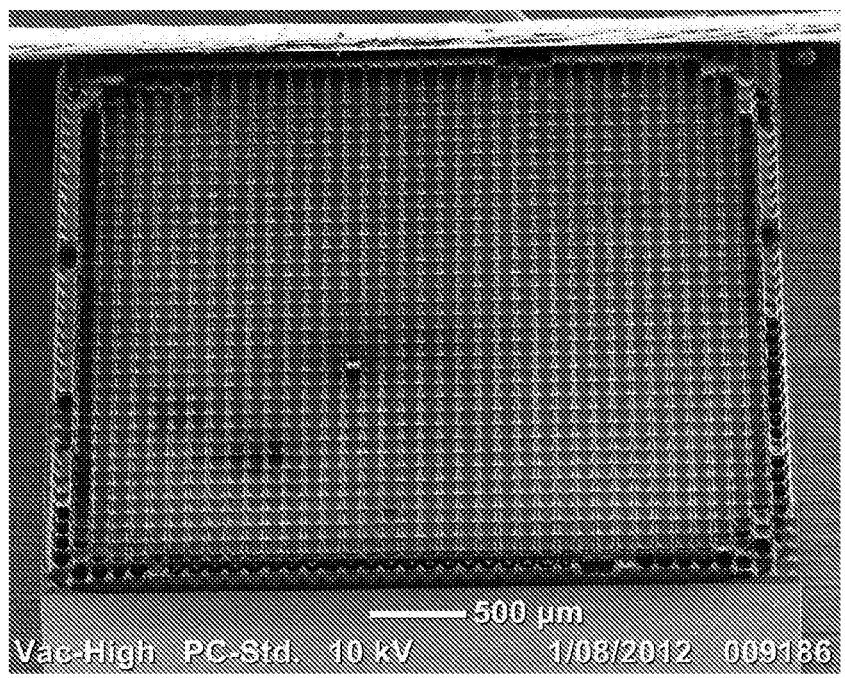
Figure 95C:
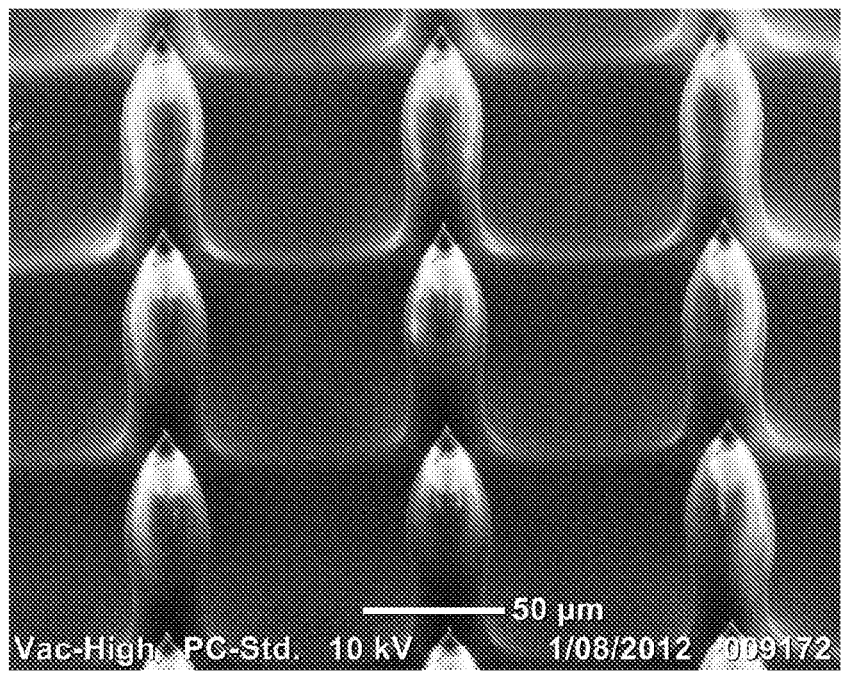
Figure 95D:
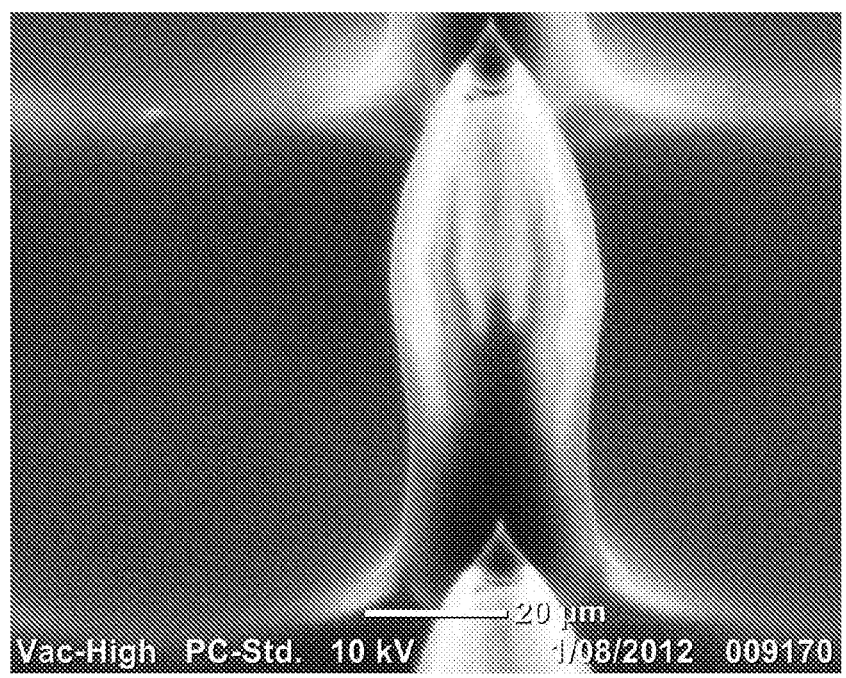
Figure 95E:
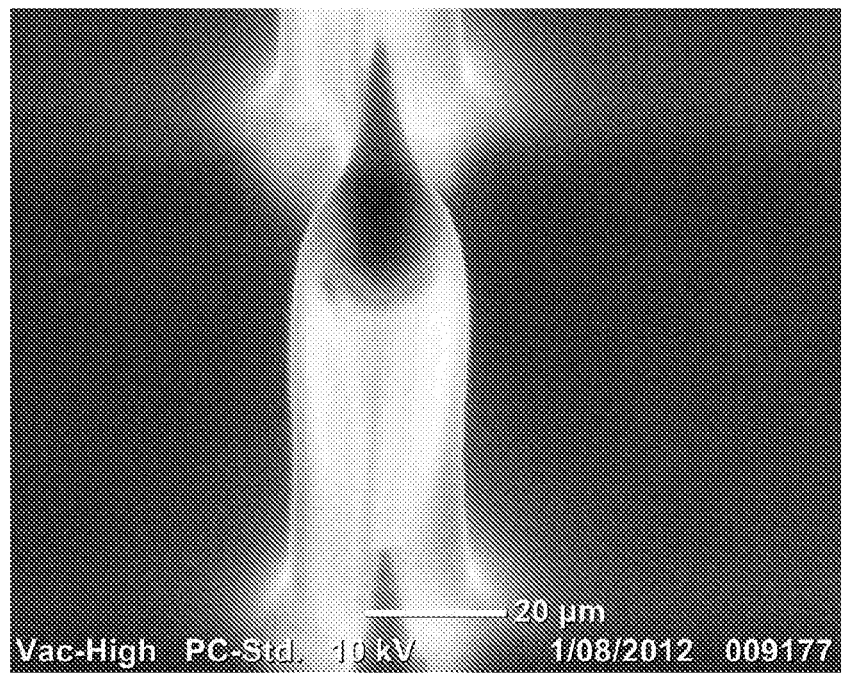

FIGS. 93A and 93B show the coating morphology of 100 μm spaced projections coated with 0.1 ng of Fluvax 2010 vaccine at magnification scales selected to focus on a single projection and the entire patch, respectively. FIGS. 94A and 94B show similar images for the coating morphology for the same projection spacing, coated with 1 ng of Fluvax 2010.

These images can be contrasted with the coating morphology for the earlier discussed 70 μm spacing cases. Changing the spacing from 70 to 100 μm between projections (thus effectively halving the number of projections per projection patch) did not adversely affect the coating morphology (representative SEM of n=4).

FIGS. 95A to 95E show further example images of a projection patch with 100 μm between projections with a 1 ng Fluvax coating, at different magnification scales, prior to delivery into murine ear skin.

Coating Delivery Efficiency

A C14 assay was used to assess coating delivery efficiency for doses ranging from 10-100 ng. These results can be seen in Table 9.

TABLE 9

| Dose | Patch | Swab | Ear |
|---|---|---|---|
| 10 ng | 68.77 ± 6.16% | 5.81 ± 3.58% | 25.42 ± 3.32% |
| 20 ng | 59.84 ± 12.19% | 6.07 ± 1.68% | 29.98 ± 8.30% |
| 50 ng | 70.31 ± 4.03% | 3.95 ± 1.24% | 25.73 ± 4.55% |
| 100 ng | 66.70 ± 4.65% | 5.29 ± 4.49% | 28.01 ± 5.28% |

It was found that coating delivery efficiency ranged with all tested Fluvax doses between ~22.6 to 30.0%.

Penetration Depth Considerations

As discussed above, penetration of projections into the dermis has been found to provide beneficial immune responses, and it has been determined that the preferred depth of penetration into the dermis can be specified based on the thickness of the epidermis in the biological subject.

Table 10 compiles epidermis thickness, preferred projection geometries and penetration depths for mice, rhesus monkeys and humans, and further shows calculated non-dimensional parameters for allowing comparisons between species. It is noted that the data in Table 10 has been determined using approximate tissue layer thickness values, and it should be appreciated that these may vary with factors such as the site of the biological subject, age, etc.

In Table 10, the epidermis thickness is calculated as the combined thickness of the stratum corneum and viable epidermis layers of the skin in each species, but it should be appreciated that the data would exhibit similar trends if based on the thickness of the viable epidermis alone, considering that this skin layer is typically significantly thicker than the stratum corneum.

TABLE 10

|  | Mouse | Rhesus Monkey | Human |
|---|---|---|---|
| Epidermis thickness - $t_E$ (μm) | 20 | 40 | 50 |
| Projection length - L (μm) | 110 | 250 | 250 |
| Total penetration depth (μm) | 40 | 90 | 100 |
| Dermal penetration depth - δ (μm) | 20 | 50 | 50 |
| $\delta/t_E$ | 1 | 1.25 | 1 |
| δ/L | 0.18 | 0.2 | 0.2 |
| $L/t_E$ | 5.5 | 6.25 | 5 |

As shown in Table 10, the $\delta/t_E$ parameter, namely the ratio of dermal penetration depth to the thickness of the epidermis of the biological subject, is on the order of 1 for each species. In other words, the projection has penetrated the dermis by a depth approximately equal to a depth of the epidermis of the biological subject, which was previously discussed as a preferred scenario.

Vaccine delivery through targeting of the dermis is expected to provide beneficial immune response outcomes across a range of $\delta/t_E$ values. A value of $\delta/t_E$ greater than 0 ensures that the tip of the projection successfully penetrates into the dermal layer of the skin. An upper threshold of $\delta/t_E$ less than 2 (maintaining i.e. a dermal penetration depth that less than twice the thickness of the epidermal layer) should generally prevent the tips of the projections from reaching nerve endings in lower portions of the dermis. Thus, the length of a projection may be selected for vaccine delivery targeting the dermis of a biological subject so that $\delta/t_E$ is between 0 and 2. In other words, the projection length should be selected so that it is sufficient to penetrate the dermis by an amount up to 2 times the thickness of the epidermal layer for the particular biological subject.

In view of findings discussed above, it will be appreciated that the dermal penetration depth δ will practically be dependent on both the configuration of the projection patch and the method of applying the patch to the skin. Whilst a range of factors will impact the penetration of the projections, the penetration depth may be controlled through selection of the projection length. It is therefore desirable to determine relationships between the length of the projections and the dermal penetration depth.

Accordingly, Table 10 also includes a row calculating δ/L for each example projection patch application. As can be seen, δ/L is around 0.2 for each species when a preferred dermal penetration depth is obtained. This relationship can be restated as a preferred projection length of approximately 5 times the dermal penetration distance.

Given that a range of dermal penetration depths are expected to provide beneficial results, a preferred range of δ/L between 0 and 0.4 has been determined. With regard to practical selection of projection length, this preferred range requires that the projection length is greater than 2.5 times a desired dermis penetration distance.

It may also be desirable to define preferred projection length ranges in terms of epidermal thickness. This can provide a particularly convenient means of initially specifying projection lengths for a biological subject based on a known epidermal layer thickness value. Accordingly, Table 10 also sets out calculated values of $L/t_E$ for the included examples. It will be seen that $L/t_E$ values range between values of 5 and 6. In other words, the length of the projections is between 5 and 7 times the epidermal thickness of the respective subject, to provide a preferred dermal penetration depth that is approximately equal to the epidermal thickness.

This relationship has been investigated under varying dermal penetration depths up to 2 times the epidermal thickness, and has revealed that a range of $L/t_E$ between 4 and 8 is suitable across species. In other words, the projection length may be selected to be between 4 and 8 times the epidermal thickness. A range of $L/t_E$ between 4 and 6 is expected to provide beneficial dermal penetration depths for human subjects, and therefore, for human application, the projection length may be selected to be between 4 and 6 times the epidermal thickness. It is noted that this range corresponds to a preferred length range of 200 μm to 300 μm, which has been suggested above.

Whilst projection penetration through the epidermis layer and into the dermis layer of the skin allows the delivery of vaccine and/or stimulus targeting cells within the dermis, it should be appreciated that there are also cases where targeting cells within the viable epidermis, without penetrating the dermis, can provide useful results. For example, targeting the viable epidermis only may be desirable for delivering biomolecules to epidermal cells, such as vaccines, allergens for allergy desensitization treatments, or the like.

Accordingly, in cases where the viable epidermis only is to be targeted, the projection geometry and application parameters should be selected to ensure that the projection tips breach the stratum corneum layer and do not penetrate into the dermal layer. The dermal penetration depth δ will thus be zero in these cases.

For example, in mouse skin, the total epidermis thickness is approximately 20 μm as identified above in Table 10. The outer stratum corneum layer is approximately 5 μm thick and the viable epidermis is approximately 15 μm thick. Accordingly, targeting the viable epidermis in mouse skin requires that the projection tips penetrate to a depth between 5 μm and 20 μm.

In human skin, the total epidermis thickness is approximately 50 μm and the outer stratum corneum is about 10 μm, thus requiring that the projection tips penetrate to a depth between 10 μm and 50 μm to ensure penetration into the viable epidermis without penetrating the dermal layer. The skin of other primates typically has a similar stratum corneum thickness but the total epidermis thickness may vary.

In any event, it will be appreciated that targeting the viable epidermis will generally require controlling the penetration depth such that it falls in a relatively narrow range compared to the above discussed dermal penetration cases.

For example, penetration into the viable epidermis only may be achieved through variation of the projection length, in a similar manner as described above for dermal penetration. In this case, the length of the projections may be selected based on the thickness of the stratum corneum—$t_{SC}$.

It has been found that the length of projections should typically be at least twice the desired total depth of penetration. Accordingly, when targeting the viable epidermis, the projection length should be at least twice the depth of the stratum corneum. The required length can be expressed independently of species by requiring that the non-dimensional parameter $L/t_{SC}$ is greater than 2. It is noted that in the human case this would correspond to a minimum projection length of 20 μm. A projection length of less than 100 μm would be expected to penetrate only the viable epidermis under similar assumptions.

However, it should be noted that specifying a particular projection length is not the only means of controlling penetration depth. Application parameters, such as the velocity at which the projection patch is applied to the skin, can also be selected to achieve a desired penetration depth.

As discussed above, the penetration depths of projections under cases of controlled velocity or projection length were investigated with reference to FIGS. 17D and 17E, respectively. With regard to FIG. 17D, it will be appreciated that controlled penetration into the viable epidermis only may achieved through the use of a low velocity of application, even when the projection length is sufficient to penetrate into the dermis at higher velocities. For example, the application velocity may be between 0.05 m/s and 1 m/s. Application velocities below 0.05 m/s are considered quasi-static (i.e. not dynamic). Thus, it may be possible to utilise patches having projections with lengths suitable for dermal targeting, such as 250 μm, and yet control the penetration depth using appropriately selected application velocity to ensure penetration into the epidermis only.

Similar techniques for targeting cells at particular penetration depths may also be used for other non-skin application cites. For example, upper epithelial cells equivalent to the epidermis or deeper epithelial cells equivalent to dermal cells may be targeted in non-skin sites such as the buccal mucosa.

It will be appreciated that, whilst many of the examples described above relate to the delivery of vaccines to particular depths within the skin of biological subjects, it will be appreciated that the described techniques will be applicable to general immunotherapeutic applications, and not solely for vaccine delivery.

Taking into account the results discussed above, the projections typically have a length selected to ensure penetration of the dermal layer, preferably without reaching nerve cells. Accordingly, the projections typically have a length of between 100 μm and 1000 μm, between 150 μm and 800 μm, and between 200 μm and 600 μm. More typically the projections have a length of between 200 μm and 300 μm, with the projections either being between 200 μm and 250 μm, or between 250 μm and 300 μm, in length.

In the event that a discontinuity is provided, this is typically located so that as the discontinuity reaches the dermis, penetration of the projection stops, with the tip extending into the dermal layer. Typically the discontinuity is located from the end of the tip at between 10 and 100 μm, between 20 and 90 μm, between 30 and 80 μm, and more typically between 40 and 60 μm.

The projection base width is selected to ensure sufficient strength, whilst avoiding the base being too wide to prevent projection penetration. Accordingly, the projections typically have a base width of between 5 μm and 100 μm, between 10 μm and 80 μm, between 20 μm and 70 μm and more typically between 30 μm and 50 μm.

To allow the tip of the projection to penetrate the skin without breaking, the tip typically has a radius of between 0.1 μm and 5 μm, between 0.1 μm and 2.5 μm, between 0.1 μm and 1 μm, and more typically between 0.1 μm and 0.5 μm.

To allow the tip to penetrate smoothly without excessive disruption to the skin, the cone angle at the tip is typically between 20° and 25°, between 15° and 20°, between 10° and 15°, and more typically between 10° and 12.5°, or 1° and 10°.

The projection spacing is selected so that material from the projections is able to at least partially, and optionally at least completely, diffuse between the projections. Accordingly, the projections are typically separated by between 10 μm and 200 μm, between 30 μm and 150 μm, between 50 μm and 120 μm and more typically between 70 μm and 100 μm, leading to patches having between 10 and 1000 projections per $mm^2$ and more typically between 100 and 3000 projections per $mm^2$, and in one specific example approximately 20,000 per $cm^2$.

As previously described, the area of the patch will have an impact on the ability to penetrate the subject, but this must be balanced by the need to induce cell damage over a sufficiently large area to induce a response. Consequently the patch typically has an area of between 0.5×0.5 mm and 20×20 mm, between 0.5×0.5 mm and 15×15 mm and more typically between 1×1 mm and 10×10 mm.

The application process is designed to ensure consistency of penetration, and so to avoid differences in tissue properties between different individuals, a preload is applied to the subject of between 0.1 N and 50 N, between 2 N and 40 N, between 5 N and 30 N, between 10 N and 20 N, between 1 N and 5 N, between 5 N and 10 N, between 10 N and 15 N and between 15 N and 20 N.

To ensure penetration and to overcome tissue stiffness the patch is typically applied with a velocity of at least 0.05 m/s, between 1 $ms^{-1}$ and 50 $ms^{-1}$, between 1 $ms^{-1}$ and 10 $ms^{-1}$, between 1 $ms^{-1}$ and 5 $ms^{-1}$, between 1 $ms^{-1}$ and 2 $ms^{-1}$, between 2 $ms^{-1}$ and 3 $ms^{-1}$, between 3 $ms^{-1}$ and 4 $ms^{-1}$, between 4 $ms^{-1}$ and 5 $ms^{-1}$ and between 5 $ms^{-1}$ and 10 $ms^{-1}$.

The projections typically have an aspect ratio (a length to width ratio) of less than about 6, to ensure that the projections are sufficiently strong to penetrate the tissue.

In the case of delivery of material to a dermis of a biological subject, the projections typically have a length that is at least one of between 4 and 8 times an epidermal thickness of the subject, between 4 and 6 times an epidermal thickness of the subject, between 6 and 8 times an epidermal thickness of the subject and more typically between 5 and 7 times an epidermal thickness of the subject.

The projections typically have a length greater than 2.5 times a desired dermis penetration distance. A ratio of the dermal penetration distance and projection length is typically between 0 and 0.4, more typically between 0.1 and 0.3 and usually about 0.18 or 0.2.

A ratio of the dermal penetration distance and epidermal thickness is typically between 0 and 2, between 0.5 and 1.5 and more typically about 1 or 1.25.

The patch is applied so that the application momentum is between 50 and 200 gram m/s, 50 and 150 gram m/s, between 50 and 100 gram m/s and between 100 and 150 gram m/s.

It will be appreciated that the application momentum for applying the patch will be dependent on the number of projections on the patch. Accordingly, the application momentum for applying the patch may be at least one of between 0.005 gram m/s and 1 gram m/s per projection, between 0.01 gram m/s and 1 gram m/s per projection, and between 0.03 gram m/s and 0.125 gram m/s per projection.

The application energy for applying the patch is typically up to 400 mJ, less than 350 mJ, less than 300 mJ, greater than 50 mJ, greater than 100 mJ, between 100 and 300 mJ and more typically between 150 and 250 mJ.

It will be appreciated that required application energy for applying the patch will be dependent on the number of projections on the patch. Accordingly, the application energy for applying the patch may be at least one of between 0.05 mJ and 2 mJ per projection, and between 0.1 mJ and 0.5 mJ per projection.

In the case of delivery of material to an epidermis of a biological subject, the projections typically have a length that is at least one of between 2 and 25 times a stratum corneum thickness of the subject, up to 6 times a desired epidermis penetration distance, and sufficient to penetrate the epidermis by an amount up to 4 times the stratum corneum thickness of the subject.

The projections typically have a length that is at least one of between 2 and 10 times a stratum corneum thickness of the subject, between 2 and 5 times a stratum corneum thickness of the subject, between 20 μm and 250 μm, and between 40 μm and 100 μm.

Material can be delivered to an epidermis of the subject by applying the device with at least one of an application velocity is at least 1 m/s, an application momentum of between 50 and 200 gram m/s, an application momentum of between 0.005 gram m/s and 1 gram m/s per projection, an application energy of up to 400 mJ, and an application energy of up to 2 mJ per projection.

Material can be delivered to an epidermis of the subject by applying the device with at least one of an application velocity is at least 0.05 m/s, an application momentum of between 35 and 150 gram m/s, an application momentum of between 0.003 gram m/s and 0.2 gram m/s per projection, an application energy of up to 200 mJ, and an application energy of up to 1 mJ per projection. The projections may have a length of between 100 μm and 250 μm and the application velocity may be between 0.05 m/s and 1 m/s. The projections may have a length of between 40 μm and 100 μm and the application velocity may be greater than 1 m/s.

The piston for use in applying the patch typically has a mass of at least one of between 5 grams and 100 grams, and 10 grams and 60 grams. It will be appreciated that the piston mass may be scaled based on patch size, such that the piston mass may be between 5 grams and 100 grams per $cm^2$.

Illustrative stimuli or material that can be delivered with the device of the present invention include any or more of: small chemical or biochemical compounds including drugs, metabolites, amino acids, sugars, lipids, saponins, and hormones; macromolecules such as complex carbohydrates, phospholipids, peptides, polypeptides, peptidomimetics, and nucleic acids; or other organic (carbon containing) or inorganic molecules; and particulate matter including whole cells, bacteria, viruses, virus-like particles, cell membranes, dendrimers and liposomes.

In some embodiments, the stimulus or material is selected from nucleic acids, illustrative examples of which include DNA, RNA, sense oligonucleotides, antisense oligonucleotides, ribozymes, small interfering oligonucleotides (siRNAs), micro RNAs (miRNAs), repeat associated RNAs (rasiRNA), effector RNAs (eRNAs), and any other oligonucleotides known in the art, which inhibit transcription and/or translation of a mutated or other detrimental protein. In illustrative examples of this type, the nucleic acid is in the form of an expression vector from which a polynucleotide of interest is expressible. The polynucleotide of interest may encode a polypeptide or an effector nucleic acid molecule such as sense or antisense oligonucleotides, siRNAs, miRNAs and eRNAs.

In other embodiments, the stimulus or material is selected from peptides or polypeptides, illustrative examples of which include insulin, proinsulin, follicle stimulating hormone, insulin like growth factor-1, insulin like growth factor-2, platelet derived growth factor, epidermal growth factor, fibroblast growth factors, nerve growth factor, colony stimulating factors, transforming growth factors, tumor necrosis factor, calcitonin, parathyroid hormone, growth hormone, bone morphogenic protein, erythropoietin, hemopoietic growth factors, luteinizing hormone, glucagon, glucagon likepeptide-1, anti-angiogenic proteins, clotting factors, anti-clotting factors, atrial natriuretic factor, plasminogen activators, bombesin, thrombin, enkephalinase, vascular endothelial growth factor, interleukins, viral antigens, non-viral antigens, transport proteins, and antibodies.

In still other embodiments, the stimulus or material is selected from receptor ligands. Illustrative examples of receptors include Fc receptor, heparin sulfate receptor, vitronectin receptor, Vcam-1 receptor, hemaglutinin receptor, Pvr receptor, Icam-1 receptor, decay-accelerating protein (CD55) receptor, Car (coxsackievirus-adenovirus) receptor, integrin receptor, sialic acid receptor, HAVCr-1 receptor, low-density lipoprotein receptor, BGP (biliary glycoprotien) receptor, aminopeptidease N receptor, MHC class-1 receptor, laminin receptor, nicotinic acetylcholine receptor, CD56 receptor, nerve growth factor receptor, CD46 receptor, asialoglycoprotein receptor Gp-2, alpha-dystroglycan receptor, galactosylceramide receptor, Cxcr4 receptor, Glvr1 receptor, Ram-1 receptor, Cat receptor, Tva receptor, BLVRcp1 receptor, MHC class-2 receptor, toll-like receptors (such as TLR-1 to -6) and complement receptors.

In specific embodiments, the stimuli or material are selected from antigens including endogenous antigens produced by a host that is the subject of the stimulus or material delivery or exogenous antigens that are foreign to that host. The antigens may be in the form of soluble peptides or polypeptides or polynucleotides from which an expression product (e.g., protein or RNA) is producible. Suitable endogenous antigens include, but are not restricted to, cancer or tumor antigens. Non-limiting examples of cancer or tumor antigens include antigens from a cancer or tumor selected from ABL1 proto-oncogene, AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, aplastic anemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous T-cell lymphoma, dermatofibrosarcoma protuberans, desmoplastic small round cell tumor, ductal carcinoma, endocrine cancers, endometrial cancer, ependymoma, oesophageal cancer, Ewing's Sarcoma, Extra-Hepatic Bile Duct Cancer, Eye Cancer, Eye: Melanoma, Retinoblastoma, Fallopian Tube cancer, Fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynecological cancers, haematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's cell histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid tumor of kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer (NSCLC), ocular cancers, esophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal tumours, pituitary cancer, polycythemia vera, prostate cancer, rare cancers and associated disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's macroglobulinemia, Wilms' tumor. In certain embodiments, the cancer or tumor relates to melanoma. Illustrative examples of melanoma-related antigens include melanocyte differentiation antigen (e.g., gp100, MART, Melan-A/MART-1, TRP-1, Tyros, TRP2, MC1R, MUC1F, MUC1R or a combination thereof) and melanoma-specific antigens (e.g., BAGE, GAGE-1, gp100In4, MAGE-1 (e.g., GenBank Accession No. X54156 and AA494311), MAGE-3, MAGE4, PRAME, TRP2IN2, NYNSO1a, NYNSO1b, LAGE1, p97 melanoma antigen (e.g., GenBank Accession No. M12154) p5 protein, gp75, oncofetal antigen, GM2 and GD2 gangliosides, cdc27, p21ras, gp100$^{Pmel117}$ or a combination thereof. Other tumour-specific antigens include, but are not limited to: etv6, aml1, cyclophilin b (acute lymphoblastic leukemia); Ig-idiotype (B cell lymphoma); E-cadherin, α-catenin, β-catenin, γ-catenin, p120ctn (glioma); p21ras (bladder cancer); p21 ras (biliary cancer); MUC family, HER2/neu, c-erbB-2 (breast cancer); p53, p21ras (cervical carcinoma); p21ras, HER2/neu, c-erbB-2, MUC family, Cripto-1protein, Pim-1 protein (colon carcinoma); Colorectal associated antigen (CRC)-CO17-1A/GA733, APC (colorectal cancer); carcinoembryonic antigen (CEA) (colorectal cancer; choriocarcinoma); cyclophilin b (epithelial cell cancer); HER2/neu, c-erbB-2, ga733 glycoprotein (gastric cancer); α-fetoprotein (hepatocellular cancer); Imp-1, EBNA-1 (Hodgkin's lymphoma); CEA, MAGE-3, NY-ESO-1 (lung cancer); cyclophilin b (lymphoid cell-derived leukemia); MUC family, p21ras (myeloma); HER2/neu, c-erbB-2 (non-small cell lung carcinoma); Imp-1, EBNA-1 (nasopharyngeal cancer); MUC family, HER2/neu, c-erbB-2, MAGE-A4, NY-ESO-1 (ovarian cancer); Prostate Specific Antigen (PSA) and its antigenic epitopes PSA-1, PSA-2, and PSA-3, PSMA, HER2/neu, c-erbB-2, ga733 glycoprotein (prostate cancer); HER2/neu, c-erbB-2 (renal cancer); viral products such as human papillomavirus proteins (squamous cell cancers of the cervix and esophagus); NY-ESO-1 (testicular cancer); and HTLV-1 epitopes (T cell leukemia).

Foreign antigens are suitably selected from transplantation antigens, allergens as well as antigens from pathogenic organisms. Transplantation antigens can be derived from donor cells or tissues from e.g., heart, lung, liver, pancreas, kidney, neural graft components, or from the donor antigen-presenting cells bearing MHC loaded with self antigen in the absence of exogenous antigen.

Non-limiting examples of allergens include Fel d 1 (i.e., the feline skin and salivary gland allergen of the domestic cat *Felis domesticus*, the amino acid sequence of which is disclosed International Publication WO 91/06571), Der p I, Der p II, Der fI or Der fII (i.e., the major protein allergens from the house dust mite dermatophagoides, the amino acid sequence of which is disclosed in International Publication WO 94/24281). Other allergens may be derived, for example from the following: grass, tree and weed (including ragweed) pollens; fungi and moulds; foods such as fish, shellfish, crab, lobster, peanuts, nuts, wheat gluten, eggs and milk; stinging insects such as bee, wasp, and hornet and the chirnomidae (non-biting midges); other insects such as the housefly, fruitfly, sheep blow fly, screw worm fly, grain weevil, silkworm, honeybee, non-biting midge larvae, bee moth larvae, mealworm, cockroach and larvae of *Tenibrio molitor* beetle; spiders and mites, including the house dust mite; allergens found in the dander, urine, saliva, blood or other bodily fluid of mammals such as cat, dog, cow, pig, sheep, horse, rabbit, rat, guinea pig, mouse and gerbil; airborne particulates in general; latex; and protein detergent additives.

Exemplary pathogenic organisms include, but are not limited to, viruses, bacteria, fungi parasites, algae and protozoa and amoebae. Illustrative viruses include viruses responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Epstein-Barr virus and other herpesviruses such as papillomavirus, Ebola virus, influenza virus, Japanese encephalitis (e.g., GenBank Accession No. E07883), dengue (e.g., GenBank Accession No. M24444), hantavirus, Sendai virus, respiratory syncytial virus, othromyxoviruses, vesicular stomatitis virus, visna virus, cytomegalovirus and human immunodeficiency virus (HIV) (e.g., GenBank Accession No. U18552). Any suitable antigen derived from such viruses are useful in the practice of the present invention. For example, illustrative retroviral antigens derived from HIV include, but are not limited to, antigens such as gene products of the gag, pol, and env genes, the Nef protein, reverse transcriptase, and other HIV components. Illustrative examples of hepatitis viral antigens include, but are not limited to, antigens such as the S, M, and L proteins of hepatitis B virus, the pre-S antigen of hepatitis B virus, and other hepatitis, e.g., hepatitis A, B, and C, viral components such as hepatitis C viral RNA. Illustrative examples of influenza viral antigens include; but are not limited to, antigens such as hemagglutinin and neuraminidase and other influenza viral components. Illustrative examples of measles viral antigens include, but are not limited to, antigens such as the measles virus fusion protein and other measles virus components. Illustrative examples of rubella viral antigens include, but are not limited to, antigens such as proteins E1 and E2 and other rubella virus components; rotaviral antigens such as VP7sc and other rotaviral components. Illustrative examples of cytomegaloviral antigens include, but are not limited to, antigens such as envelope glycoprotein B and other cytomegaloviral antigen components. Non-limiting examples of respiratory syncytial viral antigens include antigens such as the RSV fusion protein, the M2 protein and other respiratory syncytial viral antigen components. Illustrative examples of herpes simplex viral antigens include, but are not limited to, antigens such as immediate early proteins, glycoprotein D, and other herpes simplex viral antigen components. Non-limiting examples of varicella zoster viral antigens include antigens such as 9PI, gpII, and other varicella zoster viral antigen components. Non-limiting examples of Japanese encephalitis viral antigens include antigens such as proteins E, M-E, M-E-NS 1, NS 1, NS 1-NS2A, 80% E, and other Japanese encephalitis viral antigen components. Representative examples of rabies viral antigens include, but are not limited to, antigens such as rabies glycoprotein, rabies nucleoprotein and other rabies viral antigen components. Illustrative examples of papillomavirus antigens include, but are not limited to, the L1 and L2 capsid proteins as well as the E6/E7 antigens associated with cervical cancers, See Fundamental Virology, Second Edition, eds. Fields, B. N. and Knipe, D. M., 1991, Raven Press, New York, for additional examples of viral antigens.

Illustrative examples of fungi include *Acremonium* spp., *Aspergillus* spp., *Basidiobolus* spp., *Bipolaris* spp., *Blastomyces dermatidis*, *Candida* spp., *Cladophialophora carrionii*, *Coccoidiodes immitis*, *Conidiobolus* spp., *Cryptococcus* spp., *Curvularia* spp., *Epidermophyton* spp., *Exophiala jeanselmei*, *Exserohilum* spp., *Fonsecaea compacta*, *Fonsecaea pedrosoi*, *Fusarium oxysporum*, *Fusarium solani*, *Geotrichum candidum*, *Histoplasma capsulatum* var. *capsulatum*, *Histoplasma capsulatum* var. *duboisii*, *Hortaea werneckii*, *Lacazia loboi*, *Lasiodiplodia theobromae*, *Leptosphaeria senegalensis*, *Madurella grisea*, *Madurella mycetomatis*, *Malassezia furfur*, *Microsporum* spp., *Neotestudina rosatii*, *Onychocola canadensis*, *Paracoccidioides brasiliensis*, *Phialophora verrucosa*, *Piedraia hortae*, *Piedra iahortae*, *Pityriasis versicolor*, *Pseudallesheria boydii*, *Pyrenochaeta romeroi*, *Rhizopus arrhizus*, *Scopulariopsis brevicaulis*, *Scytalidium dimidiatum*, *Sporothrix schenckii*, *Trichophyton* spp., *Trichosporon* spp., *Zygomcete fungi*, *Absidia corymbifera*, *Rhizomucor pusillus* and *Rhizopus arrhizus*. Thus, representative fungal antigens that can be used in the compositions and methods of the present invention include, but are not limited to, candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Illustrative examples of bacteria include bacteria that are responsible for diseases including, but not restricted to, diphtheria (e.g., *Corynebacterium diphtheria*), pertussis (e.g., *Bordetella pertussis*, GenBank Accession No. M35274), tetanus (e.g., *Clostridium tetani*, GenBank Accession No. M64353), tuberculosis (e.g., *Mycobacterium tuberculosis*), bacterial pneumonias (e.g., *Haemophilus influenzae*.), cholera (e.g., *Vibrio cholerae*), anthrax (e.g., *Bacillus anthracis*), typhoid, plague, shigellosis (e.g., *Shigella dysenteriae*), botulism (e.g., *Clostridium botulinum*), salmonellosis (e.g., GenBank Accession No. L03833), peptic ulcers (e.g., *Helicobacter pylori*), Legionnaire's Disease, Lyme disease (e.g., GenBank Accession No. U59487), Other pathogenic bacteria include *Escherichia coli*, *Clostridium perfringens*, *Pseudomonas aeruginosa*, *Staphylococcus aureus* and *Streptococcus pyogenes*. Thus, bacterial antigens which can be used in the compositions and methods of the invention include, but are not limited to: pertussis bacterial antigens such as pertussis toxin, filamentous hemagglutinin, pertactin, F M2, FIM3, adenylate cyclase and other pertussis bacterial antigen components; diphtheria bacterial antigens such as diphtheria toxin or toxoid and other diphtheria bacterial antigen components; tetanus bacterial antigens such as tetanus toxin or toxoid and other tetanus bacterial antigen components, streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components, pneumococcal bacterial antigens such as pneumolysin, pneumococcal capsular polysaccharides and other pnermiococcal bacterial antigen components; *Haemophilus influenza* bacterial antigens such as capsular polysaccharides and other *Haemophilus influenza* bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens.

Illustrative examples of protozoa include protozoa that are responsible for diseases including, but not limited to, malaria (e.g., GenBank Accession. No. X53832), hookworm, onchocerciasis (e.g., GenBank Accession No. M27807), schistosomiasis (e.g., GenBank Accession No. LOS 198), toxoplasmosis, trypanosomiasis, leishmaniasis, giardiasis (GenBank Accession No. M33641), amoebiasis, filariasis (e.g., GenBank Accession No. J03266), borreliosis, and trichinosis. Thus, protozoal antigens which can be used in the compositions and methods of the invention include, but are not limited to: Plasmodium falciparum antigens such as merozoite surface antigens, sporozoite surface antigens, circumsporozoite antigens, gametocyte/gamete surface antigens, blood-stage antigen pf 155/RESA and other plasmodial antigen components; toxoplasma antigens such as SAG-1, p30 and other toxoplasmal antigen components; schistosomae antigens such as glutathione-S-transferase, paramyosin, and other schistosomal antigen components; Leishmania major and other leishmaniae antigens such as gp63, lipophosphoglycan and its associated protein and other leishmanial antigen components; and Trypanosoma cruzi antigens such as the 75-77 kDa antigen, the 56 kDa antigen and other trypanosomal antigen components.

The present invention also contemplates toxin components as antigens. Illustrative examples of toxins include, but are not restricted to, staphylococcal enterotoxins, toxic shock syndrome toxin; retroviral antigens (e.g., antigens derived from HIV), streptococcal antigens, staphylococcal enterotoxin-A (SEA), staphylococcal enterotoxin-B (SEB), staphylococcal enterotoxin$_{1-3}$ (SE$_{1-3}$), staphylococcal enterotoxin-D (SED), staphylococcal enterotoxin-E (SEE) as well as toxins derived from mycoplasma, mycobacterium, and herpes viruses.

In specific embodiments, the antigen is delivered to antigen-presenting cells. Such antigen-presenting cells include professional or facultative antigen-presenting cells. Professional antigen-presenting cells function physiologically to present antigen in a form that is recognised by specific T cell receptors so as to stimulate or anergise a T lymphocyte or B lymphocyte mediated immune response. Professional antigen-presenting cells not only process and present antigens in the context of the major histocompatability complex (MHC), but also possess the additional immunoregulatory molecules required to complete T cell activation or induce a tolerogenic response. Professional antigen-presenting cells include, but are not limited to, macrophages, monocytes, B lymphocytes, cells of myeloid lineage, including monocytic-granulocytic-DC precursors, marginal zone Kupffer cells, microglia, T cells, Langerhans cells and dendritic cells including interdigitating dendritic cells and follicular dendritic cells. Non-professional or facultative antigen-presenting cells typically lack one or more of the immunoregulatory molecules required to complete T lymphocyte activation or anergy. Examples of non-professional or facultative antigen-presenting cells include, but are not limited to, activated T lymphocytes, eosinophils, keratinocytes, astrocytes, follicular cells, microglial cells, thymic cortical cells, endothelial cells, Schwann cells, retinal pigment epithelial cells, myoblasts, vascular smooth muscle cells, chondrocytes, enterocytes, thymocytes, kidney tubule cells and fibroblasts. In some embodiments, the antigen-presenting cell is selected from monocytes, macrophages, B lymphocytes, cells of myeloid lineage, dendritic cells or Langerhans cells. In certain advantageous embodiments, the antigen-presenting cell expresses CD11c and includes a dendritic cell or Langerhans cell. In some embodiments the antigen-presenting cell stimulates an immune response. In other embodiments, the antigen-presenting cell induces a tolerogenic response.

The delivery of exogenous antigen to an antigen-presenting cell can be enhanced by methods known to practitioners in the art. For example, several different strategies have been developed for delivery of exogenous antigen to the endogenous processing pathway of antigen-presenting cells, especially dendritic cells. These methods include insertion of antigen into pH-sensitive liposomes (Zhou and Huang, 1994, Immunomethods, 4:229-235), osmotic lysis of pinosomes after pinocytic uptake of soluble antigen (Moore et al., 1988, Cell, 54:777-785), coupling of antigens to potent adjuvants (Aichele et al., 1990, J. Exp. Med., 171: 1815-1820; Gao et al., 1991, J. Immunol, 147: 3268-3273; Schulz et al., 1991, Proc. Natl. Acad. Sci. USA, 88: 991-993; Kuzu et al., 1993, Euro. J. Immunol., 23: 1397-1400; and Jondal et al., 1996, Immunity 5: 295-302) and apoptotic cell delivery of antigen (Albert et al. 1998, Nature 392:86-89; Albert et al. 1998, Nature Med. 4:1321-1324; and in International Publications WO 99/42564 and WO 01/85207). Recombinant bacteria (eg. *E. coli*) or transfected host mammalian cells may be pulsed onto dendritic cells (as particulate antigen, or apoptotic bodies respectively) for antigen delivery. Recombinant chimeric virus-like particles (VLPs) have also been used as vehicles for delivery of exogenous heterologous antigen to the MHC class I processing pathway of a dendritic cell line (Bachmann et al., 1996, Eur. J. Immunol., 26(11): 2595-2600).

Alternatively, or in addition, an antigen may be linked to, or otherwise associated with, a cytolysin to enhance the transfer of the antigen into the cytosol of an antigen-presenting cell of the invention for delivery to the MHC class I pathway. Exemplary cytolysins include saponin compounds such as saponin-containing Immune Stimulating Complexes (ISCOMs) (see e.g., Cox and Coulter, 1997, Vaccine 15(3): 248-256 and U.S. Pat. No. 6,352,697), phospholipases (see, e.g., Camilli et al., 1991, J. Exp. Med. 173: 751-754), pore-forming toxins (e.g., an α-toxin), natural cytolysins of gram-positive bacteria, such as listeriolysin O (LLO, e.g., Mengaud et al., 1988, Infect. Immun. 56: 766-772 and Portnoy et al., 1992, Infect. Immun. 60: 2710-2717), streptolysin O (SLO, e.g., Palmer et al., 1998, Biochemistry 37(8): 2378-2383) and perfringolysin O (PFO, e.g., Rossjohn et al., Cell 89(5): 685-692). Where the antigen-presenting cell is phagosomal, acid activated cytolysins may be advantageously used. For example, listeriolysin exhibits greater pore-forming ability at mildly acidic pH (the pH conditions within the phagosome), thereby facilitating delivery of vacuole (including phagosome and endosome) contents to the cytoplasm (see, e.g., Portnoy et al., Infect. Immun. 1992, 60: 2710-2717).

The cytolysin may be provided together with a pre-selected antigen in the form of a single composition or may be provided as a separate composition, for contacting the antigen-presenting cells. In one embodiment, the cytolysin is fused or otherwise linked to the antigen, wherein the fusion or linkage permits the delivery of the antigen to the cytosol of the target cell. In another embodiment, the cytolysin and antigen are provided in the form of a delivery vehicle such as, but not limited to, a liposome or a microbial delivery vehicle selected from virus, bacterium, or yeast. Suitably, when the delivery vehicle is a microbial delivery vehicle, the delivery vehicle is non-virulent. In a preferred embodiment of this type, the delivery vehicle is a non-virulent bacterium, as for example described by Portnoy et al. in U.S. Pat. No. 6,287,556, comprising a first polynucleotide encoding a non-secreted functional cytolysin operably linked to a regulatory polynucleotide which expresses the cytolysin in the bacterium, and a second polynucleotide encoding one or more pre-selected antigens. Non-secreted cytolysins may be provided by various mechanisms, e.g., absence of a functional signal sequence, a secretion incompetent microbe, such as microbes having genetic lesions (e.g., a functional signal sequence mutation), or poisoned microbes, etc. A wide variety of nonvirulent, non-pathogenic bacteria may be used; preferred microbes are relatively well characterised strains, particularly laboratory strains of *E. coli*, such as MC4100, MC1061, DH5α, etc. Other bacteria that can be engineered for the invention include well-characterised, nonvirulent, non-pathogenic strains of *Listeria monocytogenes, Shigella flexneri, mycobacterium, Salmonella, Bacillus subtilis*, etc. In a particular embodiment, the bacteria are attenuated to be non-replicative, non-integrative into the host cell genome, and/or non-motile inter- or intra-cellularly.

The delivery vehicles described above can be used to deliver one or more antigens to virtually any antigen-presenting cell capable of endocytosis of the subject vehicle, including phagocytic and non-phagocytic antigen-presenting cells. In embodiments when the delivery vehicle is a microbe, the subject methods generally require microbial uptake by the target cell and subsequent lysis within the antigen-presenting cell vacuole (including phagosomes and endosomes).

In other embodiments, the antigen is produced inside the antigen-presenting cell by introduction of a suitable expression vector as for example described above. The antigen-encoding portion of the expression vector may comprise a naturally-occurring sequence or a variant thereof, which has been engineered using recombinant techniques. In one example of a variant, the codon composition of an antigen-encoding polynucleotide is modified to permit enhanced expression of the antigen in a target cell or tissue of choice using methods as set forth in detail in International Publications WO 99/02694 and WO 00/42215. Briefly, these methods are based on the observation that translational efficiencies of different codons vary between different cells or tissues and that these differences can be exploited, together with codon composition of a gene, to regulate expression of a protein in a particular cell or tissue type. Thus, for the construction of codon-optimised polynucleotides, at least one existing codon of a parent polynucleotide is replaced with a synonymous codon that has a higher translational efficiency in a target cell or tissue than the existing codon it replaces. Although it is preferable to replace all the existing codons of a parent nucleic acid molecule with synonymous codons which have that higher translational efficiency, this is not necessary because increased expression can be accomplished even with partial replacement. Suitably, the replacement step affects 5, 10, 15, 20, 25, 30%, more preferably 35, 40, 50, 60, 70% or more of the existing codons of a parent polynucleotide.

The expression vector for introduction into the antigen-presenting cell will be compatible therewith such that the antigen-encoding polynucleotide is expressible by the cell. For example, expression vectors of this type can be derived from viral DNA sequences including, but not limited to, adenovirus, adeno-associated viruses, herpes-simplex viruses and retroviruses such as B, C, and D retroviruses as well as spumaviruses and modified lentiviruses. Suitable expression vectors for transfection of animal cells are described, for example, by Wu and Ataai (2000, Curr. Opin. Biotechnol. 11(2):205-208), Vigna and Naldini (2000, J. Gene Med. 2(5):308-316), Kay, et al. (2001, Nat. Med. 7(1):33-40), Athanasopoulos, et al. (2000, Int. J. Mol. Med. 6(4):363-375) and Walther and Stein (2000, Drugs 60(2): 249-271).

A number of variations and options for use with the above described devices will now be described.

Herein, the terms "projection", "micro-nanoprojection", "nanoneedle", "nanoprojection", "needle", "rod" etc are used interchangeably to describe the solid projections.

In cases where a material or agent is to be transported, projections may be coated on the outside of the nanoneedles. This provides a higher probability of delivering the coating to the depth of interest compared to microparticle delivery from a gene gun and thus is more efficient.

A further feature is that the nanoneedles may be used for delivery not only through the skin but through other body surfaces, including mucosal surfaces, to cellular sites below the outer layer or layers of such surfaces. The term "internal site", as used herein, is to be understood as indicating a site below the outer layer(s) of skin and other tissues for which the devices of the present invention are to be used.

Furthermore, these projections may be used to deliver stimuli to cells or cell components other than those resulting from the administration of bioactive agents such as drugs and antigenic materials for example. Mere penetration of cellular sites with projections may be sufficient to induce a beneficial response, as indicated hereinafter.

The device is suitable for intracellular delivery. The device is suitable for delivery to specific organelles within cells. Examples of organelles to which the device can be applied include a cell nucleus, endoplasmic reticulum, ribosome, or lysosome for example.

In a further embodiment, a bioactive material is releasably incorporated into the material of which the needle, or projection, is composed. All, or part of the projection may be constructed of a biocompatible, biodegradable polymer (such as Poly Lactic Acid (PLA), PolyGlycolic Acid (PGA) or PGLA or Poly Glucleic Acid), which is formulated with the bioactive material of choice. The projections may then be inserted into the appropriate target site and, as they dissolve, the bioactive material will enter the organelle(s)/cells.

In one example, at least the delivery end section of the needle is composed of a biodegradable material.

In an alternative embodiment of the invention, a device is also provided in which the needle has no bioactive material on or within it. The targeted cell or organelle is perturbed/stimulated by the physical disruption caused by the (delivery end of the) nanoneedle (projection). This physical stimulus may, for example, be coupled with electric stimulus as a form of specific nanoelectroporation of particular organelles or the cell.

The bioactive material or stimulus delivered by the device of the invention may be any suitable material or stimulus which gives the desired effect at the target site.

Examples of bioactive materials, which are not intended to be limiting with respect to the invention include polynucleotides and nucleic acid or protein molecules, antigens, allergens, adjuvants, molecules, elements or compounds. In addition, the device may be coated with materials such as biosensors, nanosensors or MEMS.

In one aspect, the device is provided in the form of a patch containing a plurality of needles (projections) for application to a body surface. A multiplicity of projections can allow multiple cells and organelles to be targeted and provided with a bioactive material or stimulus at the same time. The patch may be of any suitable shape, such as square or round for example. The overall number of projections per patch depends upon the particular application in which the device is to be used. Preferably, the patch has at least 10 needles per mm, and more preferably at least 100 needles per mm$^2$. Considerations and specific examples of such a patch are provided in more detail below.

Examples of specific manufacturing steps used to fabricate the device are described in greater detail below. In one preferred aspect, the device of the invention is constructed from biocompatible materials such as Titanium, Gold, Silver or Silicon, for example. This may be the entire device, or alternatively it may only be the projections or the delivery end section of the projections which are made from the biocompatible materials.

One manufacturing method for the device utilises the Deep Reactive Ion Etching (DRIE) of the patterns direct from silicon wafers, see the construction section below.

Another manufacturing method for the device utilises manufacturing from a male template constructed with X-ray lithography, electrodeposition and moulding (LIGA). The templates are then multiply inserted into a soft polymer to produce a plurality of masks. The masks are then vacuum deposited/sputtered with the material of choice for the nanoprojections, such as titanium, gold, silver, or tungsten. Magnetron sputtering may also be applied, see the construction section below.

An alternative means for producing masks is with 2 photon Stereolithography, a technique which is known in the art and is described in more detail below.

In one embodiment, the device is constructed of silicon.

The device may be for a single use or may be used and then recoated with the same or a different bioactive material or other stimulus, for example.

In one embodiment, the device comprises projections which are of differing lengths and/or diameters (or thicknesses depending on the shape of the projections) to allow targeting, of different targets within the same use of the device.

Also provided throughout the specification are numerous uses of the device, which has many useful medical applications in the treatment of a number of diseases.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. A device for delivery of a biochemical compound to a biological subject, the device comprising:
   a) a base; and,
   b) a number of solid, non-porous projections extending from the base, wherein each projection comprises a cylindrical support section which transitions into a coated, convex end section having a tip, wherein the transition forms a flat stepped surface profile between the end section and the cylindrical support section and wherein the cylindrical support section is wider at the transition than the coated end section and a discontinuity wherein the discontinuity is closer to the base than the flat stepped surface profile such that the flat stepped surface profile and the discontinuity of each projection interact with tissue of the biological subject to at least partially control penetration of the projections into the tissue thereby providing a physical adjuvant effect, when the device is applied to the tissue so that the projections penetrate the tissue,
   wherein a cone angle measured from a centerline of each projection to an edge of the coated, convex end section having a tip varies along a length of at least one of the projections and wherein the cone angle increases along the length of the end section and wherein the cone angle is between 1° and 10° at the tip.

2. The device according to claim 1, wherein the flat stepped surface profile is located at a distance from the tip of the end section, the distance being between 10 and 100 µm.

3. The device according to claim 1, wherein at least one of the projections has a length between 200 µm and 250 µm.

4. The device according to claim 1,
   wherein:
   i) the number of projections is from about 1000 to 20000;
   ii) at least one of the projections has a length of between 200 µm and 250 µm;
   iii) at least one of the projections has a base width of between 20 µm and 50 µm;
   iv) at least one of the projections has a tip radius of less than 5 µm; and
   v) the projections are separated by a spacing of between 70 µm and 100 µm.

5. The device of claim 1, wherein the coated, convex end section is coated with a first vaccine compound and wherein at least one of the projections is coated with a second vaccine compound.

6. The device of claim 1, wherein the biochemical compound is sprayed onto the projections.

7. The device of claim 1, wherein the base is 1 mm$^2$ to 100 mm$^2$.

8. The device of claim 1 wherein the physical adjuvant effect is cell damage mediated by the projections.

9. The device according to claim 1, wherein the flat stepped surface profile step is located at a distance from the tip of the end section, the distance being between 40 and 60 µm.

* * * * *